US006375955B1

(12) United States Patent
Reed et al.

(10) Patent No.: US 6,375,955 B1
(45) Date of Patent: Apr. 23, 2002

(54) LEISHMANIA ANTIGENS FOR USE IN THE THERAPY AND DIAGNOSIS OF LEISHMANIASIS

(75) Inventors: Steven G. Reed, Bellevue; Antonio Campos-Neto, Bainbridge Island, both of WA (US); John R. Webb, Manotick (CA); Davin C. Dillon, Issaquah, WA (US); Yasir A. W. Skeiky, Bellevue, WA (US); Ajay Bhatia; Peter Probst, both of Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/022,765

(22) Filed: Feb. 12, 1998

Related U.S. Application Data

(63) Continuation-in-part of application No. 08/920,609, filed on Aug. 27, 1997, which is a continuation-in-part of application No. 08/798,841, filed on Feb. 12, 1997, which is a continuation-in-part of application No. 08/533,669, filed on Sep. 22, 1995, now Pat. No. 5,834,592.

(51) Int. Cl.⁷ ...................... A61K 39/008; A61K 39/00; A61K 38/00
(52) U.S. Cl. ................................ 424/269.1; 424/265.1; 424/184.1; 930/210; 530/300; 530/350
(58) Field of Search ................................ 530/300, 350; 430/210; 424/269.1, 265.1, 184.1

(56) References Cited

U.S. PATENT DOCUMENTS

| | | | |
|---|---|---|---|
| 4,870,006 A | | 9/1989 | Dragon et al. .................. 435/7 |
| 5,411,865 A | * | 5/1995 | Reed |
| 5,719,263 A | * | 2/1998 | Reed |
| 5,834,592 A | * | 11/1998 | Reed et al. |
| 5,846,748 A | * | 12/1998 | Mandal et al. |
| 5,876,735 A | * | 3/1999 | Reed |
| 5,876,966 A | * | 3/1999 | Reed |
| 5,879,687 A | * | 3/1999 | Reed |
| 5,910,306 A | * | 6/1999 | Alving et al. |
| 5,912,166 A | * | 6/1999 | Reed et al. |
| 5,961,970 A | * | 10/1999 | Lowell et al. |
| 5,965,142 A | | 10/1999 | Dillon et al. |
| 5,980,898 A | * | 11/1999 | Glenn et al. |
| 5,985,284 A | * | 11/1999 | Lowell |
| 6,013,268 A | * | 1/2000 | Reed |
| 6,054,135 A | * | 4/2000 | Reed et al. |
| 6,228,372 B1 | * | 5/2001 | Reed et al. |

FOREIGN PATENT DOCUMENTS

| | | |
|---|---|---|
| WO | WO 95/29239 | 11/1995 |
| WO | 96/39524 | * 12/1996 |
| WO | WO 97/11180 | 3/1997 |

OTHER PUBLICATIONS

Yang et al, Immunology, 72:3–9, 1991.*
Nascimento et al, Infection & Immunity, 58/7:2198–2203, Jul. 1990.*
Osland et al, Infection & Immunity, 60/4:1368–1374, Apr. 1992.*
Myler et al, Genbank Database, EMBL # AC003679, 1998.*
Webb et al, Genbank Database, EMBL# U73845, 1997.*
Cornelissen et al., "Vaccines against protozoal diseases of veterinary importance," *FEMS Immunology and Medical Microbiology* 15(2–3):61–72, Sep. 1996.
EMBL Database Entry LDP23CSPR, Accession No. X86551, "*L. donovani* mRNA for 23kDa cell surface protein," Apr. 26, 1995.
Pir2 Database, Acession No. S54162, "*Leishmania donovani*," Jul. 8, 1995.
De Andrade et al., "Recombinant Leishmania Hsp90 and Hsp70 Are Recognized by Sera from Visceral Leishmaniasis Patients but Not Chagas' Disease Patients," *Journal Of Clinical Microbiology* 30(2):330–335, 1992.
Bixler, Jr. and Atassi, *Synthetic Vaccines Volume 1*, CRC Press, Inc., Boca Raton, Florida, 1987, Chapter 4, "B Cell Recognition Of Protein Antigens–Perspectives From The Submolecular Level," pp. 40–71.
Bowif et al., "Deciphering the Message in Protein Sequences: Tolerance to Amino Acid Substitutions," *Science* 247:1306–1310, 1990.
Campos–Neto et al., "Cloning and Expression of a *Leishmania donovani* Gene Instructed by a Peptide Isolated from Major Histocompatibility Complex Class II Molecules of Infected Macrophages," *J. Exp. Med.* 182:1423–1433, 1995.
Dillon et al., "Characterization of a *Leishmania tropica* antigen that detects immune responses in Desert Storm viscerotropic leishmaniasis patients," *Proc. Natl. Acad. Sci.* 92:7981–7985, 1995.
Frommel et al., "Vaccine–Induced Immunity against Cutaneous Leishmaniasis in BALB/c Mice," *Infection And Immunity* 56(4):843–848, 1988.
Houghten et al., "Relative Importance of Position and Individual Amino Acid Residues in Peptide Antigen–Antibody Interactions: Implications in the Mechanism of Antigenic Drift and Antigenic Shift," *Vaccines 86*, Brown et al. (eds.), Cold Spring Harbor Laboratory, 1986, pp. 21–25.

(List continued on next page.)

*Primary Examiner*—Lynette R. F. Smith
*Assistant Examiner*—Padma Baskar
(74) *Attorney, Agent, or Firm*—Seed Intellectual Property Law Group PLLC

(57) ABSTRACT

Compositions and methods for preventing, treating and detecting leishmaniasis and stimulating immune responses in patients are disclosed. The compounds provided include polypeptides that contain at least an immunogenic portion of one or more Leishmania antigens, or a variant thereof. Vaccines and pharmaceutical compositions comprising such polypeptides, or DNA molecules encoding such polypeptides, are also provided and may be used, for example, for the prevention and therapy of leishmaniasis, as well as for the detection of Leishmania infection.

14 Claims, 29 Drawing Sheets

OTHER PUBLICATIONS

Mougneau et al., "Expression Cloning of a Protective Leishmania Antigen," *Science* 268:563–566, 1995.

Shapira and Pedraza, "Sequence analysis and transcriptional activation of heat shock protein 83 of *Leishmania mexicana amazonensis*," *Molecular and Biochemical Parasitology* 42:247–256, 1990.

Skeiky et al., "A Recombinant Leishmania Antigen that Stimulates Human Peripheral Blood Mononuclear Cells to Express a Th1–Type Cytokine Profile and to Produce Interleukin 12," *J. Exp. Med.* 181:1527–1537, 1995.

Skeiky et al., "Proliferative And Cytokine Responses Of Human PBMC To Cloned *Leishmania braziliensis* Heat Shock And Ribosomal Antigens," *Journal of Immunology* 150(8pt.2):93A, Abstract #517, 1993.

* cited by examiner

```
                          ----------------------------------------------------SLTDPAVLGEETHLRVRVVPDKANKTLTVEDNGIGMTK  85
              MTETFAFQAEINQLMSLIINTFYSNKEIFLRDVISNASDACDKIRYQ.........DA.R.C.......E..............  85
              ............................................EL..........NQ....D.S...I...........T......  85
MPEETQTQDQPMEEEEV.........A....................EL...S...L.....E.....SK.DSGKE.HINLI.N.QDRA..IV.T.....  100

P                                    P
ADLVNNLGTIARSGTKAFMEALEAGGDMSMIGQFGVGFYSAYLVADRVTVVSKNNSDEAY-WESSAGGTFTITSVQESDMKRGTSTTLHLKEDQQEYLEE  184
................A........................T......V.V..............AP.....LPARI.........L....A  185
.E........................................D...T..........V.PTPDC.L....RIV............  185
...I.......K.........Q.A.I.............EK...IT.H.D..Q.A.......S..VRTDTGEP.G...KVI.......T.....  200

RRVKELIKKHSEFIGYDIELMVEKTAEKEVTDE----DEEEDESKKKSCGDEGEPKVEEVTEGG-ED-KKKKTKKVKEVKKT-YEVK---NKHKPLWTRD  274
..L................T........----....---A.ADE.GE..........-E.-............T.E-...Q---..........  272
..L.D........AT......----..D.--AAATKNEEGE.......KDDAE.GE..........TQE-FV.Q---..........  275
...I..IV....Q....P.T.F...ERD....S.DEAEEK.DKE.E.E.EEKESEDKPEI.DVGSDE..E..DGD..K.KKI.EK.ID.EEL..T..I...N  300

┌─Lbhsp83b
TKDVTKEEYAAFYKAISNDWEDTAATKHFSVEGQLEFRAIAFVPKRAPFDMFEPNKKRNNIKLYVRRVFIMDNCEDLCPDWLGFVKGVVDSEDLPLNISR  374
P...........................PP....................M.........L..............................  372
P.............EPLS............L..............S...................E..A..R..............  375
PD.I.N...GE...SLT.....HL.V.............LL....R......L..NR..K................E.I.EY.N.IR............  400

ENLQQNKILKVIRKNIVKKCLELFEEIAENKEDYKQFYEQFGKNIKLGIHEDTANRKKLMELLRFYSTESGEEMTTLKDYVTRMKPEQKSIYYITGDSKK  474
............M...V....................V............A..N..........  472
........A...........K......V.....S..........H.S....D.........EG..C...V......  475
.M...S.......L......T.L..D..N..K......S.........SQ.....S....Y.TSA..D..VS....C....EN..H......ET.D  500

KLESSPFIEKARRCGLEVLFMTEPIDEYVMQQVKDFEDKKFACLTKEGVHFEESEEEKKQREEKKAACEKLCKTMKEVLGDKVEKVTVSERLLTSPCILV  574
........Q.K.R.F..........Y.........................E..T..................S.......  572
...T.....Q..R.F........I.............T..........E.T.Y.R....A..D.........V.....A.......  575
QVAN.A.V.RL.KH....IY.I......CV...L.E..G.TLVSV....LELP.D.....KQ....TKF.N...I..DI.EK.....V..N..V....C..  600

P
TSEFGWSAHMEQIMRNQALRDSSMAQYMVSKKTMEVNPDHPIIKELRRRVEADENDKAVKDLVFLLFDTSLLTSGFQLDDPTGYAERINRMIKLGLSLDE  674
............M................M.....L..K......................................E...-..............  671
............SA..M........I..A...V...K..........Y....A......T.....S.....H..........D  675
..TY..T.N..R..KA.....N.TMG..AA..HL.I....S..ET..QKA...K...S.....I..YE.A..S...S.E..QTH.N..Y.......GI..  700

EE--EEVA-EAPPAEAAPAEVTAGTSSMEQVD  703  Lbhsp83
..E--.E.V..AV..T.............L..  701  Lahsp83
.D---NGNE..E..A.V...PV..........  704  Tchsp83
DDPTADDTSA.VTE.MP.L.GDDD..R..E..  734  Huhsp89
```

*Fig. 19*

```
GAATTCGGCACGAGGTTTCTGTACTTTATTGCTTCCAGCCTTTATTCACTCTTCGATTTCCTCTAACACCATGTCCTCCGAGCGCACCTTTATTGCCGTC  100
```
| 5'-Adaptor | Splicad-leader | 5'-UT |

```
                                                                                M  S  S  E  R  T  F  I  A  V
AAGCCGGACGGCGTGCAGCGCGGCCTCGTTGGCGAGATCATCGCCCGCTTCGAGCGCAAGGGCTACAAGCTCGTCGCCTTGAAGATACTGCAGCCGACGA  200

K  P  D  G  V  Q  R  G  L  V  G  E  I  I  A  R  F  E  R  K  G  Y  K  L  V  A  L  K  I  L  Q  P  T
CGGAGCAGGCCCAGGGTCACTATAAGGACCTTTGCTCCAAGCCGTTTTTCCCGGCCCTTGTGAAGTACTTCTCCTCTGGCCCGATCGTGTGTATGGTGTG  300

T  E  Q  A  Q  G  H  Y  K  D  L  C  S  K  P  F  F  P  A  L  V  K  Y  F  S  S  G  P  I  V  C  M  V  W
GGAGGGTAAGAACGTGGTGAAGAGCGGCCGCGTGCTGCTCGGCGCGACGAACCCGGCCGACTCACAGCCCGGCACGATCCGTGGCGACTTTGCCGTGGAT  400

E  G  K  N  V  V  K  S  G  R  V  L  L  G  A  T  N  P  A  D  S  Q  P  G  T  I  R  G  D  F  A  V  D
GTGGGCCGCAACGTGTGCCACGGGTCCGACTCTGTGGAGAGCGCGGAGCGCGAGATCGCCTTTTGGTTCAAGGCGGATGAGATCGCGAGCTGGACGTCGC  500

V  G  R  N  V  C  H  G  S  D  S  V  E  S  A  E  R  E  I  A  F  W  F  K  A  D  E  I  A  S  W  T  S
ACTCCGTGTCCCAGATCTATGAGTAACGGTGATTGCGGACACGCTTTGAGGACGTAGCTGTACCCCCAATGAATTCTTCTCTGAAAACCACATCATAAGC  600
```
| → | 3'-UT |

```
 H  S  V  S  Q  I  Y  E
CTCTTAAGAGGTTATTTTTCTTGATCGATGCCCGGTGGTGACCAGCACCATTCCTTTATCGGATTCACTCACACTCCTAGCGAATCATGTAGTGCGGTGA  700
```
| 3'-UT |

```
GAGTGGGCTCTGGAGGAGACTGTTGTGTAGCCATGGCTTCAGGAGAGAAAACAAAATACAAGGAAAGGCAATATGTAACTATGGGGTTCCCTTTTTTACT  800
```
| 3'-UT |

```
ATGCAAAGTTTTTATAACTCCTGATCGGCAAAAACAACAACAACCGCCATACACCAAGAGCAAATGCTTTCTTCTGCGGACTGTGCTTCTGTTTTTTTTT  900
```
| 3'-UT |

```
ATGAAGGAGTGACTCGCGCGATGAAAAGTGTGTGCGTGGGAGATGTATTTCCTTTTTTTGTTCATAGTGGCGACAGCTCACTGTTGACGATGACAAAAAA  1000
```
| 3'-UT |

```
AAAAAAAAAAAAACTCGAG  1019
```
| Poly A tail / Xhoi ▷ |

*Fig. 21*

LEISHMANIA ANTIGENS FOR USE IN THE THERAPY AND DIAGNOSIS OF LEISHMANIASIS

REFERENCE TO RELATED APPLICATIONS

This application is a continuation in part of U.S. patent application Ser. No. 08/920,609, filed Aug. 27, 1997, which is a continuation-in-part of U.S. patent application Ser. No. 08/798,841, filed Feb. 12, 1997, which is a continuation-in-part of U.S. patent application Ser. No. 08/533,669, filed Sep. 22, 1995 now U.S. Pat. No. 5,834,592.

TECHNICAL FIELD

The present invention relates generally to compositions and methods for preventing, treating and detecting leishmaniasis, and for stimulating immune responses in patients. The invention is more particularly related to polypeptides comprising an immunogenic portion of a Leishmania antigen or a variant thereof, and to vaccines and pharmaceutical compositions comprising one or more such polypeptides. The vaccines and pharmaceutical compositions may be used, for example, for the prevention and therapy of leishmaniasis, as well as for the detection of Leishmania infection.

BACKGROUND OF THE INVENTION

Leishmania organisms are intracellular protozoan parasites of macrophages that cause a wide range of clinical diseases in humans and domestic animals, primarily dogs. In some infections, the parasite may lie dormant for many years. In other cases, the host may develop one of a variety of forms of leishmaniasis. For example, the disease may be asymptomatic or may be manifested as subclinical visceral leishmaniasis, which is characterized by mild symptoms of malaise, diarrhea and intermittent hepatomegaly. Patients with subclinical or asymptomatic disease usually have low antibody titers, making the disease difficult to detect with standard techniques. Alternatively, leishmaniasis may be manifested as a cutaneous disease, which is a severe medical problem but is generally self-limiting, or as a highly destructive mucosal disease, which is not self-limiting. Finally, and most seriously, the disease may be manifested as an acute visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis. There are, however, no vaccines or effective treatments currently available.

Accurate diagnosis of leishmaniasis is frequently difficult to achieve. There are 20 species of Leishmania that infect humans, including *L. donovani, L. chagasi, L. infantum, L. major, L. amazonensis, L. braziliensis, L. panamensis, L. mexicana, L. tropica,* and *L guyanensis,* and there are no distinctive signs or symptoms that unambiguously indicate the presence of Leishmania infection. Parasite detection methods have been used, but such methods are neither sensitive nor clinically practical. Current skin tests typically use whole or lysed parasites. Such tests are generally insensitive, irreproducible and prone to cross-reaction with a variety of other diseases. In addition, the preparations employed in such tests are often unstable. Thus, there is a need for improved methods for the detection of Leishmania infection.

Current experimental vaccines consisting of whole organisms have not proven effective in humans. Accordingly, there remains a need in the art for vaccines to prevent leishmaniasis in humans and dogs, and for improved therapeutic compositions for the treatment of leishmaniasis.

SUMMARY OF THE INVENTION

Briefly stated, the present invention provides compositions and methods for preventing, treating and detecting leishmaniasis, as well as for stimulating immune responses in patients. In one aspect, polypeptides are provided which comprise at least an immunogenic portion of a Leishmania antigen, or a variant of such an antigen that differs only in conservative substitutions and/or modifications. In specific embodiments of the invention, the Leishmania antigen comprises an amino acid sequence selected from the group consisting of SEQ ID Nos: 2, 4, 20, 22, 24, 26, 36–38, 41, 50–53 and 82. DNA sequences encoding the above polypeptides, recombinant expression vectors comprising these DNA sequences and host cells transformed or transfected with such expression vectors are also provided.

In related aspects, the present invention provides pharmaceutical compositions which comprise one or more of the polypeptides described herein, or a DNA molecule encoding such polypeptides, and a physiologically acceptable carrier. Vaccines which comprise one or more such polypeptides or DNA molecules, together with a non-specific immune response enhancer are also provided. In specific embodiments of these aspects, the Leishmania antigen has an amino acid sequence selected from the group consisting of SEQ ID Nos: 2, 4, 20, 22, 24, 26, 36–38, 41, 50–53 and 82.

In still further related embodiments, the pharmaceutical compositions and vaccines comprise at least two different polypeptides, each polypeptide comprising an immunogenic portion of a Leishmania antigen having an amino acid sequence selected from the group consisting of sequences recited in SEQ ID Nos: 2, 4, 6, 8, 10, 20, 22, 24, 26, 36–38, 41, 50–53, 82, and variants thereof that differ only in conservative substitutions and/or modifications. In other embodiments, the inventive pharmaceutical compositions comprise one or more of the inventive polypeptides in combination with a known Leishmania antigen.

In yet other related embodiments, the pharmaceutical compositions and vaccines comprise soluble Leishmania antigens.

In another aspect, the present invention provides methods for inducing protective immunity against leishmaniasis in a patient, comprising administering to a patient a pharmaceutical composition or vaccine as described above.

In further aspects, methods and diagnostic kits are provided for detecting Leishmania infection in a patient. The methods comprise: (a) contacting dermal cells of a patient with a pharmaceutical composition as described above; and (b) detecting an immune response on the patient's skin, therefrom detecting Leishmania infection in the patient. The diagnostic kits comprise: (a) a pharmaceutical composition as described above; and (b) an apparatus sufficient to contact the pharmaceutical composition with the dermal cells of a patient.

In further aspects, the present invention provides methods for stimulating a cellular and/or humoral immune response in a patient, comprising administering to a patient a pharmaceutical composition or vaccine as described above.

In a related aspect, methods are provided for treating a patient afflicted with a disease responsive to IL-12 stimulation, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 19 presents a comparison of a Lbhsp83 sequence (SEQ ID NO:6) with homologous sequences from *L. amazonensis* (Lahsp83) (SEQ ID NO:16), *T. cruzi* (Tchsp83) (SEQ ID NO:17) and humans (Huhsp89) (SEQ ID NO:18).

FIG. 21 shows the cDNA and predicted amino acid sequence for the Leishmania antigen Lmsp1a.

FIG. 22 shows a Southern blot of genomic DNA from *L. major* digested with a panel of restriction enzymes (lanes 1 to 7) and six other Leishmania species digested with PstI (lanes 8 to 13) probed with the full-length cDNA insert of Lmsp1a.

DETAILED DESCRIPTION OF THE INVENTION

Figure 1:
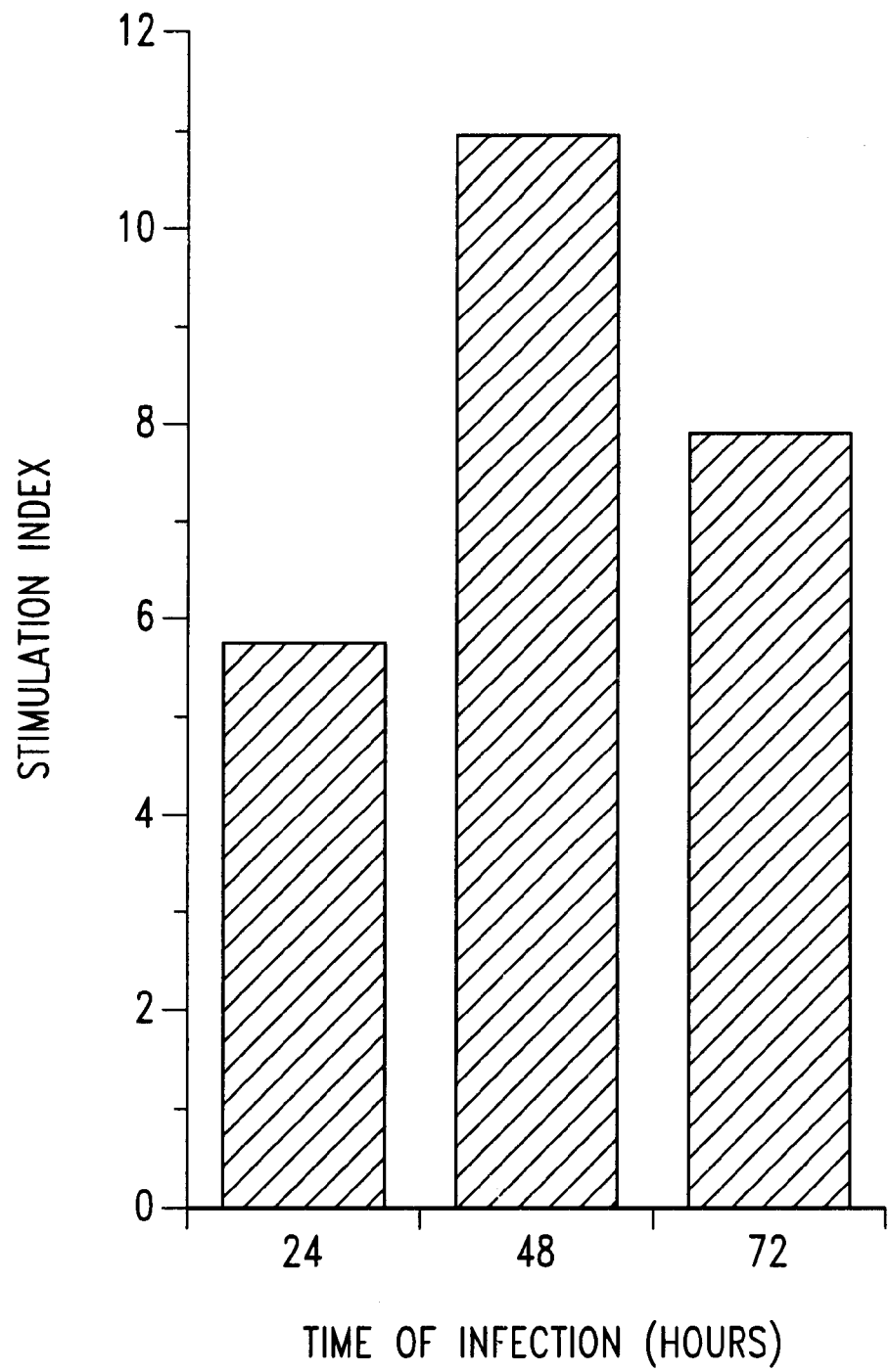
FIG. 1 shows the stimulation of proliferation of T-cells obtained from *L. donovani*-immunized BALB/c mice (represented by stimulation index) by *L. donovani*-infected macrophages after incubation for 24, 48 and 72 hours.
Figure 2A:
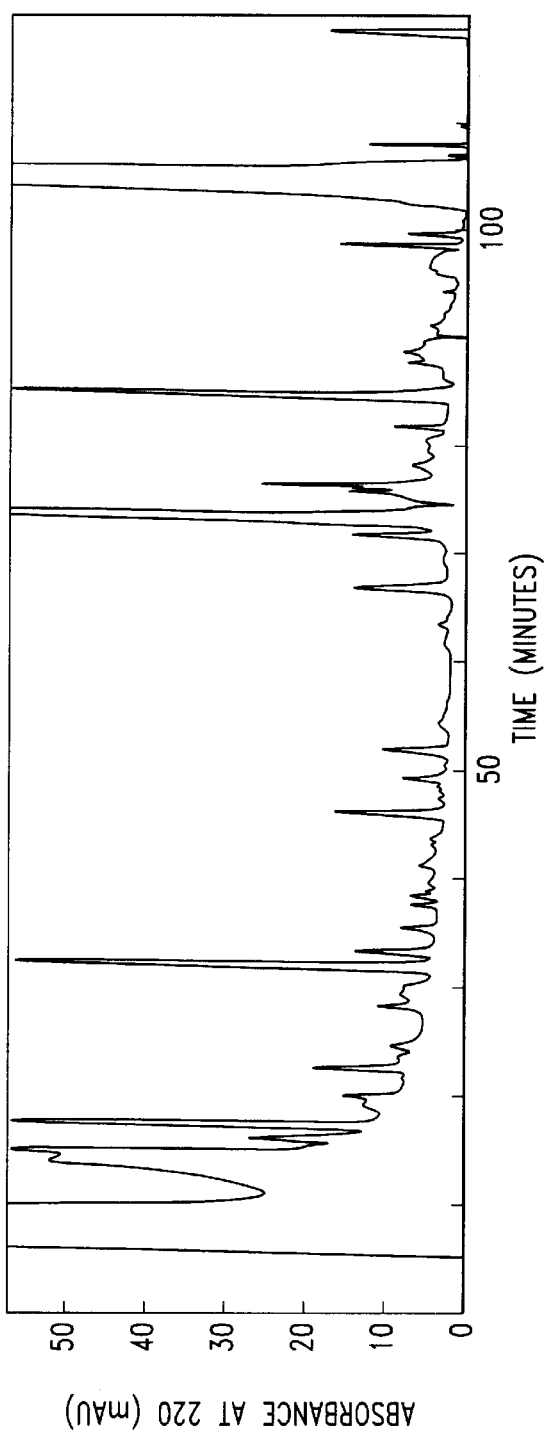
FIG. 2 illustrates representative HPLC profiles of peptides isolated from MHC class II molecules of P388D1 macrophages. Panel A shows peptides isolated from uninfected macrophages and panel B shows peptides isolated from *L. donovani* infected macrophages. The arrows in panel B indicate peptide peaks present only in the infected macrophage preparation.
Figure 2B:
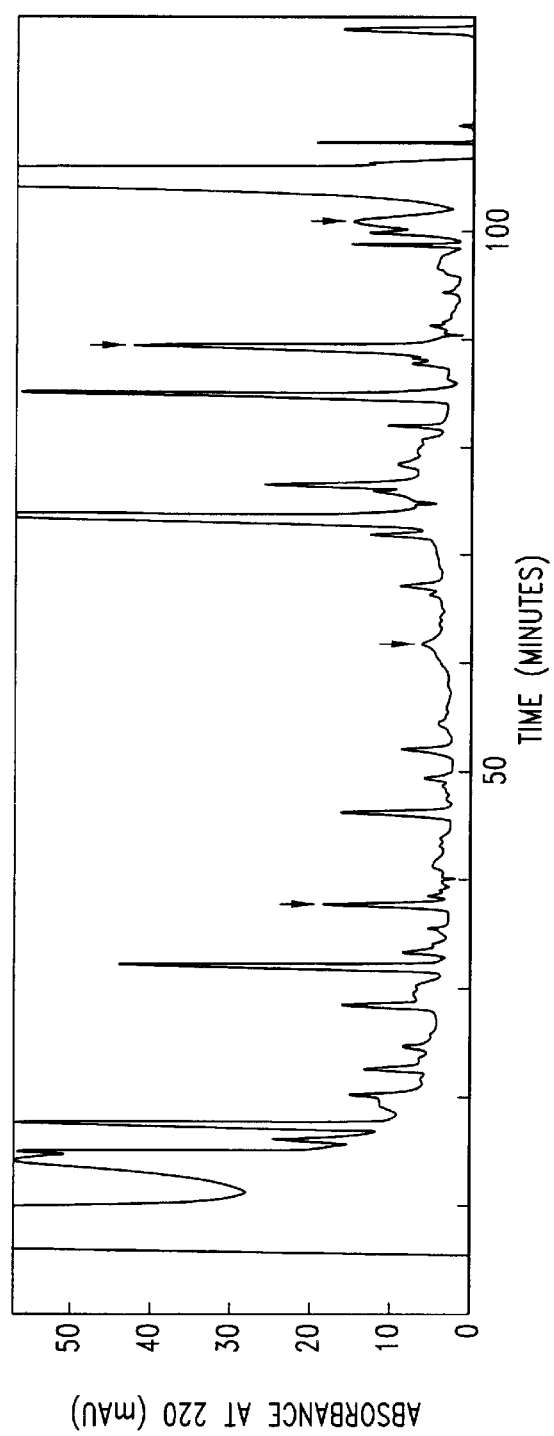

As noted above, the present invention is generally directed to compositions and methods for preventing, treating and detecting leishmaniasis, as well as for stimulating immune responses in patients. The compositions of the subject invention include polypeptides that comprise at least an immunogenic portion of a Leishmania antigen, or a variant of such an antigen that differs only in conservative substitutions and/or modifications. In one preferred embodiment, compositions of the present invention include multiple polypeptides selected so as to provide enhanced protection against a variety of Leishmania species.

Polypeptides within the scope of the present invention include, but are not limited to, polypeptides comprising immunogenic portions of Leishmania antigens comprising the sequences recited in SEQ ID NO:2 (referred to herein as M15), SEQ ID NO:4 (referred to herein as Ldp23), SEQ ID NO:6 (referred to herein as Lbhsp83), SEQ ID NO;8 (referred to herein as Lt-210), SEQ ID NO;10 (referred to herein as LbeIF4A), SEQ ID NO: 20 (referred to herein as Lmsp1a), SEQ ID NO: 22 (referred to herein as Lmsp9a), SEQ ID NOs: 24 and 26 (referred to herein as MAPS-1A), and SEQ ID NO: 36–42, 49–53 and 55. As used herein, the term "polypeptide" encompasses amino acid chains of any length, including full length proteins (i.e., antigens), wherein the amino acid residues are linked by covalent bonds. Thus, a polypeptide comprising an immunogenic portion of one of the above antigens may consist entirely of the immunogenic portion, or may contain additional sequences. The additional sequences may be derived from the native Leishmania antigen or may be heterologous, and such sequences may (but need not) be immunogenic. An antigen "having" a particular sequence is an antigen that contains, within its full length sequence, the recited sequence. The native antigen may, or may not, contain additional amino acid sequence.

An immunogenic portion of a Leishmania antigen is a portion that is capable of eliciting an immune response (i.e., cellular and/or humoral) in a presently or previously Leishmania-infected patient (such as a human or a dog) and/or in cultures of lymph node cells or peripheral blood mononuclear cells (PBMC) isolated from presently or previously Leishmania-infected individuals. The cells in which a response is elicited may comprise a mixture of cell types or may contain isolated component cells (including, but not limited to, T-cells, NK cells, macrophages, monocytes and/or B cells). In particular, immunogenic portions are capable of inducing T-cell proliferation and/or a dominantly Th1-type cytokine response (e.g., IL-2, IFN-γ, and/or TNF-α production by T-cells and/or NK cells; and/or IL-12 production by monocytes, macrophages and/or B cells). Immunogenic portions of the antigens described herein may generally be identified using techniques known to those of ordinary skill in the art, including the representative methods provided herein.

The compositions and methods of the present invention also encompass variants of the above polypeptides. A polypeptide "variant," as used herein, is a polypeptide that differs from the native antigen only in conservative substitutions and/or modifications, such that the ability of the polypeptide to include an immune response is retained. Polypeptide variants preferably exhibit at least about 70%, more preferably at least about 90% and most preferably at least about 95% identity to the identified polypeptides. Alternatively, such variants may be identified by modifying one of the above polypeptide sequences and evaluating the immunogenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the immunogenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g. poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (DNA, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. Such variant nucleotide sequences will generally hybridize to the recited nucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

"Polypeptides" as described herein also include combination polypeptides. A "combination polypeptide" is a polypeptide comprising at least one of the above immunogenic portions and one or more additional immunogenic Leishmania sequences, which are joined via a peptide linkage into a single amino acid chain. The sequences may be joined directly (i.e., with no intervening amino acids) or may be joined by way of a linker sequence (e.g., Gly-Cys-Gly) that does not significantly diminish the immunogenic properties of the component polypeptides.

In general, Leishmania antigens having immunogenic properties, and DNA sequences encoding such antigens, may be prepared using any of a variety of procedures from one or more Leishmania species including, but not limited to, *L. donovani, L. chagasi, L. infantum, L. major, L. amazonensis, L. braziliensis, L. panamensis, L. mexicana, L. tropica,* and *L. guyanensis.* Such species are available, for example, from the American Type Culture Collection (ATCC), Rockville, Md. For example, peptides isolated from MHC class II molecules of macrophages infected with a Leishmania species may be used to rescue the corresponding Leishmania donor antigens. MHC class II molecules are expressed mainly by cells of the immune system, including macrophages. These molecules present peptides, which are usually 13–17 amino acids long, derived from foreign antigens that are degraded in cellular vesicles. The bound peptide antigens are then recognized by CD4 T-cells. Accordingly, foreign peptides isolated from MHC class II molecules of, for example, Leishmania-infected murine macrophages may be used to identify immunogenic Leishmania proteins.

Briefly, peptides derived from Leishmania antigens may be isolated by comparing the reverse phase HPLC profile of peptides extracted from infected macrophages with the profile of peptides extracted from uninfected cells. Peptides giving rise to distinct HPLC peaks unique to infected macrophages may then be sequenced using, for example, Edman chemistry as described in Edman and Berg, *Eur J. Biochem,* 80:116–132 (1967). A DNA fragment corresponding to a portion of a Leishmania gene encoding the peptide may then be amplified from a Leishmania cDNA library using an oligonucleotide sense primer derived from the peptide sequence and an oligo dT antisense primer. The resulting DNA fragment may then be used as a probe to screen a Leishmania library for a full length cDNA or genomic clone that encodes the Leishmania antigen. Such screens may generally be performed using techniques well known to those of ordinary skill in the art, such as those described in Sambrook et al., *Molecular Cloning: A Laboratory Manual,* Cold Spring Harbor Laboratories, Cold Spring Harbor, N.Y. (1989).

This approach may be used to identify a 23 kD *Leishmania donovani* antigen (referred to herein as Ldp23). The sequence of a DNA molecule encoding Ldp23 is provided in SEQ ID NO:3 and the amino acid sequence of Ldp23 is provided in SEQ ID NO:4. Using the methods described herein, Ldp23 has been shown to induce a Th1 immune response in T-cells prepared from Leishmania-infected mice.

Alternatively, a Leishmania cDNA or genomic expression library may be screened with serum from a Leishmania-infected individual, using techniques well known to those of ordinary skill in the art. DNA molecules encoding reactive antigens may then be used to express the recombinant antigen for purification. The immunogenic properties of the purified Leishmania antigens may then be evaluated using, for example the representative methods described herein.

For example, sera from Leishmania-infected mice may be used to screen a cDNA library prepared from Leishmania amastigotes. Reactive clones may then be expressed and recombinant proteins assayed for the ability to stimulate T-cells or NK cells derived from Leishmania-immune individuals (i.e., individuals having evidence of infection, as documented by positive serological reactivity with Leishmania-specific antibodies and/or a Leishmania-specific DTH response, without clinical symptoms of leishmaniasis). This procedure may be used to obtain a recombinant DNA molecule encoding the Leishmania antigen designated M15. The sequence of such a DNA molecule is provided in SEQ ID NO:1, and the amino acid sequence of the encoded protein is provided in SEQ ID NO:2.

A similar approach may be used to isolate a genomic DNA molecule encoding an immunogenic *Leishmania braziliensis* antigen, referred to herein as Lbhsp83. More specifically, a genomic clone encoding Lbhsp83 may be isolated by screening a *L. braziliensis* expression library with sera from a Leishmania-infected individual. The DNA encoding Lbhsp83 is homologous to the gene encoding the eukaryotic 83 kD heat shock protein. The sequence of a DNA molecule encoding nearly all of Lbhsp83 is presented in SEQ ID NO:5, and the encoded amino acid sequence is provided in SEQ ID NO:6. Using the methods described below, Lbhsp83 has been found to stimulate proliferation, and a mixed Th1 and Th2 cytokine profile, in PBMC isolated from *L. braziliensis*-infected patients. Accordingly, Lbhsp83 is an immunogenic Leishmania antigen. Regions of Lbhsp83 that are not conserved with the mammalian gene have been found to be particularly potent for T-cell stimulation and antibody binding. Such regions may be identified, for example, by visual inspection of the sequence comparison provided in FIG. 19.

This approach may also be used to isolate a DNA molecule encoding a 210 kD immunogenic *L. tropica* antigen, referred to herein as Lt-210. The preparation and characterization of Lt-210, and immunogenic portions thereof (such as Lt-1 and immunogenic repeat and non-repeat sequences), is described in detail in U.S. patent application Ser. No. 08/511,872, filed Aug. 4, 1995. The sequence of a DNA molecule encoding Lt-1 is provided in SEQ ID NO:7 and the encoded amino acid sequence is presented in SEQ ID NO:8.

The above approach may further be used to isolate a DNA molecule encoding a *L. braziliensis* antigen referred to herein as LbeIF4A. Briefly, such a clone may be isolated by screening a *L. braziliensis* expression library with sera obtained from a patient afflicted with mucosal leishmaniasis, and analyzing the reactive antigens for the ability to stimulate proliferative responses and preferential Th1 cytokine production in PBMC isolated from Leishmania-infected patients, as described below. The preparation and characterization of LbeIF4A is described in detail in U.S. patent application Ser. Nos. 08/454,036 and 08/488,386, which are continuations-in-part of U.S. patent application Ser. No. 08/232,534, filed Apr. 22, 1994. The sequence of a DNA molecule encoding LbeIF4A is provided in SEQ ID NO:9 and the encoded amino acid sequence is presented in SEQ ID NO:10. Homologs of LbeIF4A, such as that found in *L. major,* may also be isolated using this approach, and are within the scope of the present invention.

Compositions of the present invention may also, or alternatively, contain soluble Leishmania antigens. As used herein, "soluble Leishmania antigens" refers to a mixture of at least 8 different Leishmania antigens that may be isolated from the supernatant of Leishmania promastigotes of any species grown for 8–12 hours in protein-free medium. Briefly, the organisms are grown to late log phase in complex medium with serum until they reach a density of $2-3\times10^7$ viable organisms per mL of medium. The organisms are thoroughly washed to remove medium components and resuspended at $2-3\times10^7$ viable organisms per mL of defined serum-free medium consisting of equal parts RPMI 1640 and medium 199, both from Gibco BRL, Gaithersburg, Md. After 8–12 hours, the supernatant containing soluble Leishmania antigens is removed, concentrated 10 fold and dialyzed against phosphate-buffered saline for 24 hours. The presence of at least eight different antigens within the mixture of Leishmania antigens may be confirmed using SDS-PAGE (ie., through the observation of at least 8 different bands). The immunogenic properties of the soluble Leishmania antigens may be confirmed by evaluating the ability of the preparation to elicit an immune response in cultures of lymph node cells and/or peripheral blood mononuclear cells (PBMC) isolated from presently or previously Leishmania-infected individuals. Such an evaluation may be performed as described below.

Individual antigens present within the mixture of soluble Leishmania antigens may be isolated by immunizing mice or rabbits with Leishmania culture supernatant, containing soluble antigens, and employing the resultant sera to screen a Leishmania cDNA expression library as described in detail below. This procedure may be used to isolate recombinant DNA molecules encoding the *L. major* antigens referred to herein as Lmsp1a, Lmsp9a and MAPS-1A. DNA sequences encoding Lmsp1a, Lmsp9a and MAPS-1A are provided in SEQ ID NO: 19, 21 and 23, respectively, with the corresponding predicted amino acid sequences being presented in SEQ ID NO: 20, 22 and 24, respectively. Similarly, sera from mice or rabbits immunized with *L. major* culture supernatant may be used to screen an *L. major* genomic DNA library. As detailed below, this procedure may be used to isolate DNA molecules encoding the *L. major* antigens referred to herein as LmgSP1, LmgSP3, LmgSP5, LmgSP8, LmgSP9, LmgSP13, LmgSP19, and DNA molecules encoding the *L. chagasi* antigens LcgSP1, LcgSP3, LcgSP4, LcgSP8, and LcgSP10. The DNA sequences encoding these antigens are provided in SEQ ID NO:29–35 and 44–48, respectively, with the corresponding amino acid sequences being provided in SEQ ID NO: 36–42 and 49–53. The *L. major* antigens referred to herein as 1G6-34, 1E6-44, 4A5-63, 1B11-39, 2A10-37, 4G2-82, 4H6-41 and 8G3-100 may be isolated by means of CD4+ T cell expression cloning as described below. DNA sequences encoding these antigens are provided in SEQ ID NO: 72–79, respectively, with the corresponding predicted amino acid sequences being provided in SEQ ID NO: 80–87. The immunogenic properties of the isolated Leishmania antigens may be evaluated using, for example, the representative methods described herein.

Regardless of the method of preparation, the antigens described herein are immunogenic. In other words, the antigens (and immunogenic portions thereof) are capable of eliciting an immune response in cultures of lymph node cells and/or peripheral blood mononuclear cells (PBMC) isolated from presently or previously Leishmania-infected individuals. More specifically, the antigens, and immunogenic portions thereof, have the ability to induce T-cell proliferation and/or to elicit a dominantly Th1-type cytokine response (e.g., IL-2, IFN-γ, and/or TNF-α production by T-cells and/or NK cells; and/or IL-12 production by monocytes, macrophages and/or B cells) in cells isolated from presently or previously Leishmania-infected individuals. A Leishmania-infected individual may be afflicted with a form of leishmaniasis (such as subclinical, cutaneous, mucosal or active visceral) or may be asymptomatic. Such individuals may be identified using methods known to those of ordinary skill in the art. Individuals with leishmaniasis may be identified based on clinical findings associated with at least one of the following: isolation of parasite from lesions, a positive skin test with Leishmania lysate or a positive serological test. Asymptomatic individuals are infected individuals who have no signs or symptoms of the disease. Such individuals can be identified based on a positive serological test and/or skin test with Leishmania lysate.

The term "PBMC," which refers to a preparation of nucleated cells consisting primarily of lymphocytes and monocytes that are present in peripheral blood, encompasses both mixtures of cells and preparations of one or more purified cell types. PBMC may be isolated by methods known to those in the art. For example, PBMC may be isolated by density centrifugation through, for example, Ficoll™ (Winthrop Laboratories, New York). Lymph node cultures may generally be prepared by immunizing BALB/c mice (e.g., in the rear foot pad) with Leishmania promastigotes emulsified in complete Freünd's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a polypeptide (e.g., a Leishmania antigen or a portion or other variant thereof) to induce a response in PBMC or lymph node cell cultures may be evaluated by contacting the cells with the polypeptide and measuring a suitable response. In general, the amount of polypeptide that is sufficient for the evaluation of about $2\times10^5$ cells ranges from about 10 ng to about 100 μg, and preferably is about 1–10 μg. The incubation of polypeptide with cells is typically performed at 37° C. for about 1–3 days. Following incubation with polypeptide, the cells are assayed for an appropriate response. If the response is a proliferative response, any of a variety of techniques well known to those of ordinary skill in the art may be employed. For example, the cells may be exposed to a pulse of radioactive thymidine and the incorporation of label into cellular DNA measured. In general, a polypeptide that results in at least a three fold increase in proliferation above background (ie., the proliferation observed for cells cultured without polypeptide) is considered to be able to induce proliferation.

Alternatively, the response to be measured may be the secretion of one or more cytokines (such as interferon-γ (IFN-γ), interleukin-4 (IL-4), interleukin-12 (p70 and/or p40), interleukin-2 (IL-2) and/or tumor necrosis factor-α (TNF-α)) or the change in the level of mRNA encoding one or more specific cytokines. In particular, the secretion of interferon-γ, interleukin-2, tumor necrosis factor-α and/or interleukin-12 is indicative of a Th1 response, which is responsible for the protective effect against Leishmania. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, Calif. and PharMingen, San Diego, Calif., and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1-3 \times 10^5$ cells, the production of 30 pg/mL of IL-12, IL-4, IFN-$\gamma$, TNF-$\alpha$ or IL-12 p40, or 10 pg/mL of IL-12 p70, is considered able to stimulate production of a cytokine.

Immunogenic portions of the antigens described herein may be prepared and identified using well known techniques, such as those summarized in Paul, Fundamental Immunology, 3rd ed., 243–247 (Raven Press, 1993) and references cited therein. Such techniques include screening polypeptides derived from the native antigen for immunogenic properties using, for example, the representative techniques described herein. An immunogenic portion of a polypeptide is a portion that, within such representative assays, generates an immune response (e.g., proliferation and/or cytokine production) that is substantially similar to that generated by the full length antigen. In other words, an immunogenic portion of an antigen may generate at least about 25%, and preferably at least about 50%, of the response generated by the full length antigen in the model assays described herein.

Portions and other variants of immunogenic Leishmania antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149–2146, 1963. Equipment for automated synthesis of polypeptides is commercially available from suppliers such as Perkin Elmer/Applied BioSystemsDivision, Foster City, Calif., and may be operated according to the manufacturer's instructions.

Recombinant polypeptides containing portions and/or variants of a native antigen may be readily prepared from a DNA sequence encoding the antigen. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

In general, any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast or a mammalian cell line such as COS or CHO. The DNA sequences expressed in this manner may encode naturally occurring antigens, portions of naturally occurring antigens, or other variants thereof. For example, variants of a native antigen may generally be prepared using standard mutagenesis techniques, such as oligonucleotide-directed site-specific mutagenesis, and sections of the DNA sequence may be removed to permit preparation of truncated polypeptides.

In another aspect, the present invention provides epitope repeat sequences, or antigenic epitopes, of a Leishmania antigen, together with polypeptides comprising at least two such contiguous antigenic epitopes. As used herein an "epitope" is a portion of an antigen that reacts with sera from Leishmania-infected individuals (i.e. an epitope is specifically bound by one or more antibodies present in such sera). As discussed above, epitopes of the antigens described in the present application may be generally identified using techniques well known to those of skill in the art.

In one embodiment, antigenic epitopes of the present invention comprise an amino acid sequence provided in SEQ ID NO:43, 56, 57 or 58. As discussed in more detail below, antigenic epitopes provided herein may be employed in the diagnosis and treatment of Leishmania infection, either alone or in combination with other Leishmania antigens or antigenic epitopes. Antigenic epitopes and polypeptides comprising such epitopes may be prepared by synthetic means, as described generally above and in detail in Example 15.

In certain aspects of the present invention, described in detail below, the polypeptides, antigenic epitopes and/or soluble Leishmania antigens may be incorporated into pharmaceutical compositions or vaccines. For clarity, the term "polypeptide" will be used when describing specific embodiments of the inventive therapeutic compositions and diagnostic methods. However, it will be clear to one of skill in the art that the antigenic epitopes of the present invention may also be employed in such compositions and methods.

Pharmaceutical compositions comprise one or more polypeptides, each of which may contain one or more of the above sequences (or variants thereof), and a physiologically acceptable carrier. Vaccines comprise one or more of the above polypeptides and a non-specific immune response enhancer, such as an adjuvant (e.g., LbeIF4A, interleukin-12 or other cytokines) or a liposome (into which the polypeptide is incorporated). Vaccines may additionally contain a delivery vehicle, such as a biodegradable microsphere (disclosed, for example, in U.S. Pat. Nos. 4,897,268 and 5,075,109). Pharmaceutical compositions and vaccines within the scope of the present invention may also contain other Leishmania antigens, either incorporated into a combination polypeptide or present within one or more separate polypeptides.

Alternatively, a pharmaceutical composition or vaccine may contain DNA encoding one or more of the polypeptides as described above, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993) and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897, 268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bordella pertussis* or *Mycobacterium tuberculosis*. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Preferred adjuvants include LbeIF4A, IL-12 and other cytokines such as IFN-γ or granulocyte-macrophage colony stimulating factor (GM-CSF). By virtue of its ability to induce an exclusive Th1 immune response, the use of LbeIF4A, and variants thereof, as an adjuvant in the vaccines of the present invention is particularly preferred.

In one preferred embodiment, compositions of the present invention include multiple polypeptides selected so as to provide enhanced protection against a variety of Leishmania species. Such polypeptides may be selected based on the species of origin of the native antigen or based on a high degree of conservation of amino acid sequence among different species of Leishmania. A combination of individual polypeptides may be particularly effective as a prophylactic and/or therapeutic vaccine because (1) stimulation of proliferation and/or cytokine production by individual polypeptides may be additive, (2) stimulation of proliferation and/or cytokine production by individual polypeptides may be synergistic, (3) individual polypeptides may stimulate cytokine profiles in such a way as to be complementary to each other and/or (4) individual polypeptides may be complementary to one another when certain of them are expressed more abundantly on the individual species or strain of Leishmania responsible for infection. A preferred combination contains polypeptides that comprise immunogenic portions of M15, Ldp23, Lbhsp83, Lt-1 and LbeIF4A. Alternatively, or in addition, the combination may include one or more polypeptides comprising immunogenic portions of other Leishmania antigens disclosed herein, and/or soluble Leishmania antigens.

The above pharmaceutical compositions and vaccines may be used, for example, to induce protective immunity against Leishmania in a patient, such as a human or a dog, to prevent leishmaniasis. Appropriate doses and methods of administration for this purposes are described in detail below.

The pharmaceutical compositions and vaccines described herein may also be used to stimulate an immune response, which may be cellular and/or humoral, in a patient. For Leishmania-infected patients, the immune responses that may be generated include a preferential Th1 immune response (i.e., a response characterized by the production of the cytokines interleukin-1, interleukin-2, interleukin-12 and/or interferon-γ, as well as tumor necrosis factor-α). For uninfected patients, the immune response may be the production of interleukin-12 and/or interleukin-2, or the stimulation of gamma delta T-cells. In either category of patient, the response stimulated may include IL-12 production. Such responses may also be elicited in biological samples of PBMC or components thereof derived from Leishmania-infected or uninfected individuals. As noted above, assays for any of the above cytokines may generally be performed using methods known to those of ordinary skill in the art, such as an enzyme-linked immunosorbent assay (ELISA).

Suitable pharmaceutical compositions and vaccines for use in this aspect of the present invention are those that contain at least one polypeptide comprising an immunogenic portion of a Leishmania antigen disclosed herein (or a variant thereof). Preferably, the polypeptides employed in the pharmaceutical compositions and vaccines are complementary as described above. Soluble Leishmania antigens, with or without additional polypeptides, may also be employed.

The pharmaceutical compositions and vaccines described herein may also be used to treat a patient afflicted with a disease responsive to IL-12 stimulation. The patient may be any warm-blooded animal, such as a human or a dog. Such diseases include infections (which may be, for example, bacterial, viral or protozoan) or diseases such as cancer. In one embodiment, the disease is leishmaniasis, and the patient may display clinical symptoms or may be asymptomatic. In general, the responsiveness of a particular disease to IL-12 stimulation may be determined by evaluating the effect of treatment with a pharmaceutical composition or vaccine of the present invention on clinical correlates of immunity. For example, if treatment results in a heightened Th1 response or the conversion of a Th2 to a Th1 profile, with accompanying clinical improvement in the treated patient, the disease is responsive to IL-12 stimulation. Polypeptide administration may be as described below, or may extend for a longer period of time, depending on the indication. Preferably, the polypeptides employed in the pharmaceutical compositions and vaccines are complementary, as described above. A particularly preferred combination contains polypeptides that comprise immunogenic portions of M15, Ldp23, Lbhsp83, Lt-1 and LbeIF4A, Lmsp1a, Lmsp9a, and MAPS-1A. Soluble Leishmania antigens, with or without additional polypeptides, may also be employed.

Routes and frequency of administration, as well as dosage, for the above aspects of the present invention will vary from individual to individual and may parallel those currently being used in immunization against other infections, including protozoan, viral and bacterial infections. In general, the pharmaceutical compositions and vaccines may be administered by injection (e.g., intracutaneous, intramuscular, intravenous or subcutaneous), intranasally (e.g., by aspiration) or orally. Between 1 and 12 doses may be administered over a 1 year period. For therapeutic vaccination (i.e., treatment of an infected individual), 12 doses are preferably administered, at one month intervals. For prophylactic use, 3 doses are preferably administered, at 3 month intervals. In either case, booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from leishmaniasis for at least 1–2 years. In general, the amount of polypeptide present in a dose (or produced in situ by the DNA in a dose) ranges from about 100 ng to about 1 mg per kg of host, typically from about 10 µg to about 100 µg. Suitable dose sizes will vary with the size of the patient, but will typically range from about 0.1 mL to about 5 mL.

In another aspect, this invention provides methods for using one or more of the polypeptides described above to diagnose Leishmania infection in a patient using a skin test. As used herein, a "skin test" is any assay performed directly on a patient in which a delayed-type hypersensitivity (DTH) reaction (such as induration and accompanying redness) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 72 hours after injection.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, induration that is greater than about 0.5 cm in diameter, preferably greater than about 1.0 cm in diameter, is a positive response, indicative of Leishmania infection, which may or may not be manifested as an active disease.

The polypeptides of this invention are preferably formulated, for use in a skin test, as pharmaceutical compositions containing at least one polypeptide and a physiologically acceptable carrier, as described above. Such compositions typically contain one or more of the above polypeptides in an amount ranging from about 1 µg to 100 µg, preferably from about 10 µg to 50 µg in a volume of 0.1 mL. Preferably, the carrier employed in such pharmaceutical compositions is a saline solution with appropriate preservatives, such as phenol and/or Tween 80™.

The inventive polypeptides may also be employed in combination with one or more known Leishmania antigens in the diagnosis of leishmaniasis, using, for example, the skin test described above. Preferably, individual polypeptides are chosen in such a way as to be complementary to each other. Examples of known Leishmania antigens which may be usefully employed in conjunction with the inventive polypeptides include K39 (Burns et al., *Proc. Natl. Acad. Sci. USA*, 1993 90:775–779).

The following Examples are offered by way of illustration and not by way of limitation.

EXAMPLES

Example 1

Preparation of M15

This Example illustrates the preparation of a Leishmania antigen M15, having the sequence provided in SEQ ID NO:2.

An *L. major* (Friedlan strain) amastigote cDNA expression library prepared in the λZAP II vector (Stratagene, La Jolla, Calif.) was screened according to manufacturer's instructions using sera obtained from *L. major* infected BALB/c mice (8 weeks post inoculation). Approximately 40,000 plaques were screened and four clones expressing reactive antigens were purified to homogeneity by two subsequent rounds of low density screening. Bluescript phagemid inserts were excised from positive clones for further analysis. An EcoRI/SstII restriction fragment from the 5' end of one partial cDNA insert isolated during first round screening (pLma1-1) was subsequently used as a probe to rescreen for clones containing full length cDNA inserts. The probe was labeled to high specific activity (~$10^9$ cpm/µg) with [α-$^{32}$P]dCTP using the random primer method and was used to screen ~10,000 plaques of the *L. major* expression library described above. Positive clones were compared by restriction enzyme digestion and the clone with the largest insert (pfl1-1) was chosen for subsequent analysis.

DNA sequence analyses were performed on an Applied Biosystems automated sequencer using Taq polymerase and dye coupled ddNTP terminators or dye-labeled sequencing primers. The complete sequence of the 2685 bp insert was determined using a combination of primer-directed sequencing and by sequencing a series of overlapping Exonuclease III deletion subclones generated using the Erase-a-base system (Promega, Madison, Wis.). The sequence of this insert is provided in SEQ ID NO:1, and the deduced amino acid sequence is provided in SEQ ID NO:2.

The complete insert of clone pfl-1 was excised by digestion with BamHI/KpnI and was subcloned in frame into BamHI/KpnI digested pQE31 (QUIAGEN) to generate the construct pM151A. *E. coli* containing this construct inducibly expressed high levels of the *L. major* antigen encoded by pfl1-1 (designated as M15) with the addition of a 6-histidine tag at the amino terminus. Large volume cultures (500 ml) of *E. coli* host cells containing the pM151A construct were induced to express recombinant protein by the addition of 2 mM IPTG at mid-log phase of growth. Growth was continued for 4 to 5 hours and bacteria were then pelleted and washed once with cold PBS. Bacteria were resuspended in 20 ml of lysis buffer (50 mM $Na_2HPO_4$, pH 8.0, 300 mM NaCl, 10 mM β-mercaptoethanol) containing 20 mg of lysozyme and were lysed by a 1 hour incubation at 4° C. followed by brief sonication. Insoluble material was removed by centrifugation at 10,000×g for 10 minutes and although the recombinant protein was found to be evenly distributed between the soluble and insoluble fractions the insoluble material was discarded at this point. Recombinant protein containing the amino terminal histidine tag was affinity purified using Ni-NTA resin (QIAGEN) according to the manufacturer's recommendations. Briefly, 8 ml of Ni-NTA resin resuspended in lysis buffer was added to the soluble lysate fraction and binding was conducted with constant mixing for 1 hour at 4° C. The mixture was then loaded into a gravity flow column and the non-binding material was allowed to flow through. The Ni-NTA matrix was washed 3 times with 25 ml of wash buffer (50 mM $Na_2HPO_4$, pH 6.0, 300 mM NaCl, 10 mM β-mercaptoethanol) and bound material was eluted in 25 ml of elution buffer (50 mM $Na_2HPO_4$, pH 5.0, 300 mM NaCl, 10 mM β-mercaptoethanol). The eluted material was then dialyzed against 3 changes of PBS, sterile filtered and stored at −20° C. The purified recombinant protein was shown by SDS-PAGE analysis to be free of any significant amount of *E. coli* protein. A small number of bands of lower molecular weight were assumed to be proteolytic products of the *L. major* antigen based on their reactivity by western blot analysis. A high titre polyclonal antisera against M15 was generated in rabbits by repeated subcutaneous injection of recombinant protein. Western blot analysis of lysates from *L. major* promastigotes and amastigotes using this antisera indicated that the protein is constitutively expressed throughout the parasite lifecycle.

Example 2

Preparation of LDP23

This Example illustrates the preparation of a Leishmania antigen Ldp23, having the sequence provided in SEQ ID NO:4.

A. Purification of MHC Class II-associated Peptides from P388D1 Macrophages Infected with *L. donovani*

To ascertain that in vitro infection of macrophages would load their MHC class II molecules with parasite peptides, initial experiments were carried out to test the ability of *L. donovani*-infected macrophage cell line P388D1 to present parasite antigens to *L. donovani* specific T-cells. This macrophage cell line was chosen because it has the same H-2 haplotype as the BALB/c mouse, which is a strain of mouse moderately susceptible to *L. donovani* infection and selected to conduct the in vivo experiments. Using a proportion of 3–5 parasites per cell and an initial incubation at room temperature for 4–6 hours follows by 37° C. for 24–48 hours, close to 90% of the macrophages were infected. The level of MHC class II molecule expression, as determined by FACS analysis, indicated that infection did not cause an effect on the levels of MHC class II expression when compared to non-infected control cells.

To test the ability of the *L. donovani*-infected P388D1 cells to present parasite antigens, macrophages were infected as indicated above and incubated at 26° C. for 6 hours, and then as 37° C. for either 24, 48 or 72 hours. At each of these time points the non-adherent cells and free parasites were washed out and the adherent cells were mechanically dislodged, washed and fixed with paraformaldehyde. These cells were then used as antigen presenting cells (APCs) for purified lymph node T-cells from BALB/c mice immunized with *L. donovani* promastigotes. To generate these anti-*L. donovani* specific T-cells, BALB/c mice (H-$2^d$) of both sexes (The Jackson Laboratory, Bar Harbor, Me.) were immunized at 8 to 14 weeks of age in the rear foot pad with 5–10×$10^6$ *L. donovani* promastigotes emulsified in complete Freünd's adjuvant (CFA) (Difco Laboratories, Madison, Mich.) as described in Rodrigues et al., *Parasite Immunol.* 14:49 (1992). The draining lymph nodes were excised 8 days after the immunization and T-cells were purified in an anti-mouse Ig column to remove the B cells, as described in Bunn-Moreno and Campos-Neto, *J. Immunol.* 127:427 (1981), followed by a passage through a Sephadex G10 column to remove the macrophages.

Stimulation index was calculated by dividing the cpm obtained for the cells cultured in the presence of infected P388D1 macrophages by the cpm obtained for the cells cultured in the presence of non-infected macrophages, but subjected to the same conditions as the infected macrophages. The results shown FIG. 1 indicate that *L. donovani*-infected P388D1 macrophage process parasite antigens and that optimal presentation occurs after 48 hours of infection. No stimulation of the T-cells by the non-infected macrophages was observed.

To isolate the MHC class II associated *L. donovani* peptides, P388D1 macrophages were infected with *L. donovani* promastigotes for an initial incubation of 6 hours at room temperature. The cultures were then transferred to 37° C. for the remainder of the 48 hour incubation period. At a ratio of 3–5 parasites per macrophage nearly 90% of the macrophages were infected after 24 hours of incubation at 37° C.

The MHC class II molecules were then affinity-purified. Approximately 1.5×$10^{10}$ *L. donovani*-infected or an equal number of non-infected P388D1 macrophages were used for each purification. The cells were harvested, washed with PBS and incubated for 30 minutes in cold lysis buffer (PBS, 1% Nonidet P40, 25 mM iodoacetamide, 0.04% sodium azide, 1 mM aprotinin and 1 mM PMSF). The insoluble material was removed by centrifugation at 40,000 g for 1 hour and the supernatant was recycled overnight at 4° C. over a 5 ml anti-MHC class II molecules (H-$2^d$) Sepharose column (Protein G Sepharose column to which the monoclonal antibody MK-D6 has been bound). Culture supernatants of MK-D6 hybridoma cells (American Type Culture Collection, Rockville, Md.) were employed as the source for anti-MHC class II (H-$2^d$) monoclonal antibody. The column was washed with 50 ml of lysis buffer and then with 50 ml of PBS containing 0.5% octyl glucopyranoside detergent. Bound molecules were eluted from the column with 1M acetic acid in 0.2% NaCl. The MHC/peptide molecules were separated from the IgG (MK-D6 monoclonal antibody) using a Centricon 100 filter unit (Amicon Division, W. R. Grace & Co., Beverly, Mass.). The peptides were then dissociated from the class II molecules by the addition of acetic acid to 2.5M, followed by separation using a Centricon 10 filter unit. The resulting peptide preparation, present in the low molecular weight sample, was then dried using a speed vac concentrator (Savant Instrument Inc., Farmingdale, N.Y.).

The peptides were redissolved in 200 $\mu$l of 0.05% TFA and separated by reverse-phase high performance liquid chromatography (RP-HPLC) using a 2.1 mm×25 cm Vydac C-18 column at a flow rate of 0.15 ml/min employing a 1 to 30% acetonitrile gradient (60 min) followed by a 30 to 60% gradient (30 min) and then a 60 to 80% gradient (90–110 min). Non-infected P388D1 cells were similarly processed to serve as background control for endogenous MHC class II associated peptides. FIG. 2 shows a representative experiment; four distinct peaks which are present only in the material isolated from infected macrophages (panel B), and not in the material isolated from uninfected macrophages (panel A) are indicated.

Out of three independent peptide extractions, twenty five distinct HPLC peptide peaks were isolated from *L. donovani*-infected macrophages and were subjected to protein sequence analysis using automated Edman degradation on an Applied Biosystems 477 gas-phase protein sequencer. Protein sequence and amino acid analysis were performed by the W. M. Keck Foundation, Biotechnology Resource Laboratory, Yale University, New Haven, Conn. In practically all determinations, no assignment could be made for the first position. Also, in most cases the definition of the amino acid residues of the 10–15 positions was based on the quantitative dominance of one residue over others. Using this approach, the sequences obtained for several peptides showed the presence of 3–6 different residues in many of the 10–15 sequence cycles analyzed for each determination, reflecting a mixture of peptides. In addition, sequences could not be obtained for some peaks because the peptides were blocked. Notwithstanding, three peptides sequences were determined. Amino-acid sequences were searched for identity with proteins in the GenBank database using the GENPETP, PIR and SWISSPROT programs. The sequence data base analysis revealed that one of the peptides was highly homologous to glyceraldehyde-3-phosphate dehydrogenase of various species. Another peptide had homology with elongation factor of several species, including Leishmania. The third sequence was not clearly related to any known proteins, and is shown below:

XQXPQ(L/K)VFDEXX (SEQ ID NO:11).

B. Cloning and Sequencing of the Ldp23 Gene

In order to retrieve the *L. donovani* protein that was processed into a peptide associated with the MHC class II molecules of infected macrophages, the peptide sequence of uncertain origin was chosen to guide the strategy for cloning the corresponding parasite gene. A DNA fragment was initially amplified from *L. donovani* promastigote cDNA by PCR. The sense primer was a peptide derived oligonucleotide (5'>GGAATTCCCCInCAGCTInGTInTTCGAC<3') (SEQ ID NO:12) containing an EcoRI restriction endonuclease site (underlined). The bases were selected following the preferential codon usage of *L. donovani*, as described in Langford et al., *Exp. Parasitol.* 74:360 (1992). Inosine was used for the residues of positions 4, 6 and 7 because of the low codon usage assurance for the corresponding amino acids. In addition, the carboxyl-terminal L-glutamic acid was not included for the design of the primer. The antisense primer was a poly-thymidine oligonucleotide (oligo dT, downstream primer) containing a XhoI restriction endonuclease site.

The gene fragment was amplified from a *L. donovani* promastigote cDNA preparation using the following reaction conditions; one cycle of 3 min at 94° C. immediately followed by 35 cycles of 1 min at 94° C., 1 min at 45° C. and 1 min at 72° C. The *L. donovani* cDNA was prepared from 5×10[7] washed promastigote forms harvested at the log growth phase (3 days culture). The cDNA was obtained using an Invitrogen cDNA cycle™ kit (Invitrogen Co., San Diego, Calif.). Oligonucleotide primers were synthesized by the DNA Synthesis Laboratory, Department of Pathology, Yale University School of Medicine.

The PCR products were analyzed by gel electrophoresis. Only one band of approximately 300 bp was obtained. This fragment was cloned and its sequence confirmed the sequence of the peptide-based primer including the glutamic acid codon, deliberately not included in the primer sequence.

The PCR amplified gene fragment was ligated into the pCR™ vector using the TA cloning system (Invitrogen Co., San Diego, Calif.). Transformants were selected in LB medium containing 100 µg/ml ampicillin and the plasmid DNA was isolated using the Wizard™ Minipreps DNA purification kit (Promega Co., Madison, Wis.). Insert DNA was released with the restriction enzymes EcoRI and XhoI (New England Biolabs, Beverly, Mass.), purified from an agarose gel electrophoresis and labeled with $^{32}$P using a random priming method (Megaprime Labeling Kit, Amersham Life Science, Buckinghamshire, England).

This DNA fragment was used as probe to screen a *L. donovani* promastigote cDNA library as described in Skeiky et al., *Infect. Immun.* 62:1643 (1994). An approximately 650 bp cDNA (Ldp23) was excised from the phagemid by in vivo excision using the Stratagene protocol. DNA sequencing was performed using the Sequenase version 2 system (DNA sequencing kit) in the presence or absence of 7-deaza-GTP (United States Biochemical, Cleveland, Ohio). The sequence is provided as SEQ ID NO:3, and shows complete homology with the original 300 bp PCR fragment. A 525 bp open reading frame containing an ATG codon that follows the last 4 bases of the spliced leader sequence and 3 stop codons adjacent to the poly A tail was identified. This frame also codes the carboxyl terminal sequence (KVFDE) (SEQ ID NO:13) of the purified MHC class II associated peptide. The sequence analysis of the deduced protein sequence revealed one potential glycosylation site (Asn-Cys-Ser) at positions 68–70.

Sequence analysis was performed using the University of Wisconsin Genetics Computer Group Programs and the GenBank and EMBL data bases of protein and DNA sequences. The search for homology of the Ldp23 gene with known sequences revealed no significant homology.

C. Bacterial Expression and Purification of Recombinant Protein

The recombinant *L. donovani* peptide donor protein was produced in *E. coli* transformed with the pGEX 2T expression vector in which the Ldp23 gene was subcloned in frame. PCR was used to subclone the cloned gene in frame into the expression vector pGEX 2T. Primers containing the appropriate restriction site enzymes, initiation and termination codons were: 51'>GGATCCATGGTCAAGTCCCAC-TACATCTGC<3' (SEQ ID NO:14) for the upstream primer and 5'>GAATTCAGACCGGATAGAAATAAGC-CAATGAAA<3' (SEQ ID NO: 15) for the downstream primer (restriction sites of BamHI and EcoRI are underlined respectively). PCR conditions were as indicated above for the amplification of the original peptide related DNA fragment. The template used was pBluescript plasmid containing the cloned gene from the cDNA library.

Overexpression of the recombinant fusion protein was accomplished by growing the transformed *E. coli* (DH5α) and inducing the tac promoter with 1 mM isopropyl-β-thiogalactopyranoside (IPTG) (Stratagene, La Jolla, Calif.). Cells were collected, centrifuged, and analyzed for the presence of the fusion protein by SDS-PAGE. A glutathione-S-transferase fusion protein of 43–44 kD was produced, indicating a leishmanial protein of approximately 18 kD, as glutathione-S-transferase (GST) has a MW of 26 kD. However, the fusion protein was very insoluble and therefore could not be purified by affinity chromatography using a glutathione column. The use of low concentrations of detergents like SDS, sarcosyl, deoxycolate, and octyl-glucopyranoside during the extraction steps was efficient to solubilize the protein but unfortunately prevented its binding to the glutathione column. Other maneuvers, such as the growth of the *E. coli* and incubation and induction of the tac promoter with IPTG at 33° C., did not improve the protein solubility. However, the purification was achieved by preparative SDS-PAGE. The band was visualized with 0.1M KCl, cut and electroeluted from the gel followed by extensive dialysis against PBS and concentration on Centricon 10 filters.

Figure 3A:
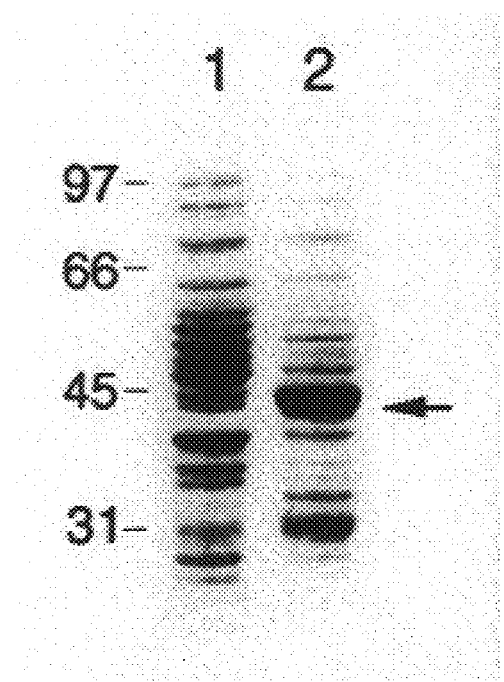
FIG. 3 illustrates the expression and purification of the Leishmania antigen Ldp23 as a recombinant fusion protein. Panel A shows a Coomassie blue-stained SDS-PAGE gel of lysed *E. coli* without (lane 1) and with (lane 2) IPTG induction of Ldp23 expression. Arrow indicates the recombinant fusion protein. Panel B shows the fusion protein following excision from a preparative SDS-PAGE gel, electroelution, dialysis against PBS and analytical SDS-PAGE.
Figure 3B:
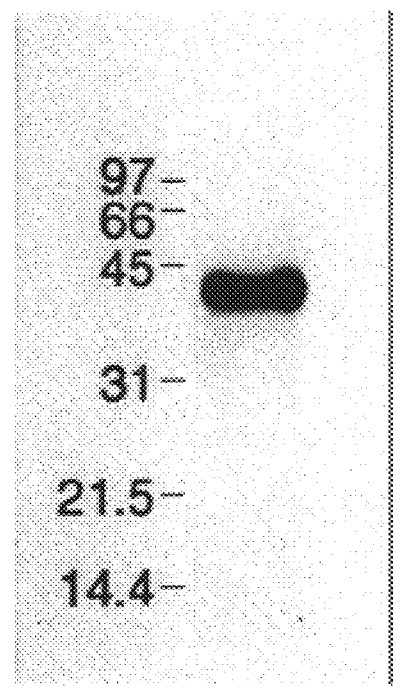

Approximately 500 µg of purified protein was obtained. The purified protein is shown in FIG. 3. In panel A, *E. coli* (DH5α) transformed with the expression vector pGEX 2T containing the Ldp23 gene was grown in LB medium and the tac promoter was induced with IPTG for 3 hours. The cells were pelleted, resuspended in loading buffer and submitted to SDS-PAGE (10%) under reducing condition. The gel was stained with Coomassie blue. Lane 1 shows the uninduced *E. coli* and land 2 shows the induced *E. coli*. The arrow indicates the recombinant protein. Panel B shows the protein prepared as in panel A and submitted to a preparative SDS-PAGE. The band corresponding to the overexpressed recombinant fusion protein was identified by KCl, cut out, electroeluted from the gel strip, dialyzed against PBS and submitted to analytical SDS-PAGE (12%). Numbers on the left side indicate the molecular weights of the markers.

Attempts to further purify the leishmanial protein by cleaving it out from the fusion protein GST with thrombin were unsuccessful.

D. Expression of Ldp23

To ascertain that the Ldp23 peptide is expressed in Leishmania organisms, a Northern blot analysis was performed using RNA prepared from different promastigote growth phases (logarithmic and stationary) and from the amastigote form of these parasites.

The RNA was prepared from $2\times10^7$ parasite cells using the Micro RNA isolation kit (Stratagene, La Jolla, Calif.) according to the company's recommended instructions. RNA was prepared from L. donovani promastigotes (logarithmic growth phase); from L. major promastigotes (logarithmic and stationary growth phases); from L. amazonensis, both promastigotes (logarithmic and stationary growth phases) and amastigotes purified from CBA/J infected mice; and from L. pifanoi, both promastigotes (logarithmic and stationary growth phases) and amastigotes (from axenic culture medium). L. donovani (1S strain), L. amazonensis (MHOM/BR/77/LTB0016), L. major (MHOM/IR/79/LRC-L251) and L. pifanoi (MHOM/VE/60/Ltrod) promastigotes were grown and maintained at 26° C. in Schneider's medium containing 20% FCS and 50 μg/ml gentamicin. The amastigote forms of L. amazonensis were obtained by differential centrifugation of a "pus-like" foot pad lesion of a CBA/J mouse infected for 6 months with this parasite. L. pifanoi amastigotes were obtained from axenic culture as previously reported by Pan et al., *J. Euk. Microbiol.* 40:213 (1993).

The hybridization was carried out at 45° C. in the presence of 50% formamide, 5×Denhardt's solution, 0.1% SDS, 100 μg/ml single stranded salmon sperm DNA and 5×SSPE using 0.45 μm Nytran membrane filters (Schleicher & Schuell, Keene, N.H.). The probe was the $^{32}P$ labeled Ldp23 gene.

Figure 4:
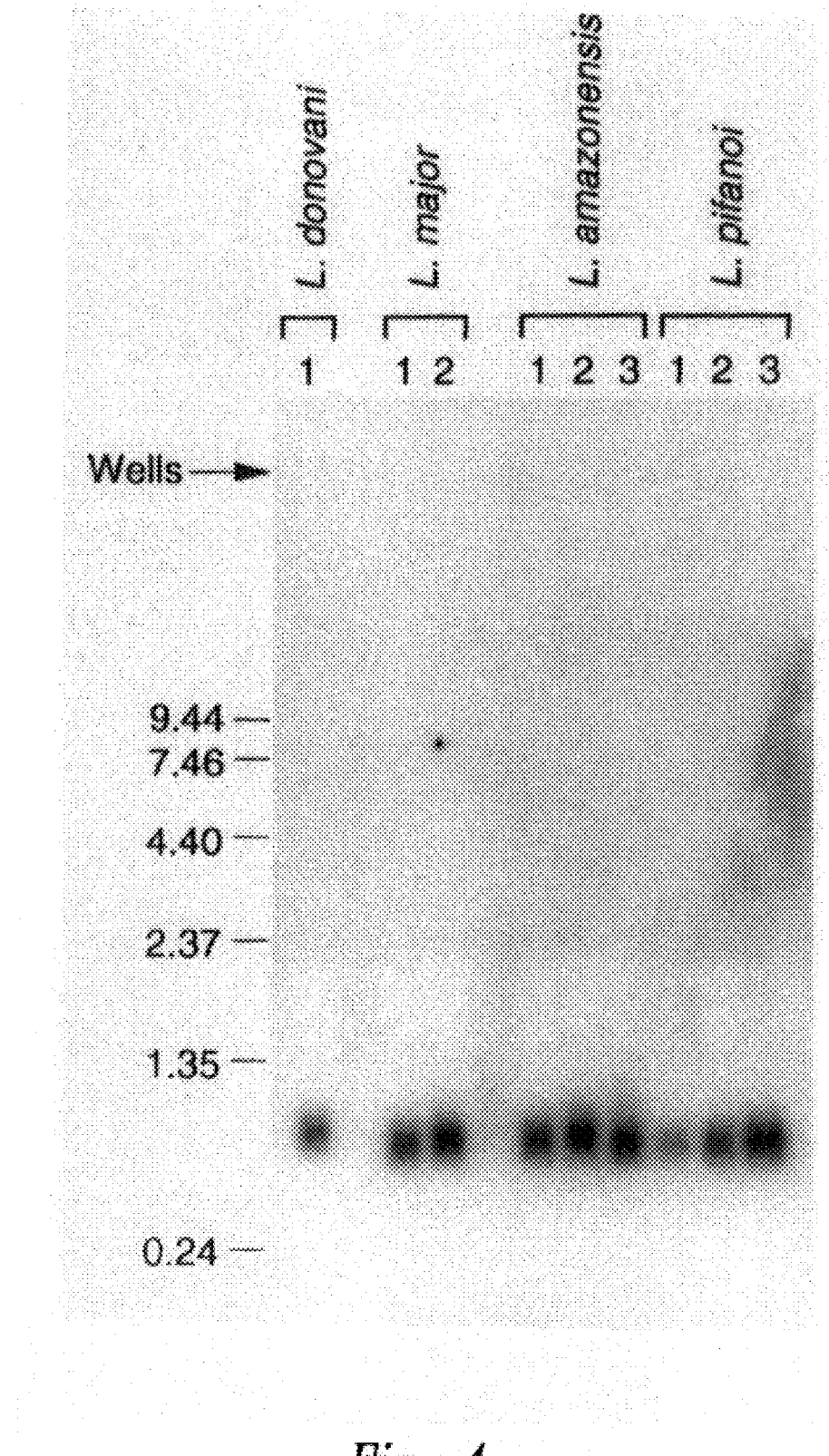
FIG. 4 presents a Northern blot analysis of total RNA prepared from *L. donovani, L. major, L. amazonensis* and *L. pifanoi* with a $^{32}$P labeled Ldp23 gene. 1, 2 and 3 refer to RNA obtained from promastigotes at the logarithmic growth phase, promastigotes at the stationary growth phase and amastigote forms, respectively.

FIG. 4 shows that one single RNA band of 680 bp was observed for all growth phases and forms of all tested Leishmania. Within FIG. 4, the numbers 1, 2 and 3 refer to RNA obtained from promastigotes at the logarithmic growth phase, promastigotes at the stationary growth phase and amastigote forms, respectively, and the numbers on the left side indicate the molecular weights of the markers in base pairs. This result is consistent with the corresponding gene size (525 bp) and with the molecular weight of the expressed protein and points to the ubiquitous distribution and expression of this gene within the genus Leishmania.

E. Induction of Anti-L. donovani Antibody Response in Mice and Rabbits by Purified Recombinant Protein In order to evaluate the immunogenicity of the recombinant leishmanial protein, and to investigate its expression in the parasites, mice and rabbits were immunized with the GST-fusion protein in CFA. BALB/c mice were immunized in the rear foot pad with 5–10 μg of protein emulsified in CFA. Protein concentration was determined using the Bio-Rad Protein Assay reagent (Bio-Rad Laboratories, Richmond, Calif.). The mice were boosted 7 days later with 5–10 μg of protein emulsified in incomplete Freünd's adjuvant (IFA) inoculated into the peritoneal cavity. The mice were bled 7 days after the second immunization. New Zealand white rabbits (Millbrook Farm, Amherst, Mass.) were immunized according to the following protocol: one intra-muscular (IM) injection of 25–30 μg of purified recombinant protein emulsified in CFA into each thigh on day one; one IM injection of 25–30 μg of purified protein emulsified in IFA into each shoulder on day 7; on day 15, 25–30 μg of the purified protein in PBS was injected into the subcutaneous tissue. The rabbit was bled 7 days after the last immunization.

Sera were prepared and the anti-Leishmania antibody response was measured by Western blot analysis and by FACScan. In both cases L. donovani promastigotes were used as antigen. Approximately $2\times10^6$ L. donovani promastigotes were grown in Schneider's medium for 3 days (log phase), were washed with PBS, lysed with SDS-PAGE loading buffer and submitted to electrophoresis under reducing conditions using a 15% polyacrylamide gel. The proteins were transferred onto 0.45μ Immobilon-P transfer membrane (Millipore Co., Bedford, Mass.) using a wet-type electroblotter (Mini Trans-Blot Electrophoretic Transfer Cell, Bio Rad Life Science Division, Richmond, Calif.) for 2 hours at 50 V. The membranes were blocked overnight at room temperature with PBS containing 3% normal goat serum (NGS), 0.2% Tween-20 and 0.05% sodium azide, followed by 3 washes with PBS. The blots were then incubated for 3–4 hours at 4° C. with a 1/200 dilution of pre-immune rabbit serum (lane A, FIG. 5) or with the same dilution of anti-fusion protein rabbit antiserum (lane B, FIG. 5). The sera was previously absorbed 2× with non-viable desiccated *Mycobacterium tuberculosis* H-37 RA (Difco Laboratories, Detroit, Mich.) and were diluted in PBS containing 1% NGS and 5% powdered non-fat bovine milk (Carnation, Nestlé Food Company, Glendale, Calif.). The membranes were then washed with PBS, incubated for 1 hour at room temperature with goat anti-rabbit IgG antibody conjugated with alkaline phosphatase (Promega, Madison, Wis.), washed once with PBS and 2× with veronal buffer pH 9.4. The reaction was visualized using the substrate mixture 5-bromo-4-chloro-3-indoyl-phosphate and nitroblue tetrazolium (Kirkegaard & Perry Laboratories Inc., Gaithersburg, Md.) according to the manufacturer's instructions.

Figure 5A:
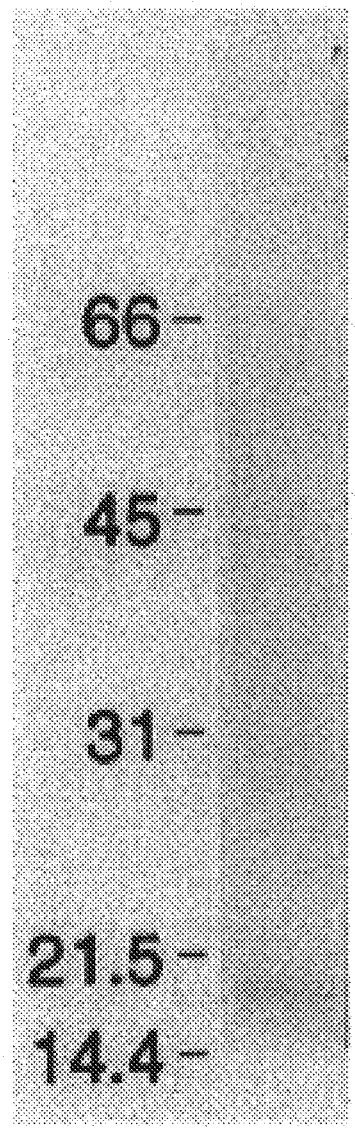
FIG. 5 shows a Western blot analysis of *L. donovani* promastigote antigens incubated with pre-immune rabbit serum (lane A) or with anti-Ldp23 rabbit antiserum (lane B).
Figure 5B:
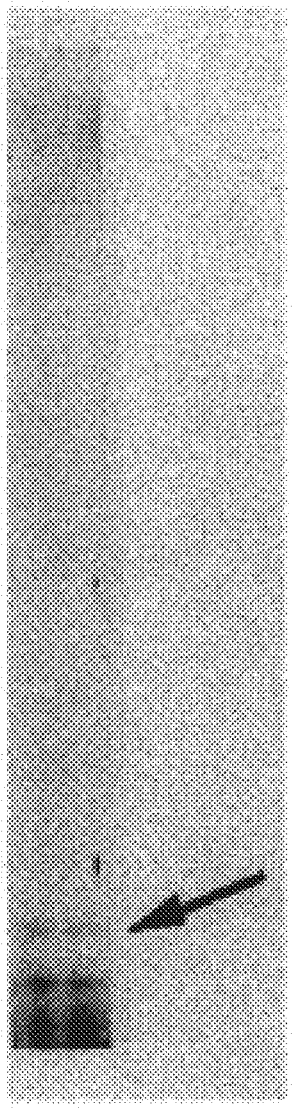
Figure 6:
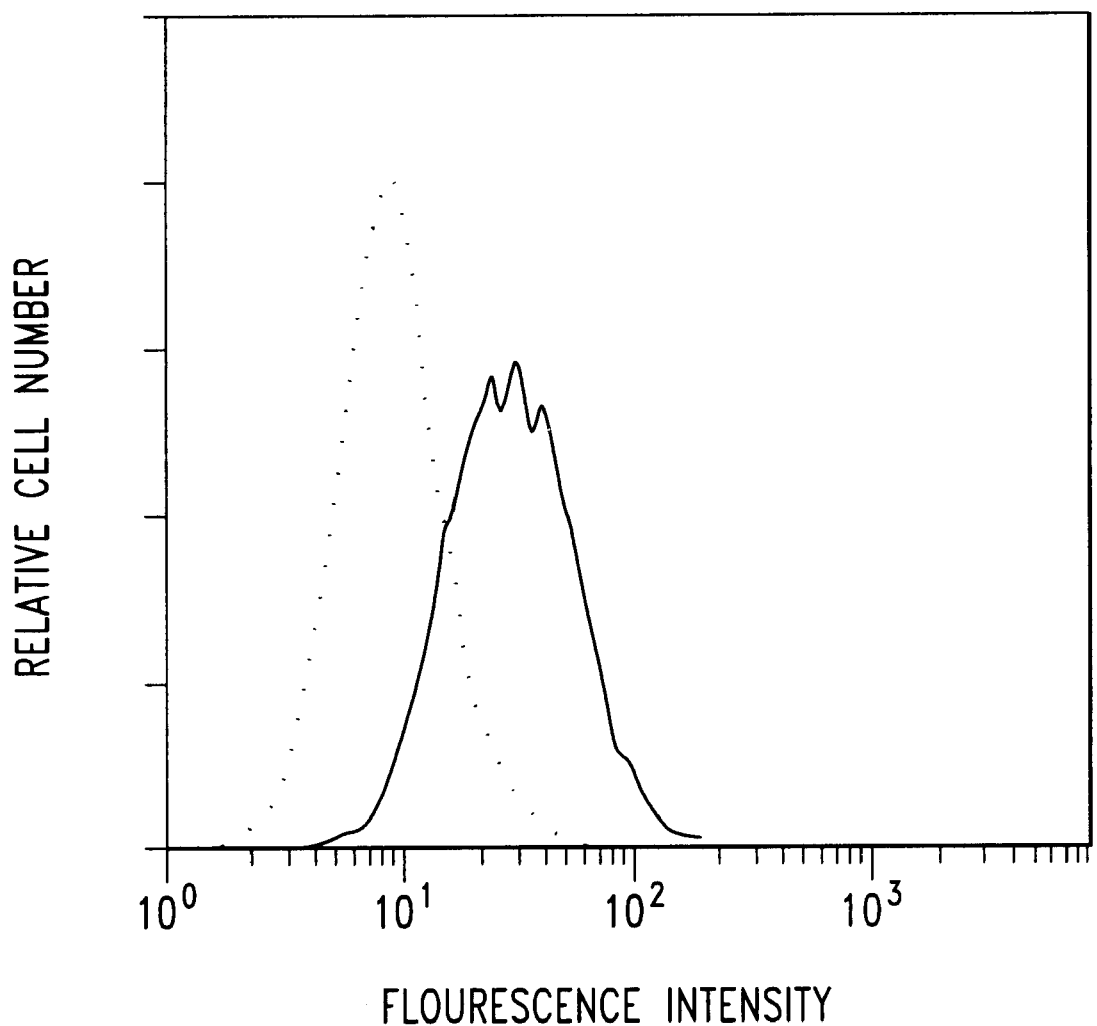
FIG. 6 illustrates the surface expression of Ldp23 on live *L. donovani* promastigotes. The dotted line shows the indirect immunofluorescence performed using pre-immune mouse serum and the solid line shows the result obtained with mouse anti-GST-Ldp23 antiserum. Fluorescence intensity was analyzed by FACScan.

FIG. 5 shows that the rabbit anti-recombinant protein antiserum detects a single protein of 23 kDa (Ldp23) in the Leishmania crude extract antigen preparation. No bands were observed when an anti-GST antiserum was used (not shown). Moreover, the FACScan analysis (FIG. 6) shows that the antibody induced by the recombinant Ldp23 reacts with intact live L. donovani promastigotes, thus pointing to a cell surface expression of this molecule on these organisms. The dotted line in FIG. 6 shows the indirect immunofluorescence performed using pre-immune mouse serum and the solid line in FIG. 6 shows the result obtained with mouse anti-GST-Ldp23 antiserum. Both sera were diluted at 1/100. Parasites were washed with staining buffer and incubated with FITC conjugated goat anti-mouse immunoglobulin antibody. Fluorescence intensity was analyzed by FACScan.

F. Recognition of Recombinant Ldp23 by Leishmania-Specific Lymph Node T-cells

Figure 7:
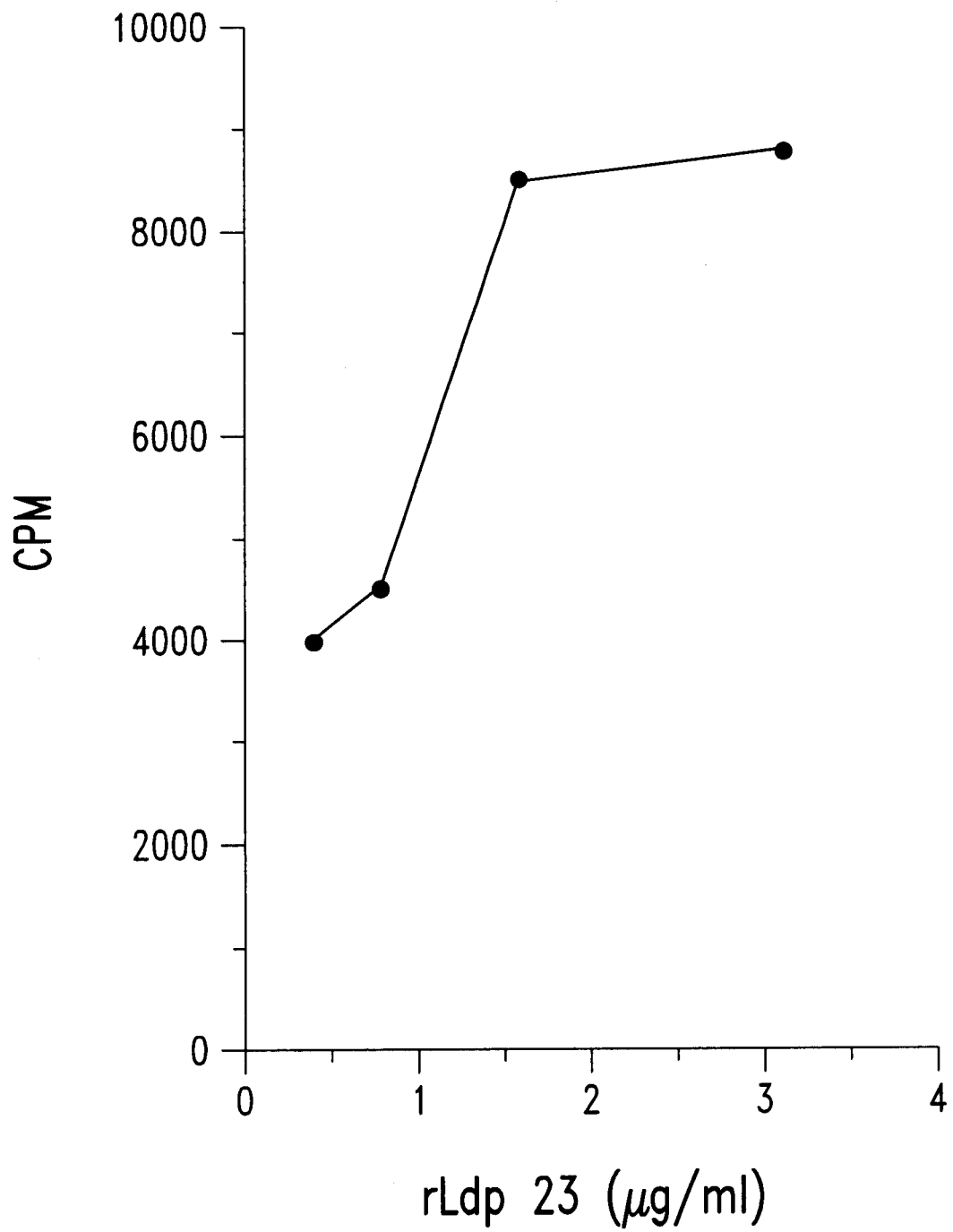
FIG. 7 shows the stimulation of Leishmania-specific T-cell proliferation by Ldp23. The results are presented as relative cell number as a function of fluorescence intensity. T-cells ($10^5$/well) were purified from lymph nodes of BALB/c mice immunized in the foot pad with *L. donovani* promastigotes in CFA and were cultured with various concentrations of the purified recombinant Ldp23 in the presence of 2×10$^5$ Mitomycin C-treated normal BALB/c spleen mononuclear cells. Proliferation of T-cells was measured at 27 hours of culture. Values are expressed as cpm and represent the mean of [$^3$H]TdR incorporation of triplicate cultures.

To test the responsiveness of T-cells to the Ldp23 protein, two sets of experiments were performed. In the first experiment, lymph node T-cells ($10^5$/well) from BALB/c mice immunized with L. donovani promastigotes (as described above) were stimulated to proliferate with $2\times10^5$ Mitomycin C-treated normal mononuclear spleen cells (APC) and pulsed with the purified recombinant fusion protein. Proliferation of T-cells was measured at 72 hours of culture. Values are expressed in FIG. 7 as cpm and represent the mean of [$^3$H]TdR incorporation of triplicate cultures. Background cpm of cells (T cells+APC) cultured in the presence of medium alone was 1291. FIG. 7 shows that Leishmania specific T-cells proliferate well and in a dose response manner to recombinant Ldp23. No response was observed when purified GST was added instead of the recombinant fusion protein nor when lymph node T-cells from mice immunized with CFA alone were stimulated to proliferate in the presence of the Leishmanial fusion protein (not shown).

The recognition of the recombinant Ldp23 protein by Leishmania-specific T-cells was also tested using two murine models of leishmaniasis, the *L. major* highly susceptible BALB/c mice and the *L. amazonensis* susceptible CBA/J mice as described in Champsi and McMahon-Pratt, *Infect. Immun.* 56:3272 (1988). These models were selected to investigate the cytokine pattern induced by Ldp23. In the mouse model of leishmaniasis, resistance is associated with Th 1 cytokines while susceptibility is linked to Th 2 responses.

Lymph node cells were obtained 3 weeks after the initiation of infection of BALB/c mice with *L. major* and the ability of these cells to recognize the recombinant Ldp23 was measured by proliferation and by the production of the cytokines IFN-γ and IL-4. 2×10⁶ cells obtained from the draining popliteal lymph node of infected mice were cultured for 72 hours in the presence of recombinant Ldp23 or Leishmania lysate. The levels of IFN-γ and IL-4 in culture supernatants were measured by ELISA as previously described (Chatelain et al., *J. Immunol.* 148:1172 (1992), Curry et al., *J. Immunol. Meth.* 104:137 (1987), and Mossman and Fong, *J. Immunol. Meth.* 116:151 (1989)) using specific anti IFN-γ and IL-4 monoclonal antibodies (PharMingen, San Diego, Calif.).

Figure 8B:
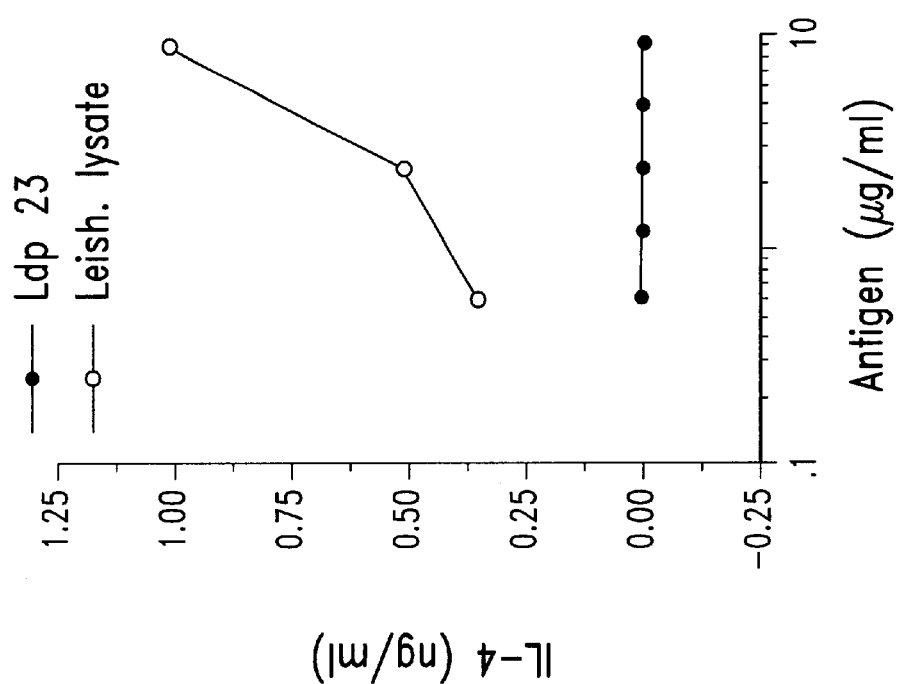
FIG. 8 illustrates Ldp23-induced cytokine production by lymph node cells of BALB/c mice. Cultures were incubated with varying amounts of Ldp23 or Leishmania lysate, presented as μg/mL, and were assayed by ELISA for the production of interferon-γ (panel A) or interleukin-4 (panel B), both of which are shown as ng/mL.
Figure 8A:
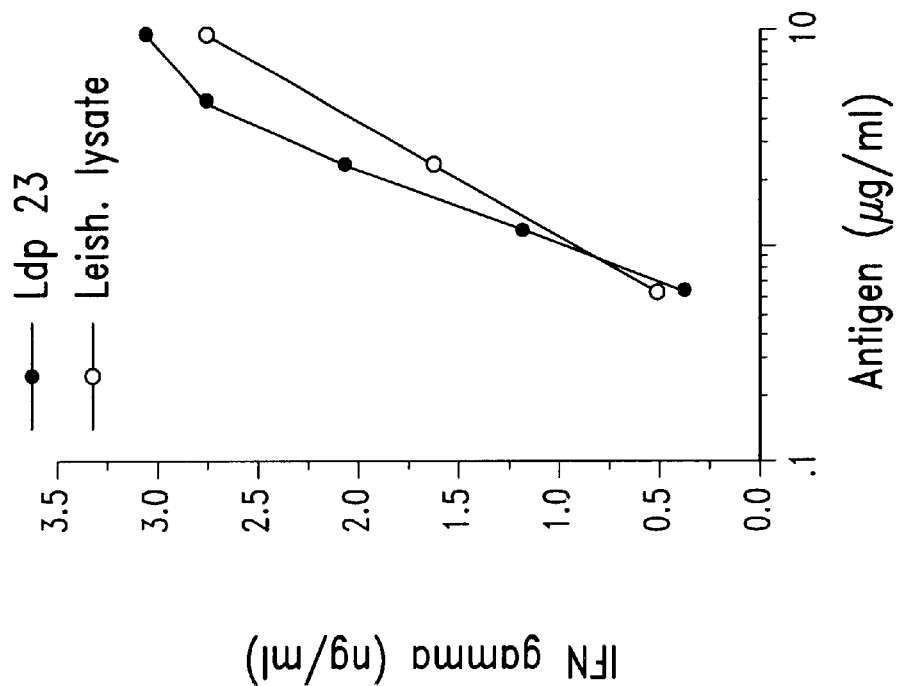

Ldp23 did stimulate these cells to proliferate (not shown) and induced a typical Th 1 type of cytokine response as indicated by the production of high levels of IFN-γ (panel A of FIG. 8) and no IL-4 (panel B of FIG. 8). Stimulation of these cells with a Leishmania crude lysate yielded a mixed Th cytokine profile. Exactly the same pattern of cytokine production was obtained from the CBA/J mice infected with *L. amazonensis* (not shown). These results clearly indicate that Ldp23 is a powerful and selective activator of the Th 1 cytokines by mouse cells.

Example 3

Preparation of Hsp83

This Example illustrates the preparation of a Leishmania antigen Hsp83, having the sequence provided in SEQ ID NO:6.

A genomic expression library was constructed with sheared DNA from *L. braziliensis* (MHOM/BR/75/M2903) in bacteriophage λZAP II (Stratagene, La Jolla, Calif.). The expression library was screened with *Escherichia coli* preadsorbed serum from an *L. braziliensis*-infected individual with ML. Immunoreactive plaques were purified, and the pBSK(−) phagemid was excised by protocols suggested by the manufacturer. Nested deletions were performed with exonuclease III to generate overlapping deletions for single-stranded template preparations and sequencing. Single-stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems automated sequencer model 373A.

Recombinant antigens produced by these clones were purified from 500 ml of isopropyl-β-D-thiogalactopyranoside (IPTG)-induced cultures as described in Skeiky et al., *J. Exp. Med.* 176:201–211 (1992). These antigens were then assayed for the ability to stimulate PBMC from Leishmania-infected individuals to proliferate and secrete cytokine. Peripheral blood was obtained from individuals living in an area (Corte de Pedra, Bahia, Brazil) where *L. braziliensis* is endemic and where epidemiological, clinical, and immunological studies have been performed for over a decade, and PBMC were isolated from whole blood by density centrifugation through Ficoll (Winthrop Laboratories, New York, N.Y.). For in vitro proliferation assays, 2×10⁵ to 4×10⁵ cells per well were cultured in complete medium (RPMI 1640 supplemented with gentamicin, 2-mercaptoethanol, L-glutamine, and 10% screened pooled A+ human serum; Trimar, Hollywood, Calif.) in 96-well flat-bottom plates with or without 10 μg of the indicated antigens per ml or 5 μg of phytohemagglutinin per ml (Sigma Immunochemicals, St. Louis, Mo.) for 5 days. The cells were then pulsed with 1 μCi of [³H]thymidine for the final 18 h of culture. For determination of cytokine production 0.5 to 1 ml of PBMC was cultured at 1×10⁶ to 2×10⁶ cells per ml with or without the Leishmania antigens for 48 and 72 h.

The supernatants and cells were harvested and analyzed for secreted cytokine or cytokine mRNAs. Aliquots of the supernatants were assayed for gamma interferon (IFN-γ), tumor necrosis factor alpha (TNF-α), interleukin-4 (IL-4), and IL-10 as described in Skeiky et al., *J. Exp. Med.* 181:1527–1537 (1995). For cytokine mRNA PCR analysis, total RNA was isolated from PBMC and cDNA was synthesized by using poly(dT) (Pharmacia, Piscataway, N.J.) and avian mycloblastosis virus reverse transcriptase. Following normalization to β-actin, diluted cDNA was amplified by PCR using Taq polymerase (Perkin-Elmer Cetus, Foster City, Calif.) with 0.2 μM concentrations of the respective 5' and 3' external primers in a reaction volume of 50 μl. The nucleotide sequences of the primary pairs and the PCR conditions used were as described in Skeiky et al., *J. Exp. Med.* 181:1527–1537 (1995). We verified that our PCR conditions were within the semiquantitative range by initially performing serial dilutions of the cDNAs and varying the number of cycles used for PCR. Plasmids containing the human sequences for IL-2, IFN-γ, IL-4, IL-10, and β-actin were digested, and the DNA inserts were purified after separation on 1% agarose gels. Radiolabeled ³²P probes were prepared by the random priming method. PCR products were analyzed by electrophoresis on 1.5% agarose gels, transferred to nylon membranes, and probed with the appropriate ³²P-labeled DNA insert.

A recombinant clone was identified in the above assays which, following sequence comparison of its predicted amino acid sequence with sequences of other proteins, was identified as a *Leishmania braziliensis* homolog of the eukaryotic 83 kD heat shock protein (Lbhsp83). The sequence of the clone is provided in SEQ ID NO:5 and the deduced protein sequence is provided in SEQ ID NO:6. On the basis of the homology, this clone, designated Lbhsp83a, appears to lack the first 47 residues of the full length 703 amino acid residues. Lbhsp83 has an overall homology of 94% (91% identity and 3% conservative substitution), 91% (84% identity and 7% conservative substitution) and 77% (61% identity and 16% conservative substitution) with *L. amazonensis* hsp83, *T. cruzi* hsp83 and human hsp89, respectively. A second clone (designated Lbhsp83b), which contained the 43 kD C-terminal portion of hsp83 (residues 331 to 703) was also isolated. FIG. 19 presents a comparison of the Lbhsp83 sequence with *L. amazonensis* hsp83 (Lahsp83), *T. cruzi* hsp83 (Tchsp83) and human hsp89 (Huhsp89).

The results of proliferation assays using Lbhsp83a are shown in Table 1. Cells from all mucosal leishmaniasis (ML) patients proliferated strongly in response to Lbhsp83a, with stimulation indices (SIs) ranging from 19 to 558 (as compared to 20 to 1,634 for parasite lysate). Proliferation of PBMC from cutaneous leishmaniasis (CL) patients was variable and except for levels in two patients (IV and VII), levels were significantly lower than those of ML patients. By comparison, the proliferative responses of individuals with self-healing CL to Lbhsp83a were similar to those of individuals with ML. However, the responses of all six self-healing individuals to Lbhsp83 were consistently higher than those to Lbhsp83b. This suggests that PBMC from self-healing CL patients preferentially recognize one or more T-cell epitopes located within the amino portion of Lbhsp83.

TABLE 1

In vitro Proliferation of PMBC from *L. braziliensis*-infected Individuals in Response to Lbhsp83

| Group and Patient | Mean [$^3$H]thymidine incorporation [$10^3$ cpm (SD)], SI with: | | |
|---|---|---|---|
| | Lysate | Lbhsp83a | Lbhsp83b |
| ML | | | |
| I | 41.3, (1.3), 294 | 32.5, (6.6), 221 | 46.7, (1.4), 318 |
| II | 44.2, (0.5), 104 | 20, (3.7), 47 | 36.7, (0.76), 86 |
| III | 27.4, (1.5), 150 | 8.1, (1.7), 44 | 9.9, (0.32), 54 |
| IV | 52.7, (3.3), 138 | 54.1, (6.2), 142 | 32.0, (1.3), 84 |
| V | 140.6, (7.6), 308 | 151.8, (57), 333 | 150.4, (7.9), 331 |
| VI | 15.8, (1.8), 20 | 21.3, (4.4), 28 | 14.4, (1.3), 19 |
| VII | 300.1, (9.4), 1634 | 102.1, (7.6), 558 | 41.7, (4.9), 228 |
| CL | | | |
| I | 0.26, (0.0), 1.5 | 0.57, (0.3), 3.3 | 0.43, (0.17), 3.3 |
| II | 55.63, (8.6), 218 | 0.42, (0.0), 1.6 | 0.8, (0.14), 3.2 |
| III | 0.39, (0.5), 4.0 | 3.4, (0.5), 9 | 2.6, (0.9), 6.6 |
| IV | 19.14, (1.3), 87 | 7.17, (0.6), 32 | 5.9, (0.9), 27 |
| V | 0.32, (0.2), 3.0 | 1.47, (0.5), 14 | 0.3, (0.1), 3.0 |
| VI | 0.77, (0.1), 4.7 | 1.44, (0.2), 9 | 1.3, (0.6), 8.0 |
| VII | 4.01, (1.0), 2.0 | 60.3, (8.5), 15 | 66.7, (3.9), 16.6 |
| Self-healing CL | | | |
| I | 19.7, (4.4), 94 | 61.3, (4.6), 293 | 5.0, (2.0), 24 |
| II | 0.6, (0.1), 6.5 | 7.0, (2.0), 79 | 1.2, (0.8), 13 |
| III | 59.6, (7.1), 519 | 49.4, (3.1), 429 | 21.4, (3.7), 186 |
| IV | 0.2, (0.1), 1.6 | 13.1, (1.7), 108 | 0.6, (0.1), 5 |
| V | 27.1, (2.0), 225 | 6.3, (2.6), 52 | 3.0, (1.5), 25 |
| VI | 130.3, (14), 340 | 28.2, (2.9), 74 | 7.7, (3.8), 20 |
| Control (uninfected) | | | |
| I | 0.19, (0.0), 1.4 | 0.18, (0.0), 1.3 | 0.40, (0.16), 2.8 |
| II | 0.31, (0.1), 1.7 | 0.19, (0.0), 1.0 | 0.27, (0.0), 1.5 |
| III | 0.44, (0.2), 4.1 | 0.48, (0.1), 5.0 | 0.51, (0.2), 5.2 |
| IV | 0.4, (0.1), 3.2 | 0.52, (0.2), 5.1 | 0.50, (0.1), 5.0 |

Figure 9A:
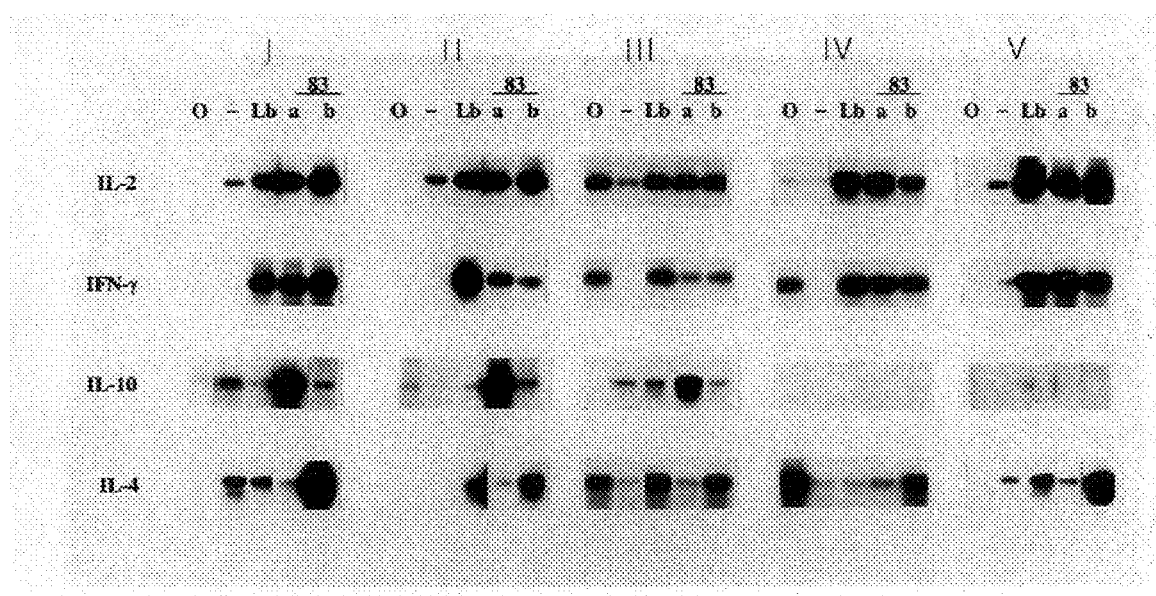
FIG. 9 shows the PCR amplification of cytokine mRNAs isolated from mucosal leishmaniasis (Panel A) and cutaneous leishmaniasis (panel B) patient PBMC before and after stimulation with representative polypeptides of the present invention. Lanes O and—indicate the level of PCR products at the initiation of culture and after 72 hours of culture, respectively, in the absence of added polypeptide; lanes Lb, 83a and 83b indicate the level of PCR products following culturing of PBMC with *L. braziliensis* lysate, and the Leishmania antigens Lbhsp83a and Lbhsp83b, respectively.
Figure 9B:
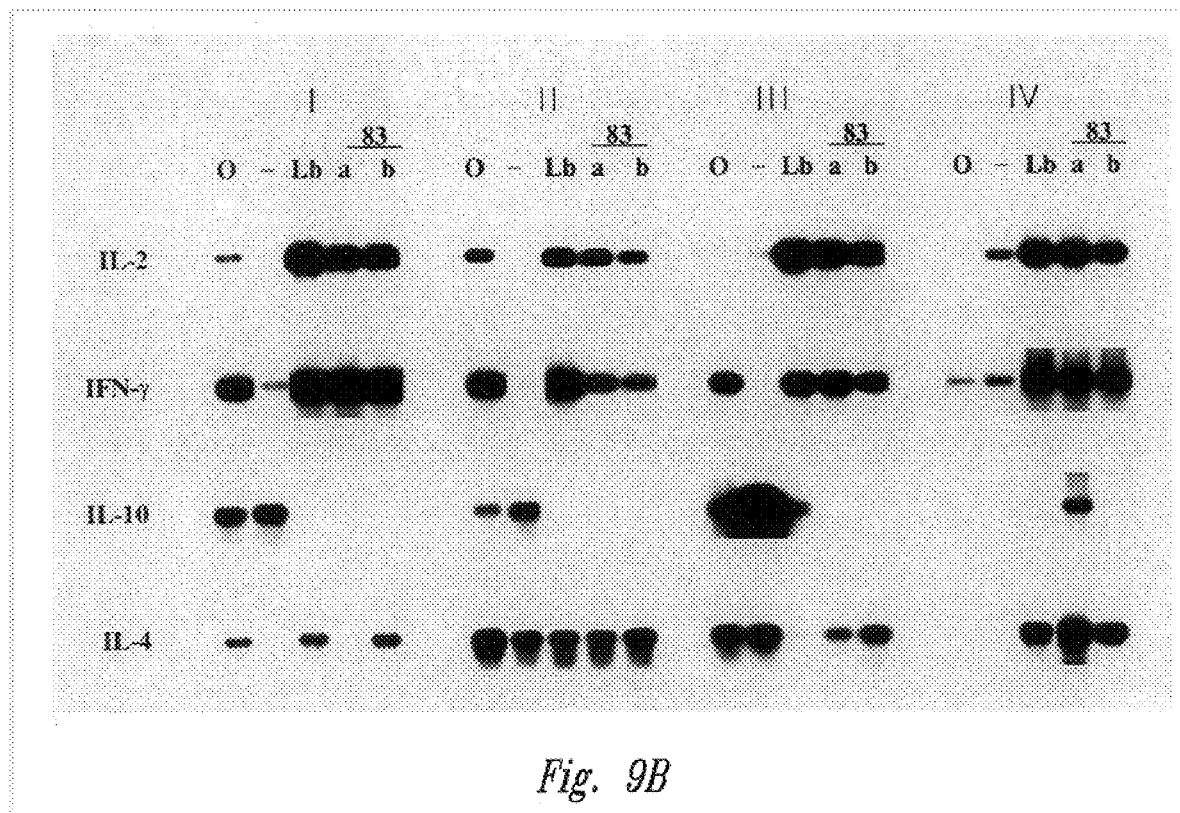

A more detailed analysis of cytokine patterns of PBMC from ML patients was performed by reverse transcriptase PCR. Cytokine mRNAs were evaluated in cells prior to culturing (FIG. 9, lanes O) or following culturing in the absence (lanes—) or presence of the indicated antigen for 48 and 72 h. FIG. 4A shows the results for five of the six ML patients whose PBMC were analyzed. In about half of the ML patients, noncultured (resting) PBMC had detectable levels of mRNA for IFN-γ, IL-2, and IL-4 but not IL-10. CL patient PBMC, however, had IL-10 mRNA in the resting state in addition to mRNAs for the other cytokines tested (FIG. 4B). Following in vitro culture without antigen, the levels of mRNA for IFN-γ, IL-2, and IL-4 in resting cells from ML patients decreased to background levels while IL-1 0 mRNA levels increased. In contrast, PBMC of most CL patients had stable or increased IL-10 mRNA, while the mRNAs for IL-2, IFN-γ, and IL-4 were reduced to barely detectable levels in the absence of antigen stimulation.

In PBMC of three ML patients, stimulation with lysate resulted in increased expression of mRNA for IFN-γ, IL-2, and IL-4 but not IL-10. By comparison, both Lbhsp83 polypeptides elicited the production of mRNA for IFN-γ and IL-2 from all ML patient PBMC tested. In contrast, profiles of mRNA for IL-10 and IL-4 differed for the two hsp83 polypeptides. Lbhsp83a stimulated the production of IL-10 but not IL-4 mRNA (patients I, II, III, and IV), while Lbhsp83b stimulated the production of IL-4 but not IL-10 mRNA in all six patients.

All CL patients tested responded to both Lbhsp83 polypeptides as well as to the parasite lysate by upregulating the synthesis of mRNAs for IL-2 and IFN-γ, and in two of four patients (I and IV), the level of IL-4 mRNA also increased, indicating stimulation of both Th1 and Th2 cytokines. Interestingly and as in the case of ML patient uncultured PBMC which did not have detectable levels of IL-10 mRNA, Lbhsp83a and not Lbhsp83b stimulated PBMC from one CL patient (IV) to synthesize IL-10 mRNA. However, in the other three patients (I, II, and III) with resting levels of IL-10 mRNA, both rLbhsp83 polypeptides as well as the parasite lysate downregulated the expression of IL-10 mRNA.

Figure 10A:
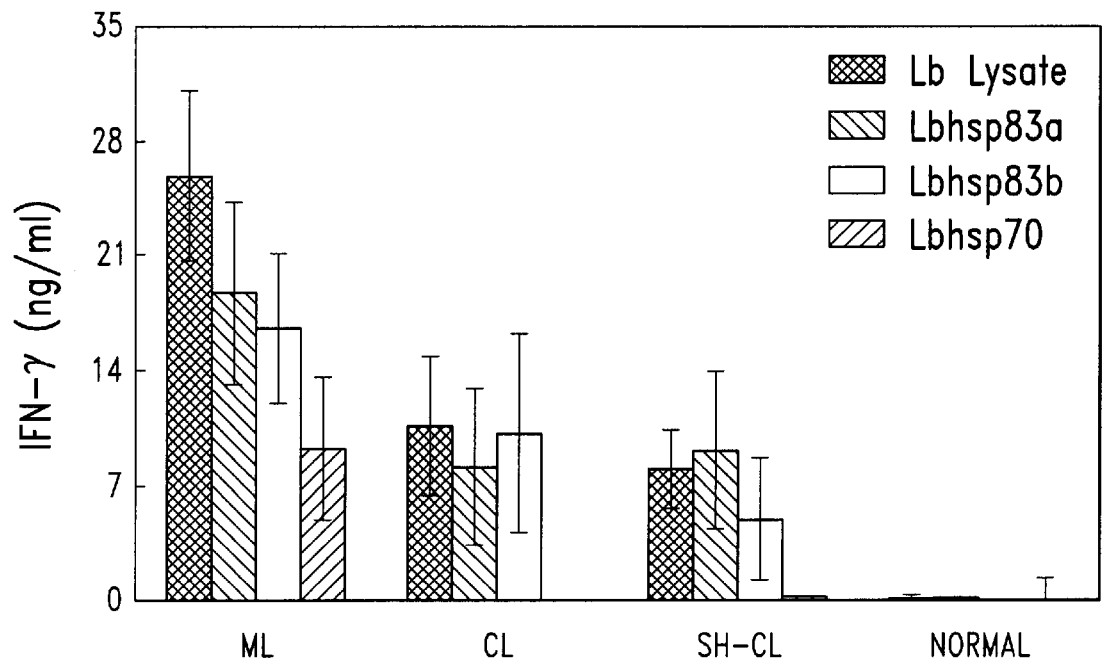
FIG. 10 presents a comparison of the levels of interferon-γ (panel A) and TNF-α (panel B) in the supernatants of 72 hour PBMC cultures from Leishmania-infected and control individuals in response to stimulation with parasite lysate or the indicated polypeptides.

PBMC supernatants were also assayed for the presence of secreted IFN-γ TNF-α, IL-4, and IL-10. Cells from all ML and self-healing CL patients (seven and six patients, respectively) and from four of seven CL patients were analyzed for secreted IFN-γ following stimulation with both rLbhsp83 polypeptides, parasite lysate and Lbhsp70, an *L. braziliensis* protein homologous to the eukaryotic 70 kD heat shock protein (FIG. 10A). In general, rLbhsp83a stimulated patient PBMC to secrete higher levels of IFN-γ than did rLbhsp83b (0.2 to 36 and 0.13 to 28 ng/ml, respectively). The presence of secreted IFN-γ correlated well with the corresponding mRNA detected by PCR.

Figure 10B:
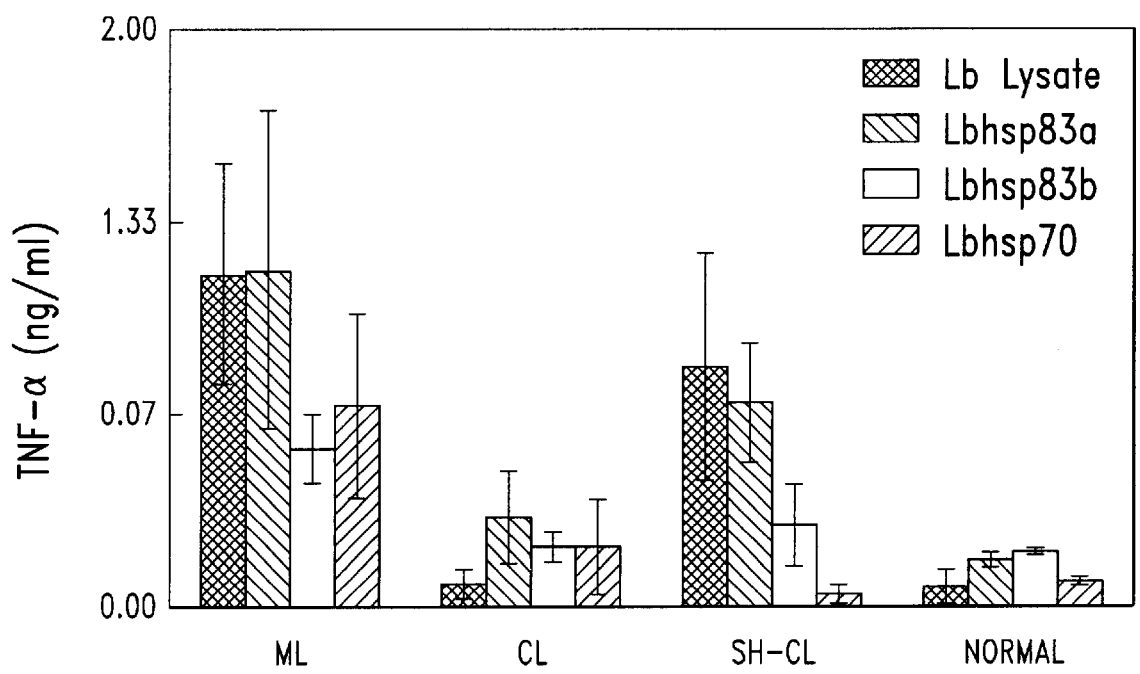

PBMC from four of five ML patients (I, II, V, and VII) had supernatant TNF-α levels (0.8 to 2.2 ng/ml) higher than those detected in cultures of PBMC from uninfected controls following stimulation with parasite lysate (FIG. 10B). Similarly, the same PBMC were stimulated by rLbhsp83 to produce levels of TNF-α in supernatant ranging from 0.61 to 2.9 ng/ml. Compared with those of uninfected controls, PBMC from three (I, V, and VI), five (I, II, IV, V, and VI), and two (II and V) of six individuals analyzed produced higher levels of TNF-α in response to parasite lysate, rLbhsp83a, and rLbhsp83b, respectively. The levels of TNF-α produced by PBMC from CL patients in response to parasite lysate were comparable to those produced by uninfected controls. However, rLbhsp83 stimulated TNF-α production in the PBMC of two of these patients. rLbhsp83a stimulated higher levels of TNF-α production than did rLbhsp83b. In the absence of antigen stimulation, only PBMC from ML patients (five of six) produced detectable levels of supernatant TNF-α (60 to 190 pg/ml).

Figure 11:
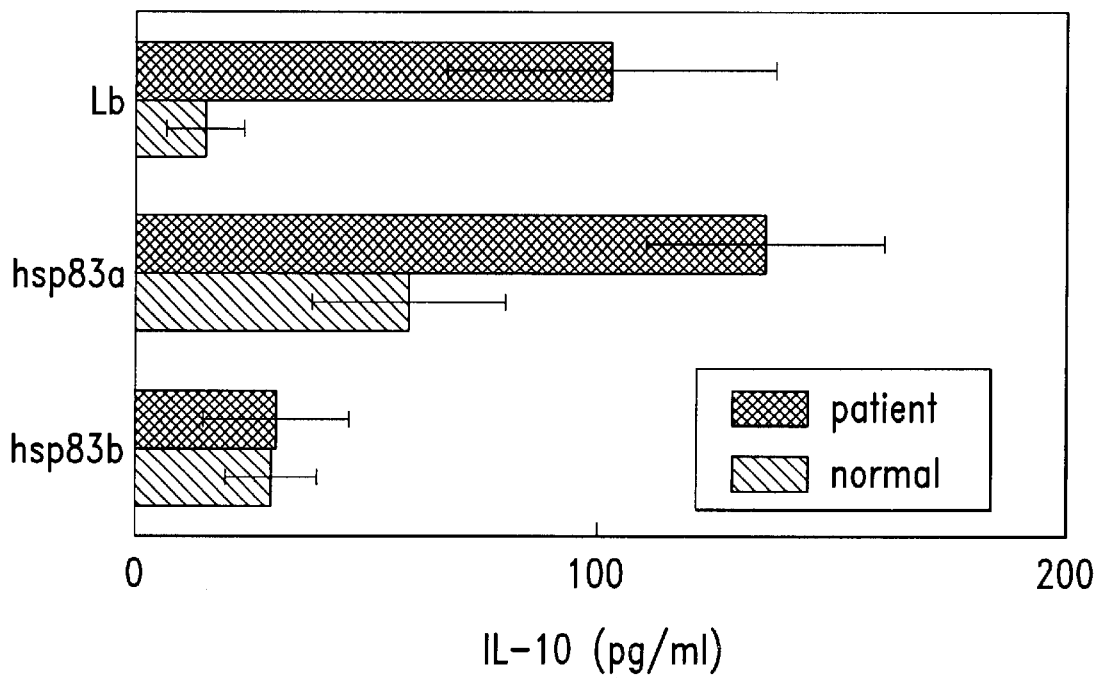
FIG. 11 illustrates the levels of IL-10 p40 (in pg/mL) in the supernatant of PBMC cultures from *L. braziliensis*-infected individuals and uninfected controls 72 hours following stimulation with parasite promastigote lysate (Lb), Lbhsp83a or Lbhsp83b.

In agreement with the IL-10 mRNA, IL-10 was detected by ELISA in the antigen-stimulated PMBC culture supernatants from ML and CL patients. The levels (49 to 190 pg) were significantly higher (up to 10-fold) following stimulation with rLbhsp83a compared with those after parallel stimulation of the same cells with rLbhsp83b (FIG. 11). Parasite lysate also stimulated PMBC from some of the patients to produce IL-10. Although rLbhsp83 stimulated PMBC from uninfected individuals to produce IL-10, with one exception, the levels were lower than those observed with patient PMBC. IL-4 was not detected in any of the supernatants analyzed. Therefore, the level of any secreted IL-4 is below the detection limit of the ELISA employed (50 pg/ml). Taken together, the results demonstrate that a predominant Th1-type cytokine profile is associated with PMBC from *L. braziliensis*-infected individuals following stimulation with rLbhsp83 polypeptides.

Figure 12:
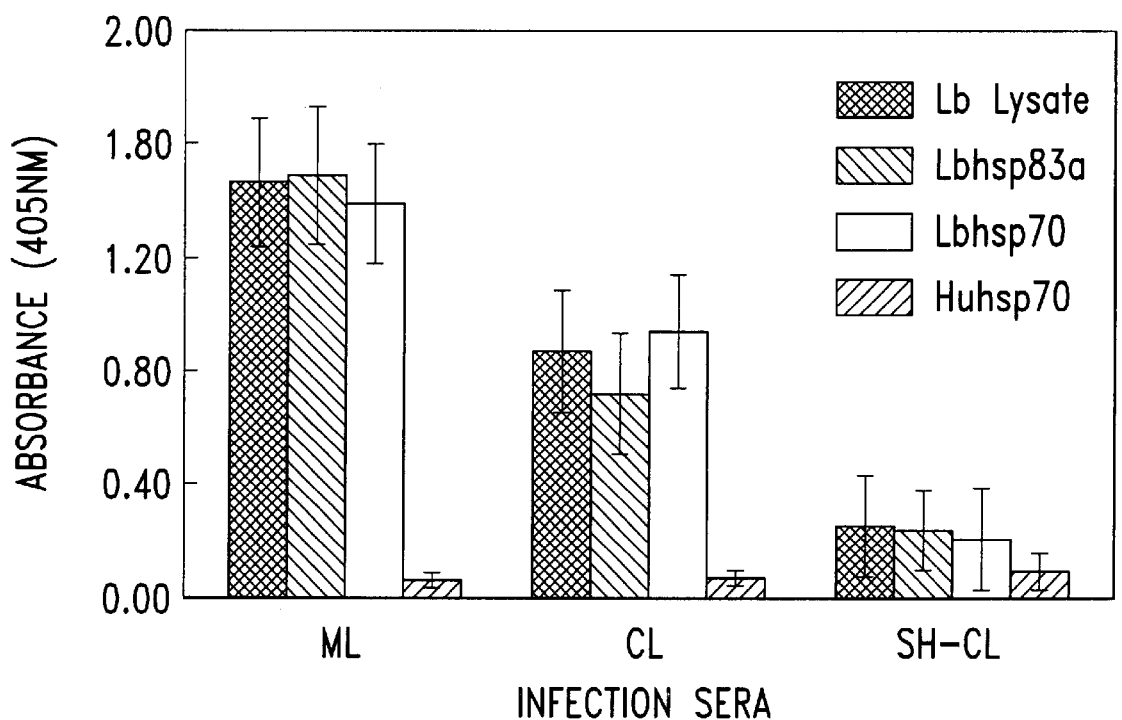
FIG. 12 presents the reactivities of sera from *L. braziliensis* infected-patients with representative polypeptides of the present invention in a standard ELISA. Values are expressed as absorbance at 405 nm.

To determine the correlation between the observed T-cell responses and antibody production to Lbhsp83, we compared the antibody (immunoglobulin G) reactivities to Lbhsp83 in sera from the three patient groups (FIG. 12). The ELISA reactivities of ML patient sera with rLbhsp83a were comparable to those observed with parasite lysate, and in general, there was a direct correlation between ML patient anti-Lbhsp83 antibody titer and T-cell proliferation. Of 23 serum samples from ML patients analyzed, 22 were positive (~96%) with absorbance values of 0.20 to >3.0. Eleven of the ML patient serum samples had optical density values that were >1. In general, CL patients had significantly lower anti-Lbhsp83 antibody titers ($\bar{x}$=0.74; standard error of the mean [SEM]=0.1) compared to those of ML patients. Therefore, ML and CL patient anti-rhsp83 antibody titers correlated with their respective T-cell proliferative responses. Anti-rLbhsp83 antibody titers were significantly higher in patients with ML ($\bar{x}$=1.5; SEM=0.2) than in self-healing CL patients ($\bar{x}$=0.35; SEM=0.056), although their T-cell proliferative responses were similar. In fact, anti-Lbhsp83 antibody titers in serum from self-healing CL patients were comparable to those from uninfected controls ($\bar{x}$=0.24; SEM=0.028). By using 2 standard deviations greater than the mean absorbance value of uninfected control (0.484) as a criterion for positive reactivity to Lbhsp83, eight of nine of the self-healing patient serum samples tested were negative.

Example 4

Preparation of Clones Encoding Lt-210

This Example illustrates the preparation of clones encoding portions of the Leishmania antigen Lt-210, and which has the sequence provided in SEQ ID NO:8.

An expression library was constructed from *L. tropica* (MHOM/SA/91/WR1063C) genomic DNA. The DNA was isolated by solubilizing *L. tropica* promastigotes in 10 mM Tris-HCl, pH 8.3, 50 mM EDTA, 1% SDS and treating with 100 $\mu$g/ml RNaseA and 100 $\mu$g/ml proteinase K. The sample was then sequentially extracted with an equal volume of phenol, phenol:chloroform (1:1), and Chloroform. DNA was precipitated by adding 0.1 volume of 3M sodium acetate (pH 5.2) and 2.5 volume 95% ethanol. The precipitate was resuspended in 10 $\mu$M Tris, 1 mM EDTA. DNA was sheared by passage through a 30-gauge needle to a size range of 2–6 kilobase, and was repaired by incubation with DNA poll in the presence of 100 $\mu$M each dATP, dCTP, dGTP, and dTTP. EcoRI adapters were ligated to the DNA fragments After removal of unligated adapters by passage over a G-25 Sephadex™ column, the fragments were inserted in EcoRI cut Lambda ZapII (Stratagene, La Jolla, Calif.).

Approximately 43,000 pfu were plated and screened with sera isolated from viscerotropic leishmaniasis (VTL) patients. Sera from VTL patients were received from Drs. M. Grogl and A. Magill. The VTL patient group included eight individuals from whom parasites were isolated and cultured, seven of which had confirmed infection with *L. tropica*. Four other patients were culture negative, but were still considered to be infected based on either PCR analysis or a positive monoclonal antibody smear (Dr. Max Grogl, personal communication). Serum samples from the 11 infected patients were pooled and anti-*E. coli* reactivity removed by affinity chromatography (Sambrook et al., supra, p. 12.27–12.28). Lambda phage expressing reactive proteins were detected after antibody binding by protein A-horseradish peroxidase and ABTS substrate.

Three clones, Lt-1, Lt-2, and Lt-3, containing a portion of the Lt-210 gene were identified and purified. The clones ranged in size from 1.4 to 3.3 kb and encoded polypeptides of 75 kD, 70 kD, and 120 kD, respectively. These three clones contain partial sequences of the Lt-210 gene. Lt-1 and Lt-2 are overlapping clones and were chosen for further study.

The DNA sequences of Lt-1 and Lt-2 were determined. Exonuclease III digestion was used to create overlapping deletions of the clones (Heinikoff, *Gene* 28:351–359, 1984). Single strand template was prepared and the sequence determined with Applied Biosystems Automated Sequencer model 373A or by Sanger dideoxy sequencing. The sequence on both strands of the coding portion of Lt-1 clone was determined. The partial sequence of one strand of Lt-2 clone was determined.

SEQ ID NO:7 presents the DNA sequence of Lt-1, and SEQ ID NO:8 provides the predicted amino acid sequence of the open reading frame. The DNA sequence of the coding portion of the Lt-1 clone includes a repeated nucleotide sequence at the 5' portion of the clone containing eight copies of a 99 bp repeat, three copies of a 60 bp repeat unit, which is part of the larger 99 bp repeat, and 800 bp of non-repeat sequence. The deduced amino acid sequence of the 99 bp repeat contains limited degeneracies. The mass of the predicted recombinant protein is 67,060 Daltons. A database search of PIR with the predicted amino acid sequence of the open reading frame yielded no significant homology to previously submitted sequences. Predicted secondary structure of the repeat portion of the clone is entirely $\alpha$-helical.

Sequence analysis of Lt-2 revealed that the 3' portion of the clone consisted of a mixture of 60 and 99 bp repeats that were identical, excepting occasional degeneracies, to the 60 and 99 bp repeats observed in Lt-1. Collectively, the sequencing data suggest that Lt-1 and Lt-2 are different portions of the same genes Lt-2 being upstream of Lt-1, with possibly a small overlap.

Hybridization analysis confirmed that rLt-2 and rLt-1 contain overlapping sequences. Genomic DNAs of various Leishmania species were restricted with a variety of enzymes, separated by agarose gel electrophoresis, and blotted on Nytran membrane filter (Schleicher & Schuell, Keene, N.H.). Inserts from rLt-l and rLt- 2 were labeled with $^{32}$P-CTP by reverse transcriptase from random oligonucleotide primers and used as probes after separation from unincorporated nucleotides on a Sephadex G-50 column. Hybridizations using the rLt-1 or the rLt-2 probe are performed in 0.2M $NaH_2PO_4$/3.6 M NaCl at 65° C., whereas hybridization using the rLt-1r probe is performed in 0.2 M $NaH_2PO_4$/3.6 M NaCl/0.2 M EDTA at 60° C. overnight. Filters are washed in 0.075 M NaCl/0.0075 M sodium citrate pH 7.0 (0.15 M NaCl/0.0150 M sodium citrate for the Lt-1r probe), plus 0.5% SDS at the same temperature as hybridization.

Genomic DNA from a number of Leishmania species including *L. tropica* were analyzed by Southern blots as described above using the Lt-1, Lt-2, and Lt-1r inserts separately as probes. Collectively, various digests of *L. tropica* DNA indicate that this gene has a low copy number. A similar, overlapping pattern was observed using either the Lt-1 or Lt-2 insert as a probe, consistent with the premise that these two clones contain sequences near or overlapping one another. In addition, sequences hybridizing with these clones are present in other Leishmania species.

*L. tropica* isolates have limited heterogeneity. Southern analyses of digested genomic DNA from four *L. tropica* parasite strains isolated from VTL patients and three *L. tropica* parasite strains isolated from CL cases (two human, one canine) were performed. The Lt-1r insert described below was labeled and used as a probe. The seven different *L. tropica* isolates yielded similar intensities and restriction patterns, with only a single restriction fragment length polymorphism among the isolates. These data, along with Southern analyses with additional enzymes, indicate limited heterogeneity in this region among the *L. tropica* isolates.

The recombinant proteins of Lt-1 and Lt-2 were expressed and purified. The nested deletion set of Lt-1 formed for sequencing included a clone referred to as Lt-1r, which contains one and one-third repeats. This polypeptide was also expressed and purified. In vivo excision of the pBluescript $SK^-$ phagemid from Lambda Zap II was performed according to the manufacturer's protocol. Phagemid virus particles were used to infect *E. coli* XL-1 Blue. Production of protein was induced by the addition of IPTG. Protein was recovered by first lysing pellets of induced bacteria in buffer (LB, 50 mM Tris-HCl, pH 8.0, 100 mM NaCl, 10 mM EDTA) using a combination of lysozyme (750 μg/mL) and sonication. rLt-1, rLt-2, and rLt-1r, were recovered from the inclusion bodies after solubilization in 8M urea (rLt-1 and rLt-2) or 4M urea (rLt-1r). Proteins rLt-1 and rLt-2 were enriched and separated by precipitation with 25%–40% ammonium sulfate and rLt-1r was enriched by precipitation with 10%–25% ammonium sulfate. The proteins were further purified by preparative gel electrophoresis in 10% SDS-PAGE. Recombinant proteins were eluted from the gels and dialyzed in phosphate-buffered saline (PBS). Concentration was measured by the Pierce (Rockford, Ill.) BCA assay, and purity assessed by Coomassie blue staining after SDS-PAGE.

Example 5

Preparation of LbeIF4A

This example illustrates the molecular cloning of a DNA sequence encoding the *L. braziliensis* ribosomal antigen LbeIF4A.

A genomic expression library was constructed with sheared DNA from *L. braziliensis* (MHOM/BR/75/M2903) in bacteriophage λZAPII (Stratagene, La Jolla, Calif.). The expression library was screened with *E. coli*-preadsorbed patient sera from an *L. braziliensis*-infected individual with mucosal leishmaniasis. Plaques containing immunoreactive recombinant antigens were purified, and the pBSK(−) phagemid excised using the manufacturer's protocols. Nested deletions were performed with Exonuclease III to generate overlapping deletions for single stranded template preparations and sequencing. Single stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems Automated Sequencer Model 373A.

The immunoreactive recombinant antigens were then analyzed in patient T-cell assays for their ability to stimulate a proliferative and cytokine production, as described in Examples 7 and 8 below.

A recombinant clone was identified in the above assays which, following sequence comparison of its predicted amino acid sequence with sequences of other proteins, was identified as a *Leishmania braziliensis* homolog of the eukaryotic initiation factor 4A (eIF4A). The isolated clone (pLeIF.1) lacked the first 48 amino acid residues (144 nucleotides) of the full length protein sequence. The pLeIF.1 insert was subsequently used to isolate the full length genomic sequence.

SEQ ID NO:9 shows the entire nucleotide sequence of the full-length LbeIF4A polypeptide. The open reading frame (nucleotides 115 to 1323) encodes a 403 amino acid protein with a predicted molecular weight of 45.3 kD. A comparison of the predicted protein sequence of LbeIF4A with the homologous proteins from tobacco (TeIF4A), mouse (MeIF4A), and yeast (YeIF4A) shows extensive sequence homology, with the first 20–30 amino acids being the most variable. The lengths (403, 413, 407, and 395 amino acids), molecular weights (45.3, 46.8, 46.4, and 44.7 kDa), and isoelectric points (5.9, 5.4, 5.5, and 4.9) of LbeIF4A, TeIF4A, MeIF4A and YeIF4A, respectively, are similar. LbeIF4A shows an overall homology of 75.5% (57% identity, 18.5% conservative substitution) with TeIF4A, 68.6% (50% identity, 18.6% conservative substitution) with MeIF4A and 67.2% (47.6% identity, 19.6% conservative substitution) with YeIF4A.

Example 6

Preparation of Soluble Leishmania Antigens

This Example illustrates the preparation of soluble Leishmania antigens from an *L. major* culture supernatant. *L. major* promastigotes were grown to late log phase in complex medium with serum until they reached a density of $2–3\times10^7$ viable organisms per mL of medium. The organisms were thoroughly washed to remove medium components and resuspended at $2–3\times10^7$ viable organisms per mL of defined serum-free medium consisting of equal parts RPMI 1640 and medium 199, both from Gibco BRL, Gaithersburg, Md. After 8–12 hours, the supernatant was removed, concentrated 10 fold and dialyzed against phosphate-buffered saline for 24 hours. Protein concentration was then determined and the presence of at least eight different antigens confirmed by SDS-PAGE. This mixture is referred to herein as "soluble Leishmania antigens."

Example 7

Comparison of Interleukin-4 and Interferon-γ Production Stimulated by Leishmania Antigens This Example illustrates the immunogenic properties of the antigens prepared according to Examples 1, 2, 5 and 6, as determined by their ability to stimulate IL-4 and IFN-γ in lymph node cultures from infected mice and in human PBMC preparations. Lymph node cultures for use in these studies were prepared from *L. major*-infected BALB/c mice 10 days after infection, as described in Example 2. PBMC were prepared using peripheral blood obtained from individuals with cured *L. donovani* infections who were immunologically responsive to Leishmania. Diagnosis of the patients was made by clinical findings associated with at least one of the following: isolation of parasite from lesions, a positive skin test with Leishmania lysate or a positive serological test. Uninfected individuals were identified based on a lack of clinical signs or symptoms, a lack of history of exposure or travel to endemic areas, and the absence of a serological or cellular response to Leishmania antigens. Peripheral blood was collected and PBMC isolated by density centrifugation through Ficoll™ (Winthrop Laboratories, New York).

Culture supernatants were assayed for the levels of secreted IL-4 and IFN-γ. IFN-γ was quantitated by a double sandwich ELISA using mouse anti-human IFN-γ mAb (Chemicon, Temucula, Calif.) and polyclonal rabbit anti-human IFN-γ serum. Human rIFN-γ (Genentech Inc., San Francisco, Calif.) was used to generate a standard curve. IL-4 was quantitated in supernatants by a double sandwich ELISA using a mouse anti-human IL-4 mAb (M1) and a polyclonal rabbit anti-human IL-4 sera (P3). Human IL-4 (Immunex Corp., Seattle, Wash.) was used to generate a standard curve ranging from 50 pg/ml to 1 ng/ml.

Figure 13A:
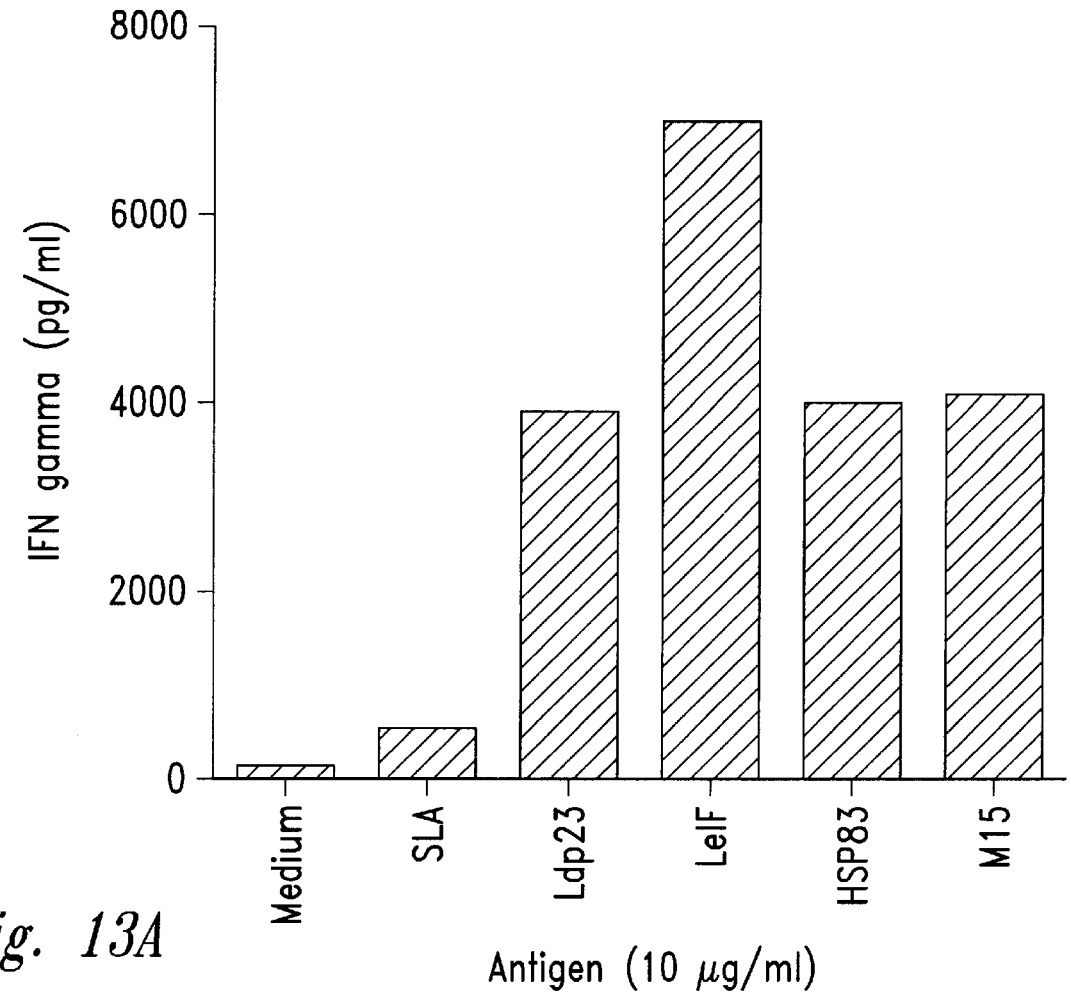
FIGS. 13A and 13B illustrate the level of secreted IL-4 and IFN-γ (in pg/mL) stimulated in mouse lymph node cultures by the addition of representative polypeptides of the present invention.
Figure 13B:
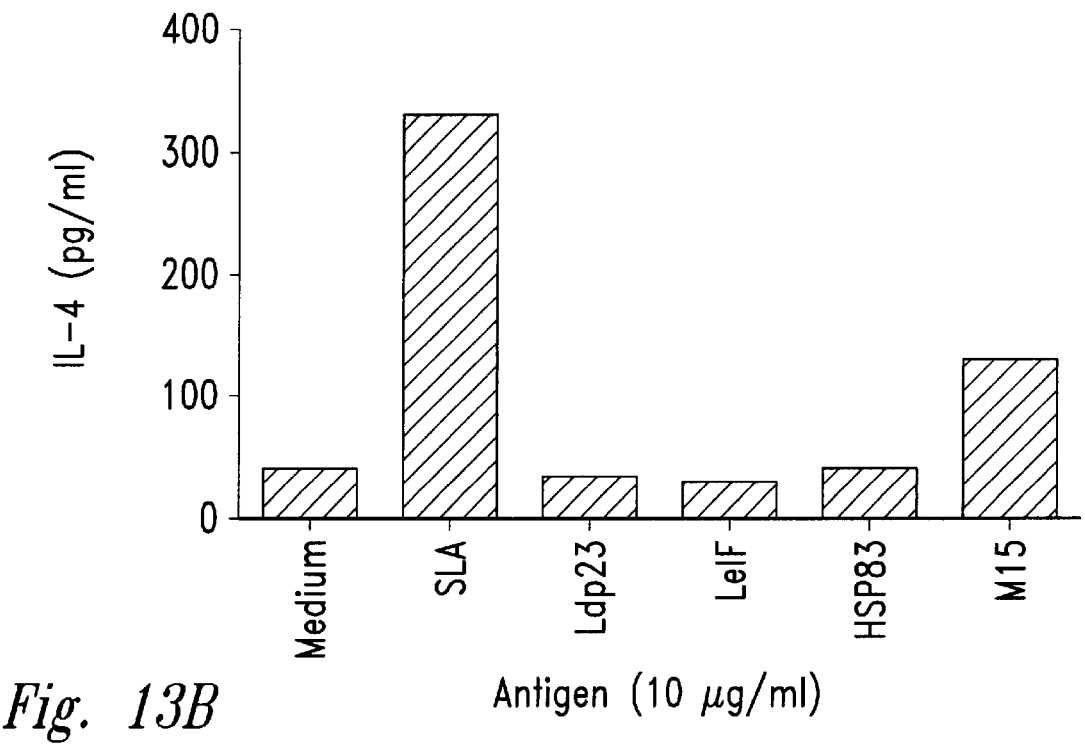

FIGS. 13A and 13B, illustrate the mean level of secreted IL-4 and IFN-γ, respectively, 72 hours after addition of 10 μg/mL of each of the following antigens to a lymph node culture prepared as described above: soluble Leishmania antigen (i.e., an extract prepared from ruptured promastigotes which contains membrane and internal antigens (SLA)), Ldp23, LbeIF4A (LeIF), Lbhsp83, M15 and LmeIF (the L. major homolog of LbeIF4A). The levels of secreted IL-4 and IFN-γ in medium alone (i.e., unstimulated) are also shown. While SLA elicits a predominantly Th2 response from lymph node cells of Leishmania-infected mice, Ldp23, LbeIF4A, Lbhsp83 and M15 elicited relatively little IL-4 and large amounts of IFN-γ, consistent with a Th1 response profile.

Figure 14:
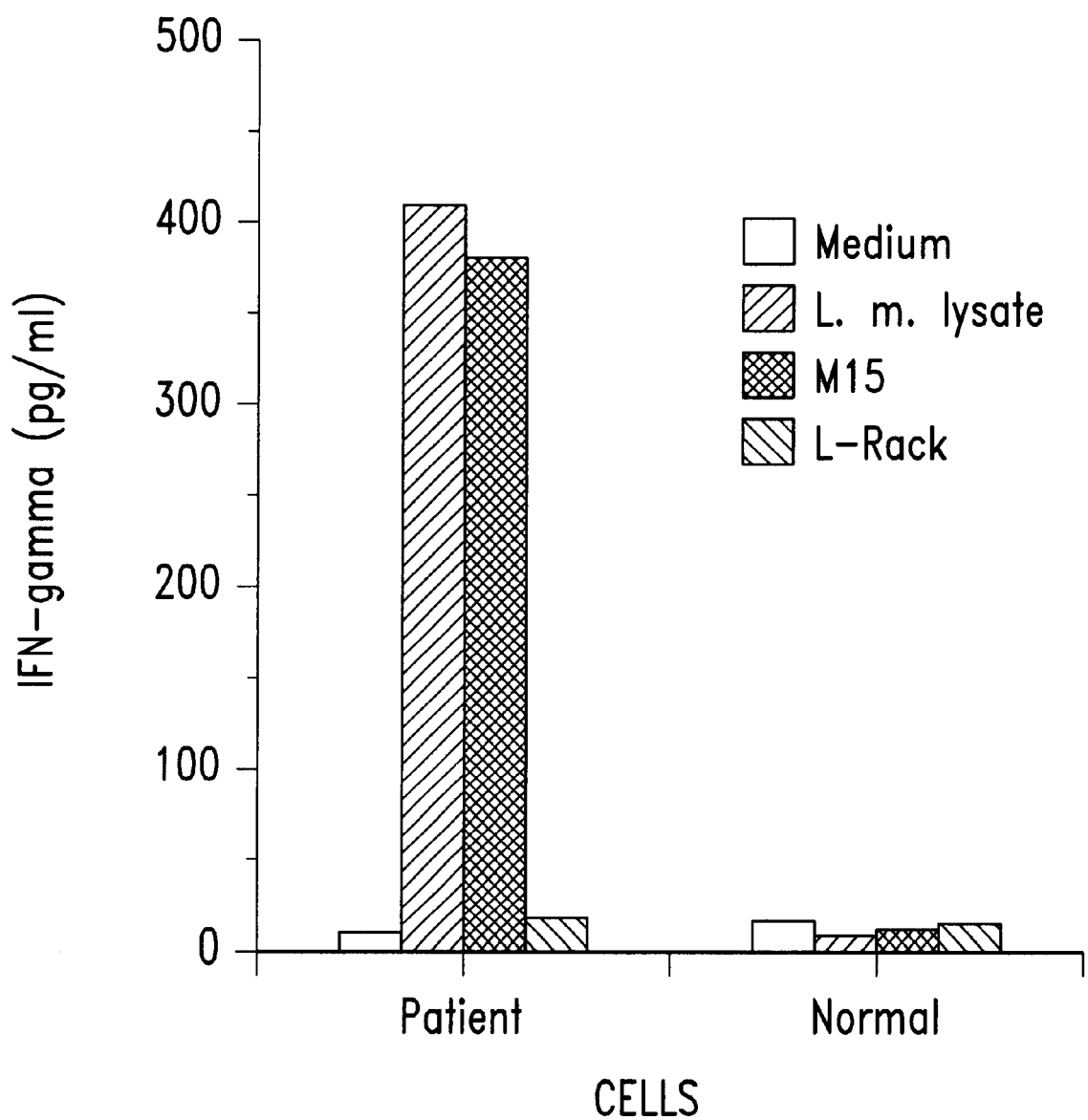
FIG. 14 shows the level of IFN-γ (in pg/mL) secreted by Leishmania-infected and uninfected human PBMC stimulated by the Leishmania antigen M15, as compared to the levels stimulated by *L. major* lysate and L-Rack, an antigen that does not appear to be recognized by Leishmania-infected humans.
Figure 15:
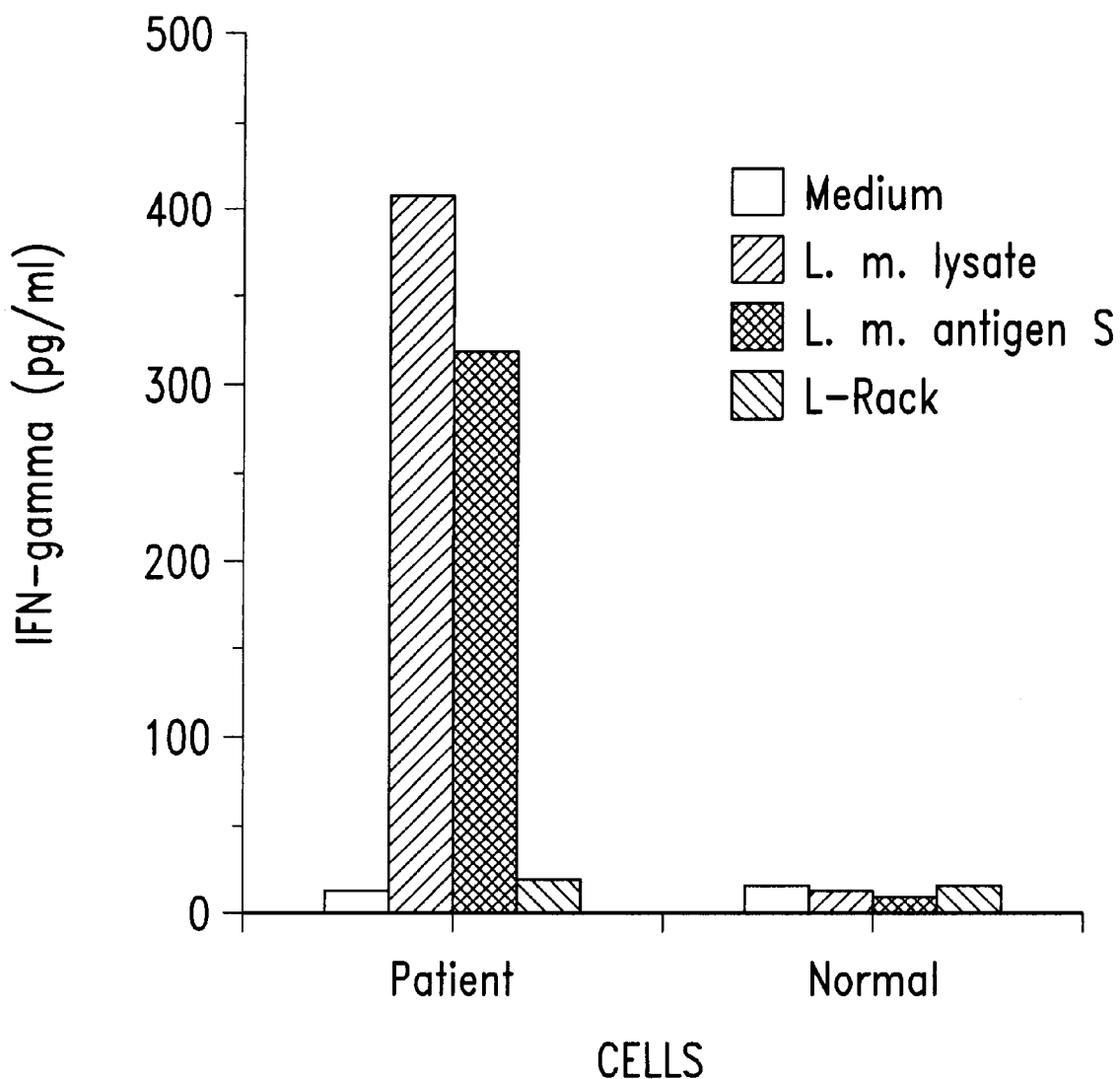
FIG. 15 shows the level of IFN-γ (in pg/mL) secreted by infected and uninfected human PBMC stimulated by soluble Leishmania antigens (S antigens), as compared to the levels stimulated by *L. major* lysate and L-Rack.

FIG. 14 shows the level of secreted IFN-γ in culture filtrate from infected and uninfected human PBMC preparations 72 hours after addition of 10 μg/mL L. major lysate, M15 or L-Rack, an immunodominant leishmanial antigen in murine leishmaniasis. Similarly, FIG. 15 illustrates the level of secreted IFN-γ in culture filtrate from infected and uninfected human PBMC preparations 72 hours after addition of 10 μg/mL L. major lysate, soluble Leishmania antigens (prepared as described in Example 6) or L-Rack. These results indicate that M15 and soluble Leishmania antigens, but not L-Rack, are potent stimulators of IFN-γ production in patient PBMC, but not in PBMC obtained from uninfected individuals. Thus, M15 and soluble Leishmania antigens elicit a dominant Th1 cytokine profile in both mice and humans infected with Leishmania.

Example 8

Comparison of Proliferation Stimulated by Leishmania Antigens

This Example illustrates the immunogenic properties of the antigens prepared according to Examples 1, 2, 5 and 6, as determined by their ability to stimulate proliferation in lymph node cultures from infected mice and in human PBMC preparations.

For in vitro proliferation assays, 2–4×10$^5$ cells/well were cultured in complete medium (RPMI 1640 supplemented with gentamycin, 2-ME, L-glutamine, and 10% screened pooled A+ human serum; Trimar, Hollywood, Calif.) in 96-well flat bottom plates with or without 10 μg/ml of the indicated antigens or 5 μg/ml PHA (Sigma Immunochemicals, St. Louis, Mo.) for five days. The cells were then pulsed with 1 μCi of [$^3$H]thymidine for the final 18 hours of culture.

Figure 16:
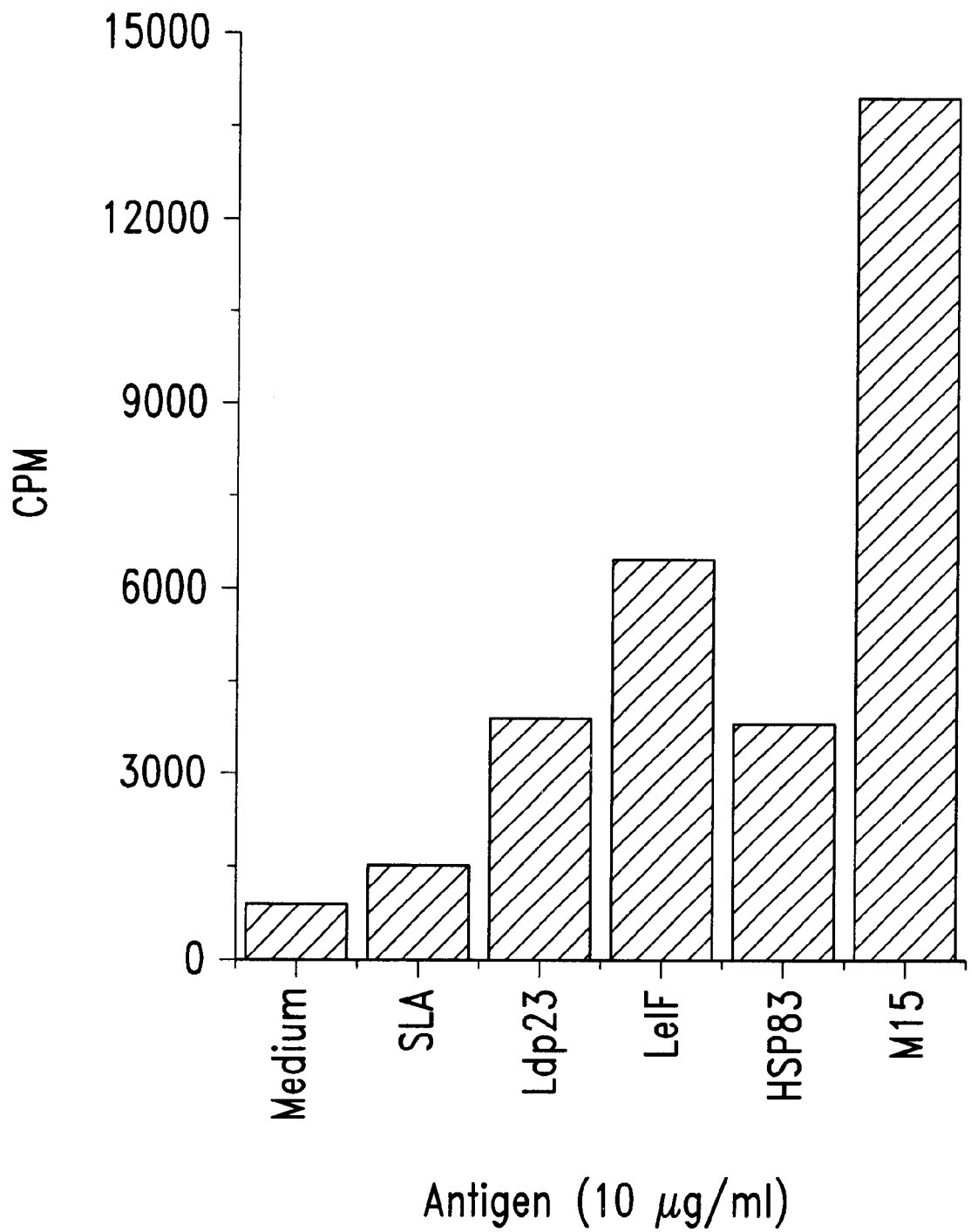
FIG. 16 illustrates the proliferation of murine lymph node cultures stimulated by the addition of representative polypeptides of the present invention. Values are expressed as cpm.

FIG. 16 illustrates the proliferation observed after addition of 10 μg/mL or 20 μg/mL of each of the following antigens to a lymph node culture prepared as described in Example 7: SLA, Ldp23, LbeIF4A, Lbhsp83, and M15. The level of proliferation without the addition of antigen is also shown. Data are represented as mean cpm. These results demonstrate that a variety of leishmanial antigens are capable of stimulatory lymph node cell proliferation from Leishmania-infected mice.

Figure 17:
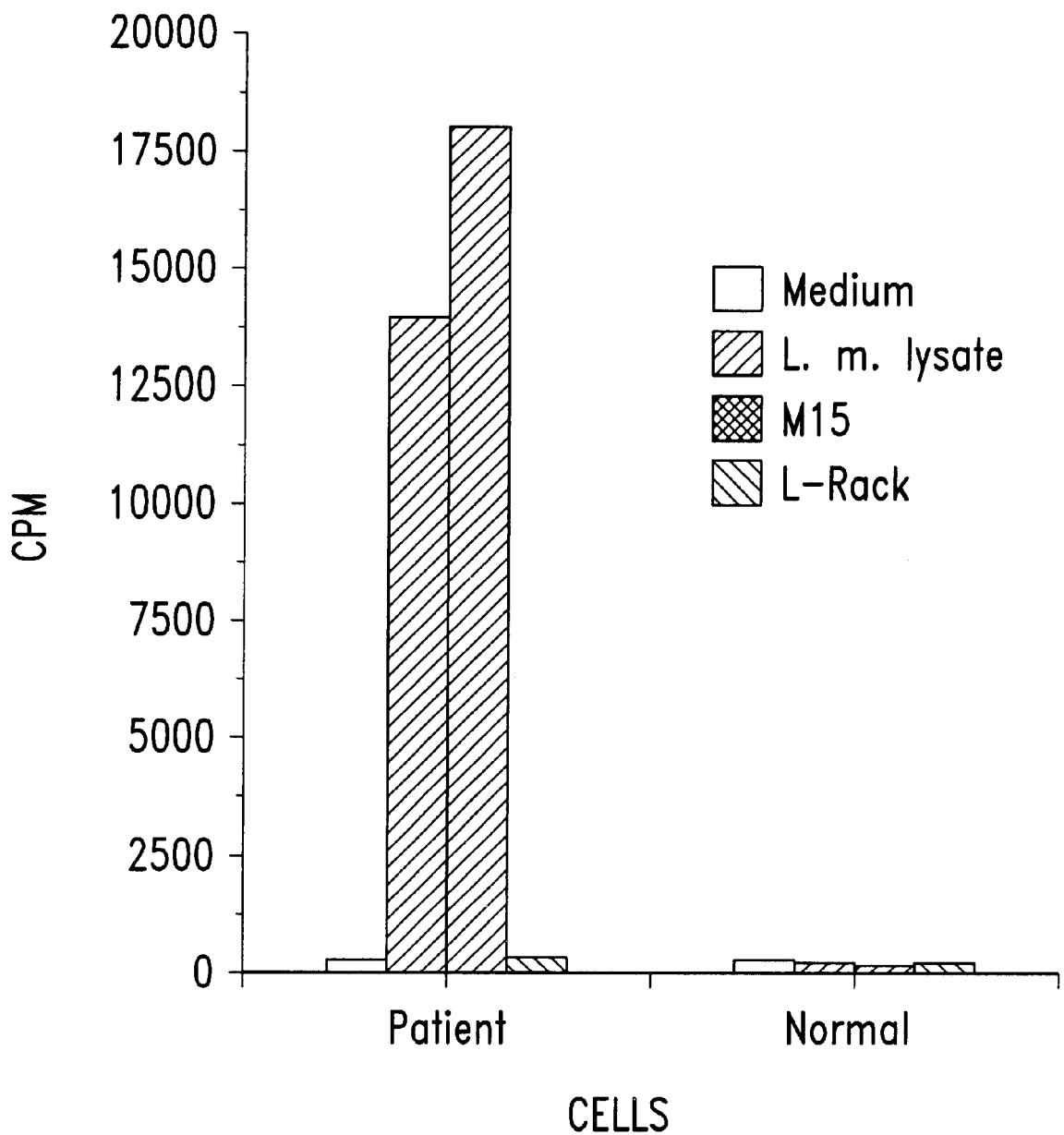
FIG. 17 shows the proliferation of human PBMC, prepared from Leishmania-immune and uninfected individuals, stimulated by M15 as compared to the proliferation stimulated by *L. major* lysate and L-Rack. Values are expressed as cpm.
Figure 18:
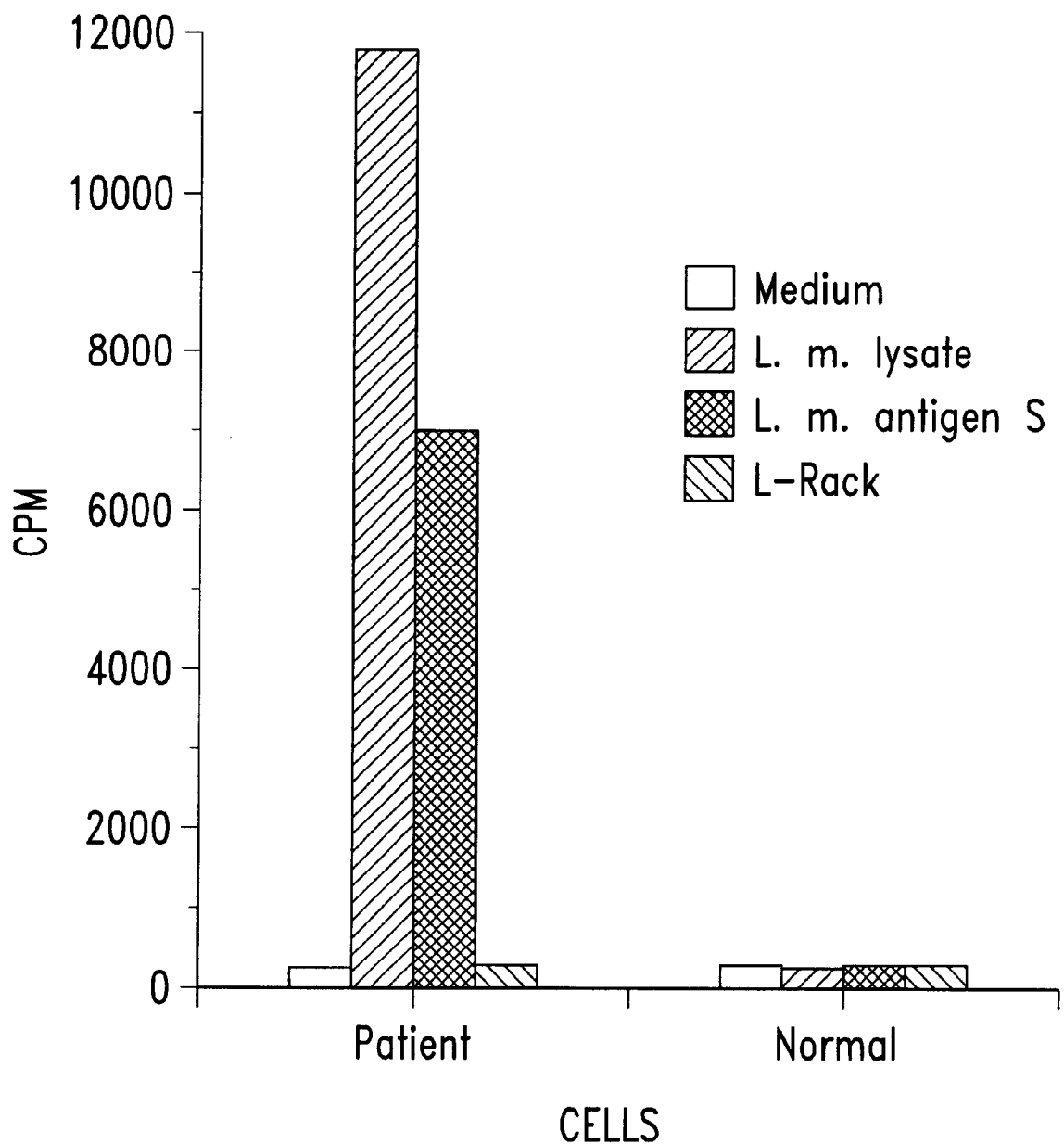
FIG. 18 illustrates the proliferation of human PBMC, prepared from Leishmania-infected and uninfected individuals, stimulated by soluble Leishmania antigens as compared to the proliferation stimulated by culture medium, *L. major* lysate and L-Rack. Values are expressed as cpm.

FIGS. 17 and 18 illustrate the proliferation observed in human PBMC preparations from Leishmania-immune and uninfected individuals following the addition of 10 μg/mL M15 and soluble Leishmania antigens, respectively. These values are compared to the proliferation observed following the addition of culture medium, L. major lysate or L-Rack. The results show that M15 and soluble Leishmania antigens stimulate proliferation in Leishmania-immune PBMC, but not in PBMC obtained from uninfected individuals, demonstrating that M15 and soluble antigens (but not L-Rack) are recognized by PBMC from individuals immune to Leishmania due to a previous infection.

Example 9

Preparation of Lmsp1A and Lmsp9A

This Example illustrates the preparation of two soluble Leishmania antigens, Lmsp1a and Lmsp9a.
A. Purification of Lmsp1a and Lmsp9a from a Mixture of Soluble L. major Antigens A high titer rabbit sera was raised against L. major soluble antigens, prepares as described above in Example 6. Specifically, a New Zealand white rabbit was immunized subcutaneously at multiple sites with 180 μg of L. major soluble antigens in a suspension containing 100 μg muramyl dipeptide and 50% incomplete Freund's adjuvant. Six weeks later the rabbit was given a subcutaneous boost of 100 μg of the same soluble antigen preparation in incomplete Freund's adjuvant. This was followed by two intravenous boosts spaced two weeks apart, each with 100 μg of the soluble antigen preparation. Sera was collected from the rabbit 11 days after the final boost.

Figure 20:
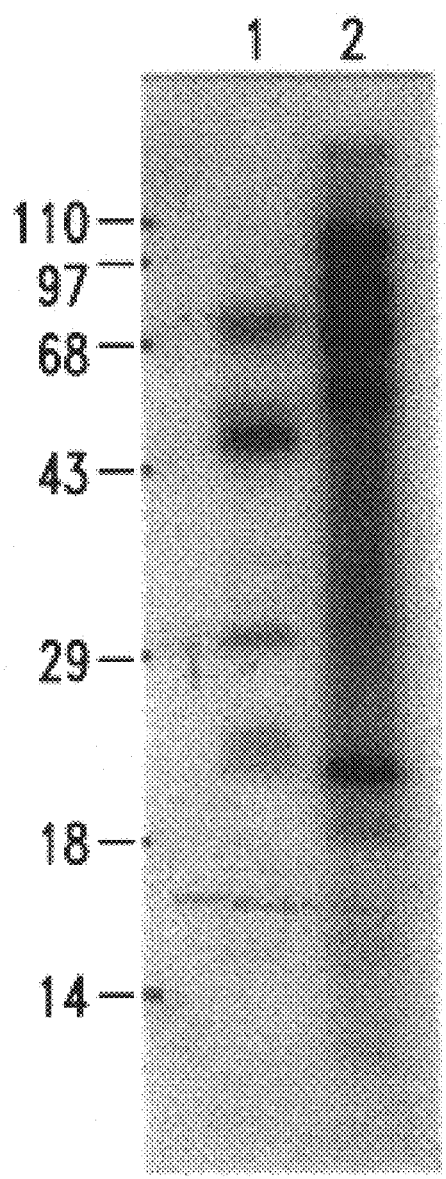
FIG. 20 illustrates the reactivity of rabbit sera raised against soluble Leishmania antigens with Leishmania promastigote lysate (lane 1) and soluble Leishmania antigens (lane 2).

Anti E. coli antibody reactivities were removed from the rabbit sera by pre-adsorbing on nitrocellulose filters containing lysed E. coli. Adsorbed sera were evaluated by Western blot analysis using 10 μg Leishmania promastigote lysate (lane 1) and 1 μg soluble L. major antigen mixture (lane 2). As shown in FIG. 20, the rabbit sera was found to be reactive with seven dominant antigens of the soluble L. major antigen mixture with molecular weights ranging from 18 to >200 kDa. A four times longer exposure of the same blot revealed three additional immunoreactive species with molecular weights less than 18 kDa. The same sera reacted with approximately 10 antigens of the promastigote lysate, but with a pattern significantly different from that observed with the soluble L. major antigens (FIG. 20). This is suggestive of potential post-translational modification of the same antigen before (intracellular localization) and after secretion/shedding. Such modifications may include cleavage of a leader sequence and/or the addition of carbohydrate molecules to the secreted/shed antigens.

The rabbit sera described above was subsequently used to screen an L. major cDNA expression library prepared from L. major promastigote RNA using the unidirectional Lambda ZAP (uni-ZAP) kit (Stratagene) according to the manufacturer's protocol. A total of 70,000 pfu of the amplified cDNA library was screened with the rabbit sera at a 1:250 dilution. Nineteen positive clones were confirmed in the tertiary screening. The phagemid were excised and DNA from each of the 19 clones was sequenced using a Perkin Elmer/Applied Biosystems Division automated sequencer Model 373A. All 19 clones were found to represent two distinct sequences, referred to as Lmsp1a and Lmsp9a. The determined cDNA sequences for Lmsp1a and Lmsp9a are provided in SEQ ID NO: 19 and 21, respectively, with the corresponding amino acid sequences being provided in SEQ ID NO: 20 and 22, respectively.

B. Characterization of Lmsp1a and Lmsp9a

FIG. 21 shows the full-length cDNA (SEQ ID NO: 19) and predicted amino acid sequence (SEQ ID NO: 20) for the antigen Lmsp1a. The EcoRI/XhoI insert is 1019 bp long and contains the following features: a) the last 17 nt of the spliced leader sequence characteristic of all trypanosoma nuclearly encoded mRNA; b) 39 nt of 5' untranslated sequence; c) an open reading frame of 453 nt long coding for a 151 deduced amino acid sequence with a predicted molecular mass of 16.641 kDa; and d) 471 nt of 3' untranslated sequence terminating with a poly A tail. The predicted amino acid sequence contains three potential phosphorylation sites at amino acid residues 3, 85 and 102. In addition, Lmsp1a contains an RGD sequence at residue 104, a sequence that may play a role in parasite invasion of the macrophage. RGD sequences have been shown to mediate the binding of various adhesion proteins to their cell surface receptors. There is no obvious leader sequence (secretory signal) at the amino terminal portion suggesting that the protein might be shed or excreted. Lmsp1a appears to be one of the most abundant antigens found in the culture supernatant of live promastigote, since 17 of the 19 clones contain sequences of variable lengths identical to Lmsp1a.

Comparison of the amino acid sequence of Lmps1a with known sequences using the DNA STAR system (Version 87) revealed that Lmsp1a shares between 65% to 70% homology with the eukaryotic nucleoside diphosphate kinase protein, also referred to in the mouse and human as a tumor metastasis inhibitor gene.

Figure 22:
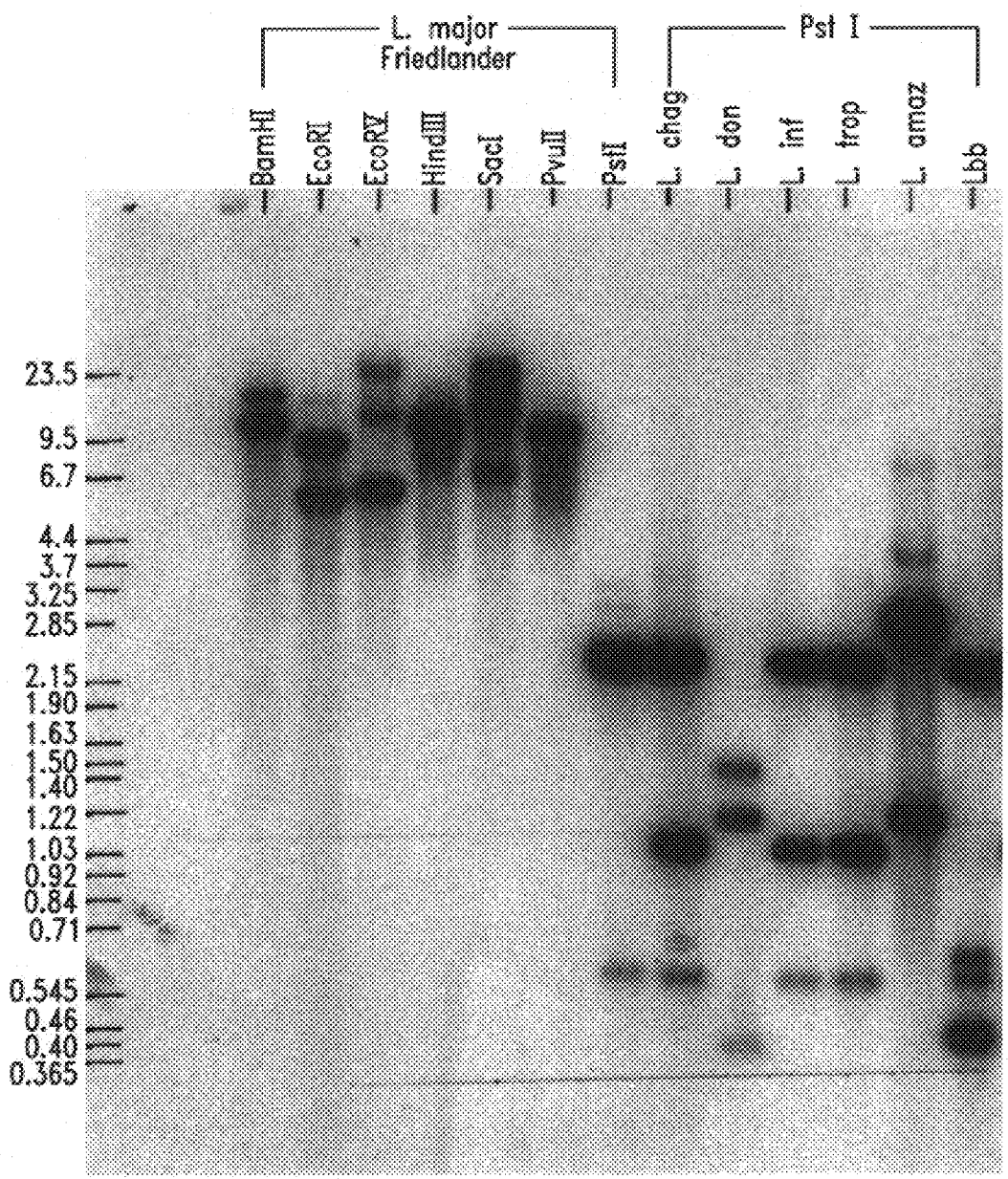

Southern blot analysis of genomic DNA from *L. major* (Friedlander strain) digested with a panel of restriction enzymes (lanes 1 to 7) and six other Leishmania species of different geographic locations digested with PstI (lanes 8 to 13) using the full-length cDNA insert of Lmpsla, demonstrated that Lmsp1a is present in all the species characterized with a high degree of conservation (FIG. 22). This suggests evolutionary significance for the maintenance of Lmsp1a and the existence of homologous species among all the Leishmania species.

The remaining two cDNA clones isolated from the soluble *L. major* antigen mixture represent identical sequences (referred to as Lmsp9a; SEQ ID NO: 21), suggesting that the two copies resulted from amplification of the primary library. Sequencing of the Lmsp9a cDNA revealed that the clone does not contain the full length 5' sequence since it is lacking both the spliced leader and 5' untranslated sequences. The 3' end of the cDNA contains a poly A stretch, as would be expected for a Leishmania mRNA. Of the predicted translated sequence (SEQ ID NO: 22), 34 of the 201 amino acids (17%) represent cysteine residues. Comparison of the predicted protein sequence with those of known proteins as described above, revealed some homology with other cysteine rich proteins such as the major surface trophozoite antigen of *Giardia lamblia* and furin proteases.

Example 10

Preparation and Characterization of MAPS-1A

This Example illustrates the preparation and characterization of the Leishmania antigen MAPS-1A (SEQ ID NO: 24).

A pool of sera was obtained from 5 BALB/c mice that had been given a primary immunization and two boosts with crude *L. major* promastigote culture supernatant as described below in Example 12. These mice were subsequently shown to be protected when challenged with a dose of live *L. major* promastigotes generally found to be lethal. The mouse sera thus obtained were used to screen an *L. major* amastigote cDNA expression library prepared as described in Example 1. Several seroreactive clones were isolated and sequenced using a Perkin Elmer/Applied Biosystems Division automated sequencer Model 373A (Foster City, Calif.).

One of these clones, referred to herein as MAPS-1A, was found to be full-length. Comparison of the cDNA and deduced amino acid sequences for MAPS-1A (SEQ ID Nos: 23 and 24, respectively) with known sequences in the gene bank using the DNA STAR system revealed no significant homologies to known Leishmania sequences, although some sequence similarity was found to a group of proteins, known as thiol-specific antioxidants, found in other organisms.

Figure 23:
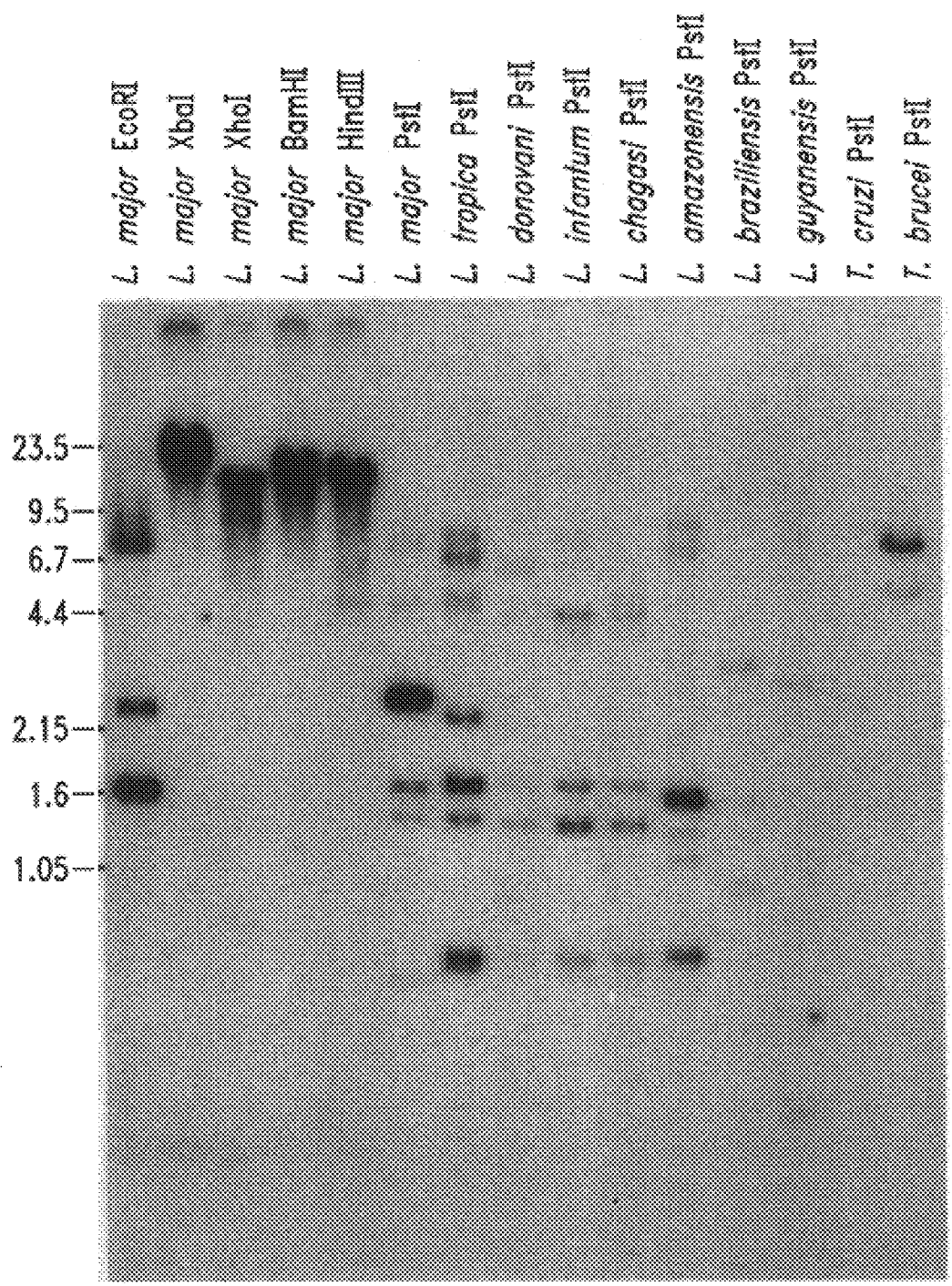
FIG. 23 shows a Southern blot of genomic DNA from *L. major* digested with a panel of restriction enzymes, six other Leishmania species digested with PstI and the infectious pathogens *T. cruzi* and *T. brucei*, probed with the full-length cDNA insert of the Leishmania antigen MAPS-1A.

Recombinant MAPS-1A protein having an amino-terminal HIS-Tag was prepared using a high level *E. coli* expression system and recombinant protein was purified by affinity chromatography as described in Example 1. Southern blot analysis of genomic DNA from *L. major* digested with a panel of restriction enzymes, seven other Leishmania species digested with PstI, and two other infectious-disease pathogens (*T. cruzi* and *T. brucei*), using the full length insert of MAPS-1A, demonstrated that MAPS-1A is present in all eight Leishmania species tested (FIG. 23). Northern blot analysis of *L. major* promastigote and amastigote RNAs indicated that MAPS-1A is constitutively expressed.

Using oligonucleotide primers (SEQ ID NOs:27 and 28) based on the MAPS-1A cDNA sequence provided in SEQ ID NO: 23, the corresponding gene was isolated from *L. tropica* by means of PCR (using 30 cycles of the following temperature step sequence: 94° C., 1 minute; 50° C., 1 minute; 72° C., 1 minute) The determined cDNA sequence for the *L. tropica* MAPS-1A protein is provided in SEQ ID NO: 25, with the corresponding amino acid sequence being provided in SEQ ID NO: 26.

Figure 24:
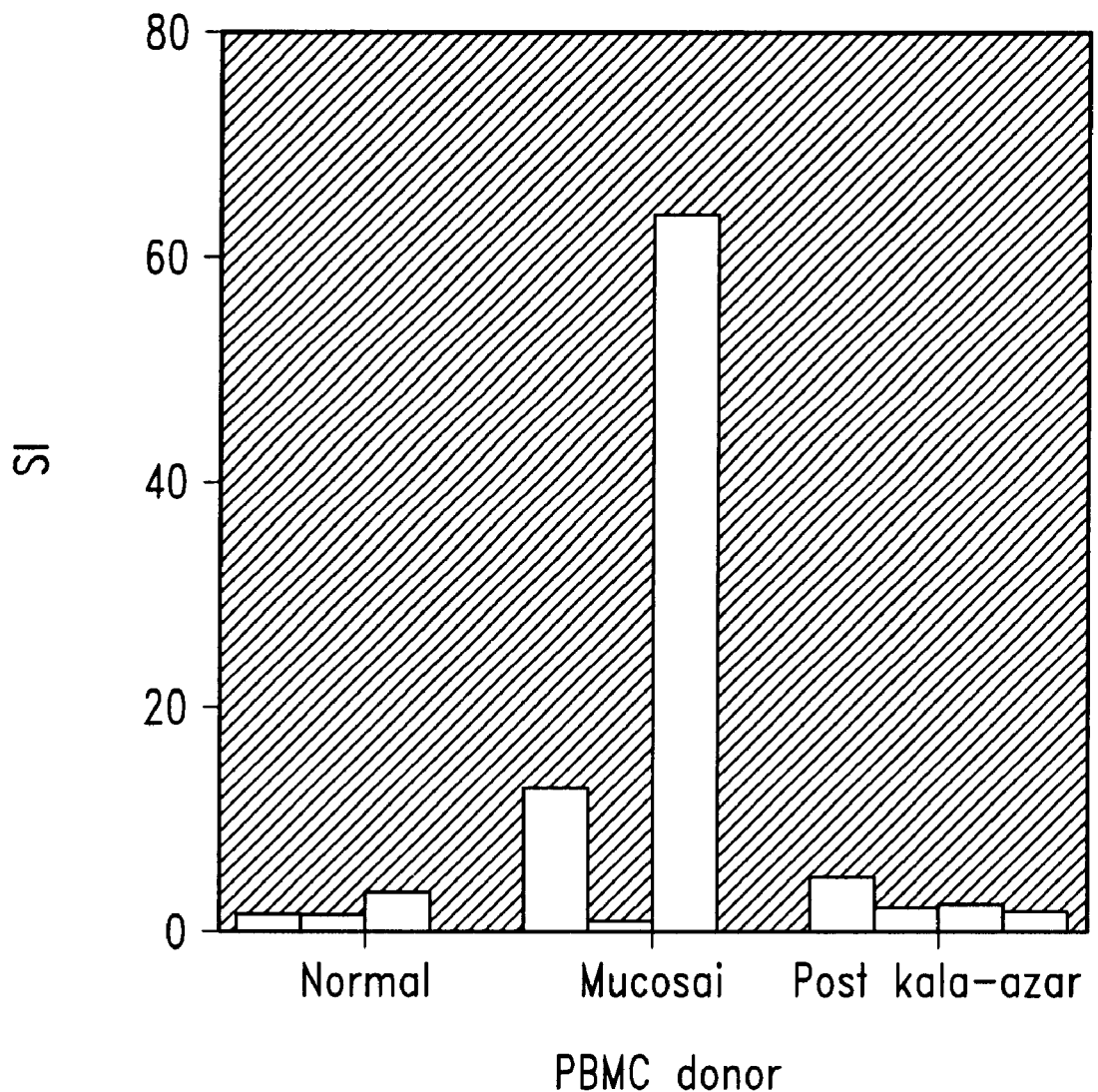
FIG. 24 illustrates the proliferation of PBMC isolated from uninfected-individuals, patients with active mucosal leishmaniasis and patients post kala-azar infection, stimulated by MAPS-1A.

The ability of recombinant MAPS-1A to stimulate cell proliferation was investigated as follows. PBMC from 3 *L. braziliensis*-infected patients having active mucosal leishmaniasis, from 4 patients post kala-azar infection (previously infected with *L. chagasi* and/or *L. donovani*) and from 3 uninfected-individuals were prepared as described above in Example 7. The ability of MAPS-1A to stimulate proliferation of these PBMC was determined as described in Example 8 above. As shown in FIG. 24, significant levels of MAPS-1A specific PBMC proliferation were seen in 2 of the 7 Leishmania patients.

Figure 25:
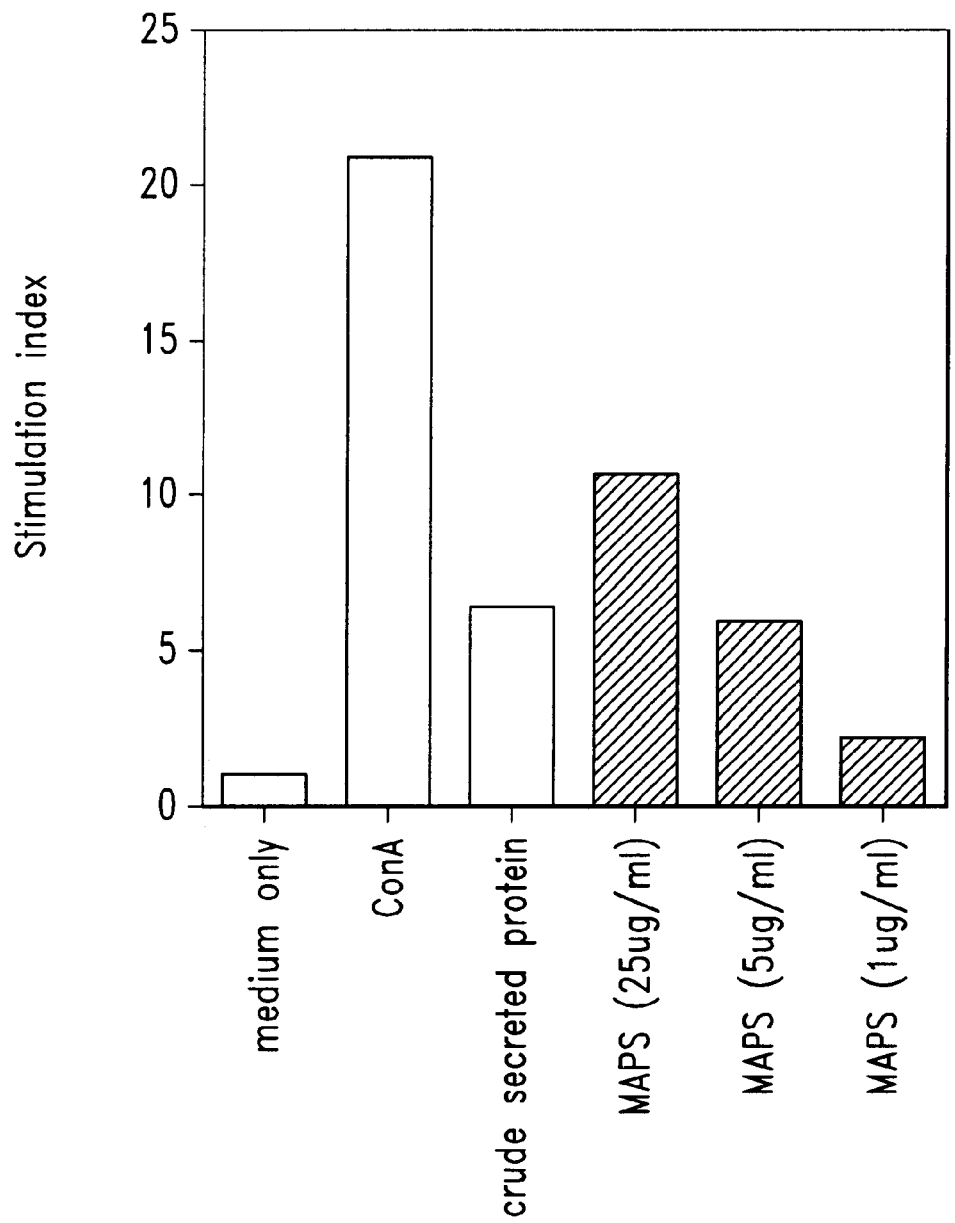
FIG. 25 illustrates the proliferation of murine lymph node cultures stimulated by MAPS-1A.

The ability of MAPS-1A to stimulate proliferation in mice lymph node cultures was determined as described in Example 8. FIG. 25 shows the amount of proliferation stimulated by MAPS-1A (at 25 $\mu$g/ml, 5 $\mu$g/ml and 1 $\mu$g/ml) as compared to that stimulated by the positive control ConA and by crude *L. major* promastigote supernatant proteins, 20 days post-infection with *L. major*. Cells isolated 20 days post-infection were highly responsive to MAPS-1A, whereas cells isolated 10 days post-infection were unresponsive.

Example 11

Immunoreactivity of Soluble Leishmania Antigens with Sera from Leishmania-infected Patients The reactivity of MAPS-1A with sera from uninfected individuals, from human leishmaniasis patients with cutaneous infection, from human patients with acute visceral leishmaniasis, and from *L. major*-infected BALB/c mice was determined as follows.

Assays were performed in 96-well plates coated with 200 ng antigen diluted to 50 μL in carbonate coating buffer, pH 9.6. The wells were coated overnight at 4° C. (or 2 hours at 37° C.). The plate contents were then removed and the wells were blocked for 2 hours with 200 μL of PBS/1% BSA. After the blocking step, the wells were washed five times with PBS/0.1% Tween 20™. 50 μL sera, diluted 1:100 in PBS/0.1% Tween 20™/0.1% BSA, was then added to each well and incubated for 30 minutes at room temperature. The plates were then washed again five times with PBS/0.1% Tween 20™.

The enyzme conjugate (horseradish peroxidase—Protein A, Zymed, San Francisco, Calif.) was then diluted 1:10,000 in PBS/0.1% Tween 20™/0.1% BSA, and 50 μL of the diluted conjugate was added to each well and incubated for 30 minutes at room temperature. Following incubation, the wells were washed five times with PBS/0.1% Tween 20™. 100 μL of tetramethylbenzidine peroxidase (TMB) substrate (Kirkegaard and Perry Laboratories, Gaithersburg, Md.) was added, undiluted, and incubated for about 15 minutes. The reaction was stopped with the addition of 100 μL of 1 N $H_2SO_4$ to each well, and the plates were read at 450 nm.

Figure 26:
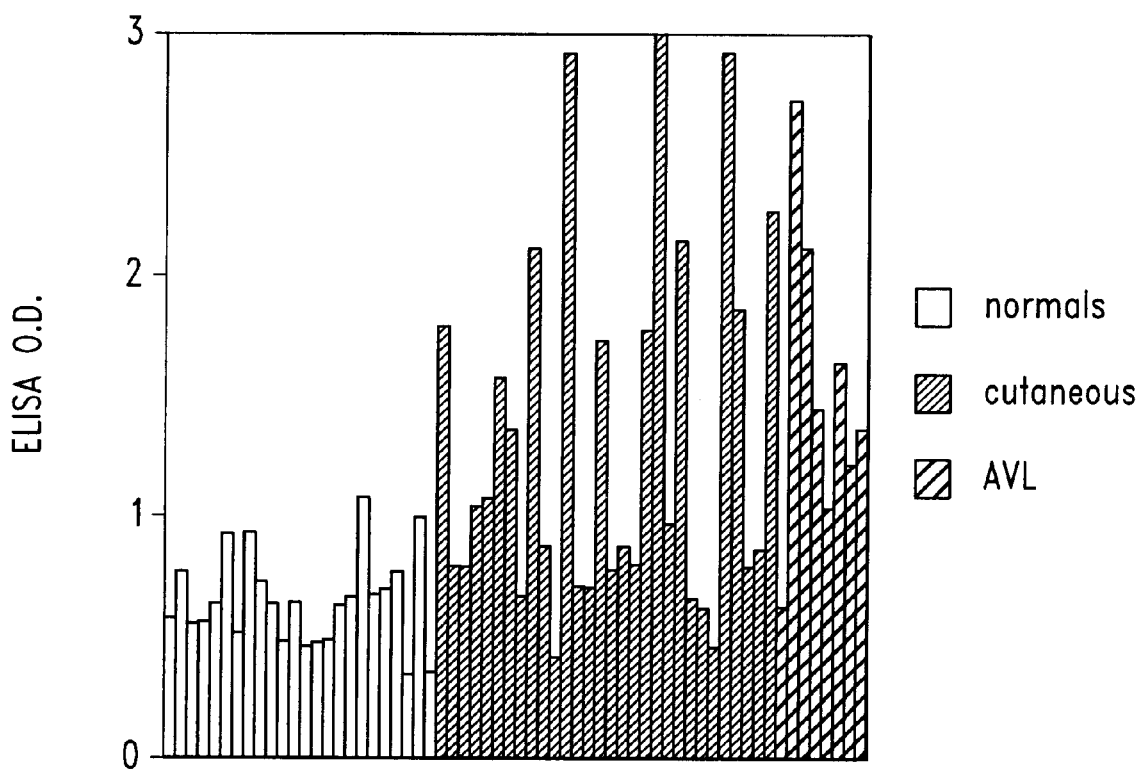
FIG. 26 illustrates the reactivity of MAPS-1A with sera from human leishmaniasis patients.
Figure 27:
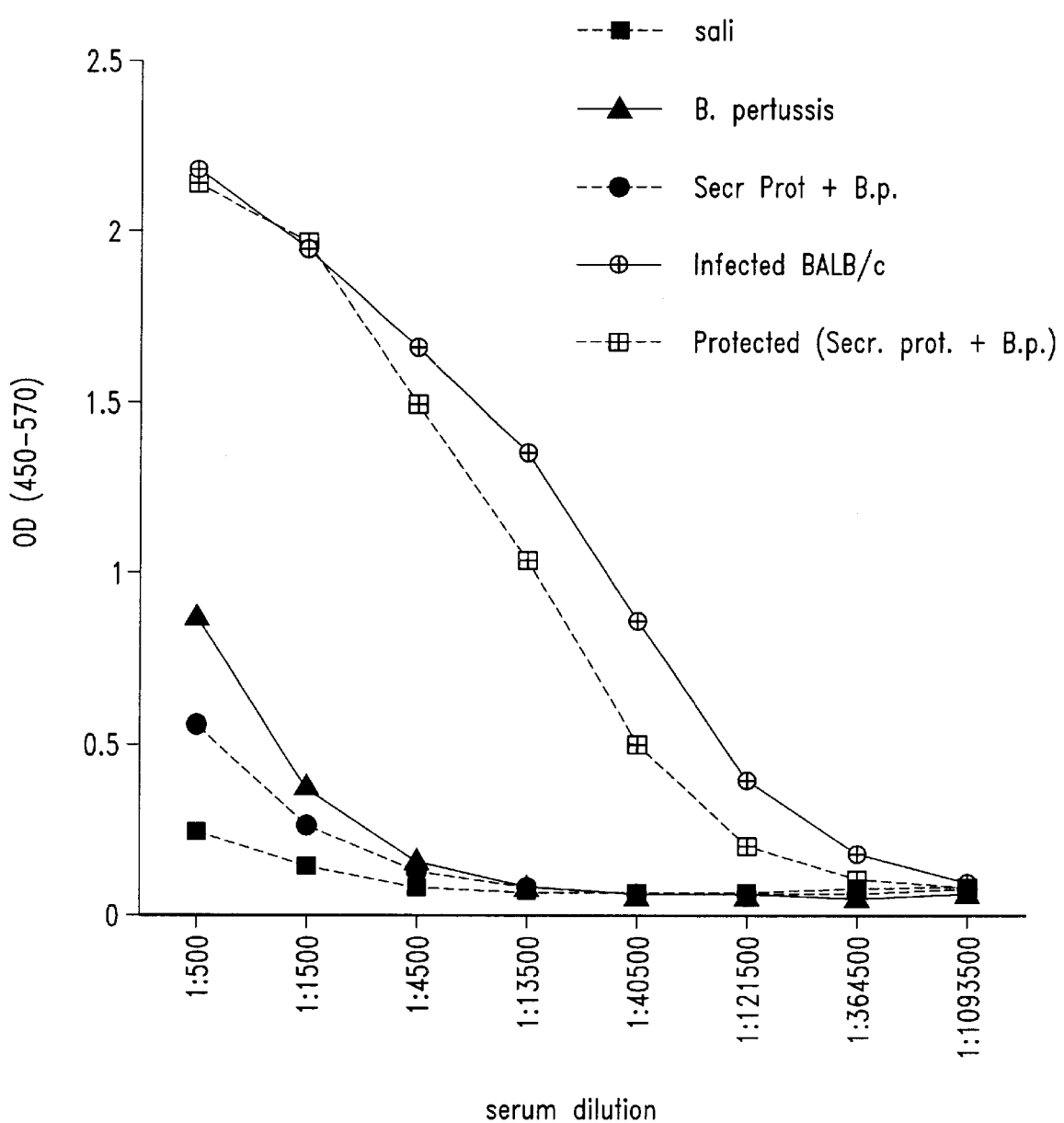
FIG. 27 illustrates the reactivity of MAPS-1A with sera from mice immunized against and/or infected with leishmaniasis.

As shown in FIG. 26, approximately 50% of the samples from human leishmaniasis patients showed reactivities with recombinant MAPS-1A substantially above background. FIG. 27 shows the reactivity of MAPS-1A with increasing dilutions of sera from BALB/c mice previously administered either (i) saline solution; (ii) the adjuvant *B. pertussis;* (iii) soluble Leishmania antigens plus *B. pertussis;* (iv) live *L. major* promastigotes; or (v) soluble Leishmania antigens plus *B. pertussis* followed by live *L. major* promastigotes (as described below in Example 12). Considerably higher absorbances were seen with sera from mice infected with live *L. major* promastigotes and with mice infected with live *L. major* promastigotes following immunization with soluble Leishmania antigens plus *B. pertussis,* than with sera from the other three groups of mice, indicating that anti-MAPS-1A antibody titers increase following Leishmania infection.

Example 12

Use of Leishmania Antigens for Vaccination Against Leishmania Infection

This example illustrates the effectiveness of Leishmania antigens in conferring protection against disease in the experimental murine leishmaniasis model system. For a discussion of the murine leishmaniasis model system see, for example, Reiner et al. *Annu. Rev. Immunol.,* 13:151–77, 1995.

Figure 28:
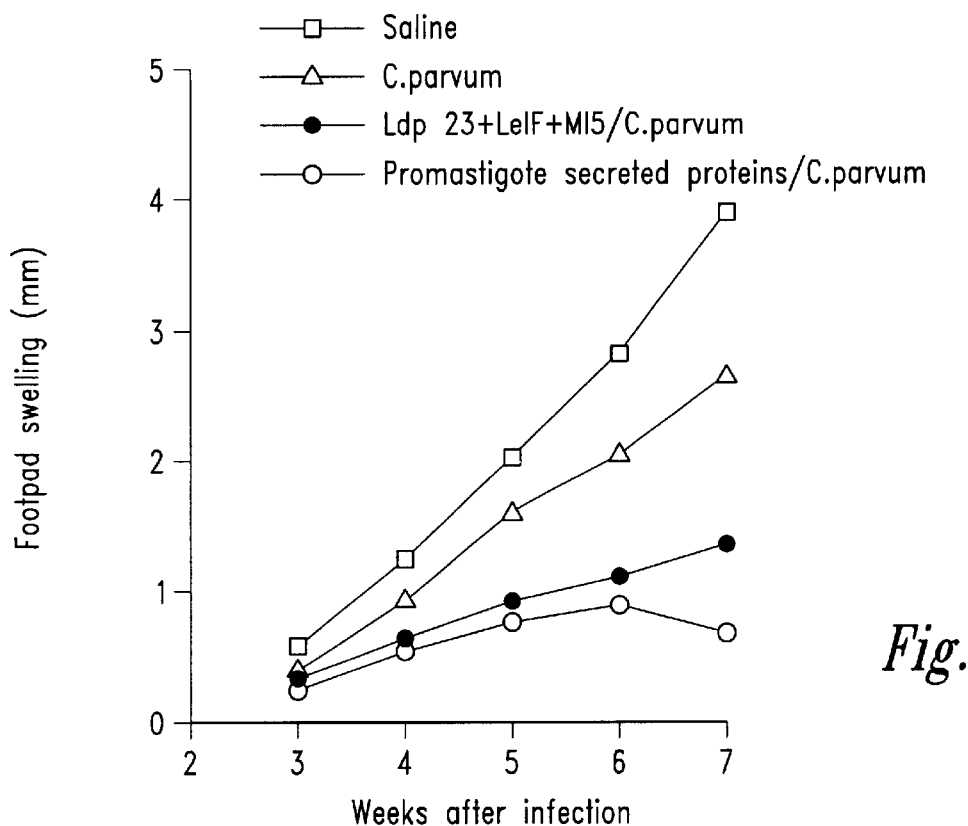
FIG. 28 illustrates the effectiveness of immunization with either soluble Leishmania antigens or a mixture of Ldp23, LbeiF4A and M15 plus adjuvant in conferring protection against infection (as measured by footpad swelling) in a murine leishmaniasis model system, as compared to the administration of adjuvant alone.
Figure 29:
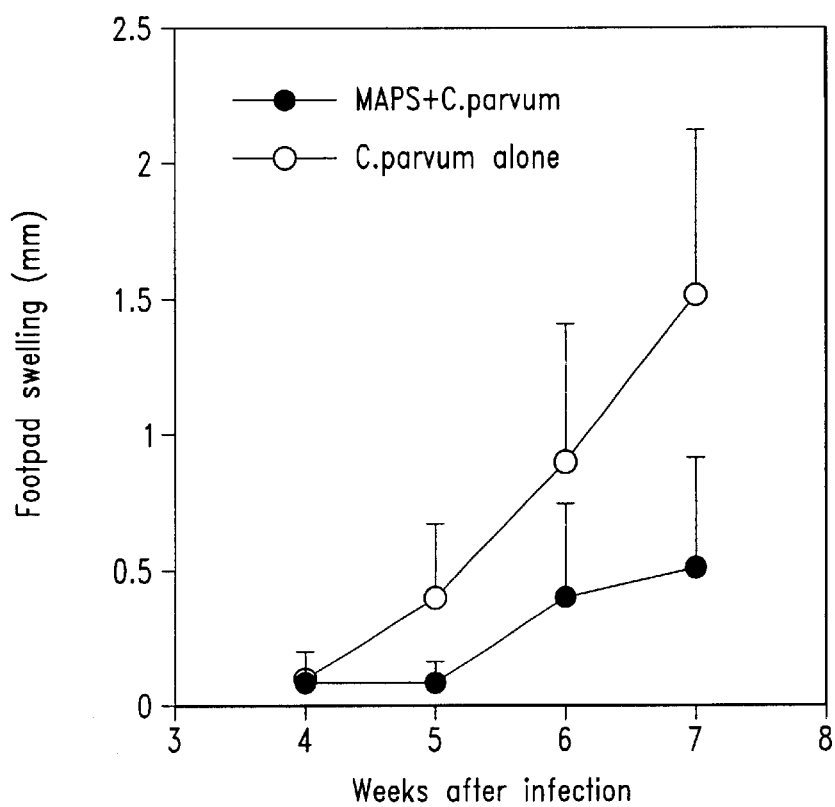
FIG. 29 illustrates the effectiveness of immunization with MAPS-1A plus adjuvant in conferring protection against infection (as measured by footpad swelling) in a murine leishmaniasis model system, as compared to the administration of adjuvant alone.
Figure 30A:
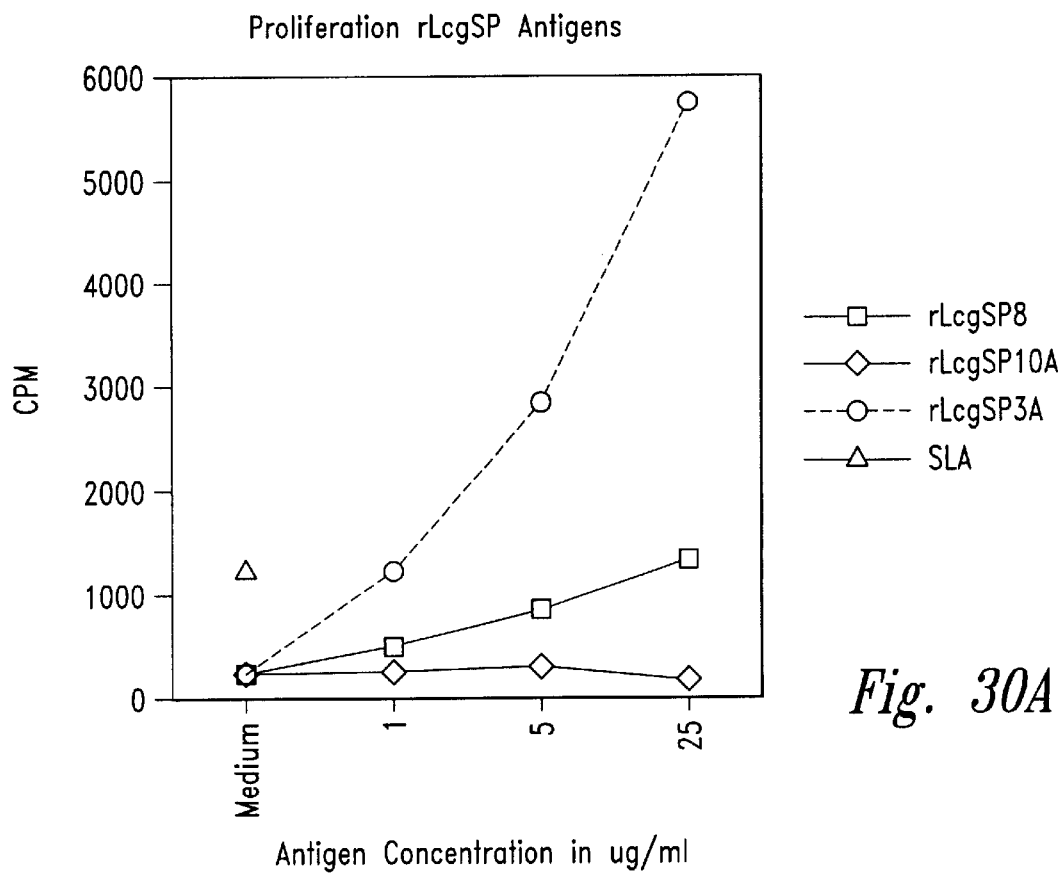
FIGS. 30A and B illustrate the proliferation of murine lymph node cultures stimulated with either LcgSP8, LcgSP10 or LcgSP3.
Figure 30B:
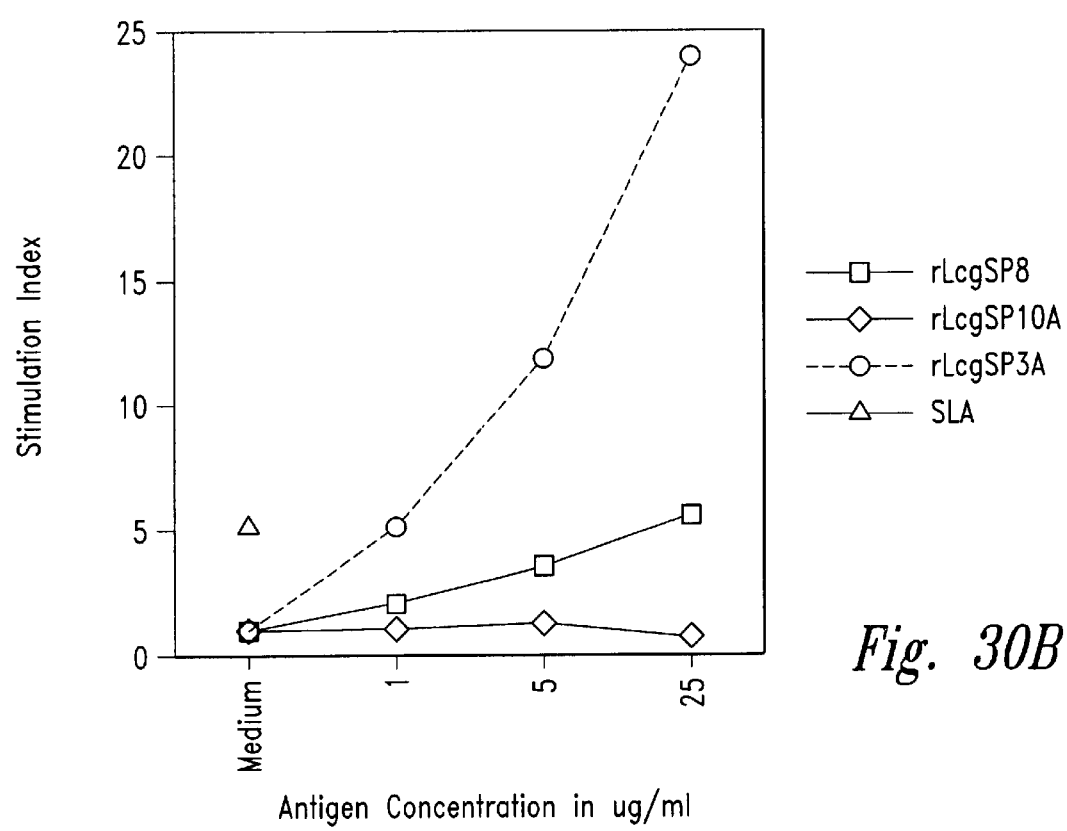

The effectiveness of (i) crude soluble Leishmania antigens, (ii) MAPS-1A, and (iii) a mixture of Ldp23, LbeIF4A and M15, as vaccines against Leishmania infection was determined as follows. BALB/c mice (5 per group) were immunized intra-peritoneally three times at biweekly intervals with either (i) 30 μg crude soluble Leishmania antigens, (ii)20 μg MAPS-1A or (iii) a mixture containing 10 μg each of LeIF, Ldp23 and M15, together with 100 μg of the adjuvant *C. parvum*. Two control groups were immunized with either saline or *C. parvum* alone. Two weeks after the last immunization, the mice were challenged with $2 \times 10^5$ late-log phase promastigotes of *L. major*. Infection was monitored weekly by measurement of footpad swelling. The amount of footpad swelling seen in mice immunized with either crude soluble Leishmania antigens, a mixture of Ldp23, LbeiF4A and M15 (FIG. 28), or MAPS-1A (FIG. 29) was significantly less than that seen in mice immunized with *C. parvum* alone. These results demonstrate that the Leishmania antigens of the present invention are effective in conferring protection against Leishmania infection.

Example 13

Isolation of DNA Encoding for Soluble Antigens from an *L. Major* Genomic DNA Library This example illustrates the isolation of seven soluble Leishmania antigen genes from an *L. major* genomic DNA library.

An *L. major* genomic DNA expression library was prepared from *L. major* promastigotes using the unidirectional Lambda ZAP (uni-ZAP) kit (Stratagene) according to the manufacturer's protocol. This library was screened with a high titer rabbit sera raised against *L. major* soluble antigens, as described above in Example 9. Seven positive clones were identified. The phagemid were excised and DNA from each of the seven clones was sequenced using a Perkin Elmer/Applied Biosystems Division automated sequencer Model 373A. The DNA sequences for these antigens, referred to as LmgSP1, LmgSP3, LmgSP5, LmgSP8, LmgSP9, LmgSP13, LmgSP19, are provided in SEQ ID NO:29–35, respectively, with the corresponding amino acid sequences being provided in SEQ ID NO: 36–42, respectively. LmgSP13 was found to contain a 39 amino acid repeat sequence shown in SEQ ID NO:43.

Subsequent studies resulted in the isolation of a full-length sequence for LmgSP9. The full-length DNA sequence is provided in SEQ ID NO: 54, with the corresponding predicted amino acid sequence being provided in SEQ ID NO: 55. The amino acid sequence was found to contain six 14 amino acid repeat units (SEQ ID NO: 56), with each unit being further divided into two 7 amino acid units, provided in SEQ ID NO; 57 and 58.

Comparison of the DNA and amino acid sequences for the isolated antigens as described above, revealed no significant homologies to LmgSP1, LmgSP3, and LmgSP13. LmgSP5 was found to be related to the known PSA2 family. LmgSP8 was found to bear some homology to a sequence previously identified in *E. coli* (2-succinyl-6-hydroxy-2,4-cyclohexadiene-1-carboxylic acid synthase). LmgSP9 and LmgSP19 were found to be homologous to a *L. major* hydrophilic surface protein referred to as Gene B (Flinn, H. M. et al. *Mol. Biochem. Parasit.* 65:259–270, 1994), and to ubiquitin, respectively. To the best of the inventors' knowledge, none of these antigens have been previously shown to elicit T or B cell responses.

The reactivity of recombinant LmgSP9 with sera from patients with visceral leishmaniasis, (from both Sudan and Brazil) and from normal donors was evaluated by ELISA as described above. The absorbance values were compared with those obtained using the known Leishmania antigen K39 described above, with *L. chagasi* lysate being employed as a positive control. Representative results of these assays are provided below in Table 2, wherein all the patients from Brazil and those from the Sudan designated as "VL" were inflicted with visceral leishmaniasis. The results demonstrated that LmgSP9 specifically detects antibody in most individuals with visceral leishmaniasis, regardless of geographical location. In several cases, the absorbance values of the antibody reactivity to LmgSP9 were comparable to that observed with K39. In addition, LmgSP9 detected several cases of leishmaniasis that were not detected using K39. These results indicate that LmgSP9 can be used to complement the reactivity of K39.

TABLE 2

REACTIVITY OF LMGSP9 WITH SERA FROM LEISHMANIA PATIENTS

| Patient No. | L. chagasi lysate | K39 | LmgSP9 |
|---|---|---|---|
| Sudanese samples: | | | |
| B19 | 1.067 | 0.306 | 0.554 |
| B25 | 1.884 | 3.435 | 0.974 |
| B43 | 1.19 | 3.225 | 0.86 |
| B47 | 2.405 | 2.892 | 0.375 |
| B50 | 0.834 | 0.748 | 0.432 |
| B58 | 0.921 | 0.235 | 0.92 |
| B63 | 1.291 | 0.303 | 0.764 |
| B70 | 0.317 | 0.089 | 3.056 |
| VL4 | 1.384 | 3.035 | 2.965 |
| VL11 | 0.382 | 0.144 | 0.142 |
| VL12 | 0.277 | 0.068 | 0.098 |
| VL13 | 0.284 | 0.12 | 0.194 |
| Brazilian samples: | | | |
| 105 | 3.508 | 3.53 | 0.374 |
| 106 | 2.979 | 3.373 | 2.292 |
| 107 | 2.535 | 3.444 | 0.46 |
| 109 | 1.661 | 3.415 | 3.319 |
| 111 | 3.595 | 3.537 | 0.781 |
| 112 | 2.052 | 3.469 | 0.63 |
| 113 | 3.352 | 3.429 | 0.963 |
| 114 | 2.316 | 3.437 | 1.058 |
| 115 | 2.073 | 3.502 | 1.186 |
| 116 | 3.331 | 3.461 | 0.96 |
| Normal Donors: | | | |
| 129 | 0.157 | 0.104 | 0.08 |
| 130 | 0.195 | 0.076 | 0.095 |
| 131 | 0.254 | 0.134 | 0.086 |
| 132 | 0.102 | 0.035 | 0.043 |

In order to obtain a higher specificity for the detection of antibodies in sera from visceral leishmaniasis patients, a homologue of LmgSP9 was isolated from *L. chagasi*, one of the causative agents of visceral leishmaniasis. A total of 80,000 pfu of an amplified *L. chagasi* genomic library were screened with the entire coding region of LmgSP9 (amplified from *L. major* genomic DNA). Seven hybridizing clones were purified to homogeneity. The determined DNA sequences for two of these clones, referred to as Lc Gene A and LcGene B, are provided in SEQ ID NO: 59 and 60, respectively, with the corresponding predicted amino acid sequences being provided in SEQ ID NO: 61 and 62, respectively. The open reading frame for Lc Gene A was found to show some homology to Gene A/C, previously isolated from *L. major* (McKlean et al., *Mol. Bio. Parasitol.*, 85:221–231, 1997). The open reading frame for Lc Gene B showed some homology to Gene B of *L. major*, discussed above, and was found to contain eleven repeats of a 14 amino acid repeat unit (SEQ ID NO: 63); with each repeat being further divided into two 7 amino acid units, provided in SEQ ID NO: 64 and 65.

The diagnostic potentials of Lc Gene A and Lc Gene B were evaluated by ELISA as described above using sera from visceral leishmaniasis patients from Sudan and Brazil, and from uninfected controls. Absorbance values were compared to those obtained using LmgSP9. Much higher absorbance values were obtained with Lc Gene A and Lc Gene B than with LmgSP9, with Lc Gene B appearing to be more effective that Lc Gene A in detecting antibodies in certain cases. These results indicate that Lc Gene B is highly effective in the diagnosis of visceral leishmaniasis.

In order to assess the diagnostic potential of the repeats found within Lc Gene B, a series of 6 peptides were synthesized (SEQ ID NO: 66–71; referred to as Pep 1–6), differing in an R or H residue. An ELISA was carried out using the full-length LcGene B protein and the six peptides. The absorbance values obtained with Pep 3 were higher than those obtained with the other 5 peptides, however they were not as high as those obtained with the full length protein.

Example 14

Isolation and Characterization of DNA Encoding for Soluble Antigens from an *L. Chagasi* Genomic DNA Library This example illustrates the preparation of five soluble Leishmania antigen genes from an *L. chagasi* genomic DNA library.

An *L. chagasi* genomic DNA expression library was prepared from *L. chagasi* promastigotes using the unidirectional Lambda ZAP (uni-ZAP) kit (Stratagene) according to the manufacturer's protocol. This library was screened with a high titer rabbit sera raised against *L. major* soluble antigens, as described above in Example 9. Five positive clones were identified. The phagemid were excised and DNA from each of the Five clones was sequenced using a Perkin Elmer/Applied Biosystems Division automated sequencer Model 373A. The DNA sequences for these antigens, referred to as LcgSP1, LcgSP3, LcgSP4, LcgSP8, and LcgSP10 are provided in SEQ ID NO:44–48, respectively, with the corresponding amino acid sequences being provided in SEQ ID NO:49–53, respectively.

Comparison of these sequences with known sequences in the gene bank as described above, revealed no known homologies to LcgSP3, LcgSP4, LcgSP8 and LcgSP10. LcgSP1 was found to be homologous to the known antigen HSP70.

FIGS. 30A and B illustrate the proliferative response of murine lymph nodes to recombinant LcgSP8, LcgSP10 and LcgSP3. Lymph nodes were taken BALB/c mice 17 days after infection with *L. major.* Infection occurred by footpad injection of $2\times10^6$ parasites/footpad. The cells were stimulated with recombinant antigen and proliferation was measured at 72 hours using $^3$H-thymidine. FIG. 30A shows the CPM, a direct measurement of mitotic activity in response to the antigens, and FIG. 30B shows the stimulation index, which measures the proliferative response relative to the negative control.

Example 15

Isolation of DNA Encoding for *L. Major* Antigens by CD4+ T Cell Expression Cloning This example illustrates the isolation of T cell antigens of *L. major* using a direct T cell screening approach.

Leishmania-specific CD4+ T cell lines were derived from the PBMC of an individual who tested positive in a Leishmania skin test but had no clinical history of disease. These T cell lines were used to screen a *L. major* amastigote cDNA expression library prepared as described in Example 1. Immunoreactive clones were isolated and sequenced as described above. The determined cDNA sequences for the 8 isolated clones referred to as 1G6-34, 1E6-44, 4A5-63, 1B11-39, 2A10-37, 4G2-83, 4H6-41, 8G3-100 are provided in SEQ ID NO: 72–79, respectively, with the corresponding predicted amino acid sequences being provided in SEQ ID NO: 80–87, respectively. The cDNA sequences provided for 1E6-44, 2A10-37, 4G2-83, 4H6-41 and 8G3-100 are believe to represent partial clones. All of these clones were shown to stimulate T cell proliferation.

Comparison of these sequences with those in the gene bank as described above revealed no known homologies to the antigen 4A5-63. 1G6-34 was found to have some homology to histone H2B previously identified in L. enrietti. Antigens 1E6-44, 1B11-39 and 8G3-100 showed some homology to sequences previously identified in other eukaryotes, in particular Saccharomyces cerevisae. 2A10-37 and 4H6-41 were found to be homologous to the two previously identified proteins alpha tubulin from L. donovani and beta tubulin from L. major, respectively, and 4G2-83 was found to be homologous to elongation initiation factor 2 previously identified in T. cruzi.

Example 15

Synthesis of Polypeptides

Polypeptides may be synthesized on a Perkin Elmer/ Applied Biosystems Division 430A peptide synthesizer using FMOC chemistry with HPTU (O-Benzotriazole-N,N, N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising an immunogenic portion of a Leishmania antigen, wherein said antigen comprises an amino acid sequence of SEQ ID NO: 82.

2. A pharmaceutical composition comprising a polypeptide according to claim 1, and a physiologically acceptable carrier, wherein the polypeptide is present in an amount effective for the treatment of Leishmaniasis.

3. A pharmaceutical composition according to claim 2, further comprising soluble Leishmania antigens.

4. A pharmaceutical composition according to claim 2, further comprising a K39 Leishmania antigen.

5. A pharmaceutical composition comprising a polypeptide and a physiologically acceptable carrier, the polypeptide comprising an immunogenic portion of a Leishmania antigen, wherein said antigen comprises an amino acid sequence selected from the group consisting of SEQ ID NO:80, 81, and 83–87, the polypeptide being present in an amount effective for the treatment of Leishmaniasis.

6. A pharmaceutical composition according to claim 5 further comprising a K39 Leishmania antigen.

7. An isolated polypeptide comprising an amino acid sequence of SEQ ID NO:61, wherein said polypeptide comprises an immunogenic portion of a Leishmania antigen, said immunogenic portion of Leishmania antigen selectively binds to anti-leishmania antibodies.

8. An isolated polypeptide comprising an amino acid sequence of SEQ ID NO:62, wherein said polypeptide comprises an immunogenic portion of a Leishmania antigen, said immunogenic portion of Leishmania antigen selectively binds to anti-leishmania antibodies.

9. An isolated polypeptide comprising SEQ ID NO:80.

10. An isolated polypeptide comprising SEQ ID NO:81.

11. An isolated polypeptide comprising SEQ ID NO:83.

12. An isolated polypeptide comprising SEQ ID NO:84.

13. An isolated polypeptide comprising SEQ ID NO:85.

14. An isolated polypeptide comprising a sequence selected from the group consisting of SEQ ID NO: 86 and 87.

\* \* \* \* \*

SEQUENCE LISTING (1) GENERAL INFORMATION:

(iii) NUMBER OF SEQUENCES: 87

(2) INFORMATION FOR SEQ ID NO:1:

(i) SEQUENCE CHARACTERISTICS:
      (A) LENGTH: 3134 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 421..2058

(xi) SEQUENCE DESCRIPTION: SKEQ ID NO:1:

```
CAAGTGTCGA AGGACAGTGT TCNCCGTGTG AGATCGCCGG CTGTGCGTGT GAAGGCGGTG      60

CCATCGGANA AACAACACCG GTGGANCCGC AGGAAACCAT CTTTCTCCGC AGGTCTCTTT     120

TTGTTGTCGA TTGAGAGTGC NCCAAACCCT GCTGGTGCCC TTCTCACATA TCATGTTTTT     180

CGTTGTGCGC TCGCTTTGCC TTTCCTCTCC TTTCCCTCTC TTCCGTGGTG CCGTGTATAC     240

TTCTGGCACC CGCTACGTCA CTTCGCTGGT TTGAACAGAA CCACTGTGAA CACCCACGGG     300

CGATCGCACA CATACACATC CCTCACTCAC ACACACAGCT ACATCTATCC TACATAAAGC     360

TGAAAAAAAA GTCTACGAAC AATTTTGTTT TTACAGTGCG TTGCCGCACA TTTCTCCGTA     420

ATG GAC GCA ACT GAG CTG AAG AAC AAG GGG AAC GAA GAG TTC TCC GCC      468
Met Asp Ala Thr Glu Leu Lys Asn Lys Gly Asn Glu Glu Phe Ser Ala
 1               5                  10                  15

GGC CGC TAT GTG GAG GCG GTG AAC TAC TTC TCA AAG GCG ATC CAG TTG      516
Gly Arg Tyr Val Glu Ala Val Asn Tyr Phe Ser Lys Ala Ile Gln Leu
             20                  25                  30

GAT GAG CAG AAC AGT GTC CTC TAC AGC AAC CGC TCC GCC TGT TTT GCA      564
Asp Glu Gln Asn Ser Val Leu Tyr Ser Asn Arg Ser Ala Cys Phe Ala
         35                  40                  45

GCC ATG CAG AAA TAC AAG GAC GCG CTG GAC GAC GCC GAC AAG TGC ATC      612
Ala Met Gln Lys Tyr Lys Asp Ala Leu Asp Asp Ala Asp Lys Cys Ile
```

-continued

```
            50                    55                    60
TCG ATC AAG CCG AAT TGG GCC AAG GGC TAC GTG CGC CGA GGA GCA GCT           660
Ser Ile Lys Pro Asn Trp Ala Lys Gly Tyr Val Arg Arg Gly Ala Ala
 65              70                  75                  80

CTC CAT GGC ATG CGC CGC TAC GAC GAT GCC ATT GCC GCG TAT GAA AAG           708
Leu His Gly Met Arg Arg Tyr Asp Asp Ala Ile Ala Ala Tyr Glu Lys
                 85                  90                  95

GGG CTC AAG GTG GAC CCT TCC AAC AGC GGC TGC GCG CAG GGC GTG AAG           756
Gly Leu Lys Val Asp Pro Ser Asn Ser Gly Cys Ala Gln Gly Val Lys
                100                 105                 110

GAC GTG CAG GTA GCC AAG GCC CGC GAA GCA CGT GAC CCC ATC GCT CGC           804
Asp Val Gln Val Ala Lys Ala Arg Glu Ala Arg Asp Pro Ile Ala Arg
            115                 120                 125

GTC TTC ACC CCG GAG GCG TTC CGC AAG ATC CAA GAG AAT CCC AAG CTG           852
Val Phe Thr Pro Glu Ala Phe Arg Lys Ile Gln Glu Asn Pro Lys Leu
        130                 135                 140

TCT CTA CTT ATG CTG CAG CCG GAC TAC GTG AAG ATG GTA GAC ACC GTC           900
Ser Leu Leu Met Leu Gln Pro Asp Tyr Val Lys Met Val Asp Thr Val
145                 150                 155                 160

ATC CGC GAC CCT TCG CAG GGC CGG CTG TAC ATG GAA GAC CAG CGC TTT           948
Ile Arg Asp Pro Ser Gln Gly Arg Leu Tyr Met Glu Asp Gln Arg Phe
                165                 170                 175

GCC CTG ACG CTC ATG TAC CTG AGC GGA ATG AAG ATT CCC AAC GAT GGT           996
Ala Leu Thr Leu Met Tyr Leu Ser Gly Met Lys Ile Pro Asn Asp Gly
                180                 185                 190

GAT GGC GAG GAG GAG GAA CGT CCG TCT GCG AAG GCG GCA GAG ACA GCG          1044
Asp Gly Glu Glu Glu Glu Arg Pro Ser Ala Lys Ala Ala Glu Thr Ala
            195                 200                 205

AAG CCA AAA GAG GAG AAG CCT CTC ACC GAC AAC GAG AAG GAG GCC CTG          1092
Lys Pro Lys Glu Glu Lys Pro Leu Thr Asp Asn Glu Lys Glu Ala Leu
        210                 215                 220

GCG CTC AAG GAG GAG GGC AAC AAG CTG TAC CTC TCG AAG AAG TTT GAG          1140
Ala Leu Lys Glu Glu Gly Asn Lys Leu Tyr Leu Ser Lys Lys Phe Glu
225                 230                 235                 240

GAG GCG CTG ACC AAG TAC CAA GAG GCG CAG GTG AAA GAC CCC AAC AAC          1188
Glu Ala Leu Thr Lys Tyr Gln Glu Ala Gln Val Lys Asp Pro Asn Asn
                245                 250                 255

ACT TTA TAC ATT CTG AAC GTG TCG GCC GTG TAC TTC GAG CAG GGT GAC          1236
Thr Leu Tyr Ile Leu Asn Val Ser Ala Val Tyr Phe Glu Gln Gly Asp
                260                 265                 270

TAC GAC AAG TGC ATC GCC GAG TGC GAG CAC GGT ATC GAG CAC GGT CGC          1284
Tyr Asp Lys Cys Ile Ala Glu Cys Glu His Gly Ile Glu His Gly Arg
            275                 280                 285

GAG AAC CAC TGC GAC TAC ACA ATC ATT GCG AAG CTC ATG ACC CGG AAC          1332
Glu Asn His Cys Asp Tyr Thr Ile Ile Ala Lys Leu Met Thr Arg Asn
        290                 295                 300

GCC TTG TGC CTC CAG AGG CAG AGG AAG TAC GAG GCT GCT ATC GAC CTT          1380
Ala Leu Cys Leu Gln Arg Gln Arg Lys Tyr Glu Ala Ala Ile Asp Leu
305                 310                 315                 320

TAC AAG CGC GCC CTT GTC GAG TGG CGT AAC CCT GAC ACC CTC AAG AAG          1428
Tyr Lys Arg Ala Leu Val Glu Trp Arg Asn Pro Asp Thr Leu Lys Lys
                325                 330                 335

CTG ACG GAG TGC GAG AAG GAG CAC CAA AAG GCG GTG GAG GAA GCC TAC          1476
Leu Thr Glu Cys Glu Lys Glu His Gln Lys Ala Val Glu Glu Ala Tyr
                340                 345                 350

ATC GAT CCT GAG ATC GCG AAG CAG AAG AAA GAC GAA GGT AAC CAG TAC          1524
Ile Asp Pro Glu Ile Ala Lys Gln Lys Lys Asp Glu Gly Asn Gln Tyr
            355                 360                 365

TTC AAG GAG GAT AAG TTC CCC GAG GCC GTG GCA GCG TAC ACG GAG GCC          1572
```

```
Phe Lys Glu Asp Lys Phe Pro Glu Ala Val Ala Ala Tyr Thr Glu Ala
    370                 375                 380

ATC AAG CGC AAC CCT GCC GAG CAC ACC TCC TAC AGC AAT CGC GCG GCC    1620
Ile Lys Arg Asn Pro Ala Glu His Thr Ser Tyr Ser Asn Arg Ala Ala
385                 390                 395                 400

GCG TAC ATC AAG CTT GGA GCC TTC AAC GAC GCC CTC AAG GAC GCG GAG    1668
Ala Tyr Ile Lys Leu Gly Ala Phe Asn Asp Ala Leu Lys Asp Ala Glu
                405                 410                 415

AAG TGC ATT GAG CTG AAG CCC GAC TTT GTT AAG GGC TAC GCG CGC AAG    1716
Lys Cys Ile Glu Leu Lys Pro Asp Phe Val Lys Gly Tyr Ala Arg Lys
            420                 425                 430

GGT CAT GCT TAC TTT TGG ACC AAG CAG TAC AAC CGC GCG CTG CAG GCG    1764
Gly His Ala Tyr Phe Trp Thr Lys Gln Tyr Asn Arg Ala Leu Gln Ala
        435                 440                 445

TAC GAT GAG GGC CTC AAG GTG GAC CCG AGC AAT GCG GAC TGC AAG GAT    1812
Tyr Asp Glu Gly Leu Lys Val Asp Pro Ser Asn Ala Asp Cys Lys Asp
    450                 455                 460

GGG CGG TAT CGC ACA ATC ATG AAG ATT CAG GAG ATG GCA TCT GGC CAA    1860
Gly Arg Tyr Arg Thr Ile Met Lys Ile Gln Glu Met Ala Ser Gly Gln
465                 470                 475                 480

TCC GCG GAT GGC GAC GAG GCG GCG CGC CGG GCC ATG GAC GAT CCT GAA    1908
Ser Ala Asp Gly Asp Glu Ala Ala Arg Arg Ala Met Asp Asp Pro Glu
                485                 490                 495

ATC GCG GCA ATC ATG CAA GAT AGC TAC ATG CAA CTA GTG TTG AAG GAG    1956
Ile Ala Ala Ile Met Gln Asp Ser Tyr Met Gln Leu Val Leu Lys Glu
            500                 505                 510

ATG CAG AAC GAT CCC ACG CGC ATT CAG GAG TAC ATG AAG GAC TCC GGG    2004
Met Gln Asn Asp Pro Thr Arg Ile Gln Glu Tyr Met Lys Asp Ser Gly
        515                 520                 525

ATC TCA TCG AAG ATC AAC AAG CTG ATT TCA GCT GGC ATC ATT CGT TTT    2052
Ile Ser Ser Lys Ile Asn Lys Leu Ile Ser Ala Gly Ile Ile Arg Phe
    530                 535                 540

GGT CAG TAGACTTCTA CGCTGCCTCA TCTTTTCCGT GTCTTTGCGT CGGCGGGTAT    2108
Gly Gln
545

CGTAAAGCAC AATAAAGCAG CGATTCACAT GCACGAGTAA AGTGCTGCGC CTCTCAAACA    2168

CGACGTCGAG GCTGTGGTGC AGATGCGCGT CCTGCATGAA GGTAGTGAAG AGGAAAGTAA    2228

GGGATGTTGT TTGTGGGCCT TCGTGGCTGC GCACACACCT CTTATCTCCT TCGCTTGGTA    2288

CCTTCTCCCT TTTTCGTCTT CACCCCCCTT TCTCTTCTCA CGCTCTCCCT GGCGCGGTGG    2348

TGCAACGATT TCGTTTTATT TACGTCTGTG TAGCTCCTCT ATTCAACGGT GCGATGACGC    2408

TAACGAAGCT GGCCTGTATT CGGCTAAGGC GAAGGCAAAA GACTAGGAGG GGGGGGGGAA    2468

GGAGACGGCG TGACCATCAC TGCGAAGAAA CAAGCCGAAG AAAAGGCCCC GAACGCCTGC    2528

ATTTCCGCGC GCCCTCGCCC GCCTTCCTTC CTTCCTTCGC TCTCTCTCTC TCTCTCTCTC    2588

GCTATCTTCT CAACGGAGAC ATGAAAGGCG TTTGTTAGGA AAAGAGGGGG GGGGGAAGAG    2648

TGGGACGACG CGCTGCGTCT TTTGGGCACT GGTCACGTGC GTCACCCTCT TTTTTTATCT    2708

CTATTGGCAC TGTCTTGTTT CTTTTCCCTT TCCTATCATA CGCGTCTCGC AAACGACTCC    2768

GCGCTGAGCA GCCATGTGCT GCGGCGTGGA GGAAGTACAC AGACATCACG GATGCATATG    2828

TGCGCGTCCG TGTACGCGCT TGTATGGGGC TTCTAACAGC GCCTGTGTGT GTTTGTGTGT    2888

GTGTGTGTGT GTGTGTCTGT GTATTTCGAG CGTCTGTATG CTATTCTATT AAGCACCGAA    2948

GAAGAGACAC ACACGACAGC GAAGGAGATG GTGTCGGCTT TTCGGCTAAT CACTCCCTTC    3008

CATAGCTTCT CTGAAGGAGG CTCTCTTCCA GAGGAATAGA CTGCAGATGG GGTCCACGTT    3068
```

```
TATCTGAGGA GTCAACGGAA AAAAAAAAAA AAAAAAAAAA AAAAAAAAAA AAAAAAAAAA    3128

CTCGAG                                                               3134
```

(2) INFORMATION FOR SEQ ID NO:2:

(i) SEQUENCE CHARACTERISTICS:
        (A) LENGTH: 546 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Ala Thr Glu Leu Lys Asn Lys Gly Asn Glu Glu Phe Ser Ala
 1               5                  10                  15

Gly Arg Tyr Val Glu Ala Val Asn Tyr Phe Ser Lys Ala Ile Gln Leu
            20                  25                  30

Asp Glu Gln Asn Ser Val Leu Tyr Ser Asn Arg Ser Ala Cys Phe Ala
        35                  40                  45

Ala Met Gln Lys Tyr Lys Asp Ala Leu Asp Asp Ala Asp Lys Cys Ile
    50                  55                  60

Ser Ile Lys Pro Asn Trp Ala Lys Gly Tyr Val Arg Arg Gly Ala Ala
65                  70                  75                  80

Leu His Gly Met Arg Arg Tyr Asp Asp Ala Ile Ala Ala Tyr Glu Lys
                85                  90                  95

Gly Leu Lys Val Asp Pro Ser Asn Ser Gly Cys Ala Gln Gly Val Lys
            100                 105                 110

Asp Val Gln Val Ala Lys Ala Arg Glu Ala Arg Asp Pro Ile Ala Arg
        115                 120                 125

Val Phe Thr Pro Glu Ala Phe Arg Lys Ile Gln Glu Asn Pro Lys Leu
    130                 135                 140

Ser Leu Leu Met Leu Gln Pro Asp Tyr Val Lys Met Val Asp Thr Val
145                 150                 155                 160

Ile Arg Asp Pro Ser Gln Gly Arg Leu Tyr Met Glu Asp Gln Arg Phe
                165                 170                 175

Ala Leu Thr Leu Met Tyr Leu Ser Gly Met Lys Ile Pro Asn Asp Gly
            180                 185                 190

Asp Gly Glu Glu Glu Arg Pro Ser Ala Lys Ala Ala Glu Thr Ala
        195                 200                 205

Lys Pro Lys Glu Glu Lys Pro Leu Thr Asp Asn Glu Lys Glu Ala Leu
    210                 215                 220

Ala Leu Lys Glu Glu Gly Asn Lys Leu Tyr Leu Ser Lys Lys Phe Glu
225                 230                 235                 240

Glu Ala Leu Thr Lys Tyr Gln Glu Ala Gln Val Lys Asp Pro Asn Asn
                245                 250                 255

Thr Leu Tyr Ile Leu Asn Val Ser Ala Val Tyr Phe Glu Gln Gly Asp
            260                 265                 270

Tyr Asp Lys Cys Ile Ala Glu Cys Glu His Gly Ile Glu His Gly Arg
        275                 280                 285

Glu Asn His Cys Asp Tyr Thr Ile Ile Ala Lys Leu Met Thr Arg Asn
    290                 295                 300

Ala Leu Cys Leu Gln Arg Gln Arg Lys Tyr Glu Ala Ala Ile Asp Leu
305                 310                 315                 320

Tyr Lys Arg Ala Leu Val Glu Trp Arg Asn Pro Asp Thr Leu Lys Lys
                325                 330                 335
```

```
Leu Thr Glu Cys Glu Lys Glu His Gln Lys Ala Val Glu Glu Ala Tyr
             340                 345                 350
Ile Asp Pro Glu Ile Ala Lys Gln Lys Lys Asp Glu Gly Asn Gln Tyr
             355                 360                 365
Phe Lys Glu Asp Lys Phe Pro Glu Ala Val Ala Ala Tyr Thr Glu Ala
             370                 375                 380
Ile Lys Arg Asn Pro Ala Glu His Thr Ser Tyr Ser Asn Arg Ala Ala
385                 390                 395                 400
Ala Tyr Ile Lys Leu Gly Ala Phe Asn Asp Ala Leu Lys Asp Ala Glu
                 405                 410                 415
Lys Cys Ile Glu Leu Lys Pro Asp Phe Val Lys Gly Tyr Ala Arg Lys
             420                 425                 430
Gly His Ala Tyr Phe Trp Thr Lys Gln Tyr Asn Arg Ala Leu Gln Ala
             435                 440                 445
Tyr Asp Glu Gly Leu Lys Val Asp Pro Ser Asn Ala Asp Cys Lys Asp
             450                 455                 460
Gly Arg Tyr Arg Thr Ile Met Lys Ile Gln Glu Met Ala Ser Gly Gln
465                 470                 475                 480
Ser Ala Asp Gly Asp Glu Ala Ala Arg Arg Ala Met Asp Asp Pro Glu
                 485                 490                 495
Ile Ala Ala Ile Met Gln Asp Ser Tyr Met Gln Leu Val Leu Lys Glu
             500                 505                 510
Met Gln Asn Asp Pro Thr Arg Ile Gln Glu Tyr Met Lys Asp Ser Gly
             515                 520                 525
Ile Ser Ser Lys Ile Asn Lys Leu Ile Ser Ala Gly Ile Ile Arg Phe
             530                 535                 540
Gly Gln
545

(2) INFORMATION FOR SEQ ID NO:3:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 26..550

(xi) SEQUENCE DESCRIPTION: SEQ ID NO:3:

AATTCGGCAC GAGGCATTGT GCATA ATG GTC AAG TCC CAC TAC ATC TGC GCG         52
                           Met Val Lys Ser His Tyr Ile Cys Ala
                                       550                 555

GGC CGC CTG GTG CGC ATC CTG CGT GGC CCC CGC CAG GAC CGC GTT GGT        100
Gly Arg Leu Val Arg Ile Leu Arg Gly Pro Arg Gln Asp Arg Val Gly
                560                 565                 570

GTG ATC GTC GAC ATT GTC GAC GCG AAC CGC GTG CTG GTG GAG AAC CCG        148
Val Ile Val Asp Ile Val Asp Ala Asn Arg Val Leu Val Glu Asn Pro
                575                 580                 585

GAG GAC GCG AAG ATG TGG CGC CAC GTG CAG AAC CTG AAG AAC GTG GAG        196
Glu Asp Ala Lys Met Trp Arg His Val Gln Asn Leu Lys Asn Val Glu
                590                 595                 600

CCG CTG AAG TAC TGC GTG AGC GTC AGC CGC AAC TGC AGC GCG AAG GCG        244
Pro Leu Lys Tyr Cys Val Ser Val Ser Arg Asn Cys Ser Ala Lys Ala
             605                 610                 615

CTG AAG GAT GCG CTG GCC TCG TCG AAG GCG CTG GAG AAG TAC GCG AAG        292
Leu Lys Asp Ala Leu Ala Ser Ser Lys Ala Leu Glu Lys Tyr Ala Lys
```

```
                620                   625                    630                      635
ACG CGC ACT GCT GCG CGC GTG GAG GCG AAG AAG GCG TGC GCC GCG TCG      340
Thr Arg Thr Ala Ala Arg Val Glu Ala Lys Lys Ala Cys Ala Ala Ser
                640                   645                    650

ACG GAC TTC GAG CGC TAC CAG CTG CGC GTT GCG CGC CGT TCT CGC GCG      388
Thr Asp Phe Glu Arg Tyr Gln Leu Arg Val Ala Arg Arg Ser Arg Ala
                655                   660                    665

CAC TGG GCG CGC AAG GTG TTC GAC GAG AAG GAC GCG AAG ACG CCC GTG      436
His Trp Ala Arg Lys Val Phe Asp Glu Lys Asp Ala Lys Thr Pro Val
                670                   675                    680

TCG TGG CAC AAG GTT GCG CTG AAG AAG ATG CAG AAG AAG GCC GCA AAG      484
Ser Trp His Lys Val Ala Leu Lys Lys Met Gln Lys Lys Ala Ala Lys
                685                   690                    695

ATG GAC TCG ACC GAG GGC GCT AAG AGG CGC ATG CAG AAG GCG ATC GCT      532
Met Asp Ser Thr Glu Gly Ala Lys Arg Arg Met Gln Lys Ala Ile Ala
700                 705                   710                    715

GCC CGC AAG GCG AAA AAG TAAGGCCATA CCCTCACTTC GCTTGTTTCG             580
Ala Arg Lys Ala Lys Lys
                720

TGATTTTTCG TGGGAGTCGG TGGCCCTACC AGCGGTCTTT CATTGGCTTA TTTCTATCCG    640

GTCTGAAAGA GGTACAAAAA AAAAAAAAAA AAAAAA                              676

(2) INFORMATION FOR SEQ ID NO:4:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO:4:

Met Val Lys Ser His Tyr Ile Cys Ala Gly Arg Leu Val Arg Ile Leu
1               5                   10                  15

Arg Gly Pro Arg Gln Asp Arg Val Gly Val Ile Val Asp Ile Val Asp
                20                  25                  30

Ala Asn Arg Val Leu Val Glu Asn Pro Glu Asp Ala Lys Met Trp Arg
            35                  40                  45

His Val Gln Asn Leu Lys Asn Val Glu Pro Leu Lys Tyr Cys Val Ser
        50                  55                  60

Val Ser Arg Asn Cys Ser Ala Lys Ala Leu Lys Asp Ala Leu Ala Ser
65                  70                  75                  80

Ser Lys Ala Leu Glu Lys Tyr Ala Lys Thr Arg Thr Ala Ala Arg Val
                85                  90                  95

Glu Ala Lys Lys Ala Cys Ala Ala Ser Thr Asp Phe Glu Arg Tyr Gln
                100                 105                 110

Leu Arg Val Ala Arg Arg Ser Arg Ala His Trp Ala Arg Lys Val Phe
            115                 120                 125

Asp Glu Lys Asp Ala Lys Thr Pro Val Ser Trp His Lys Val Ala Leu
        130                 135                 140

Lys Lys Met Gln Lys Lys Ala Ala Lys Met Asp Ser Thr Glu Gly Ala
145                 150                 155                 160

Lys Arg Arg Met Gln Lys Ala Ile Ala Ala Arg Lys Ala Lys Lys
                165                 170                 175

(2) INFORMATION FOR SEQ ID NO:5:

(i) SEQUENCE CHARACTERISTICS:
```

(A) LENGTH: 2040 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 62..2029

(xi) SEQUENCE DESCRIPTION: SEQ ID NO:5:

CGCGGTGGCG GCCGCTCTAG AACTAGTGGA TCCCCCGGGC TGCAGGAATT CGGCACGAGA      60

G AGC CTG ACG GAC CCG GCG GTG CTG GGC GAG GAG ACT CAC CTG CGC        106
  Ser Leu Thr Asp Pro Ala Val Leu Gly Glu Glu Thr His Leu Arg
              180                 185                 190

GTC CGC GTG GTG CCG GAC AAG GCG AAC AAG ACG CTG ACG GTG GAG GAT      154
Val Arg Val Val Pro Asp Lys Ala Asn Lys Thr Leu Thr Val Glu Asp
                195                 200                 205

AAC GGC ATC GGC ATG ACC AAG GCG GAC CTC GTG AAC AAT CTG GGC ACG      202
Asn Gly Ile Gly Met Thr Lys Ala Asp Leu Val Asn Asn Leu Gly Thr
            210                 215                 220

ATC GCG CGC TCC GGC ACG AAG GCT TTC ATG GAG GCA CTG GAG GCC GGC      250
Ile Ala Arg Ser Gly Thr Lys Ala Phe Met Glu Ala Leu Glu Ala Gly
        225                 230                 235

GGC GAC ATG AGC ATG ATC GGC CAG TTC GGT GTC GGC TTC TAC TCC GCG      298
Gly Asp Met Ser Met Ile Gly Gln Phe Gly Val Gly Phe Tyr Ser Ala
    240                 245                 250

TAC CTT GTG GCG GAC CGC GTG ACG GTG GTG TCG AAG AAC AAC TCG GAC      346
Tyr Leu Val Ala Asp Arg Val Thr Val Val Ser Lys Asn Asn Ser Asp
255                 260                 265                 270

GAG GCG TAC TGG GAA TCG TCT GCG GGG GGC ACG TTC ACC ATC ACG AGC      394
Glu Ala Tyr Trp Glu Ser Ser Ala Gly Gly Thr Phe Thr Ile Thr Ser
                275                 280                 285

GTG CAG GAG TCG GAC ATG AAG CGC GGC ACG AGT ACA ACG CTG CAC CTA      442
Val Gln Glu Ser Asp Met Lys Arg Gly Thr Ser Thr Thr Leu His Leu
            290                 295                 300

AAG GAG GAC CAG CAG GAG TAC CTG GAG GAG CGC CGG GTG AAG GAG CTG      490
Lys Glu Asp Gln Gln Glu Tyr Leu Glu Glu Arg Arg Val Lys Glu Leu
        305                 310                 315

ATC AAG AAG CAC TCC GAG TTC ATC GGC TAC GAC ATC GAG CTG ATG GTG      538
Ile Lys Lys His Ser Glu Phe Ile Gly Tyr Asp Ile Glu Leu Met Val
    320                 325                 330

GAG AAG ACG GCG GAG AAG GAG GTG ACG GAC GAG GAC GAG GAG GAG GAC      586
Glu Lys Thr Ala Glu Lys Glu Val Thr Asp Glu Asp Glu Glu Glu Asp
335                 340                 345                 350

GAG TCG AAG AAG AAG TCC TGC GGG GAC GAG GGC GAG CCG AAG GTG GAG      634
Glu Ser Lys Lys Lys Ser Cys Gly Asp Glu Gly Glu Pro Lys Val Glu
                355                 360                 365

GAG GTG ACG GAG GGC GGC GAG GAC AAG AAG AAG AAG ACG AAG AAG GTG      682
Glu Val Thr Glu Gly Gly Glu Asp Lys Lys Lys Thr Lys Lys Val
            370                 375                 380

AAG GAG GTG AAG AAG ACG TAC GAG GTC AAG AAC AAG CAC AAG CCG CTC      730
Lys Glu Val Lys Lys Thr Tyr Glu Val Lys Asn Lys His Lys Pro Leu
        385                 390                 395

TGG ACG CGC GAC ACG AAG GAC GTG ACG AAG GAG GAG TAC GCG GCC TTC      778
Trp Thr Arg Asp Thr Lys Asp Val Thr Lys Glu Glu Tyr Ala Ala Phe
    400                 405                 410

TAC AAG GCC ATC TCC AAC GAC TGG GAG GAC ACG GCG GCG ACG AAG CAC      826
Tyr Lys Ala Ile Ser Asn Asp Trp Glu Asp Thr Ala Ala Thr Lys His
415                 420                 425                 430

TTC TCG GTG GAG GGC CAG CTG GAG TTC CGC GCG ATC GCG TTC GTG CCG      874
Phe Ser Val Glu Gly Gln Leu Glu Phe Arg Ala Ile Ala Phe Val Pro

-continued

```
                   435                 440                 445
AAG CGC GCG CCG TTC GAC ATG TTC GAG CCG AAC AAG AAG CGC AAC AAC     922
Lys Arg Ala Pro Phe Asp Met Phe Glu Pro Asn Lys Lys Arg Asn Asn
            450                 455                 460

ATC AAG CTG TAC GTG CGC CGC GTG TTC ATC ATG GAC AAC TGC GAG GAC     970
Ile Lys Leu Tyr Val Arg Arg Val Phe Ile Met Asp Asn Cys Glu Asp
            465                 470                 475

CTG TGC CCG GAC TGG CTC GGC TTC GTG AAG GGC GTC GTG GAC AGC GAG    1018
Leu Cys Pro Asp Trp Leu Gly Phe Val Lys Gly Val Val Asp Ser Glu
            480                 485                 490

GAC CTG CCG CTG AAC ATC TCG CGC GAG AAC CTG CAG CAG AAC AAG ATC    1066
Asp Leu Pro Leu Asn Ile Ser Arg Glu Asn Leu Gln Gln Asn Lys Ile
495                 500                 505                 510

CTG AAG GTG ATC CGC AAG AAC ATC GTG AAG AAG TGC CTG GAG CTG TTC    1114
Leu Lys Val Ile Arg Lys Asn Ile Val Lys Lys Cys Leu Glu Leu Phe
            515                 520                 525

GAA GAG ATA GCG GAG AAC AAG GAG GAC TAC AAG CAG TTC TAC GAG CAG    1162
Glu Glu Ile Ala Glu Asn Lys Glu Asp Tyr Lys Gln Phe Tyr Glu Gln
            530                 535                 540

TTC GGC AAG AAC ATC AAG CTG GGC ATC CAC GAG GAC ACG GCG AAC CGC    1210
Phe Gly Lys Asn Ile Lys Leu Gly Ile His Glu Asp Thr Ala Asn Arg
            545                 550                 555

AAG AAG CTG ATG GAG TTG CTG CGC TTC TAC AGC ACC GAG TCG GGG GAG    1258
Lys Lys Leu Met Glu Leu Leu Arg Phe Tyr Ser Thr Glu Ser Gly Glu
            560                 565                 570

GAG ATG ACG ACA CTG AAG GAC TAC GTG ACG CGC ATG AAG CCG GAG CAG    1306
Glu Met Thr Thr Leu Lys Asp Tyr Val Thr Arg Met Lys Pro Glu Gln
575                 580                 585                 590

AAG TCG ATC TAC TAC ATC ACT GGC GAC AGC AAG AAG AAG CTG GAG TCG    1354
Lys Ser Ile Tyr Tyr Ile Thr Gly Asp Ser Lys Lys Lys Leu Glu Ser
            595                 600                 605

TCG CCG TTC ATC GAG AAG GCG AGA CGC TGC GGG CTC GAG GTG CTG TTC    1402
Ser Pro Phe Ile Glu Lys Ala Arg Arg Cys Gly Leu Glu Val Leu Phe
            610                 615                 620

ATG ACG GAG CCG ATC GAC GAG TAC GTG ATG CAG CAG GTG AAG GAC TTC    1450
Met Thr Glu Pro Ile Asp Glu Tyr Val Met Gln Gln Val Lys Asp Phe
            625                 630                 635

GAG GAC AAG AAG TTC GCG TGC CTG ACG AAG GAA GGC GTG CAC TTC GAG    1498
Glu Asp Lys Lys Phe Ala Cys Leu Thr Lys Glu Gly Val His Phe Glu
            640                 645                 650

GAG TCC GAG GAG GAG AAG AAG CAG CGC GAG GAG AAG AAG GCG GCG TGC    1546
Glu Ser Glu Glu Glu Lys Lys Gln Arg Glu Glu Lys Lys Ala Ala Cys
655                 660                 665                 670

GAG AAG CTG TGC AAG ACG ATG AAG GAG GTG CTG GGC GAC AAG GTG GAG    1594
Glu Lys Leu Cys Lys Thr Met Lys Glu Val Leu Gly Asp Lys Val Glu
            675                 680                 685

AAG GTG ACC GTG TCG GAG CGC CTG TTG ACG TCG CCG TGC ATC CTG GTG    1642
Lys Val Thr Val Ser Glu Arg Leu Leu Thr Ser Pro Cys Ile Leu Val
            690                 695                 700

ACG TCG GAG TTT GGG TGG TCG GCG CAC ATG GAA CAG ATC ATG CGC AAC    1690
Thr Ser Glu Phe Gly Trp Ser Ala His Met Glu Gln Ile Met Arg Asn
            705                 710                 715

CAG GCG CTG CGC GAC TCC AGC ATG GCG CAG TAC ATG GTG TCC AAG AAG    1738
Gln Ala Leu Arg Asp Ser Ser Met Ala Gln Tyr Met Val Ser Lys Lys
            720                 725                 730

ACG ATG GAG GTG AAC CCC GAC CAC CCC ATC ATC AAG GAG CTG CGC CGC    1786
Thr Met Glu Val Asn Pro Asp His Pro Ile Ile Lys Glu Leu Arg Arg
735                 740                 745                 750

CGC GTG GAG GCG GAC GAG AAC GAC AAG GCC GTG AAG GAC CTC GTC TTC    1834
```

-continued

```
                                                                          1882
Arg Val Glu Ala Asp Glu Asn Asp Lys Ala Val Lys Asp Leu Val Phe
            755                 760                 765
CTG CTC TTC GAC ACG TCG CTG CTC ACG TCC GGC TTC CAG CTG GAT GAC           1882
Leu Leu Phe Asp Thr Ser Leu Leu Thr Ser Gly Phe Gln Leu Asp Asp
            770                 775                 780

CCC ACC GGC TAC GCC GAG CGC ATC AAC CGC ATG ATC AAG CTC GGC CTG           1930
Pro Thr Gly Tyr Ala Glu Arg Ile Asn Arg Met Ile Lys Leu Gly Leu
            785                 790                 795

TCG CTC GAC GAG GAG GAG GAG GAG GTC GCC GAG GCG CCG CCG GCC GAG           1978
Ser Leu Asp Glu Glu Glu Glu Glu Val Ala Glu Ala Pro Pro Ala Glu
800                 805                 810

GCA GCC CCC GCG GAG GTC ACC GCC GGC ACC TCC AGC ATG GAG CAG GTG           2026
Ala Ala Pro Ala Glu Val Thr Ala Gly Thr Ser Ser Met Glu Gln Val
815                 820                 825                 830

GAC TGAGCCGGTA A                                                          2040
Asp
```

(2) INFORMATION FOR SEQ ID NO:6:

(i) SEQUENCE CHARACTERISTICS:
        (A) LENGTH: 656 amino acids
        (B) TYPE: amino acid
        (D) TOPOLOGY: linear (ii) MOLECULE TYPE: protein (xi) SEQUENCE DESCRIPTION: SEQ ID NO:6:

```
Ser Leu Thr Asp Pro Ala Val Leu Gly Glu Glu Thr His Leu Arg Val
1               5                   10                  15

Arg Val Val Pro Asp Lys Ala Asn Lys Thr Leu Thr Val Glu Asp Asn
                20                  25                  30

Gly Ile Gly Met Thr Lys Ala Asp Leu Val Asn Asn Leu Gly Thr Ile
            35                  40                  45

Ala Arg Ser Gly Thr Lys Ala Phe Met Glu Ala Leu Glu Ala Gly Gly
        50                  55                  60

Asp Met Ser Met Ile Gly Gln Phe Gly Val Gly Phe Tyr Ser Ala Tyr
65                  70                  75                  80

Leu Val Ala Asp Arg Val Thr Val Val Ser Lys Asn Asn Ser Asp Glu
                85                  90                  95

Ala Tyr Trp Glu Ser Ser Ala Gly Gly Thr Phe Thr Ile Thr Ser Val
            100                 105                 110

Gln Glu Ser Asp Met Lys Arg Gly Thr Ser Thr Thr Leu His Leu Lys
        115                 120                 125

Glu Asp Gln Gln Glu Tyr Leu Glu Glu Arg Arg Val Lys Glu Leu Ile
130                 135                 140

Lys Lys His Ser Glu Phe Ile Gly Tyr Asp Ile Glu Leu Met Val Glu
145                 150                 155                 160

Lys Thr Ala Glu Lys Glu Val Thr Asp Glu Asp Glu Glu Glu Asp Glu
                165                 170                 175

Ser Lys Lys Lys Ser Cys Gly Asp Glu Gly Glu Pro Lys Val Glu Glu
            180                 185                 190

Val Thr Glu Gly Gly Glu Asp Lys Lys Lys Thr Lys Lys Val Lys
        195                 200                 205

Glu Val Lys Lys Thr Tyr Glu Val Lys Asn Lys His Lys Pro Leu Trp
210                 215                 220

Thr Arg Asp Thr Lys Asp Val Thr Lys Glu Glu Tyr Ala Ala Phe Tyr
225                 230                 235                 240
```

-continued

```
Lys Ala Ile Ser Asn Asp Trp Glu Asp Thr Ala Ala Thr Lys His Phe
            245                 250                 255

Ser Val Glu Gly Gln Leu Glu Phe Arg Ala Ile Ala Phe Val Pro Lys
        260                 265                 270

Arg Ala Pro Phe Asp Met Phe Glu Pro Asn Lys Lys Arg Asn Asn Ile
        275                 280                 285

Lys Leu Tyr Val Arg Arg Val Phe Ile Met Asp Asn Cys Glu Asp Leu
        290                 295                 300

Cys Pro Asp Trp Leu Gly Phe Val Lys Gly Val Val Asp Ser Glu Asp
305                 310                 315                 320

Leu Pro Leu Asn Ile Ser Arg Glu Asn Leu Gln Gln Asn Lys Ile Leu
                325                 330                 335

Lys Val Ile Arg Lys Asn Ile Val Lys Lys Cys Leu Glu Leu Phe Glu
                340                 345                 350

Glu Ile Ala Glu Asn Lys Glu Asp Tyr Lys Gln Phe Tyr Glu Gln Phe
            355                 360                 365

Gly Lys Asn Ile Lys Leu Gly Ile His Glu Asp Thr Ala Asn Arg Lys
        370                 375                 380

Lys Leu Met Glu Leu Leu Arg Phe Tyr Ser Thr Glu Ser Gly Glu Glu
385                 390                 395                 400

Met Thr Thr Leu Lys Asp Tyr Val Thr Arg Met Lys Pro Glu Gln Lys
                405                 410                 415

Ser Ile Tyr Tyr Ile Thr Gly Asp Ser Lys Lys Lys Leu Glu Ser Ser
                420                 425                 430

Pro Phe Ile Glu Lys Ala Arg Arg Cys Gly Leu Glu Val Leu Phe Met
            435                 440                 445

Thr Glu Pro Ile Asp Glu Tyr Val Met Gln Gln Val Lys Asp Phe Glu
        450                 455                 460

Asp Lys Lys Phe Ala Cys Leu Thr Lys Glu Gly Val His Phe Glu Glu
465                 470                 475                 480

Ser Glu Glu Glu Lys Lys Gln Arg Glu Glu Lys Lys Ala Ala Cys Glu
                485                 490                 495

Lys Leu Cys Lys Thr Met Lys Glu Val Leu Gly Asp Lys Val Glu Lys
            500                 505                 510

Val Thr Val Ser Glu Arg Leu Leu Thr Ser Pro Cys Ile Leu Val Thr
        515                 520                 525

Ser Glu Phe Gly Trp Ser Ala His Met Glu Gln Ile Met Arg Asn Gln
        530                 535                 540

Ala Leu Arg Asp Ser Ser Met Ala Gln Tyr Met Val Ser Lys Lys Thr
545                 550                 555                 560

Met Glu Val Asn Pro Asp His Pro Ile Ile Lys Glu Leu Arg Arg Arg
                565                 570                 575

Val Glu Ala Asp Glu Asn Asp Lys Ala Val Lys Asp Leu Val Phe Leu
                580                 585                 590

Leu Phe Asp Thr Ser Leu Leu Thr Ser Gly Phe Gln Leu Asp Asp Pro
            595                 600                 605

Thr Gly Tyr Ala Glu Arg Ile Asn Arg Met Ile Lys Leu Gly Leu Ser
        610                 615                 620

Leu Asp Glu Glu Glu Glu Val Ala Glu Ala Pro Ala Glu Ala
625                 630                 635                 640

Ala Pro Ala Glu Val Thr Ala Gly Thr Ser Ser Met Glu Gln Val Asp
                645                 650                 655
```

(2) INFORMATION FOR SEQ ID NO:7:

(i) SEQUENCE CHARACTERISTICS:
        (A) LENGTH: 1771 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1698

(xi) SEQUENCE DESCRIPTION: SEQ ID NO:7:

```
CAG GCC CGC GTC CAG GCC CTC GAG GAG GCA GCG CGT CTC CGC GCG GAG       48
Gln Ala Arg Val Gln Ala Leu Glu Glu Ala Ala Arg Leu Arg Ala Glu
 1               5                  10                  15

CTG GAG GCG GCC GAG GAG GCG GCC CGC CTG GAT GTC ATG CAT GCG GCC       96
Leu Glu Ala Ala Glu Glu Ala Ala Arg Leu Asp Val Met His Ala Ala
            20                  25                  30

GAG CAG GCC CGT GTC CAG GCC CTC GAG GAG GCA GCG CGT CTC CGC GCG      144
Glu Gln Ala Arg Val Gln Ala Leu Glu Glu Ala Ala Arg Leu Arg Ala
        35                  40                  45

GAG CTG GAG GAG GCC GAG GAG GCG GCC CGC CTG GAT GTC ATG CAT GCG      192
Glu Leu Glu Glu Ala Glu Glu Ala Ala Arg Leu Asp Val Met His Ala
    50                  55                  60

GCC GAG CAG GCC CGC GTC CAG GCC CTC GAG GAG GCA GCG CGT CTC CGC      240
Ala Glu Gln Ala Arg Val Gln Ala Leu Glu Glu Ala Ala Arg Leu Arg
65                  70                  75                  80

GCG GAG CTG GAG GCT GCC GAG GAG GCG GCG CGC CTG GAG GCC ATG CAC      288
Ala Glu Leu Glu Ala Ala Glu Glu Ala Ala Arg Leu Glu Ala Met His
                85                  90                  95

GAG GCC GAG CAG GCC CGC TCC CAG GCC CTC GAG GAG GCA GCG CGT CTC      336
Glu Ala Glu Gln Ala Arg Ser Gln Ala Leu Glu Glu Ala Ala Arg Leu
            100                 105                 110

CGC GCG GAG CTG GAG GAA GCC GAG GAG GCG GCC CGC CTG GAT GTC ATG      384
Arg Ala Glu Leu Glu Glu Ala Glu Glu Ala Ala Arg Leu Asp Val Met
        115                 120                 125

CAT GCG GCC GAG CAG GCC CGC GTC CAG GCC CTC GAG GAG GCA GCG CGT      432
His Ala Ala Glu Gln Ala Arg Val Gln Ala Leu Glu Glu Ala Ala Arg
    130                 135                 140

CTC CGC GCG GAG CTG GAG GAG GCC GAG GAG GCG GCC CGC CTG GAG GCC      480
Leu Arg Ala Glu Leu Glu Glu Ala Glu Glu Ala Ala Arg Leu Glu Ala
145                 150                 155                 160

ATG CAC GAG GCC GAG CAG GCC CGC TCC CAG GCC CTC GAG GAG GCA GCG      528
Met His Glu Ala Glu Gln Ala Arg Ser Gln Ala Leu Glu Glu Ala Ala
                165                 170                 175

CGT CTC CGC GCG GAG CTG GAG GCG GCC GAG GAG GCG GCC CGC CTG GAT      576
Arg Leu Arg Ala Glu Leu Glu Ala Ala Glu Glu Ala Ala Arg Leu Asp
            180                 185                 190

GTC ATG CAC GAG GCC GAG CAG GCC CGT GTC CAG GCC CTC GAG GAG GCG      624
Val Met His Glu Ala Glu Gln Ala Arg Val Gln Ala Leu Glu Glu Ala
        195                 200                 205

GCG CGC CTG GAT GTC ATG CAC GAG GCC GAG CAG GCC CGC GTC CAG GCC      672
Ala Arg Leu Asp Val Met His Glu Ala Glu Gln Ala Arg Val Gln Ala
    210                 215                 220

CTC GAG GAG GCA GCG CGT CTC CGC GCG GAG CTG GAG GCG GCC GAG GAG      720
Leu Glu Glu Ala Ala Arg Leu Arg Ala Glu Leu Glu Ala Ala Glu Glu
225                 230                 235                 240

GCG GCC CGC CTG GAT GTC ATG CAC GAG GCC GAG CAG GCC CGC GTC CAG      768
Ala Ala Arg Leu Asp Val Met His Glu Ala Glu Gln Ala Arg Val Gln
                245                 250                 255

GCC CTC GAG GAG GCA GCG CGT CTC CGC GCG GAG CTG GAG GCG GCC GAG      816
```

```
                Ala Leu Glu Glu Ala Ala Arg Leu Arg Ala Glu Leu Glu Ala Ala Glu
                                260                 265                 270

GAG GCG GCC CGC CTG GAT GTC ATG CAC GAG GGC GAG CAG GCC CGT GTC                    864
Glu Ala Ala Arg Leu Asp Val Met His Glu Gly Glu Gln Ala Arg Val
            275                 280                 285

CAG GCC CTC GAG GAG GCG GCC CGC CTG GAG GCC ATG CAC GAG GCC GAG                    912
Gln Ala Leu Glu Glu Ala Ala Arg Leu Glu Ala Met His Glu Ala Glu
        290                 295                 300

CAG GCC CGC TCC CAG GCC CTC GAG GAG GCA GCG CGT CTC TGC GCG GAG                    960
Gln Ala Arg Ser Gln Ala Leu Glu Glu Ala Ala Arg Leu Cys Ala Glu
305                 310                 315                 320

CTG GAG GCT GAG GAG GAG GAA AAA GAT GAG CGG CCG GCG ACG TCG AGC                   1008
Leu Glu Ala Glu Glu Glu Lys Asp Glu Arg Pro Ala Thr Ser Ser
                325                 330                 335

TAC AGC GAG GAG TGC AAA GGG CGA CTG CTA TCG AGG GCG CGG CCG GAT                   1056
Tyr Ser Glu Glu Cys Lys Gly Arg Leu Leu Ser Arg Ala Arg Pro Asp
            340                 345                 350

CCG CGG AGG CCG CTG CCG CGG CCG TTC ATT GGG ATG TCA CTG TTG GAG                   1104
Pro Arg Arg Pro Leu Pro Arg Pro Phe Ile Gly Met Ser Leu Leu Glu
        355                 360                 365

GAT GTG GAG AAG AGT ATT CTC ATT GTG GAC GGG CTC TAC AGG GAT GGG                   1152
Asp Val Glu Lys Ser Ile Leu Ile Val Asp Gly Leu Tyr Arg Asp Gly
    370                 375                 380

CCG GCG TAC CAG ACG GGC ATC CGC CTC GGG GAT GTC CTC TTG CGT ATC                   1200
Pro Ala Tyr Gln Thr Gly Ile Arg Leu Gly Asp Val Leu Leu Arg Ile
385                 390                 395                 400

GCG GGG GTT TAC GTG GAT TCA ATA GCG AAG GCG AGG CAG GTG GTC GAT                   1248
Ala Gly Val Tyr Val Asp Ser Ile Ala Lys Ala Arg Gln Val Val Asp
                405                 410                 415

GCG CGT TGC CGC TGC GGC TGC GTC GTT CCC GTG ACG CTG GCG ACG AAG                   1296
Ala Arg Cys Arg Cys Gly Cys Val Val Pro Val Thr Leu Ala Thr Lys
            420                 425                 430

ATG AAC CAG CAG TAC AGC GTG GCT CTG TAT ATC ATG ACG GTG GAT CCG                   1344
Met Asn Gln Gln Tyr Ser Val Ala Leu Tyr Ile Met Thr Val Asp Pro
        435                 440                 445

CAG CAC AAC GAC AAG CCC TTT TTT TTT GAT GTG CAC ATC CAC CAC CGC                   1392
Gln His Asn Asp Lys Pro Phe Phe Phe Asp Val His Ile His His Arg
    450                 455                 460

ATC GAG AGC TCG CAC ATG GGG AAG AAG GCG CAG TGG ATG GAA GTT CTT                   1440
Ile Glu Ser Ser His Met Gly Lys Lys Ala Gln Trp Met Glu Val Leu
465                 470                 475                 480

GAG AGC CCA TCC GTA TCT TCG GCT GCC ACC ACC CCT CTC GTG CCG CTC                   1488
Glu Ser Pro Ser Val Ser Ser Ala Ala Thr Thr Pro Leu Val Pro Leu
                485                 490                 495

TTG CGT GAG CCG ACG CCG CGT AGG GGC TCA GAG CTG CAG TCA AGT GCT                   1536
Leu Arg Glu Pro Thr Pro Arg Arg Gly Ser Glu Leu Gln Ser Ser Ala
            500                 505                 510

CGT TCC GCC TTC GTT GCC ACG TCT TAC TTC TCG AGC GCG CGC AGG TCG                   1584
Arg Ser Ala Phe Val Ala Thr Ser Tyr Phe Ser Ser Ala Arg Arg Ser
        515                 520                 525

GTC AGC TCA GAA AGT GAG CGA CCG CGC GGG TCC TCT AGC GTG GCT ATG                   1632
Val Ser Ser Glu Ser Glu Arg Pro Arg Gly Ser Ser Ser Val Ala Met
    530                 535                 540

GCG GAG GAG GCG ATC GCG CTG GCG CCG CAA GGG TAT ACC CCA CCC AAC                   1680
Ala Glu Glu Ala Ile Ala Leu Ala Pro Gln Gly Tyr Thr Pro Pro Asn
545                 550                 555                 560

CAA GTG CGC GGC CGT AGT TGACGTCTCT GTGTGAGTGT GTGTCGCTCC                          1728
Gln Val Arg Gly Arg Ser
                565
```

GTCTCCTTCC TTTTTCGTCA TGTGTTTTAT TCATTTCTTT TTC    1771

(2) INFORMATION FOR SEQ ID NO:8:

(i) SEQUENCE CHARACTERISTICS:
      (A) LENGTH: 566 amino acids
      (B) TYPE: amino acid
      (D) TOPOLOGY: linear (ii) MOLECULE TYPE: protein (xi) SEQUENCE DESCRIPTION: SEQ ID NO:8:

Gln Ala Arg Val Gln Ala Leu Glu Glu Ala Ala Arg Leu Arg Ala Glu
 1               5                  10                  15

Leu Glu Ala Ala Glu Glu Ala Ala Arg Leu Asp Val Met His Ala Ala
            20                  25                  30

Glu Gln Ala Arg Val Gln Ala Leu Glu Glu Ala Ala Arg Leu Arg Ala
        35                  40                  45

Glu Leu Glu Glu Ala Glu Glu Ala Ala Arg Leu Asp Val Met His Ala
    50                  55                  60

Ala Glu Gln Ala Arg Val Gln Ala Leu Glu Glu Ala Ala Arg Leu Arg
65                  70                  75                  80

Ala Glu Leu Glu Ala Ala Glu Glu Ala Ala Arg Leu Glu Ala Met His
                85                  90                  95

Glu Ala Glu Gln Ala Arg Ser Gln Ala Leu Glu Glu Ala Ala Arg Leu
            100                 105                 110

Arg Ala Glu Leu Glu Glu Ala Glu Glu Ala Ala Arg Leu Asp Val Met
        115                 120                 125

His Ala Ala Glu Gln Ala Arg Val Gln Ala Leu Glu Glu Ala Ala Arg
    130                 135                 140

Leu Arg Ala Glu Leu Glu Glu Ala Glu Glu Ala Ala Arg Leu Glu Ala
145                 150                 155                 160

Met His Glu Ala Glu Gln Ala Arg Ser Gln Ala Leu Glu Glu Ala Ala
                165                 170                 175

Arg Leu Arg Ala Glu Leu Glu Ala Ala Glu Glu Ala Ala Arg Leu Asp
            180                 185                 190

Val Met His Glu Ala Glu Gln Ala Arg Val Gln Ala Leu Glu Glu Ala
        195                 200                 205

Ala Arg Leu Asp Val Met His Glu Ala Glu Gln Ala Arg Val Gln Ala
    210                 215                 220

Leu Glu Glu Ala Ala Arg Leu Arg Ala Glu Leu Glu Ala Ala Glu Glu
225                 230                 235                 240

Ala Ala Arg Leu Asp Val Met His Glu Ala Glu Gln Ala Arg Val Gln
                245                 250                 255

Ala Leu Glu Glu Ala Ala Arg Leu Arg Ala Glu Leu Glu Ala Ala Glu
            260                 265                 270

Glu Ala Ala Arg Leu Asp Val Met His Glu Gly Glu Gln Ala Arg Val
        275                 280                 285

Gln Ala Leu Glu Glu Ala Ala Arg Leu Glu Ala Met His Glu Ala Glu
    290                 295                 300

Gln Ala Arg Ser Gln Ala Leu Glu Glu Ala Ala Arg Leu Cys Ala Glu
305                 310                 315                 320

Leu Glu Ala Glu Glu Glu Glu Lys Asp Glu Arg Pro Ala Thr Ser Ser
                325                 330                 335

Tyr Ser Glu Glu Cys Lys Gly Arg Leu Leu Ser Arg Ala Arg Pro Asp
            340                 345                 350

```
Pro Arg Arg Pro Leu Pro Arg Pro Phe Ile Gly Met Ser Leu Leu Glu
        355                 360                 365
Asp Val Glu Lys Ser Ile Leu Ile Val Asp Gly Leu Tyr Arg Asp Gly
        370                 375                 380
Pro Ala Tyr Gln Thr Gly Ile Arg Leu Gly Asp Val Leu Leu Arg Ile
385                 390                 395                 400
Ala Gly Val Tyr Val Asp Ser Ile Ala Lys Ala Arg Gln Val Val Asp
                405                 410                 415
Ala Arg Cys Arg Cys Gly Cys Val Val Pro Val Thr Leu Ala Thr Lys
            420                 425                 430
Met Asn Gln Gln Tyr Ser Val Ala Leu Tyr Ile Met Thr Val Asp Pro
        435                 440                 445
Gln His Asn Asp Lys Pro Phe Phe Asp Val His Ile His His Arg
    450                 455                 460
Ile Glu Ser Ser His Met Gly Lys Lys Ala Gln Trp Met Glu Val Leu
465                 470                 475                 480
Glu Ser Pro Ser Val Ser Ser Ala Ala Thr Thr Pro Leu Val Pro Leu
                485                 490                 495
Leu Arg Glu Pro Thr Pro Arg Arg Gly Ser Glu Leu Gln Ser Ser Ala
            500                 505                 510
Arg Ser Ala Phe Val Ala Thr Ser Tyr Phe Ser Ser Ala Arg Arg Ser
        515                 520                 525
Val Ser Ser Glu Ser Glu Arg Pro Arg Gly Ser Ser Val Ala Met
        530                 535                 540
Ala Glu Glu Ala Ile Ala Leu Ala Pro Gln Gly Tyr Thr Pro Asn
545                 550                 555                 560
Gln Val Arg Gly Arg Ser
                565
```

(2) INFORMATION FOR SEQ ID NO:9:

(i) SEQUENCE CHARACTERISTICS:
        (A) LENGTH: 1618 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 115..1323

(xi) SEQUENCE DESCRIPTION: SEQ ID NO:9:

```
CCACTCTCTC GGTCGTCTGT CTCCCACGCG CGCACGCAGT TGATTTCCGC CTTCTTAAAC      60

GCTCTCTTTT TTTTTATTTT TCACCTGACC AACCGCACCA CGTCGGCCTC CATC ATG       117
                                                             Met
                                                               1

TCG CAG CAA GAC CGA GTT GCC CCA CAG GAC CAG GAC TCG TTC CTC GAC       165
Ser Gln Gln Asp Arg Val Ala Pro Gln Asp Gln Asp Ser Phe Leu Asp
         5                  10                  15

GAC CAG CCC GGC GTC CGC CCG ATC CCG TCC TTC GAT GAC ATG CCG TTG       213
Asp Gln Pro Gly Val Arg Pro Ile Pro Ser Phe Asp Asp Met Pro Leu
     20                  25                  30

CAC CAG AAC CTT CTG CGC GGC ATC TAC TCG TAC GGC TTC GAG AAA CCG       261
His Gln Asn Leu Leu Arg Gly Ile Tyr Ser Tyr Gly Phe Glu Lys Pro
 35                  40                  45

TCC AGC ATC CAG CAG CGC GCC ATC GCC CCC TTC ACG CGC GGC GGC GAC       309
```

-continued

| | |
|---|---|
| Ser Ser Ile Gln Gln Arg Ala Ile Ala Pro Phe Thr Arg Gly Gly Asp<br>50                              55                        60                        65 | |
| ATC ATC GCG CAG GCG CAG TCC GGT ACC GGC AAG ACG GGC GCC TTC TCC<br>Ile Ile Ala Gln Ala Gln Ser Gly Thr Gly Lys Thr Gly Ala Phe Ser<br>                   70                        75                        80 | 357 |
| ATC GGC CTG CTG CAG CGC CTG GAC TTC CGC CAC AAC CTG ATC CAG GGC<br>Ile Gly Leu Leu Gln Arg Leu Asp Phe Arg His Asn Leu Ile Gln Gly<br>                85                       90                        95 | 405 |
| CTC GTG CTC TCC CCG ACC CGC GAG CTG GCC CTG CAG ACG GCG GAG GTG<br>Leu Val Leu Ser Pro Thr Arg Glu Leu Ala Leu Gln Thr Ala Glu Val<br>         100                    105                    110 | 453 |
| ATC AGC CGC ATC GGC GAG TTC CTG TCG AAC AGC GCG AAG TTC TGT GAG<br>Ile Ser Arg Ile Gly Glu Phe Leu Ser Asn Ser Ala Lys Phe Cys Glu<br>115                            120                    125 | 501 |
| ACC TTT GTG GGT GGC ACG CGC GTG CAG GAT GAC CTG CGC AAG CTG CAG<br>Thr Phe Val Gly Gly Thr Arg Val Gln Asp Asp Leu Arg Lys Leu Gln<br>130                            135                    140                    145 | 549 |
| GCT GGC GTC GTC GTC GCC GTG GGG ACG CCG GGC CGC GTG TCC GAC GTG<br>Ala Gly Val Val Val Ala Val Gly Thr Pro Gly Arg Val Ser Asp Val<br>                   150                    155                    160 | 597 |
| ATC AAG CGC GGC GCG CTG CGC ACC GAG TCC CTG CGC GTG CTG GTG CTC<br>Ile Lys Arg Gly Ala Leu Arg Thr Glu Ser Leu Arg Val Leu Val Leu<br>         165                    170                    175 | 645 |
| GAC GAG GCT GAT GAG ATG CTG TCT CAG GGC TTC GCG GAT CAG ATT TAC<br>Asp Glu Ala Asp Glu Met Leu Ser Gln Gly Phe Ala Asp Gln Ile Tyr<br>         180                    185                    190 | 693 |
| GAG ATC TTC CGC TTC CTG CCG AAG GAC ATC CAG GTC GCG CTC TTC TCC<br>Glu Ile Phe Arg Phe Leu Pro Lys Asp Ile Gln Val Ala Leu Phe Ser<br>195                            200                    205 | 741 |
| GCC ACG ATG CCG GAG GAG GTG CTG GAG CTG ACA AAG AAG TTC ATG CGC<br>Ala Thr Met Pro Glu Glu Val Leu Glu Leu Thr Lys Lys Phe Met Arg<br>210                            215                    220                    225 | 789 |
| GAC CCC GTA CGC ATT CTC GTG AAG CGC GAG AGC CTG ACG CTG GAG GGC<br>Asp Pro Val Arg Ile Leu Val Lys Arg Glu Ser Leu Thr Leu Glu Gly<br>                   230                    235                    240 | 837 |
| ATC AAG CAG TTC TTC ATC GCC GTC GAG GAG GAG CAC AAG CTG GAC ACG<br>Ile Lys Gln Phe Phe Ile Ala Val Glu Glu Glu His Lys Leu Asp Thr<br>         245                    250                    255 | 885 |
| CTG ATG GAC CTG TAC GAG ACC GTG TCC ATC GCG CAG TCC GTC ATC TTC<br>Leu Met Asp Leu Tyr Glu Thr Val Ser Ile Ala Gln Ser Val Ile Phe<br>260                            265                    270 | 933 |
| GCC AAC ACC CGC CGC AAG GTG GAC TGG ATC GCC GAG AAG CTG AAT CAG<br>Ala Asn Thr Arg Arg Lys Val Asp Trp Ile Ala Glu Lys Leu Asn Gln<br>275                            280                    285 | 981 |
| AGC AAC CAC ACC GTC AGC AGC ATG CAC GCC GAG ATG CCC AAG AGC GAC<br>Ser Asn His Thr Val Ser Ser Met His Ala Glu Met Pro Lys Ser Asp<br>290                            295                    300                    305 | 1029 |
| CGC GAG CGC GTC ATG AAC ACC TTC CGC AGC GGC AGC TCC CGC GTG CTC<br>Arg Glu Arg Val Met Asn Thr Phe Arg Ser Gly Ser Ser Arg Val Leu<br>         310                    315                    320 | 1077 |
| GTA ACG ACC GAC CTC GTG GCC CGC GGC ATC GAC GTG CAC CAC GTG AAC<br>Val Thr Thr Asp Leu Val Ala Arg Gly Ile Asp Val His His Val Asn<br>         325                    330                    335 | 1125 |
| ATC GTC ATC AAC TTC GAC CTG CCG ACG AAC AAG GAG AAC TAC CTG CAC<br>Ile Val Ile Asn Phe Asp Leu Pro Thr Asn Lys Glu Asn Tyr Leu His<br>         340                    345                    350 | 1173 |
| CGC ATT GGC CGC GGC GGC CGC TAC GGC GTA AAG GGT GTT GCC ATC AAC<br>Arg Ile Gly Arg Gly Gly Arg Tyr Gly Val Lys Gly Val Ala Ile Asn<br>355                            360                    365 | 1221 |

```
TTC GTG ACG GAG AAA GAC GTG GAG CTG CTG CAC GAG ATC GAG GGG CAC    1269
Phe Val Thr Glu Lys Asp Val Glu Leu Leu His Glu Ile Glu Gly His
370                 375                 380                 385

TAC CAC ACG CAG ATC GAT GAG CTC CCG GTG GAC TTT GCC GCC TAC CTC    1317
Tyr His Thr Gln Ile Asp Glu Leu Pro Val Asp Phe Ala Ala Tyr Leu
                390                 395                 400

GGC GAG TGA GCGGGCCCCT GCCCCCCTTC CCTGCCCCCC TCTCGCGACG            1366
Gly Glu

AGAGAACGCA CATCGTAACA CAGCCACGCG AACGATAGTA AGGGCGTGCG GCGGCGTTCC   1426

CCTCCTCCTG CCAGCGGCCC CCCTCCGCAG CGCTTCTCTT TGAGAGGGG GGCAGGGGGA    1486

GGCGCTGCGC CTGGCTGGAT GTGTGCTTGA GCTTGCATTC CGTCAAGCAA GTGCTTTGTT   1546

TTAATTATGC GCGCCGTTTT GTTGCTCGTC CCTTTCGTTG GTGTTTTTTC GGCCGAAACG   1606

GCGTTTAAAG CA                                                      1618

(2) INFORMATION FOR SEQ ID NO:10:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO:10:

Met Ser Gln Gln Asp Arg Val Ala Pro Gln Asp Gln Asp Ser Phe Leu
1               5                   10                  15

Asp Asp Gln Pro Gly Val Arg Pro Ile Pro Ser Phe Asp Asp Met Pro
                20                  25                  30

Leu His Gln Asn Leu Leu Arg Gly Ile Tyr Ser Tyr Gly Phe Glu Lys
            35                  40                  45

Pro Ser Ser Ile Gln Gln Arg Ala Ile Ala Pro Phe Thr Arg Gly Gly
        50                  55                  60

Asp Ile Ile Ala Gln Ala Gln Ser Gly Thr Gly Lys Thr Gly Ala Phe
65                  70                  75                  80

Ser Ile Gly Leu Leu Gln Arg Leu Asp Phe Arg His Asn Leu Ile Gln
                85                  90                  95

Gly Leu Val Leu Ser Pro Thr Arg Glu Leu Ala Leu Gln Thr Ala Glu
            100                 105                 110

Val Ile Ser Arg Ile Gly Glu Phe Leu Ser Asn Ser Ala Lys Phe Cys
        115                 120                 125

Glu Thr Phe Val Gly Gly Thr Arg Val Gln Asp Asp Leu Arg Lys Leu
    130                 135                 140

Gln Ala Gly Val Val Val Ala Val Gly Thr Pro Gly Arg Val Ser Asp
145                 150                 155                 160

Val Ile Lys Arg Gly Ala Leu Arg Thr Glu Ser Leu Arg Val Leu Val
                165                 170                 175

Leu Asp Glu Ala Asp Glu Met Leu Ser Gln Gly Phe Ala Asp Gln Ile
            180                 185                 190

Tyr Glu Ile Phe Arg Phe Leu Pro Lys Asp Ile Gln Val Ala Leu Phe
        195                 200                 205

Ser Ala Thr Met Pro Glu Glu Val Leu Glu Leu Thr Lys Lys Phe Met
    210                 215                 220

Arg Asp Pro Val Arg Ile Leu Val Lys Arg Glu Ser Leu Thr Leu Glu
225                 230                 235                 240

Gly Ile Lys Gln Phe Phe Ile Ala Val Glu Glu Glu His Lys Leu Asp
```

```
                        245                 250                 255
Thr Leu Met Asp Leu Tyr Glu Thr Val Ser Ile Ala Gln Ser Val Ile
                260                 265                 270

Phe Ala Asn Thr Arg Arg Lys Val Asp Trp Ile Ala Glu Lys Leu Asn
                275                 280                 285

Gln Ser Asn His Thr Val Ser Ser Met His Ala Glu Met Pro Lys Ser
                290                 295                 300

Asp Arg Glu Arg Val Met Asn Thr Phe Arg Ser Gly Ser Ser Arg Val
305                 310                 315                 320

Leu Val Thr Thr Asp Leu Val Ala Arg Gly Ile Asp Val His His Val
                325                 330                 335

Asn Ile Val Ile Asn Phe Asp Leu Pro Thr Asn Lys Glu Asn Tyr Leu
                340                 345                 350

His Arg Ile Gly Arg Gly Gly Arg Tyr Gly Val Lys Gly Val Ala Ile
                355                 360                 365

Asn Phe Val Thr Glu Lys Asp Val Glu Leu Leu His Glu Ile Glu Gly
                370                 375                 380

His Tyr His Thr Gln Ile Asp Glu Leu Pro Val Asp Phe Ala Ala Tyr
385                 390                 395                 400

Leu Gly Glu
```

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 6
        (D) OTHER INFORMATION: /note= "Where Xaa is either a Leu
            or Lys Residue"

(xi) SEQUENCE DESCRIPTION: SEQ ID NO:11:

```
Xaa Gln Xaa Pro Gln Xaa Val Phe Asp Glu Xaa Xaa
1               5                   10
```

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: -
        (B) LOCATION: 11
        (D) OTHER INFORMATION: /note= "Where n is inosine"

(ix) FEATURE:
        (A) NAME/KEY: -
        (B) LOCATION: 17
        (D) OTHER INFORMATION: /note= "Where n is inosine"

(ix) FEATURE:
        (A) NAME/KEY: -
        (B) LOCATION: 20
        (D) OTHER INFORMATION: /note= "Where n is inosine"

(xi) SEQUENCE DESCRIPTION: SEQ ID NO:12:

```
GGAATTCCCC NCAGCTNGTN TTCGAC                                       26
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:13:

```
Lys Val Phe Asp Glu
1               5
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:14:

```
GGATCCATGG TCAAGTCCCA CTACATCTGC                              30
```

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:15:

```
GAATTCAGAC CGGATAGAAA TAAGCCAATG AAA                          33
```

(2) INFORMATION FOR SEQ ID NO:16:

(i) SEQUENCE CHARACTERISTICS:
        (A) LENGTH: 701 amino acids
        (B) TYPE: amino acid
        (C) STRANDEDNESS:
        (D) TOPOLOGY: linear (xi) SEQUENCE DESCRIPTION: SEQ ID NO:16:

```
Met Thr Glu Thr Phe Ala Phe Gln Ala Glu Ile Asn Gln Leu Met Ser
1               5                   10                  15

Leu Ile Ile Asn Thr Phe Tyr Ser Asn Lys Glu Ile Phe Leu Arg Asp
                20                  25                  30

Val Ile Ser Asn Ala Ser Asp Ala Cys Asp Lys Ile Arg Tyr Gln Ser
            35                  40                  45

Leu Thr Asp Pro Ala Val Leu Gly Asp Ala Thr Arg Leu Cys Val Arg
        50                  55                  60

Val Val Pro Asp Lys Glu Asn Lys Thr Leu Thr Val Glu Asp Asn Gly
65                  70                  75                  80

Ile Gly Met Thr Lys Ala Asp Leu Val Asn Asn Leu Gly Thr Ile Ala
                85                  90                  95

Arg Ser Gly Thr Lys Ala Phe Met Glu Ala Leu Glu Ala Gly Ala Asp
                100                 105                 110

Met Ser Met Ile Gly Gln Phe Gly Val Gly Phe Tyr Ser Ala Tyr Leu
            115                 120                 125

Val Ala Asp Arg Val Thr Val Thr Ser Lys Asn Asn Ser Asp Glu Val
        130                 135                 140

Tyr Val Trp Glu Ser Ser Ala Gly Gly Thr Phe Thr Ile Thr Ser Ala
```

```
145                 150                 155                 160
Pro Glu Ser Asp Met Lys Leu Pro Ala Arg Ile Thr Leu His Leu Lys
                165                 170                 175
Glu Asp Gln Leu Glu Tyr Leu Glu Ala Arg Arg Leu Lys Glu Leu Ile
                180                 185                 190
Lys Lys His Ser Glu Phe Ile Gly Tyr Asp Ile Glu Leu Met Val Glu
                195                 200                 205
Lys Thr Thr Glu Lys Glu Val Thr Asp Glu Asp Glu Glu Ala Lys
210                 215                 220
Lys Ala Asp Glu Asp Gly Glu Glu Pro Lys Val Glu Glu Val Thr Glu
225                 230                 235                 240
Gly Glu Glu Asp Lys Lys Lys Thr Lys Lys Val Lys Glu Val Thr
                245                 250                 255
Lys Glu Tyr Glu Val Gln Asn Lys His Lys Pro Leu Trp Thr Arg Asp
                260                 265                 270
Pro Lys Asp Val Thr Lys Glu Tyr Ala Ala Phe Tyr Lys Ala Ile
                275                 280                 285
Ser Asn Asp Trp Glu Asp Pro Pro Ala Thr Lys His Phe Ser Val Glu
                290                 295                 300
Gly Gln Leu Glu Phe Arg Ala Ile Met Phe Val Pro Lys Arg Ala Pro
305                 310                 315                 320
Phe Asp Met Leu Glu Pro Asn Lys Lys Arg Asn Asn Ile Lys Leu Tyr
                325                 330                 335
Val Arg Arg Val Phe Ile Met Asp Asn Cys Glu Asp Leu Cys Pro Asp
                340                 345                 350
Trp Leu Gly Phe Val Lys Gly Val Val Asp Ser Glu Asp Leu Pro Leu
                355                 360                 365
Asn Ile Ser Arg Glu Asn Leu Gln Gln Asn Lys Ile Leu Lys Val Ile
                370                 375                 380
Arg Lys Asn Ile Val Lys Lys Cys Leu Glu Met Phe Glu Glu Val Ala
385                 390                 395                 400
Glu Asn Lys Glu Asp Tyr Lys Gln Phe Tyr Glu Gln Phe Gly Lys Asn
                405                 410                 415
Ile Lys Leu Gly Ile His Glu Asp Thr Ala Asn Arg Lys Lys Leu Met
                420                 425                 430
Glu Leu Leu Arg Phe Tyr Ser Thr Glu Ser Gly Glu Val Met Thr Thr
                435                 440                 445
Leu Lys Asp Tyr Val Thr Arg Met Lys Ala Glu Gln Asn Ser Ile Tyr
                450                 455                 460
Tyr Ile Thr Gly Asp Ser Lys Lys Leu Glu Ser Ser Pro Phe Ile
465                 470                 475                 480
Glu Gln Ala Lys Arg Arg Gly Phe Glu Val Leu Phe Met Thr Glu Pro
                485                 490                 495
Tyr Asp Glu Tyr Val Met Gln Gln Val Lys Asp Phe Glu Asp Lys Lys
                500                 505                 510
Phe Ala Cys Leu Thr Lys Glu Gly Val His Phe Glu Glu Ser Glu Glu
                515                 520                 525
Glu Lys Lys Gln Arg Glu Glu Glu Lys Ala Thr Cys Glu Lys Leu Cys
                530                 535                 540
Lys Thr Met Lys Glu Val Leu Gly Asp Lys Val Glu Lys Val Thr Val
545                 550                 555                 560
Ser Glu Arg Leu Ser Thr Ser Pro Cys Ile Leu Val Thr Ser Glu Phe
                565                 570                 575
```

```
Gly Trp Ser Ala His Met Glu Gln Met Met Arg Asn Gln Ala Leu Arg
            580                 585                 590

Asp Ser Ser Met Ala Gln Tyr Met Met Ser Lys Lys Thr Met Glu Leu
            595                 600                 605

Asn Pro Lys His Pro Ile Ile Lys Glu Leu Arg Arg Arg Val Glu Ala
            610                 615                 620

Asp Glu Asn Asp Lys Ala Val Lys Asp Leu Val Phe Leu Leu Phe Asp
625                 630                 635                 640

Thr Ser Leu Leu Thr Ser Gly Phe Gln Leu Glu Asp Pro Thr Tyr Ala
                645                 650                 655

Glu Arg Ile Asn Arg Met Ile Lys Leu Gly Leu Ser Leu Asp Glu Glu
            660                 665                 670

Glu Glu Glu Glu Ala Val Glu Ala Ala Val Ala Glu Thr Ala Pro Ala
            675                 680                 685

Glu Val Thr Ala Gly Thr Ser Ser Met Glu Leu Val Asp
            690                 695                 700

(2) INFORMATION FOR SEQ ID NO:17:

(i) SEQUENCE CHARACTERISTICS:
        (A) LENGTH: 704 amino acids
        (B) TYPE: amino acid
        (C) STRANDEDNESS:
        (D) TOPOLOGY: linear (xi) SEQUENCE DESCRIPTION: SEQ ID NO:17:

Met Thr Glu Thr Phe Ala Phe Gln Ala Glu Ile Asn Gln Leu Met Ser
1               5                   10                  15

Leu Ile Ile Asn Thr Phe Tyr Ser Asn Lys Glu Ile Phe Leu Arg Glu
            20                  25                  30

Leu Ile Ser Asn Ala Ser Asp Ala Cys Asp Lys Ile Arg Tyr Gln Ser
            35                  40                  45

Leu Thr Asn Gln Ala Val Leu Gly Asp Glu Ser His Leu Arg Ile Arg
50                  55                  60

Val Val Pro Asp Lys Ala Asn Lys Thr Leu Thr Val Glu Asp Thr Gly
65                  70                  75                  80

Ile Gly Met Thr Lys Ala Glu Leu Val Asn Asn Leu Gly Thr Ile Ala
            85                  90                  95

Arg Ser Gly Thr Lys Ala Phe Met Glu Ala Leu Glu Ala Gly Gly Asp
            100                 105                 110

Met Ser Met Ile Gly Gln Phe Gly Val Gly Phe Tyr Ser Ala Tyr Leu
            115                 120                 125

Val Ala Asp Arg Val Thr Val Val Ser Lys Asn Asn Asp Asp Glu Ala
130                 135                 140

Tyr Thr Trp Glu Ser Ser Ala Gly Gly Thr Phe Thr Val Thr Pro Thr
145                 150                 155                 160

Pro Asp Cys Asp Leu Lys Arg Gly Thr Arg Ile Val Leu His Leu Lys
            165                 170                 175

Glu Asp Gln Gln Glu Tyr Leu Glu Glu Arg Arg Leu Lys Asp Leu Ile
            180                 185                 190

Lys Lys His Ser Glu Phe Ile Gly Tyr Asp Ile Glu Leu Met Val Glu
            195                 200                 205

Lys Ala Thr Glu Lys Glu Val Thr Asp Glu Asp Glu Asp Glu Ala Ala
            210                 215                 220

Ala Thr Lys Asn Glu Glu Gly Glu Glu Pro Lys Val Glu Glu Val Lys
```

-continued

```
                225                 230                 235                 240
Asp Asp Ala Glu Glu Gly Glu Lys Lys Lys Thr Lys Lys Val Lys
                245                 250                 255
Glu Val Thr Gln Glu Phe Val Val Gln Asn Lys His Lys Pro Leu Trp
                260                 265                 270
Thr Arg Asp Pro Lys Asp Val Thr Lys Glu Glu Tyr Ala Ala Phe Tyr
            275                 280                 285
Lys Ala Ile Ser Asn Asp Trp Glu Glu Pro Leu Ser Thr Lys His Phe
            290                 295                 300
Ser Val Glu Gly Gln Leu Glu Phe Arg Ala Ile Leu Phe Val Pro Lys
305                 310                 315                 320
Arg Ala Pro Phe Asp Met Phe Glu Pro Ser Lys Lys Arg Asn Asn Ile
                325                 330                 335
Lys Leu Tyr Val Arg Arg Val Phe Ile Met Asp Asn Cys Glu Asp Leu
                340                 345                 350
Cys Pro Glu Trp Leu Ala Phe Val Arg Gly Val Val Asp Ser Glu Asp
            355                 360                 365
Leu Pro Leu Asn Ile Ser Arg Glu Asn Leu Gln Gln Asn Lys Ile Leu
    370                 375                 380
Lys Val Ile Arg Lys Asn Ile Val Lys Lys Ala Leu Glu Leu Phe Glu
385                 390                 395                 400
Glu Ile Ala Glu Asn Lys Glu Asp Tyr Lys Lys Phe Tyr Glu Gln Phe
                405                 410                 415
Gly Lys Asn Val Lys Leu Gly Ile His Glu Asp Ser Ala Asn Arg Lys
                420                 425                 430
Lys Leu Met Glu Leu Leu Arg Phe His Ser Ser Glu Ser Gly Glu Asp
            435                 440                 445
Met Thr Thr Leu Lys Asp Tyr Val Thr Arg Met Lys Glu Gly Gln Lys
        450                 455                 460
Cys Ile Tyr Tyr Val Thr Gly Asp Ser Lys Lys Lys Leu Glu Thr Ser
465                 470                 475                 480
Pro Phe Ile Glu Gln Ala Arg Arg Arg Gly Phe Glu Val Leu Phe Met
                485                 490                 495
Thr Glu Pro Ile Asp Glu Tyr Val Met Gln Gln Val Lys Asp Phe Glu
            500                 505                 510
Asp Lys Lys Phe Ala Cys Leu Thr Lys Glu Gly Val His Phe Glu Glu
        515                 520                 525
Thr Glu Glu Glu Lys Lys Gln Arg Glu Glu Lys Thr Ala Tyr Glu
    530                 535                 540
Arg Leu Cys Lys Ala Met Lys Asp Val Leu Gly Asp Lys Val Glu Lys
545                 550                 555                 560
Val Val Val Ser Glu Arg Leu Ala Thr Ser Pro Cys Ile Leu Val Thr
                565                 570                 575
Ser Glu Phe Gly Trp Ser Ala His Met Glu Gln Ile Met Arg Asn Gln
            580                 585                 590
Ala Leu Arg Asp Ser Ser Met Ser Ala Tyr Met Ser Lys Lys Thr
        595                 600                 605
Met Glu Ile Asn Pro Ala His Pro Ile Val Lys Glu Leu Lys Arg Arg
    610                 615                 620
Val Glu Ala Asp Glu Asn Asp Lys Ala Val Lys Asp Leu Val Tyr Leu
625                 630                 635                 640
Leu Phe Asp Thr Ala Leu Leu Thr Ser Gly Phe Thr Leu Asp Asp Pro
                645                 650                 655
```

```
Thr Ser Tyr Ala Glu Arg Ile His Arg Met Ile Lys Leu Gly Leu Ser
            660                 665                 670

Leu Asp Asp Glu Asp Asn Gly Asn Glu Glu Ala Glu Pro Ala Ala Ala
            675                 680                 685

Val Pro Ala Glu Pro Val Ala Gly Thr Ser Ser Met Glu Gln Val Asp
            690                 695                 700

(2) INFORMATION FOR SEQ ID NO:18:

(i) SEQUENCE CHARACTERISTICS:
        (A) LENGTH: 732 amino acids
        (B) TYPE: amino acid
        (C) STRANDEDNESS:
        (D) TOPOLOGY: linear (xi) SEQUENCE DESCRIPTION: SEQ ID NO:18:

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Ser Leu
    50                  55                  60

Thr Asp Pro Ser Lys Leu Asp Ser Gly Lys Glu Leu His Ile Asn Leu
65                  70                  75                  80

Ile Pro Asn Lys Gln Asp Arg Ala Leu Thr Ile Val Asp Thr Gly Ile
                85                  90                  95

Gly Met Thr Lys Ala Asp Leu Ile Asn Asn Leu Gly Thr Ile Ala Lys
                100                 105                 110

Ser Gly Thr Lys Ala Phe Met Glu Ala Leu Gln Ala Gly Ala Asp Ile
            115                 120                 125

Ser Met Ile Gly Gln Phe Gly Val Gly Phe Tyr Ser Ala Tyr Leu Val
        130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Asp Glu Lys Lys Asp Gly
            260                 265                 270

Asp Lys Lys Lys Lys Lys Lys Ile Lys Glu Lys Tyr Ile Asp Lys Glu
        275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
```

```
                  305                 310                 315                 320
Glu Asp His Leu Ala Val Lys His Phe Ser Val Gly Gln Leu Glu
                325                 330                 335
Phe Arg Ala Leu Leu Phe Val Pro Arg Arg Ala Pro Phe Asp Leu Phe
            340                 345                 350
Glu Asn Arg Lys Lys Lys Asn Asn Ile Lys Leu Tyr Val Arg Arg Val
            355                 360                 365
Phe Ile Met Asp Asn Cys Glu Glu Leu Ile Pro Glu Tyr Leu Asn Phe
    370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                405                 410                 415
Val Lys Lys Cys Leu Glu Leu Phe Thr Glu Leu Ala Glu Asp Lys Glu
            420                 425                 430
Asn Tyr Lys Lys Phe Tyr Glu Gln Phe Ser Lys Asn Ile Lys Leu Gly
            435                 440                 445
Ile His Glu Asp Ser Gln Asn Arg Lys Lys Leu Ser Glu Leu Leu Arg
    450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
                485                 490                 495
Glu Thr Lys Asp Gln Val Ala Asn Ser Ala Phe Val Glu Arg Leu Arg
            500                 505                 510
Lys His Gly Leu Glu Val Ile Tyr Met Ile Glu Pro Ile Asp Glu Tyr
            515                 520                 525
Cys Val Gln Gln Leu Lys Glu Phe Glu Gly Lys Thr Leu Val Ser Val
    530                 535                 540
Thr Lys Glu Gly Leu Glu Leu Pro Glu Asp Glu Glu Lys Lys Lys
545                 550                 555                 560
Gln Glu Glu Lys Lys Thr Lys Phe Glu Asn Leu Cys Lys Ile Met Lys
                565                 570                 575
Asp Ile Leu Glu Lys Lys Val Glu Lys Val Val Val Ser Asn Arg Leu
            580                 585                 590
Val Thr Ser Pro Cys Cys Leu Val Thr Ser Thr Tyr Gly Trp Thr Ala
        595                 600                 605
Asn Met Glu Arg Ile Met Lys Ala Gln Ala Leu Arg Asp Asn Ser Thr
    610                 615                 620
Met Gly Tyr Met Ala Ala Lys Lys His Leu Glu Ile Asn Pro Asp His
625                 630                 635                 640
Ser Ile Ile Glu Thr Leu Arg Gln Lys Ala Glu Ala Asp Lys Asn Asp
                645                 650                 655
Lys Ser Val Lys Asp Leu Val Ile Leu Leu Tyr Glu Thr Ala Leu Leu
            660                 665                 670
Ser Ser Gly Phe Ser Leu Glu Asp Pro Gln Thr His Ala Asn Arg Ile
            675                 680                 685
Tyr Arg Met Ile Lys Leu Gly Leu Gly Ile Asp Glu Asp Pro Thr
    690                 695                 700
Ala Asp Asp Thr Ser Ala Ala Val Thr Glu Glu Met Pro Pro Leu Glu
705                 710                 715                 720
Gly Asp Asp Asp Thr Ser Arg Met Glu Glu Val Asp
                725                 730
```

(2) INFORMATION FOR SEQ ID NO:19:

(i) SEQUENCE CHARACTERISTICS:
        (A) LENGTH: 1019 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Leishmania major (ix) FEATURE:
        (A) NAME/KEY: CDS
        (B) LOCATION: 71..523

(xi) SEQUENCE DESCRIPTION: SEQ ID NO:19:

```
GAATTCGGCA CGAGGTTTCT GTACTTTATT GCTTCCAGCC TTTATTCACT CTTCGATTTC      60

CTCTAACACC ATG TCC TCC GAG CGC ACC TTT ATT GCC GTC AAG CCG GAC        109
           Met Ser Ser Glu Arg Thr Phe Ile Ala Val Lys Pro Asp
             1               5                  10

GGC GTG CAG CGC GGC CTC GTT GGC GAG ATC ATC GCC CGC TTC GAG CGC        157
Gly Val Gln Arg Gly Leu Val Gly Glu Ile Ile Ala Arg Phe Glu Arg
 15                  20                  25

AAG GGC TAC AAG CTC GTC GCC TTG AAG ATA CTG CAG CCG ACG ACG GAG        205
Lys Gly Tyr Lys Leu Val Ala Leu Lys Ile Leu Gln Pro Thr Thr Glu
 30                  35                  40                  45

CAG GCC CAG GGT CAC TAT AAG GAC CTT TGC TCC AAG CCG TTT TTC CCG        253
Gln Ala Gln Gly His Tyr Lys Asp Leu Cys Ser Lys Pro Phe Phe Pro
                 50                  55                  60

GCC CTT GTG AAG TAC TTC TCC TCT GGC CCG ATC GTG TGT ATG GTG TGG        301
Ala Leu Val Lys Tyr Phe Ser Ser Gly Pro Ile Val Cys Met Val Trp
         65                  70                  75

GAG GGT AAG AAC GTG GTG AAG AGC GGC CGC GTG CTG CTC GGC GCG ACG        349
Glu Gly Lys Asn Val Val Lys Ser Gly Arg Val Leu Leu Gly Ala Thr
 80                  85                  90

AAC CCG GCC GAC TCA CAG CCC GGC ACG ATC CGT GGC GAC TTT GCC GTG        397
Asn Pro Ala Asp Ser Gln Pro Gly Thr Ile Arg Gly Asp Phe Ala Val
 95                 100                 105

GAT GTG GGC CGC AAC GTG TGC CAC GGG TCC GAC TCT GTG GAG AGC GCG        445
Asp Val Gly Arg Asn Val Cys His Gly Ser Asp Ser Val Glu Ser Ala
110                 115                 120                 125

GAG CGC GAG ATC GCC TTT TGG TTC AAG GCG GAT GAG ATC GCG AGC TGG        493
Glu Arg Glu Ile Ala Phe Trp Phe Lys Ala Asp Glu Ile Ala Ser Trp
                130                 135                 140

ACG TCG CAC TCC GTG TCC CAG ATC TAT GAG TAACGGTGAT TGCGGACACG          543
Thr Ser His Ser Val Ser Gln Ile Tyr Glu
                145                 150

CTTTGAGGAC GTAGCTGTAC CCCCAATGAA TTCTTCTCTG AAAACCACAT CATAAGCCTC      603

TTAAGAGGTT ATTTTTCTTG ATCGATGCCC GGTGGTGACC AGCACCATTC CTTTATCGGA      663

TTCACTCACA CTCCTAGCGA ATCATGTAGT GCGGTGAGAG TGGGCTCTGG AGGAGACTGT      723

TGTGTAGCCA TGGCTTCAGG AGAGAAAACA AAATACAAGG AAAGGCAATA TGTAACTATG      783

GGGTTCCCTT TTTTACTATG CAAAGTTTTT ATAACTCCTG ATCGGCAAAA ACAACAACAA      843

CCGCCATACA CCAAGAGCAA ATGCTTTCTT CTGCGGACTG TGCTTCTGTT TTTTTTTATG      903

AAGGAGTGAC TCGCGCGATG AAAAGTGTGT GCGTGGGAGA TGTATTTCCT TTTTTTGTTC      963

ATAGTGGCGA CAGCTCACTG TTGACGATGA CAAAAAAAA AAAAAAAAA CTCGAG          1019
```

(2) INFORMATION FOR SEQ ID NO:20:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ser Ser Glu Arg Thr Phe Ile Ala Val Lys Pro Asp Gly Val Gln
  1               5                  10                  15

Arg Gly Leu Val Gly Glu Ile Ile Ala Arg Phe Glu Arg Lys Gly Tyr
             20                  25                  30

Lys Leu Val Ala Leu Lys Ile Leu Gln Pro Thr Thr Glu Gln Ala Gln
         35                  40                  45

Gly His Tyr Lys Asp Leu Cys Ser Lys Pro Phe Pro Ala Leu Val
 50                  55                  60

Lys Tyr Phe Ser Ser Gly Pro Ile Val Cys Met Val Trp Glu Gly Lys
 65                  70                  75                  80

Asn Val Val Lys Ser Gly Arg Val Leu Leu Gly Ala Thr Asn Pro Ala
                 85                  90                  95

Asp Ser Gln Pro Gly Thr Ile Arg Gly Asp Phe Ala Val Asp Val Gly
             100                 105                 110

Arg Asn Val Cys His Gly Ser Asp Ser Val Glu Ser Ala Glu Arg Glu
         115                 120                 125

Ile Ala Phe Trp Phe Lys Ala Asp Glu Ile Ala Ser Trp Thr Ser His
130                 135                 140

Ser Val Ser Gln Ile Tyr Glu
145                 150
```

(2) INFORMATION FOR SEQ ID NO:21:

(i) SEQUENCE CHARACTERISTICS:
        (A) LENGTH: 1523 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Leishmania major (ix) FEATURE:
        (A) NAME/KEY: CDS
        (B) LOCATION: 14..973

(xi) SEQUENCE DESCRIPTION: SEQ ID NO:21:

```
GAATTCGGCA CGA GTG CTG CCC GAC ATG ACA TGC TCG CTG ACC GGA CTT       49
           Val Leu Pro Asp Met Thr Cys Ser Leu Thr Gly Leu
            1               5                  10

CAG TGC ACA GAC CCG AAC TGC AAG ACC TGC ACA ACT TAC GGT CAG TGC      97
Gln Cys Thr Asp Pro Asn Cys Lys Thr Cys Thr Thr Tyr Gly Gln Cys
         15                  20                  25

ACA GAC TGC AAC GAC GGC TAC GGT CTC ACC TCC TCC AGC GTT TGC GTG     145
Thr Asp Cys Asn Asp Gly Tyr Gly Leu Thr Ser Ser Ser Val Cys Val
 30                  35                  40

CGC TGC AGT GTA GCG GGC TGC AAG AGC TGC CCC GTC GAC GCT AAC GTC     193
Arg Cys Ser Val Ala Gly Cys Lys Ser Cys Pro Val Asp Ala Asn Val
 45                  50                  55                  60

TGC AAA GTG TGT CTC GGC GGC AGC GAG CCG ATC AAC AAT ATG TGC CCC     241
```

```
                                                              -continued

Cys Lys Val Cys Leu Gly Gly Ser Glu Pro Ile Asn Asn Met Cys Pro
             65                  70                  75
TGC ACC GAC CCC AAC TGC GCC AGC TGC CCC AGC GAC GCT GGC ACG TGC             289
Cys Thr Asp Pro Asn Cys Ala Ser Cys Pro Ser Asp Ala Gly Thr Cys
             80                  85                  90
ACT CAG TGC GCG AAC GGC TAC GGT CTC GTG GAC GGC GCC TGT GTG AGA             337
Thr Gln Cys Ala Asn Gly Tyr Gly Leu Val Asp Gly Ala Cys Val Arg
             95                 100                 105
TGC CAG GAG CCC AAC TGC TTC AGC TGC GAC AGC GAC GCG AAT AAG TGC             385
Cys Gln Glu Pro Asn Cys Phe Ser Cys Asp Ser Asp Ala Asn Lys Cys
            110                 115                 120
ACA CAA TGT GCG CCG AAC TAC TAC CTC ACC CCG CTC TTG ACC TGC TCC             433
Thr Gln Cys Ala Pro Asn Tyr Tyr Leu Thr Pro Leu Leu Thr Cys Ser
125                 130                 135                 140
CCG GTG GCC TGC AAC ATC GAG CAC TGC ATG CAG TGC GAC CCA CAG ACG             481
Pro Val Ala Cys Asn Ile Glu His Cys Met Gln Cys Asp Pro Gln Thr
                    145                 150                 155
CCG TCG CGC TGC CAG GAG TGC GTG TCC CCC TAC GTG GTT GAC AGC TAC             529
Pro Ser Arg Cys Gln Glu Cys Val Ser Pro Tyr Val Val Asp Ser Tyr
            160                 165                 170
GAC GGC CTC TGC AGG CTC TCC GAT GCC TGC TCC GTG CCC AAC TGC AAG             577
Asp Gly Leu Cys Arg Leu Ser Asp Ala Cys Ser Val Pro Asn Cys Lys
            175                 180                 185
AAG TGC GAG ACC GGT ACC TCC AGG CTC TGC GCC GAG TGC GAC ACC GGC             625
Lys Cys Glu Thr Gly Thr Ser Arg Leu Cys Ala Glu Cys Asp Thr Gly
190                 195                 200
TAC AGT CTC TCC GCC GAC GCG ACG AGC TGC AGC AGT CCA ACC ACG CAG             673
Tyr Ser Leu Ser Ala Asp Ala Thr Ser Cys Ser Ser Pro Thr Thr Gln
205                 210                 215                 220
CCG TGC GAG GTG GAG CAC TGC AAC ACA TGT GTG AAC GGC GAT AGC ACC             721
Pro Cys Glu Val Glu His Cys Asn Thr Cys Val Asn Gly Asp Ser Thr
                    225                 230                 235
CGC TGT GCC TAC TGC AAC ACC GGC TAC TAC GTC TCC GAT GGC AAG TGC             769
Arg Cys Ala Tyr Cys Asn Thr Gly Tyr Tyr Val Ser Asp Gly Lys Cys
            240                 245                 250
AAG GCC ATG CAG GGC TGC TAC GTG TCG AAC TGC GCG CAG TGC ATG CTG             817
Lys Ala Met Gln Gly Cys Tyr Val Ser Asn Cys Ala Gln Cys Met Leu
            255                 260                 265
CTT GAC AGC ACC AAG TGC TCC ACG TGC GTG AAA GGG TAC CTG CTC ACG             865
Leu Asp Ser Thr Lys Cys Ser Thr Cys Val Lys Gly Tyr Leu Leu Thr
            270                 275                 280
TCG TCC TAC AGT TGC GTC TCG CAG AAA GTC ATC AAC AGT GCG GCC GCG             913
Ser Ser Tyr Ser Cys Val Ser Gln Lys Val Ile Asn Ser Ala Ala Ala
285                 290                 295                 300
CCC TAC TCT CTG TGG GTG GCC GCC GCC GTG CTC CTC ACC TCT TTT GCC             961
Pro Tyr Ser Leu Trp Val Ala Ala Ala Val Leu Leu Thr Ser Phe Ala
                    305                 310                 315
ATG CAC CTA GCA TAGTGCGCAG CGGCATGCGA ACAACCCCAC TCTCATTCTC                1013
Met His Leu Ala
            320
CAACATGTGC ATACACACAC ACACAGACAG CGGGGCAGCA CCCCCTCCCC ACACACACAC          1073
ACGCACTTCC CCCTTGTCTT GTTCTTCTTT CCTCGTTCGC ATTTCTTTCT CTCGTGCGCT          1133
GGCGCCGGCC TCCTGCACGT CGCTCCCCTC CCCCTAACCT CTATTCTCTC TCTCTCTCTC          1193
TCTCGCCGGC ATCATTGCTT CTTACCCTTT TCTGATCCTT GCTCGCGTGG GCGGACACTG          1253
CCACAGTCCC ACAGCGCAGA CACACGTGTT TAAACGGCGC AGGCATCCCT CCCTATCACT          1313
TCATTTCTCC TAAAGCCACT CACCAAGTCG CACACCGCCC TCCCCCATCG GCCGCCCTTC          1373
```

-continued

```
CGGGCGCAGC TGTGCGGAAT GGGTGTGTGC TCGACCTCGT TCCTGGCAGC TCACTCGCAT      1433

GTGTACAGCC ACTCCAACCA CGAAAGCTCT CTTCTGCGCA CATAAAAAAA AAAAAAAAAA      1493

AAAAACTCGA GGGGGGGCCC GGTACCCAAA                                       1523
```

(2) INFORMATION FOR SEQ ID NO:22:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:22:

```
Val Leu Pro Asp Met Thr Cys Ser Leu Thr Gly Leu Gln Cys Thr Asp
 1               5                  10                  15

Pro Asn Cys Lys Thr Cys Thr Thr Tyr Gly Gln Cys Thr Asp Cys Asn
                20                  25                  30

Asp Gly Tyr Gly Leu Thr Ser Ser Val Cys Val Arg Cys Ser Val
            35                  40                  45

Ala Gly Cys Lys Ser Cys Pro Val Asp Ala Asn Val Cys Lys Val Cys
        50                  55                  60

Leu Gly Ser Glu Pro Ile Asn Asn Met Cys Pro Cys Thr Asp Pro
65                  70                  75                  80

Asn Cys Ala Ser Cys Pro Ser Asp Ala Gly Thr Cys Thr Gln Cys Ala
                85                  90                  95

Asn Gly Tyr Gly Leu Val Asp Gly Ala Cys Val Arg Cys Gln Glu Pro
            100                 105                 110

Asn Cys Phe Ser Cys Asp Ser Asp Ala Asn Lys Cys Thr Gln Cys Ala
        115                 120                 125

Pro Asn Tyr Tyr Leu Thr Pro Leu Leu Thr Cys Ser Pro Val Ala Cys
    130                 135                 140

Asn Ile Glu His Cys Met Gln Cys Asp Pro Gln Thr Pro Ser Arg Cys
145                 150                 155                 160

Gln Glu Cys Val Ser Pro Tyr Val Val Asp Ser Tyr Asp Gly Leu Cys
                165                 170                 175

Arg Leu Ser Asp Ala Cys Ser Val Pro Asn Cys Lys Lys Cys Glu Thr
            180                 185                 190

Gly Thr Ser Arg Leu Cys Ala Glu Cys Asp Thr Gly Tyr Ser Leu Ser
        195                 200                 205

Ala Asp Ala Thr Ser Cys Ser Ser Pro Thr Thr Gln Pro Cys Glu Val
    210                 215                 220

Glu His Cys Asn Thr Cys Val Asn Gly Asp Ser Thr Arg Cys Ala Tyr
225                 230                 235                 240

Cys Asn Thr Gly Tyr Tyr Val Ser Asp Gly Lys Cys Lys Ala Met Gln
                245                 250                 255

Gly Cys Tyr Val Ser Asn Cys Ala Gln Cys Met Leu Leu Asp Ser Thr
            260                 265                 270

Lys Cys Ser Thr Cys Val Lys Gly Tyr Leu Leu Thr Ser Ser Tyr Ser
        275                 280                 285

Cys Val Ser Gln Lys Val Ile Asn Ser Ala Ala Pro Tyr Ser Leu
    290                 295                 300

Trp Val Ala Ala Val Leu Leu Thr Ser Phe Ala Met His Leu Ala
305                 310                 315                 320
```

(2) INFORMATION FOR SEQ ID NO:23:

(i) SEQUENCE CHARACTERISTICS:
        (A) LENGTH: 797 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Leishmania major (ix) FEATURE:
        (A) NAME/KEY: CDS
        (B) LOCATION: 27..623

(xi) SEQUENCE DESCRIPTION: SEQ ID NO:23:

```
CTGTACTTTA TTGCCACCAG CCAGCC ATG TCC TGC GGT AAC GCC AAG ATC AAC         53
                            Met Ser Cys Gly Asn Ala Lys Ile Asn
                              1               5

TCT CCC GCG CCG TCC TTC GAG GAG GTG GCG CTC ATG CCC AAC GGC AGC        101
Ser Pro Ala Pro Ser Phe Glu Glu Val Ala Leu Met Pro Asn Gly Ser
 10              15                  20                  25

TTC AAG AAG ATC AGC CTC TCC TCC TAC AAG GGC AAG TGG GTC GTG CTC        149
Phe Lys Lys Ile Ser Leu Ser Ser Tyr Lys Gly Lys Trp Val Val Leu
                 30                  35                  40

TTC TTC TAC CCG CTC GAC TTT AGC TTC GTG TGC CCG ACA GAG GTC ATC        197
Phe Phe Tyr Pro Leu Asp Phe Ser Phe Val Cys Pro Thr Glu Val Ile
             45                  50                  55

GCG TTC TCC GAC AGC GTG AGT CGC TTC AAC GAG CTC AAC TGC GAG GTC        245
Ala Phe Ser Asp Ser Val Ser Arg Phe Asn Glu Leu Asn Cys Glu Val
         60                  65                  70

CTC GCG TGC TCG ATA GAC AGC GAG TAC GCG CAC CTG CAG TGG ACG CTG        293
Leu Ala Cys Ser Ile Asp Ser Glu Tyr Ala His Leu Gln Trp Thr Leu
     75                  80                  85

CAG GAC CGC AAG AAG GGC GGC CTC GGG ACC ATG GCG ATC CCA ATG CTA        341
Gln Asp Arg Lys Lys Gly Gly Leu Gly Thr Met Ala Ile Pro Met Leu
 90                  95                 100                 105

GCC GAC AAG ACC AAG AGC ATC GCT CGT TCC TAC GGC GTG CTG GAG GAG        389
Ala Asp Lys Thr Lys Ser Ile Ala Arg Ser Tyr Gly Val Leu Glu Glu
                110                 115                 120

AGC CAG GGC GTG GCC TAC CGC GGT CTC TTC ATC ATC GAC CCC CAT GGC        437
Ser Gln Gly Val Ala Tyr Arg Gly Leu Phe Ile Ile Asp Pro His Gly
            125                 130                 135

ATG CTG CGT CAG ATC ACC GTC AAT GAC ATG CCG GTG GGC CGC AGC GTG        485
Met Leu Arg Gln Ile Thr Val Asn Asp Met Pro Val Gly Arg Ser Val
        140                 145                 150

GAG GAG GTT CTA CGC CTG CTG GAG GCT TTT CAG TTC GTG GAG AAG CAC        533
Glu Glu Val Leu Arg Leu Leu Glu Ala Phe Gln Phe Val Glu Lys His
    155                 160                 165

GGC GAG GTG TGC CCC GCG AAC TGG AAG AAG GGC GCC CCC ACG ATG AAG        581
Gly Glu Val Cys Pro Ala Asn Trp Lys Lys Gly Ala Pro Thr Met Lys
170                 175                 180                 185

CCG GAA CCG AAT GCG TCT GTC GAG GGA TAC TTC AGC AAG CAG                623
Pro Glu Pro Asn Ala Ser Val Glu Gly Tyr Phe Ser Lys Gln
                190                 195

TAAACCTGTG AGCGTCGCAG GAGTCAGTGT GACCTCACCC GCCTCTGCCA GTGGGTGCGA       683

GAGGGCGTGA GGGATTGTGG GAAGGCTGTT GGATATGATG CAGACAGCGA TGAATGCAAC       743

TCCCACACAC TGGCCCTCCT CAGCCCTCTC CACACAGACA CACGCACGCA TGTG             797
```

(2) INFORMATION FOR SEQ ID NO:24:

(i) SEQUENCE CHARACTERISTICS:
    (A) LENGTH: 199 amino acids
    (B) TYPE: amino acid
    (D) TOPOLOGY: linear (ii) MOLECULE TYPE: protein (xi) SEQUENCE DESCRIPTION: SEQ ID NO:24:

```
Met Ser Cys Gly Asn Ala Lys Ile Asn Ser Pro Ala Pro Ser Phe Glu
  1               5                  10                  15

Glu Val Ala Leu Met Pro Asn Gly Ser Phe Lys Lys Ile Ser Leu Ser
             20                  25                  30

Ser Tyr Lys Gly Lys Trp Val Val Leu Phe Phe Tyr Pro Leu Asp Phe
         35                  40                  45

Ser Phe Val Cys Pro Thr Glu Val Ile Ala Phe Ser Asp Ser Val Ser
     50                  55                  60

Arg Phe Asn Glu Leu Asn Cys Glu Val Leu Ala Cys Ser Ile Asp Ser
 65                  70                  75                  80

Glu Tyr Ala His Leu Gln Trp Thr Leu Gln Asp Arg Lys Lys Gly Gly
                 85                  90                  95

Leu Gly Thr Met Ala Ile Pro Met Leu Ala Asp Lys Thr Lys Ser Ile
                100                 105                 110

Ala Arg Ser Tyr Gly Val Leu Glu Glu Ser Gln Gly Val Ala Tyr Arg
            115                 120                 125

Gly Leu Phe Ile Ile Asp Pro His Gly Met Leu Arg Gln Ile Thr Val
        130                 135                 140

Asn Asp Met Pro Val Gly Arg Ser Val Glu Glu Val Leu Arg Leu Leu
145                 150                 155                 160

Glu Ala Phe Gln Phe Val Glu Lys His Gly Glu Val Cys Pro Ala Asn
                165                 170                 175

Trp Lys Lys Gly Ala Pro Thr Met Lys Pro Glu Pro Asn Ala Ser Val
            180                 185                 190

Glu Gly Tyr Phe Ser Lys Gln
            195
```

(2) INFORMATION FOR SEQ ID NO:25:

(i) SEQUENCE CHARACTERISTICS:
        (A) LENGTH: 637 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Leishmania tropica (ix) FEATURE:
        (A) NAME/KEY: CDS
        (B) LOCATION: 7..624

(xi) SEQUENCE DESCRIPTION: SEQ ID NO:25:

```
TTACAT ATG CAT CAC CAC CAC CAC CAC ATG TCC TGC GGT AAC GCC AAG         48
       Met His His His His His His Met Ser Cys Gly Asn Ala Lys
         1               5                  10

ATC AAC TCT CCC GCG CCG CCC TTC GAG GAG ATG GCG CTC ATG CCC AAC         96
Ile Asn Ser Pro Ala Pro Pro Phe Glu Glu Met Ala Leu Met Pro Asn
 15                  20                  25                  30

GGC AGC TTC AAG AAG ATC AGC CTC TCC GCC TAC AAG GGC AAG TGG GTC        144
Gly Ser Phe Lys Lys Ile Ser Leu Ser Ala Tyr Lys Gly Lys Trp Val
```

-continued

```
                       35                  40                  45
GTG CTC TTC TTC TAC CCG CTC GAC TTC ACC TTC GTG TGC CCG ACA GAG      192
Val Leu Phe Phe Tyr Pro Leu Asp Phe Thr Phe Val Cys Pro Thr Glu
                50                  55                  60

ATC ATC GCG TTC TCC GAC AAC GTG AGT CGC TTC AAC GAG CTC AAC TGC      240
Ile Ile Ala Phe Ser Asp Asn Val Ser Arg Phe Asn Glu Leu Asn Cys
            65                  70                  75

GAG GTC CTC GCG TGC TCG ATG GAC AGC GAG TAC GCG CAC CTG CAG TGG      288
Glu Val Leu Ala Cys Ser Met Asp Ser Glu Tyr Ala His Leu Gln Trp
        80                  85                  90

ACG CTG CAG GAC CGC AAG AAG GGC GGC CTC GGG GCC ATG GCG ATC CCA      336
Thr Leu Gln Asp Arg Lys Lys Gly Gly Leu Gly Ala Met Ala Ile Pro
    95                 100                 105                 110

ATG CTG GCC GAC AAG ACT AAG AGC ATC GCT CGT TCC TAC GGC GTG CTG      384
Met Leu Ala Asp Lys Thr Lys Ser Ile Ala Arg Ser Tyr Gly Val Leu
               115                 120                 125

GAG GAG AGC CAG GGC GTG GCC TAC CGC GGT CTC TTC ATC ATC GAC CCC      432
Glu Glu Ser Gln Gly Val Ala Tyr Arg Gly Leu Phe Ile Ile Asp Pro
           130                 135                 140

CGT GGC ATG GTG CGT CAG ATC ACC GTC AAC GAC ATG CCG GTG GGC CGC      480
Arg Gly Met Val Arg Gln Ile Thr Val Asn Asp Met Pro Val Gly Arg
       145                 150                 155

AAC GTG GAG GAG GCT CTG CGC CTG CTG GAG GCT TTG CAG TTC GTG GAG      528
Asn Val Glu Glu Ala Leu Arg Leu Leu Glu Ala Leu Gln Phe Val Glu
   160                 165                 170

AAG CAC GGC GAG GTG TGC CCC GCG AAC TGG AAG AAG GGC GCC CCC ACG      576
Lys His Gly Glu Val Cys Pro Ala Asn Trp Lys Lys Gly Ala Pro Thr
175                 180                 185                 190

ATG AAG CCG GAA CCG AAG GCG TCT GTC GAG GGA TAC TTC AGC AAG CAG      624
Met Lys Pro Glu Pro Lys Ala Ser Val Glu Gly Tyr Phe Ser Lys Gln
               195                 200                 205

TAAGAATTCC ATG                                                       637
```

(2) INFORMATION FOR SEQ ID NO:26:

(i) SEQUENCE CHARACTERISTICS:
        (A) LENGTH: 206 amino acids
        (B) TYPE: amino acid
        (D) TOPOLOGY: linear (ii) MOLECULE TYPE: protein (xi) SEQUENCE DESCRIPTION: SEQ ID NO:26:

```
Met His His His His His His Met Ser Cys Gly Asn Ala Lys Ile Asn
 1               5                  10                  15

Ser Pro Ala Pro Pro Phe Glu Glu Met Ala Leu Met Pro Asn Gly Ser
            20                  25                  30

Phe Lys Lys Ile Ser Leu Ser Ala Tyr Lys Gly Lys Trp Val Val Leu
        35                  40                  45

Phe Phe Tyr Pro Leu Asp Phe Thr Phe Val Cys Pro Thr Glu Ile Ile
    50                  55                  60

Ala Phe Ser Asp Asn Val Ser Arg Phe Asn Glu Leu Asn Cys Glu Val
65                  70                  75                  80

Leu Ala Cys Ser Met Asp Ser Glu Tyr Ala His Leu Gln Trp Thr Leu
                85                  90                  95

Gln Asp Arg Lys Lys Gly Gly Leu Gly Ala Met Ala Ile Pro Met Leu
           100                 105                 110

Ala Asp Lys Thr Lys Ser Ile Ala Arg Ser Tyr Gly Val Leu Glu Glu
       115                 120                 125
```

```
Ser Gln Gly Val Ala Tyr Arg Gly Leu Phe Ile Ile Asp Pro Arg Gly
    130                 135                 140

Met Val Arg Gln Ile Thr Val Asn Asp Met Pro Val Gly Arg Asn Val
145                 150                 155                 160

Glu Glu Ala Leu Arg Leu Leu Glu Ala Leu Gln Phe Val Glu Lys His
                165                 170                 175

Gly Glu Val Cys Pro Ala Asn Trp Lys Lys Gly Ala Pro Thr Met Lys
                180                 185                 190

Pro Glu Pro Lys Ala Ser Val Glu Gly Tyr Phe Ser Lys Gln
        195                 200                 205
```

(2) INFORMATION FOR SEQ ID NO:27:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "5 PCR primer (MAPS-1-5 His)
            to simultaneously amplify MAPS-1 cDNA for both L. major
            and L. tropica while adding 6 His residues to amino
            terminal end of encoded protein."

(xi) SEQUENCE DESCRIPTION: SEQ ID NO:27:

```
CAATTACATA TGCATCACCA TCACCATCAC ATGTCCTGCG GTAACGCCAA G          51
```

(2) INFORMATION FOR SEQ ID NO:28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' PCR primer (MAPS-1-3 R1) to
            simultaneously amplify MAPS-1 cDNA for both L. major
            and L. tropica.

(xi) SEQUENCE DESCRIPTION: SEQ ID NO:28:

```
CATGGAATTC TTACTGCTTG CTGAAGTATC C                                 31
```

(2) INFORMATION FOR SEQ ID NO:29:

(i) SEQUENCE CHARACTERISTICS:
        (A) LENGTH: 520 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Leishmania major (xi) SEQUENCE DESCRIPTION: SEQ ID NO:29:

```
GGCACGAGCC CTTGCCTACA TTTGCTCGCC GATATTCGCG GGGAGTTCTT CAATTTGCGT    60

CGCGTAGAAC TGCTCAATGT CGCGCAACAA GCGCAGCTCG TCGTGGCGCA CGAAGGTGAT   120

GGCCAGTCCA GTGCGGCCCA TGCGGCCAGT GCGGCCGATG CGGTGAATGT ACTGCTCACG   180

CGCGAGCGGC AAATCGTAGC TGAGGACGAG CGAGACGCGC TCCACATCAA TGCCACGCGC   240

CCACAGGTCC GTTGTAATGA NCACGCGGCT GTGTCCATTA CGGAATGCCG CATAATCTCG   300
```

```
TCGCGCTCCG CCTGGGGCAT GTCGCCGTGC ATGGCGGACA CAGCGAAATT CTCGCGCGTC     360

ATCTTCTTGG CAAGCTGCTC CACCTTTTTG CGGGTGTTGC ANAAAACCAC NGCGTGGGCG     420

ATCGTTAAGC TGTCGTACAA ACTCCATCAA GAAATCGAAT TTGTTTTTCT CTTCGTCNAC     480

NGANACAAAN TACTGTTTAA CGCTNTCCAC GGTGATCTCA                           520
```

(2) INFORMATION FOR SEQ ID NO:30:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Leishmania major (xi) SEQUENCE DESCRIPTION: SEQ ID NO:30:

```
GGCACAAGGT TTTCGGGTTA TCTTCACGCA TGGTGGAGCG CAGATGGGTG AAGTAAATAC      60

GCGGACCGAA CTGCTTGATC ATATCAACCA GATCGTTGTC AGCACGCACG CCGTANGAAC     120

CGGTGCACAT GGTAAAACCG TNTGCCATGC TGTTTACGGT ATCAACCATC CACTGCATAT     180

CTTCAATGGT GGAAACAATG CGCGGCAGGC CGAGGATCCG GCGCGGCTCA TCATNNAGNT     240

NATNAACCAN TCGCACGTCT ANTTCTGCAC TAAAACTACAA NTATCGGTNA CATATNATAA    300

GGCCNATTTT CGGTCCAGGA NTATGTNCTN TCAAAATGCC NCGTTANNCA CTCTTAAATG     360

TCTCANGNGN AAANTNGTTC TAAAGGGTGT CCAAAANNTN NTTACCNTTC CCCNCTTACT     420

TCAANANCTC CTCNAATTCC CNGGCCCTTN GACNANNATT TNCTATTAAA ANATANAANN     480

TTCAAATTNA TTCCCNACCT NCCNTNNCCA AANNTANCNA ATAATCANNC CCCTNTCANN     540

ANNTCCCANC TTACCCTCCN NTNGNNGGGN NNNCCNATTN CCCCAANCCC NCNCTAAATA     600
```

(2) INFORMATION FOR SEQ ID NO:31:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Leishmania major (xi) SEQUENCE DESCRIPTION: SEQ ID NO:31:

```
GGCACGAGCC TCAGTGGAGC TCAATGAAGA TATTGCAGTA TCTTACTCTG GATGGCACTC      60

AGGTCTCCGG CACGCTGCCG CCCCAGTGGA GCGCGATGGC ATCGGTGCGA ATTCTTAACC     120

TGNAGGGTAC TGAGGTCTCT GGTACGCTGC CGCCTGAGTG GATATCNATG ANCAGGCTGC     180

AAACTCTGAA TCTGCGGCGC ACGAAANTAT CCGGCACTCT GCCGCCCGAA TGGANTTCTA     240

TGAACAGCCT GGAGTACTTT CACCTTTATC TTACTCAGGT CTCCGGCACG CTGCCGCCCG     300

AGTGGAGTGG GATGTCNAAG GCCGCATACT TCTGGCTGGA ATACTGCGAC CTGTCCGGCA     360

NTCTGCCGCC CNAGTGGTCG TCNATGCCAA AGCTGCGCGG TATCTCACTG ANCGGCAACA     420

AATTCTTGCG NGTGTNTNCC NGACTCNTGG GATTCAGAAA GGTGGTCCTT GTTGTTGGGC     480

ATCNAAGGAN CAAACCCCAA NGGGCCCNCN AATTGCTTGG GCNTGCTTAA GGANTTGCAC     540

NAACCAACNC CNCCAAAAAC CCCCCCCACC NCNAAANNAC NANCCCCCAC TTAANNCCCN     600
```

(2) INFORMATION FOR SEQ ID NO:32:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Leishmania major (xi) SEQUENCE DESCRIPTION: SEQ ID NO:32:

```
NGCACGAGAA GCGCAACTGG CGCATCGCAT CTGTGACTAT CTGCCTGAAC AGGGGCAATN      60

GTTTGTTGGT AACAGCCTGG TGGTACGTCT GATTGATNCG CTTNCGCAAN TTCCGGCAGG     120

TTACCCGGTG TACANCAACC GTGGGGCCAN CGGTATCNAC NGGCTGCTTT CGACCGCCGC     180

CGGNGTTCAN CGGGCAANCG GCAAACCGAC GCTGGCGATT GTGGGCGATC TCTCCGCACT     240

TTACGATCTC AACGCNCTGG CGTTATTGCG TCAGGTTTCT GCGCCGCTGG TATTAATTGT     300

GGTGAACAAC AACGGCNGGG CAAAATTTTC TCGCTGTTGC CAACGCCCCC AAAGCNAGCG     360

TGAAGCGTTT CTATCTGATG CCGCAAAACG TCCATTTTGA AACACGCCGC CNCCCATGTT     420

TCGANCTGAA AATATCATCG TCCGCAAAAC TGGCANGAAA CTTNGAAAAC CGCATTTTGC     480

CGACNCCCTG GCNCACGCCC AACCCACCCA CCGGTTGATT GAAAATGGTG GGTTAACGAA     540

NCCNNATGGG TGCCCCAAAN CNCNNCCANC CAAATTTCTG GGCCCAGGTT AAANCCCTTT     600
```

(2) INFORMATION FOR SEQ ID NO:33:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Leishmania major (xi) SEQUENCE DESCRIPTION: SEQ ID NO:33:

```
ACGATGACCA TGCCCCGAAG GAGGATGGCC ATGCGCCGAA GAACGATGAC CATGCCCCGA      60

AGGAGGATGG CCATGCGCCG AAGAACGATG ACCATGCCCC GAAGGAGGAT GGCCATGCGC     120

CGAAGAACGA CGGGGATGTG CAGAANAAGA GCGAAGATGG AGACAACGTG GGAGAGGGAG     180

GCAAGGGCAA TGAGGATGGT AACGATGATC AGCCGAAGGA GCACGCTGCC GGCAACTAGT     240

GGGCTGCGTC CGGGCTTGTG TGCGANCCGT GCTCTGCACC CCGCCGCTCG TGCATCCTCG     300

CATGTGGACT GCGTGTGTCT CTCCCGCTTT GTCTCTCTCC CCCACACAGT GGCTGATGCC     360

TGCACGGGGT TGCTGTGGCT GCACCTCCTG ACCACTGCCA GCTTTCTTGG CTTGCCTCCC     420

CTCTGCGCCT CCGCTCGTGC CGCTCGTGCC GAATTCGATA TCAAGCTTAT CGATACCGTC     480

NACCTCGAAG GGGGGCCCGG TTACCCATTC GCCCTATANT GAGTCNTATT ACAATTCCTG     540

GCGTCGTTTT ACACGTCGTG ACTGGGAAAA ACCCTGGCGT TCCCCACTTA TCGCCTTGCA     600
```

(2) INFORMATION FOR SEQ ID NO:34:

(i) SEQUENCE CHARACTERISTICS:
        (A) LENGTH: 516 base pairs
        (B) TYPE: nucleic acid (C) STRANDEDNESS: double
        (D) TOPOLOGY: linear (ii) MOLECULE TYPE: DNA (genomic)

(vi) ORIGINAL SOURCE:
        (A) ORGANISM: Leishmania major (xi) SEQUENCE DESCRIPTION: SEQ ID NO:34:

```
AGCTGCAGCA GCGCCTAGAC ACCGCCACGC AGCAGCGCGC CGAGCTGGAG GCACGGGTGG      60

CACGGCTGGC CGCGGACCGC GACGAGGCGC GCCAGCAGCT GGCCGCGAAC GCCGAGGAGC     120

TGCAGCAGCG CCTAGACACC GCCACGCAGC AGCGCGCCGA GCTGGAGGCA CGGGTGGCAC     180

GGCTGGCCGC GGACGGCGAC GAGGCCCGCC AGCAGCTGGC CGCGAACGCC GAGGAGCTGC     240

AGCAGCGCCT AGACACCGCC ACGCAGCAGC GCGCCGAGCT GGAGGCACAG GTGGCACGGC     300

TGGCCGCGAA CGCCGAGGAG CTGCAGCAGC GCCTAGACAC CGCCACGCAG CAGCGCGCCG     360

AGCTGGAGGC ACGGGTGGCA CGGCTGGCCG CGGACCGCGA CGAGGCGCGC CAGCAGCTGG     420

CCGCGAACGC CGAGGAGCTG CAGCAGCGCC TAGACACCGC CACGCAGCAG CGCGCCGAGC     480

TGGARGCACA GGTGGCACGG CTGGCCGCGA AMGCCG                               516
```

(2) INFORMATION FOR SEQ ID NO:35:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Leishmania major (xi) SEQUENCE DESCRIPTION: SEQ ID NO:35:

```
GGCACGANAG ATCTTCGTGA AGACGCTGAC CGGCAANACG ATCGCGCTGG AGGTGGAGCC      60

GAGCGACACG ATCGAGAACG TGAAGGCCAA GATCCAGGAC AAGGAGGGCA TCCCGCCGGA     120

CCAGCAGCGC CTGATCTTCG CCGGCAAGCA GCTGGAGGAN GGCCGCACGC TCTCGGACTA     180

CAACATCCAG AAGGAGTCCA CGCTGCACCT GGTGCTGCGC CTGCGCGGCG GCATGCANAT     240

CTTCGTGAAA ACGCTNACCG GCAANACAAT CGCGCTGGAA GTGGAGCCGA ACGACCNATC     300

GAAAACGTGA AGGCCNANAT CCANGACAAG GAAGGCNTCC CGCCGGANCA GCACGCCTGA     360

TCTTCCNCCG GCAACCACTT GANGAAGGGC NCACGCTCTC NGACTACNAC ATCCANAAAG     420

GATTCCNCCC TGCACCTTGT TGCTTGCNCC TTGCTCGGGG GGCATGCCNA ATCTTCCTTN     480

AAAACCTCAA CCGGCAANAA CAATCCCCCN CNGAAGTTGG AACCCAACCA NCCCATTCNA     540

AAACTTTAAA GGCCNNNATT CCNGAACAAN GAAGGGCTTC CCCCCCGGAC CNNCAANCNC     600

CCTGATTNTT CCCCCGGNNN NCANTTTGGA ANGAAGGGCC CCNCCCTCCN CCGAATTNCN     660

ACNTCCCNAA ANGGATTCCC CCCCTNCCCT TGNTTTTTGC GCCNNNNNNC GGCNNCNTNC     720

CNAAATTCCG NCCNAAGGNC CCCANTANAN CNACTTTCCC NTTCCCCCCC NNNNTTTTGC     780

NTAAANTTTT TNCCCCCNNA AANNTCCCNT TTNCNANTTN AN                        822
```

(2) INFORMATION FOR SEQ ID NO:36:

(i) SEQUENCE CHARACTERISTICS:
        (A) LENGTH: 146 amino acids
        (B) TYPE: amino acid
        (C) STRANDEDNESS: single (D) TOPOLOGY: linear (ii) MOLECULE TYPE: peptide (vi) ORIGINAL SOURCE:
         (A) ORGANISM: Leishmania major (xi) SEQUENCE DESCRIPTION: SEQ ID NO:36:

```
Gly Thr Ser Pro Cys Leu His Leu Leu Ala Asp Ile Arg Gly Glu Phe
1               5                   10                  15

Phe Asn Leu Arg Arg Val Glu Leu Leu Asn Val Ala Gln Gln Ala Gln
                20                  25                  30

Leu Val Val Ala His Glu Gly Asp Gly Gln Ser Ser Ala Ala His Ala
                35                  40                  45

Ala Ser Ala Ala Asp Ala Val Asn Val Leu Leu Thr Arg Glu Arg Gln
    50                  55                  60

Ile Val Ala Glu Asp Glu Arg Asp Ala Leu His Ile Asn Ala Thr Arg
65                  70                  75                  80

Pro Gln Val Arg Cys Asn Xaa His Ala Ala Val Ser Ile Thr Glu Cys
                85                  90                  95

Arg Ile Ile Ser Ser Arg Ser Ala Trp Gly Met Ser Pro Cys Met Ala
                100                 105                 110

Asp Thr Ala Lys Phe Ser Arg Val Ile Phe Leu Ala Ser Cys Ser Thr
                115                 120                 125

Phe Leu Arg Val Leu Xaa Lys Thr Thr Ala Trp Ala Ile Val Lys Leu
    130                 135                 140

Ser Tyr
145
```

(2) INFORMATION FOR SEQ ID NO:37:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Leishmania major (xi) SEQUENCE DESCRIPTION: SEQ ID NO:37:

```
Ala Gln Gly Phe Arg Val Ile Phe Thr His Gly Ala Gln Met Gly
1               5                   10                  15

Glu Val Asn Thr Arg Thr Glu Leu Leu Asp His Ile Asn Gln Ile Val
                20                  25                  30

Val Ser Thr His Ala Val Xaa Thr Gly Ala His Gly Lys Thr Val Cys
                35                  40                  45

His Ala Val Tyr Gly Ile Asn His Pro Leu His Ile Phe Asn Gly Gly
    50                  55                  60

Asn Asn Ala Arg Gln Ala Glu Asp Pro Ala Arg Leu Ile
65                  70                  75
```

(2) INFORMATION FOR SEQ ID NO:38:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: peptide (vi) ORIGINAL SOURCE:
    (A) ORGANISM: Leishmania major (xi) SEQUENCE DESCRIPTION: SEQ ID NO:38:

```
His Gln Pro Gln Trp Ser Ser Met Lys Ile Leu Gln Tyr Leu Thr Leu
1               5                  10                  15

Asp Gly Thr Gln Val Ser Gly Thr Leu Pro Pro Gln Trp Ser Ala Met
            20                  25                  30

Ala Ser Val Arg Ile Leu Asn Leu Xaa Gly Thr Glu Val Ser Gly Thr
        35                  40                  45

Leu Pro Pro Glu Trp Ile Ser Met Xaa Arg Leu Gln Thr Leu Asn Leu
    50                  55                  60

Arg Arg Thr Lys
65
```

(2) INFORMATION FOR SEQ ID NO:39:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Leishmania major (xi) SEQUENCE DESCRIPTION: SEQ ID NO:39:

```
Ala Arg Glu Ala Gln Leu Ala His Arg Ile Cys Asp Tyr Leu Pro Glu
1               5                  10                  15

Gln Gly Gln Xaa Phe Val Gly Asn Ser Leu Val Val Arg Leu Ile Asp
            20                  25                  30

Xaa Leu Xaa Gln Xaa Pro Ala Gly Tyr Pro Val Tyr Xaa Asn Arg Gly
        35                  40                  45

Ala Xaa Gly Ile Xaa Xaa Leu Leu Ser Thr Ala Ala Gly Val Xaa Arg
    50                  55                  60

Ala
65
```

(2) INFORMATION FOR SEQ ID NO:40:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Leishmania major (xi) SEQUENCE DESCRIPTION: SEQ ID NO:40:

```
Asp Asp His Ala Pro Lys Glu Asp Gly His Ala Pro Lys Asn Asp Asp
1               5                  10                  15

His Ala Pro Lys Glu Asp Gly His Ala Pro Lys Asn Asp Asp His Ala
            20                  25                  30

Pro Lys Glu Asp Gly His Ala Pro Lys Asn Asp Gly Asp Val Gln Xaa
        35                  40                  45

Lys Ser Glu Asp Gly Asp Asn Val Gly Glu Gly Gly Lys Gly Asn Glu
```

```
              50                  55                  60
Asp Gly Asn Asp Asp Gln Pro Lys Glu His Ala Ala Gly Asn
 65                  70                  75
```

(2) INFORMATION FOR SEQ ID NO:41:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Leishmania major (xi) SEQUENCE DESCRIPTION: SEQ ID NO:41:

```
Leu Gln Gln Arg Leu Asp Thr Ala Thr Gln Gln Arg Ala Glu Leu Glu
 1               5                  10                  15

Ala Arg Val Ala Arg Leu Ala Ala Asp Arg Asp Glu Ala Arg Gln Gln
                20                  25                  30

Leu Ala Ala Asn Ala Glu Glu Leu Gln Gln Arg Leu Asp Thr Ala Thr
                35                  40                  45

Gln Gln Arg Ala Glu Leu Glu Ala Arg Val Ala Arg Leu Ala Ala Asp
 50                  55                  60

Gly Asp Glu Ala Arg Gln Gln Leu Ala Ala Asn Ala Glu Glu Leu Gln
 65                  70                  75                  80

Gln Arg Leu Asp Thr Ala Thr Gln Gln Arg Ala Glu Leu Glu Ala Gln
                85                  90                  95

Val Ala Arg Leu Ala Ala Asn Ala Glu Glu Leu Gln Gln Arg Leu Asp
                100                 105                 110

Thr Ala Thr Gln Gln Arg Ala Glu Leu Glu Ala Arg Val Ala Arg Leu
                115                 120                 125

Ala Ala Asp Arg Asp Glu Ala Arg Gln Gln Leu Ala Ala Asn Ala Glu
                130                 135                 140

Glu Leu Gln Gln Arg Leu Asp Thr Ala Thr Gln Gln Arg Ala Glu Leu
 145                 150                 155                 160

Glu Ala Gln Val Ala Arg Leu Ala Ala
                165
```

(2) INFORMATION FOR SEQ ID NO:42:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Leishmania major (xi) SEQUENCE DESCRIPTION: SEQ ID NO:42:

```
Ala Arg Xaa Ile Phe Val Lys Thr Leu Thr Gly Xaa Thr Ile Ala Leu
 1               5                  10                  15

Glu Val Glu Pro Ser Asp Thr Ile Glu Asn Val Lys Ala Lys Ile Gln
                20                  25                  30

Asp Lys Glu Gly Ile Pro Pro Asp Gln Gln Arg Leu Ile Phe Ala Gly
                35                  40                  45
```

```
Lys Gln Leu Glu Xaa Gly Arg Thr Leu Ser Asp Tyr Asn Ile Gln Lys
    50                  55                  60

Glu Ser Thr Leu His Leu Val Leu Arg Leu Arg Gly Gly Met Xaa Ile
65                  70                  75                  80

Phe Val Lys Thr Leu Thr Gly Xaa Thr Ile Ala Leu Glu Val Glu Pro
                85                  90                  95

Asn Asp
```

(2) INFORMATION FOR SEQ ID NO:43:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Leishmania major (xi) SEQUENCE DESCRIPTION: SEQ ID NO:43:

```
Leu Gln Gln Arg Leu Asp Thr Ala Thr Gln Gln Arg Ala Glu Leu Glu
1               5                   10                  15

Ala Arg Val Ala Arg Leu Ala Ala Asp Arg Asp Glu Ala Arg Gln Gln
                20                  25                  30

Leu Ala Ala Asn Ala Glu Glu
            35
```

(2) INFORMATION FOR SEQ ID NO:44:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Leishmania chagasi (xi) SEQUENCE DESCRIPTION: SEQ ID NO:44:

```
CGGCCGCCTC AGCGAGGAGG AGATCGAGCG CATGGTGCGC GAGGCTGCCG AGTTCGAGGA      60

TGAGGACCGC AAGGTGCGCG AACGTGTCGA AGCGAAGAAC TCGCTAGAGA GCATCGCGTA     120

CTCGCTTCGC AACCAGATCA ACGACAAGGA CAAGCTTGGT GACAAGCTCG CCGCGGACGA     180

CAAGAAGGCG ATCGAGGAGG CTGTGAAGGA TGCCCTCGAC TTTGTCCACG AGAACCCCAA     240

TGCAGACCGT GAGGAGTTCG AGGCTGCTCG CACGAAGCTG CAGAGTGTGA CGAACCCCAT     300

CATTCAAAAG GTGTACCAGG GCGCCGCCGG CTCTGGTGCA GAAGAGGCGG ACGCGATGGA     360

TGACTTGTTA GTCGGCCGCG TGAAAAGAAA AACAGGGAAA GCGGGAACAT NCCACAANAA     420

CCNAAGAAGA AAGGGGGTNG CGACACCGCT CGAACACCGA CGGCNCACAT NCNTCATGGG     480

CATGCTCAGC TTTCCTCTCC CCAACAAACC AGAAGGTTTT CTCCAAACNC CGTCTCNGCN     540

CCCAAAATAC GGAAANGTTA ANCGAAAAAN CCCCTTCCAC CAATTGNNGT TCTTTTGTTT     600
```

(2) INFORMATION FOR SEQ ID NO:45:

(i) SEQUENCE CHARACTERISTICS:
        (A) LENGTH: 1748 base pairs
        (B) TYPE: nucleic acid
        (C) STRANDEDNESS: double (D) TOPOLOGY: linear (ii) MOLECULE TYPE: DNA (genomic)

(vi) ORIGINAL SOURCE:
    (A) ORGANISM: Leishmania chagasi (xi) SEQUENCE DESCRIPTION: SEQ ID NO:45:

```
CTAGTGGATC CCCCGGGCTG CAGGAATTCA CGGAATACGT ACCTCCTCCC CCTTCTTGGT     60
AGAAGAACAA CAACAACGTT CAAGACGACG CCGCGCCTTC TTGTACCGCA TTTGCTTCTG    120
AGCACGTTCA ATCCGTGCCT TGCAAACATG GAGGCGTACA AGAAGCTGGA AACGATCTTT    180
ACGAAGGTCT ACCGCCTGGA CCACTTCCTC GGTCTGGGCA ACTGGGACAT GAACACAAAC    240
ATGCCCCCCA AGGGCGAGGA ATCACGCGGT GAGGCGATGG CGATGCTCTC GGAGCTCCGC    300
TTTGGCTTCA TCACGGCACC GGAGGTGAAA AGCCTGATTG AGAGTGCCAC CAAGGGCAGC    360
GAGGAGCTGA ATGCGGTGCA GCGCGCTAAC TTGCGGGAGA TGAGGCGTGC GTGGAAGAGC    420
GCCACCGCCT TGCCGGCTGA GTTTGTGGGC CGCAAGATGC GCCTCACGAC ACACGCGCAC    480
AGCGTGTGGC GCGACAGCCG CAAAGCAAAT GACTTCGCCA AGTTCCTACC GGTGCTCAGG    540
GACCTGGTGG CGCTCGCCCG TGAGGAGGGC TCATACCTCG CCGCCGGCAC CTCCCTCTCC    600
CCGTATGAGG CGCTCATGAA CGAGTACGAG CCAGGAATCA CGACACAAAA GCTGGATGAG    660
GTGTACGCAA ATGTAAAGTC GTGGCTGCCG CAGCTGCTAA AGGACATTGT GCAGAAGCAG    720
TCCGGCGAGT CGGTGATTGC GTTCTCGCAT AAGTTCCCGC AGGACAAGCA GGAAGCACTG    780
TGCAAGGAAT TCATGAAGAT CTGGCACTTC GACACCGATG CCGGTCGCCT CGACGTCAGC    840
CCCCACCCTT TCACGGGAAT GACGAAGGAG GACTGCCGAC TCACAACAAA CTACATCGAA    900
GACACGTTTG TTCAGAGCTT GTATGGCGTC ATCCACGAGA GTGGGCATGG CAAGTACGAG    960
CAGAACTGTG GCCCACGCGA GCACATCACG CAGCCGGTGT GCAACGCCCG CTCTCTTGGC   1020
CTGCATGAGA GCCAGAGCCT CTTTGCGGAG TTTCAGATCG GCCACGCGAC GCCCTTCATC   1080
GACTACCTCA CAACTCGCCT TCCTGAGTTC TTCGAGGCGC AGCCAGCGTT CTCGCAGGAC   1140
AACATGCGCA AGTCGCTGCA GCAGGTGAAG CCGGGCTACA TTCGCGTCGA TGCCGATGAG   1200
GTGTGCTACC CTCTGCACGT GATCCTGCGC TACGAGATCG AGCGCGACTT GATGGAGGGC   1260
AAAATGGAGG TGGAAGACGT GCCGCGCGCG TGGAACGCAA AGATGCAGGA GTACTTGGGT   1320
CTCTCAACGG AGGGCCGTGA CGACGTTGGG TGCCTGCAGG ACGTGCATTG GTCCATGGTG   1380
CGCTCGGCTA CTCTCCGACG TACTCGCTCG GCGCCATGTA TGCGGCGCAG ATCATGGCGA   1440
GCATCCGAAA GGAGCTGGGA GACGACAAGG TGGATGAGTG CCTGCGCACC GGTGAGCTCG   1500
GCCCCCTCCT GGAAAAGCAG CAGGAGAAGA TCTGGGATCA TGGGTGCCTG TACGAGACGG   1560
ACGACCTCAT GACGCGTGCG ACGGGCGAGA CGCTGAACCC CGAGTACCTG CGCCGCCACC   1620
TGGAGGCGCG CTACATAAAC GCCTGAGTCG CGAGCGGTTG ACACACGCGC TCGCTAGCAC   1680
ATGACGCGTC TTTATTATTC TTTGTTGTGC ATTCGGAATT CCGCGGAATT CGATATCAAG   1740
CTTATCGA                                                            1748
```

(2) INFORMATION FOR SEQ ID NO:46:

(i) SEQUENCE CHARACTERISTICS:
        (A) LENGTH: 560 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
    (A) ORGANISM: Leishmania chagasi (xi) SEQUENCE DESCRIPTION: SEQ ID NO:46:

```
CGGAAGGAGG ATGGCCATAC ACAGAAAAAT GACGGCGATG CCCTAAGGA GGACGGCCGT    60

ACACAGAAAA ACGACGACGG TGGCCCTAAG GAGGACGGCC ATACACAGAA AAATGACGGC   120

GATGGCCCTA AGGAGGACGG CCGTACACAG AAAAATAACG GCGATGGCCC TNAGGAGGAC   180

GGCCATACAC AGAAAAATGA CGGCGATGCC CCTNAGGAGG ACGGCCGTAC ACANAAAAAT   240

GACGGCNATG GCCCTNAGGA GGACGGCCGT ACACAGAAAA ATGACNGCCA TGGCCCTTAG   300

GANGACGCCG TACACAGAAA AATGACGCNA TGGCCCTNAG GGAGGACGGC CATACCCANA   360

AAAATTGACG GCNATNGCCC TTAGGANGAC GGCCGTNCCC ANAAANANTG ACNGCGGTNG   420

CCCTTAAGGA AGATGAAAAT CTGCCACCAA AACNATTGGG AATGCNCAGG AAAANAACNA   480

ANATNGACCC CACGTGGGGG ATGGANCTTA CNGCNATTAA NATTGTTACC ATTATCNACC   540

NAAGGACNNG TTGCCGNCAA                                               560
```

(2) INFORMATION FOR SEQ ID NO:47:

(i) SEQUENCE CHARACTERISTICS:
       (A) LENGTH: 600 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: Leishmania chagasi (xi) SEQUENCE DESCRIPTION: SEQ ID NO:47:

```
CGTCCGAGAA ACCCGTACAT GTATGCTGCT GGTAGAAGGC GCAGAGCTGG TCCCTCTGAT    60

GCACAAGCAT GAGGTCGTAC ATTGCCTGGT TCGTCATTTT CCAGAGCACA ACGAGCAGCG   120

TCATCATACA GCATCCAATA GCCGCCAGAG TGAATGCGAT GCGCACACCA AGTCGAAAGT   180

GGTCGACCAG TAGGGGAATG TGACCCTGGC TGGCGTGCAA CATGATCGCC ACGCCAGCGG   240

TGGGCCACAC CACAACAGAG GCGACGAAAG AGAAACATGAA CTTGCTCACG AAGCTNACAA   300

TAAGGGCGTC GCTNGTGATG CTAAGAACCA CGCCNAGGTA GACGGCGAAG ANCAAACTAA   360

ACACAAGCGT GACGATCCCG AAAAGAAGGA TCTCTGCGGA ATTTTCGTGA GATAGANAAT   420

GCCCGTACTG GAAAAANAAG CCGGCAGGCG CGCGATAACG CTGCAACTTG CCGCTCCTCG   480

CGGGCGCGTT TTCGCTCCTT CTCCGACTTG ATGGCGCNGT CNGNCTTGAC AAAACGGTTA   540

AGCTCCTCAT GCCCCAGCCG ATTCCCAGCT CACGGTCCAC TTCCGGCCAT GCCCACGGAC   600
```

(2) INFORMATION FOR SEQ ID NO:48:

(i) SEQUENCE CHARACTERISTICS:
       (A) LENGTH: 1053 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: Leishmania chagasi (xi) SEQUENCE DESCRIPTION: SEQ ID NO:48:

```
GGGAAAAAAG TGGAGCTCCA CCGCGGTGGC GGCCGCTCTA GAACTAGTGG ATCCCCCGGG    60
```

```
CTGCAGGAAT TCCGCGGAAT TCCGCGGAAT TCCGCGGAAT TCCGTCCGAC GCGGCACCCG      120

CACAGGGGTC GACAGTGACG CAACCTCCTC CACCACTGCG GCCTACGACG GCGCCGGCTC      180

CGCGCCAGTG ATGGTTGACG CCAATGTGAG CCACCCTCCG TACGCGGGGC ATGACCAAGT      240

GTACATGCAC GTCGGCAAGC CCATCGTGGG CAACACCCTC GACGGATACA ACGGGTGCGT      300

GTTCGCCTAC GGGCANACGG GCAGCGGCAA AACCTTCACG ATGCTCGGNT ACGCGCCGAG      360

CACGANCGAC ATCCGCGCTC GCAAAGGGTC CGTCCCCTGC GGGGCCAGCA GCATGGAGAA      420

CAGCACTCCT CTTGACAGCG CTGTGGAGCC GTTTGAGAGC GATGACGGCG ACGACGTGGT      480

GGACAAGACG GGGCTGGATC CGAACGAGCT GCAAGGCATC ATCCCGCGCG CGTGCACGGA      540

CCTGTTCGAT GGTCTCCGTG CGAAGCGCGC CAAGGACTCC GACTTCACGT ACCGCGTGGA      600

GGTGTCTTAC TACGAGATCT ACAACGAGAA GGTGTTCGAT CTCATCCGGC CGCAGCGCAA      660

CACGGACCTG AGGATACGTA ACTCGCCCAA CTCCGGTCCA TTTATCGAAG GCCTGACGTG      720

GAAGATGGTG TCCAAGGAGG AAGACGTCGC CCGCGTGATT CGCAAGGGCA TGCAGGAGCG      780

CCACACGGCT GCGACCAAGT TCAACGACCG CAGCAGCCGC AGCACGCCA TCCTCACCTT       840

CAACATTGTG CAGCTGTCGA TGGACGACTC CGACAACGCG TTCCAGATGC GCAGCAAGCT      900

GAACCTGGTG GACCTTGCTG GGTCGGAGCC CACTGGTGCG GCCGGAGCCG AGGGCAATGA      960

GTTCCACGAC GGTGTGAAGA TCAACCACTC GCTGACGGTG CTGGGCGCG TGATCGACCG      1020

TCTGGCGGAC CTCTCGCAGA ACAAGGGAGG GGG                                 1053
```

(2) INFORMATION FOR SEQ ID NO:49:

(i) SEQUENCE CHARACTERISTICS:
    (A) LENGTH: 136 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Leishmania chagasi (xi) SEQUENCE DESCRIPTION: SEQ ID NO:49:

```
Gly Arg Leu Ser Glu Glu Glu Ile Glu Arg Met Val Arg Glu Ala Ala
1               5                   10                  15

Glu Phe Glu Asp Glu Asp Arg Lys Val Arg Glu Arg Val Glu Ala Lys
            20                  25                  30

Asn Ser Leu Glu Ser Ile Ala Tyr Ser Leu Arg Asn Gln Ile Asn Asp
        35                  40                  45

Lys Asp Lys Leu Gly Asp Lys Leu Ala Ala Asp Asp Lys Lys Ala Ile
    50                  55                  60

Glu Glu Ala Val Lys Asp Ala Leu Asp Phe Val His Glu Asn Pro Asn
65                  70                  75                  80

Ala Asp Arg Glu Glu Phe Glu Ala Ala Arg Thr Lys Leu Gln Ser Val
                85                  90                  95

Thr Asn Pro Ile Ile Gln Lys Val Tyr Gln Gly Ala Ala Gly Ser Gly
            100                 105                 110

Ala Glu Glu Ala Asp Ala Met Asp Asp Leu Leu Val Gly Arg Val Lys
        115                 120                 125

Arg Lys Thr Gly Lys Ala Gly Thr
    130                 135
```

-continued (2) INFORMATION FOR SEQ ID NO:50:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Leishmania chagasi (xi) SEQUENCE DESCRIPTION: SEQ ID NO:50:

```
Tyr Leu Leu Pro Leu Gly Arg Arg Thr Thr Thr Phe Lys Thr
1               5                   10                  15

Thr Pro Arg Leu Leu Val Pro His Leu Leu Ser Thr Phe Asn Pro
            20                  25                  30

Cys Leu Ala Asn Met Glu Ala Tyr Lys Lys Leu Glu Thr Ile Phe Thr
            35                  40                  45

Lys Val Tyr Arg Leu Asp His Phe Leu Gly Leu Gly Asn Trp Asp Met
        50                  55                  60

Asn Thr Asn Met Pro Pro Lys Gly Glu Glu Ser Arg Gly Glu Ala Met
65                  70                  75                  80

Ala Met Leu Ser Glu Leu Arg Phe Gly Phe Ile Thr Ala Pro Glu Val
                85                  90                  95

Lys Ser Leu Ile Glu Ser Ala Thr Lys Gly Ser Glu Glu Leu Asn Ala
            100                 105                 110

Val Gln Arg Ala Asn Leu Arg Glu Met Arg Arg Ala Trp Lys Ser Ala
            115                 120                 125

Thr Ala Leu Pro Ala Glu Phe Val Gly Arg Lys Met Arg Leu Thr Thr
            130                 135                 140

His Ala His Ser Val Trp Arg Asp Ser Arg Lys Ala Asn Asp Phe Ala
145                 150                 155                 160

Lys Phe Leu Pro Val Leu Arg Asp Leu Val Ala Leu Ala Arg Glu Glu
                165                 170                 175

Gly Ser Tyr Leu Ala Ala Gly Thr Ser Leu Ser Pro Tyr Glu Ala Leu
            180                 185                 190

Met Asn Glu Tyr Glu Pro Gly Ile Thr Thr Gln Lys Leu Asp Glu Val
            195                 200                 205

Tyr Ala Asn Val Lys Ser Trp Leu Pro Gln Leu Leu Lys Asp Ile Val
        210                 215                 220

Gln Lys Gln Ser Gly Glu Ser Val Ile Ala Phe Ser His Lys Phe Pro
225                 230                 235                 240

Gln Asp Lys Gln Glu Ala Leu Cys Lys Glu Phe Met Lys Ile Trp His
                245                 250                 255

Phe Asp Thr Asp Ala Gly Arg Leu Asp Val Ser Pro His Pro Phe Thr
            260                 265                 270

Gly Met Thr Lys Glu Asp Cys Arg Leu Thr Thr Asn Tyr Ile Glu Asp
            275                 280                 285

Thr Phe Val Gln Ser Leu Tyr Gly Val Ile His Glu Ser Gly His Gly
        290                 295                 300

Lys Tyr Glu Gln Asn Cys Gly Pro Arg Glu His Ile Thr Gln Pro Val
305                 310                 315                 320

Cys Asn Ala Arg Ser Leu Gly Leu His Glu Ser Gln Ser Leu Phe Ala
                325                 330                 335

Glu Phe Gln Ile Gly His Ala Thr Pro Phe Ile Asp Tyr Leu Thr Thr
```

```
                    340                 345                 350
Arg Leu Pro Glu Phe Phe Glu Ala Gln Pro Ala Phe Ser Gln Asp Asn
            355                 360                 365
Met Arg Lys Ser Leu Gln Gln Val Lys Pro Gly Tyr Ile Arg Val Asp
    370                 375                 380
Ala Asp Glu Val Cys Tyr Pro Leu His Val Ile Leu Arg Tyr Glu Ile
385                 390                 395                 400
Glu Arg Asp Leu Met Glu Gly Lys Met Glu Val Glu Asp Val Pro Arg
                405                 410                 415
Ala Trp Asn Ala Lys Met Gln Glu Tyr Leu Gly Leu Ser Thr Glu Gly
            420                 425                 430
Arg Asp Asp Val Gly Cys Leu Gln Asp Val His Trp Ser Met Val Arg
        435                 440                 445
Ser Ala Thr Leu Arg Arg Thr Arg Ser Ala Pro Cys Met Arg Arg Arg
450                 455                 460
Ser Trp Arg Ala Ser Glu Arg Ser Trp Glu Thr Thr Arg Trp Met Ser
465                 470                 475                 480
Ala Cys Ala Pro Val Ser Ser Ala Pro Ser Trp Lys Ser Ser Arg Arg
                485                 490                 495
Arg Ser Gly Ile Met Gly Ala Cys Thr Arg Arg Thr Thr Ser
            500                 505                 510

(2) INFORMATION FOR SEQ ID NO:51:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Leishmania chagasi (xi) SEQUENCE DESCRIPTION: SEQ ID NO:51:

Gly Arg Arg Met Ala Ile His Arg Lys Met Thr Ala Met Ala Leu Arg
1               5                   10                  15
Arg Thr Ala Val His Arg Lys Thr Thr Thr Val Ala Leu Arg Arg Thr
            20                  25                  30
Ala Ile His Arg Lys Met Thr Ala Met Ala Leu Arg Arg Thr Ala Val
        35                  40                  45
His Arg Lys Ile Thr Ala Met Ala Leu Arg Arg Thr Ala Ile His Arg
    50                  55                  60
Lys Met Thr Ala Met Pro Leu Arg Arg Thr Ala Val His Xaa Lys Met
65                  70                  75                  80
Thr Ala Met Ala Leu Arg Arg Thr Ala Val His Arg Lys Met Thr Ala
                85                  90                  95
Met Ala Leu Arg Xaa Thr Pro Tyr Thr Glu Lys
            100                 105

(2) INFORMATION FOR SEQ ID NO:52:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: peptide
```

(vi) ORIGINAL SOURCE:
    (A) ORGANISM: Leishmania chagasi (xi) SEQUENCE DESCRIPTION: SEQ ID NO:52:

```
Val Arg Glu Thr Arg Thr Cys Met Leu Leu Val Glu Gly Ala Glu Leu
1               5                   10                  15

Val Pro Leu Met His Lys His Glu Val Val His Cys Leu Val Arg His
                20                  25                  30

Phe Pro Glu His Asn Glu Gln Arg His His Thr Ala Ser Asn Ser Arg
            35                  40                  45

Gln Ser Glu Cys Asp Ala His Thr Lys Ser Lys Val Val Asp Gln
50                  55                  60
```

(2) INFORMATION FOR SEQ ID NO:53:

(i) SEQUENCE CHARACTERISTICS:
        (A) LENGTH: 324 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Leishmania chagasi (xi) SEQUENCE DESCRIPTION: SEQ ID NO:53:

```
Phe Arg Gly Ile Pro Arg Asn Ser Val Arg Arg Gly Thr Arg Thr Gly
1               5                   10                  15

Val Asp Ser Asp Ala Thr Ser Ser Thr Thr Ala Ala Tyr Asp Gly Ala
                20                  25                  30

Gly Ser Ala Pro Val Met Val Asp Ala Asn Val Ser His Pro Pro Tyr
            35                  40                  45

Ala Gly His Asp Gln Val Tyr Met His Val Gly Lys Pro Ile Val Gly
        50                  55                  60

Asn Thr Leu Asp Gly Tyr Asn Gly Cys Val Phe Ala Tyr Gly Xaa Thr
65                  70                  75                  80

Gly Ser Gly Lys Thr Phe Thr Met Leu Gly Tyr Ala Pro Ser Thr Xaa
                85                  90                  95

Asp Ile Arg Ala Arg Lys Gly Ser Val Pro Cys Gly Ala Ser Ser Met
            100                 105                 110

Glu Asn Ser Thr Pro Leu Asp Ser Ala Val Glu Pro Phe Glu Ser Asp
        115                 120                 125

Asp Gly Asp Asp Val Val Asp Lys Thr Gly Leu Asp Pro Asn Glu Leu
130                 135                 140

Gln Gly Ile Ile Pro Arg Ala Cys Thr Asp Leu Phe Asp Gly Leu Arg
145                 150                 155                 160

Ala Lys Arg Ala Lys Asp Ser Asp Phe Thr Tyr Arg Val Glu Val Ser
                165                 170                 175

Tyr Tyr Glu Ile Tyr Asn Glu Lys Val Phe Asp Leu Ile Arg Pro Gln
            180                 185                 190

Arg Asn Thr Asp Leu Arg Ile Arg Asn Ser Pro Asn Ser Gly Pro Phe
        195                 200                 205

Ile Glu Gly Leu Thr Trp Lys Met Val Ser Lys Glu Glu Asp Val Ala
    210                 215                 220

Arg Val Ile Arg Lys Gly Met Gln Glu Arg His Thr Ala Ala Thr Lys
225                 230                 235                 240
```

```
Phe Asn Asp Arg Ser Ser Arg Ser His Ala Ile Leu Thr Phe Asn Ile
            245                 250                 255

Val Gln Leu Ser Met Asp Asp Ser Asp Asn Ala Phe Gln Met Arg Ser
            260                 265                 270

Lys Leu Asn Leu Val Asp Leu Ala Gly Ser Glu Arg Thr Gly Ala Ala
            275                 280                 285

Gly Ala Glu Gly Asn Glu Phe His Asp Gly Val Lys Ile Asn His Ser
        290                 295                 300

Leu Thr Val Leu Gly Arg Val Ile Asp Arg Leu Ala Asp Leu Ser Gln
305                 310                 315                 320

Asn Lys Gly Gly (2) INFORMATION FOR SEQ ID NO:54:

(i) SEQUENCE CHARACTERISTICS:
        (A) LENGTH: 1585 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:54:

AAAGCTGGAG CTCCACCGCG GTGGCGGCCG CTCTAGAACT AGTGGATCCC CCGGGCTGCA      60

GGAATTCGGC ACGAGTGCTG CCCGACATGA CATGCTCGCT GACCGGACTT CAGTGCACAG     120

ACCCGAACTG CAAGACCTGC ACAACTTACG GTCAGTGCAC AGACTGCAAC GACGGCTACG     180

GTCTCACCTC CTCCAGCGTT TGCGTGCGCT GCAGTGTAGC GGGCTGCAAG AGCTGCCCCG     240

TCGACGCTAA CGTCTGCAAA GTGTGTCTCG GCGGCAGCGA GCCGATCAAC AATATGTGCC     300

CCTGCACCGA CCCCAACTGC GCCAGCTGCC CCAGCGACGC TGGCACGTGC ACTCAGTGCG     360

CGAACGGCTA CGGTCTCGTG GACGGCGCCT GTGTGAGATG CCAGGAGCCC AACTGCTTCA     420

GCTGCGACAG CGACGCGAAT AAGTGCACAC AATGTGCGCC GAACTACTAC CTCACCCCGC     480

TCTTGACCTG CTCCCCGGTG GCCTGCAACA TCGAGCACTG CATGCAGTGC GACCCACAGA     540

CGCCGTCGCG CTGCCAGGAG TGCGTGTCCC CCTACGTGGT TGACAGCTAC GACGGCCTCT     600

GCAGGCTCTC CGATGCCTGC TCCGTGCCCA ACTGCAAGAA GTGCGAGACC GGTACCTCCA     660

GGCTCTGCGC CGAGTGCGAC ACCGGCTACA GTCTCTCCGC CGACGCGACG AGCTGCAGCA     720

GTCCAACCAC GCAGCCGTGC GAGGTGGAGC ACTGCAACAC ATGTGTGAAC GGCGATAGCA     780

CCCGCTGTGC CTACTGCAAC ACCGGCTACT ACGTCTCCGA TGGCAAGTGC AAGGCCATGC     840

AGGGCTGCTA CGTGTCGAAC TGCGCGCAGT GCATGCTGCT TGACAGCACC AAGTGCTCCA     900

CGTGCGTGAA AGGGTACCTG CTCACGTCGT CCTACAGTTG CGTCTCGCAG AAAGTCATCA     960

ACAGTGCGGC CGCGCCCTAC TCTCTGTGGG TGGCCGCCGC CGTGCTCCTC ACCTCTTTTG    1020

CCATGCACCT AGCATAGTGC GCAGCGGCAT GCGAACAACC CCACTCTCAT TCTCCAACAT    1080

GTGCATACAC ACACACACAG ACAGCGGGGC AGCACCCCCT CCCCACACAC ACACACGCAC    1140

TTCCCCCTTG TCTTGTTCTT CTTTCCTCGN TTCGCATTTC TTTCTCTCGT GCGCTGGCGC    1200

CGGCCTCCTG CACGTCGCTC CCCTCCCCCT AACCTCTATT CTCTCTCTCT CTCTCTCTCG    1260

CCGGCATCAT TGCTTCTTAC CCTTTTCTGA TCCTTGCTCG CGTGGGCGGA CACTGCCACA    1320

GTCCACAGC GCAGACACAC GTGTTTAAAC GGCGCAGGCA TCCCTCCCTA TCACTTCATT    1380

TCTCCTAAAG CCACTCACCA AGTCGCACAC CGCCCTCCCC CATCGGCCGC CCTTCCGGGC    1440

GCAGCTGTGC GGAATGGGTG TGTGCTCGAC CTCGTTCCTG GCAGCTCACT CGCATGTGTA    1500
```

```
CAGCCACTCC AACCACGAAA GCTCTCTTCT GCGCACATAA AAAAAAAAAA AAAAAAAAAA    1560

CTCGAGGGGG GGCCCGGTAC CCAAA                                         1585
```

(2) INFORMATION FOR SEQ ID NO:55:

(i) SEQUENCE CHARACTERISTICS:
        (A) LENGTH: 320 amino acids
        (B) TYPE: amino acid
        (C) STRANDEDNESS:
        (D) TOPOLOGY: linear (ii) MOLECULE TYPE: protein (v) FRAGMENT TYPE: internal (xi) SEQUENCE DESCRIPTION: SEQ ID NO:55:

```
Val Leu Pro Asp Met Thr Cys Ser Leu Thr Gly Leu Gln Cys Thr Asp
1               5                  10                  15

Pro Asn Cys Lys Thr Cys Thr Thr Tyr Gly Gln Cys Thr Asp Cys Asn
            20                  25                  30

Asp Gly Tyr Gly Leu Thr Ser Ser Ser Val Cys Val Arg Cys Ser Val
        35                  40                  45

Ala Gly Cys Lys Ser Cys Pro Val Asp Ala Asn Val Cys Lys Val Cys
    50                  55                  60

Leu Gly Gly Ser Glu Pro Ile Asn Asn Met Cys Pro Cys Thr Asp Pro
65                  70                  75                  80

Asn Cys Ala Ser Cys Pro Ser Asp Ala Gly Thr Cys Thr Gln Cys Ala
                85                  90                  95

Asn Gly Tyr Gly Leu Val Asp Gly Ala Cys Val Arg Cys Gln Glu Pro
            100                 105                 110

Asn Cys Phe Ser Cys Asp Ser Asp Ala Asn Lys Cys Thr Gln Cys Ala
        115                 120                 125

Pro Asn Tyr Tyr Leu Thr Pro Leu Leu Thr Cys Ser Pro Val Ala Cys
    130                 135                 140

Asn Ile Glu His Cys Met Gln Cys Asp Pro Gln Thr Pro Ser Arg Cys
145                 150                 155                 160

Gln Glu Cys Val Ser Pro Tyr Val Val Asp Ser Tyr Asp Gly Leu Cys
                165                 170                 175

Arg Leu Ser Asp Ala Cys Ser Val Pro Asn Cys Lys Lys Cys Glu Thr
            180                 185                 190

Gly Thr Ser Arg Leu Cys Ala Glu Cys Asp Thr Gly Tyr Ser Leu Ser
        195                 200                 205

Ala Asp Ala Thr Ser Cys Ser Ser Pro Thr Thr Gln Pro Cys Glu Val
    210                 215                 220

Glu His Cys Asn Thr Cys Val Asn Gly Asp Ser Thr Arg Cys Ala Tyr
225                 230                 235                 240

Cys Asn Thr Gly Tyr Tyr Val Ser Asp Gly Lys Cys Lys Ala Met Gln
                245                 250                 255

Gly Cys Tyr Val Ser Asn Cys Ala Gln Cys Met Leu Leu Asp Ser Thr
            260                 265                 270

Lys Cys Ser Thr Cys Val Lys Gly Tyr Leu Leu Thr Ser Ser Tyr Ser
        275                 280                 285

Cys Val Ser Gln Lys Val Ile Asn Ser Ala Ala Ala Pro Tyr Ser Leu
    290                 295                 300

Trp Val Ala Ala Ala Val Leu Leu Thr Ser Phe Ala Met His Leu Ala
305                 310                 315                 320
```

(2) INFORMATION FOR SEQ ID NO:56:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:56:

Pro Lys Glu Asp Gly His Ala Pro Lys Asn Asp Asp His Ala
1               5                   10

(2) INFORMATION FOR SEQ ID NO:57:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:57:

Pro Lys Glu Asp Gly His Ala
1               5

(2) INFORMATION FOR SEQ ID NO:58:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:58:

Pro Lys Asn Asp Asp His Ala
1               5

(2) INFORMATION FOR SEQ ID NO:59:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (xi) SEQUENCE DESCRIPTION: SEQ ID NO:59:

```
ATGCACCATC ATCACCATCA CATGGGAAGC TCCTGCACGA AGGACTCCGC AAAGGAGCCC    60

CAGAAGCGTG CTGATAACAT CGATACGACC ACTCGAAGCG ATGAGAAGGA CGGCATCCAT   120

GTCCAGGAGA GCGCCGGTCC TGTGCAGGAG AACTTCGGGG ATGCGCAGGA GAAGAACGAA   180

GATGGACACA ACGTGGGGGA TGGAGCTAAC GACAATGAGG ATGGTAACGA TGATCAGCCG   240

AAGGAGCAGG TTGCCGGCAA CTAG                                         264
```

(2) INFORMATION FOR SEQ ID NO:60:

(i) SEQUENCE CHARACTERISTICS:
    (A) LENGTH: 744 base pairs
    (B) TYPE: nucleic acid
    (C) STRANDEDNESS: single
    (D) TOPOLOGY: linear (xi) SEQUENCE DESCRIPTION: SEQ ID NO:60:

```
ATGGGAGCCT ACTGCACGAA GGACTCCGCA AAGGAGCCCC AGAAGCGTGC TGATAACATC    60
CATAAAACCA CTGAGGCCAA TCACAGAGGC GCCGCCGGTG TGCCCCCGAA GCACGCCGGC   120
GGTGCGATGA ACGACTCTGC CCCGAAGGAG GATGGCCATA CACAGAAAAA TGACGGCGAT   180
GGCCCTAAGG AGGACGGCCG TACACAGAAA AACGACGACG GTGGCCCTAA GGAGGACGGC   240
CATACACAGA AAAATGACGG CGATGGCCCT AAGGAGGACG GCCGTACACA GAAAAATAAC   300
GGCGATGGCC CTAAGGAGGA CGGCCATACA CAGAAAAATG ACGGCGATGC CCCTAAGGAG   360
GACGGCCGTA CACAGAAAAA TGACGGCGAT GGCCCTAAGG AGGACGGCCG TACACAGAAA   420
AATGACGGCG ATGGCCCTAA GGAGGACGGC CGTACACAGA AAAATGACGG CGATGGCCCT   480
AAGGAGGACG GCCGTACACA GAAAAATGAC GGCGATGGCC CTAAGGAGGA CGGCCATACA   540
CAGAAAAATG ACGGCGATGG CCCTAAGGAG GACGGCCGTA CACAGAAAAA TGACGGCGGT   600
GGCCCTAAGG AGGATGAGAA TCTGCAGCAA AACGATGGGA ATGCGCAGGA GAAGAACGAA   660
GATGGACACA ACGTGGGGGA TGGAGCTAAC GGCAATGAGG ATGGTAACGA TGATCAGCCG   720
AAGGAGCAGG TTGCCGGCAA CTAG                                         744
```

(2) INFORMATION FOR SEQ ID NO:61:

(i) SEQUENCE CHARACTERISTICS:
        (A) LENGTH: 80 amino acids
        (B) TYPE: amino acid
        (C) STRANDEDNESS:
        (D) TOPOLOGY: linear (xi) SEQUENCE DESCRIPTION: SEQ ID NO:61:

```
Met Gly Ser Ser Cys Thr Lys Asp Ser Ala Lys Glu Pro Gln Lys Arg
1               5                   10                  15

Ala Asp Asn Ile Asp Thr Thr Thr Arg Ser Asp Glu Lys Asp Gly Ile
            20                  25                  30

His Val Gln Glu Ser Ala Gly Pro Val Gln Glu Asn Phe Gly Asp Ala
        35                  40                  45

Gln Glu Lys Asn Glu Asp Gly His Asn Val Gly Asp Gly Ala Asn Asp
    50                  55                  60

Asn Glu Asp Gly Asn Asp Asp Gln Pro Lys Glu Gln Val Ala Gly Asn
65                  70                  75                  80
```

(2) INFORMATION FOR SEQ ID NO:62:

(i) SEQUENCE CHARACTERISTICS:
        (A) LENGTH: 247 amino acids
        (B) TYPE: amino acid
        (C) STRANDEDNESS:
        (D) TOPOLOGY: linear (xi) SEQUENCE DESCRIPTION: SEQ ID NO:62:

```
Met Gly Ala Tyr Cys Thr Lys Asp Ser Ala Lys Glu Pro Gln Lys Arg
1               5                   10                  15

Ala Asp Asn Ile His Lys Thr Thr Glu Ala Asn His Arg Gly Ala Ala
            20                  25                  30

Gly Val Pro Pro Lys His Ala Gly Gly Ala Met Asn Asp Ser Ala Pro
        35                  40                  45
```

```
Lys Glu Asp Gly His Thr Gln Lys Asn Asp Gly Asp Gly Pro Lys Glu
     50                  55                  60
Asp Gly Arg Thr Gln Lys Asn Asp Asp Gly Gly Pro Lys Glu Asp Gly
 65                  70                  75                  80
His Thr Gln Lys Asn Asp Gly Asp Gly Pro Lys Glu Asp Gly Arg Thr
                 85                  90                  95
Gln Lys Asn Asn Gly Asp Gly Pro Lys Glu Asp Gly His Thr Gln Lys
            100                 105                 110
Asn Asp Gly Asp Ala Pro Lys Glu Asp Gly Arg Thr Gln Lys Asn Asp
            115                 120                 125
Gly Asp Gly Pro Lys Glu Asp Gly Arg Thr Gln Lys Asn Asp Gly Asp
            130                 135                 140
Gly Pro Lys Glu Asp Gly Arg Thr Gln Lys Asn Asp Gly Asp Gly Pro
145                 150                 155                 160
Lys Glu Asp Gly Arg Thr Gln Lys Asn Asp Gly Asp Gly Pro Lys Glu
                165                 170                 175
Asp Gly His Thr Gln Lys Asn Asp Gly Asp Gly Pro Lys Glu Asp Gly
                180                 185                 190
Arg Thr Gln Lys Asn Asp Gly Gly Gly Pro Lys Glu Asp Glu Asn Leu
                195                 200                 205
Gln Gln Asn Asp Gly Asn Ala Gln Glu Lys Asn Glu Asp Gly His Asn
            210                 215                 220
Val Gly Asp Gly Ala Asn Gly Asn Glu Asp Gly Asn Asp Asp Gln Pro
225                 230                 235                 240
Lys Glu Gln Val Ala Gly Asn
                245

(2) INFORMATION FOR SEQ ID NO:63:

(i) SEQUENCE CHARACTERISTICS:
        (A) LENGTH: 14 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 6
        (D) OTHER INFORMATION: /note= "Xaa can be either His or
            Arg"

(ix) FEATURE:
        (A) NAME/KEY: Modified-site
        (B) LOCATION: 12
        (D) OTHER INFORMATION: /note= "Xaa can be either Gly or
            Asp"

(ix) FEATURE:
        (A) NAME/KEY: Modified-site
        (B) LOCATION: 13
        (D) OTHER INFORMATION: /note= "Xaa can be either Asp or
            Gly"

(xi) SEQUENCE DESCRIPTION: SEQ ID NO:63:

Pro Lys Glu Asp Gly Xaa Thr Gln Lys Asn Asp Xaa Xaa Gly
 1               5                  10

(2) INFORMATION FOR SEQ ID NO:64:

(i) SEQUENCE CHARACTERISTICS:
        (A) LENGTH: 7 amino acids
        (B) TYPE: amino acid
        (C) STRANDEDNESS:
```

```
        (D) TOPOLOGY: linear (ix) FEATURE:
        (A) NAME/KEY: Modified-site
        (B) LOCATION: 6
        (D) OTHER INFORMATION: /note= "Xaa can be either His or
            Arg"

(xi) SEQUENCE DESCRIPTION: SEQ ID NO:64:

Pro Lys Glu Asp Gly Xaa Thr
1               5

(2) INFORMATION FOR SEQ ID NO:65:

(i) SEQUENCE CHARACTERISTICS:
        (A) LENGTH: 7 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 5
        (D) OTHER INFORMATION: /note= "Xaa can be either Gly or
            Asp"

(ix) FEATURE:
        (A) NAME/KEY: Modified-site
        (B) LOCATION: 6
        (D) OTHER INFORMATION: /note= "Xaa can be either Asp or
            Gly"

(xi) SEQUENCE DESCRIPTION: SEQ ID NO:65:

Gln Lys Asn Asp Xaa Xaa Gly
1               5

(2) INFORMATION FOR SEQ ID NO:66:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:66:

Gly Cys Gly Pro Lys Glu Asp Gly Arg Thr Gln Lys Asn Asp Gly Asp
1               5                   10                  15
Gly (2) INFORMATION FOR SEQ ID NO:67:

(i) SEQUENCE CHARACTERISTICS:
        (A) LENGTH: 31 amino acids
        (B) TYPE: amino acid
        (C) STRANDEDNESS:
        (D) TOPOLOGY: linear (xi) SEQUENCE DESCRIPTION: SEQ ID NO:67:

Gly Cys Gly Pro Lys Glu Asp Gly Arg Thr Gln Lys Asn Asp Gly Asp
1               5                   10                  15
Gly Pro Lys Glu Asp Gly Arg Thr Gln Lys Asn Asp Gly Asp Gly
            20                  25                  30

(2) INFORMATION FOR SEQ ID NO:68:

(i) SEQUENCE CHARACTERISTICS:
        (A) LENGTH: 45 amino acids
        (B) TYPE: amino acid
        (C) STRANDEDNESS:
```

(D) TOPOLOGY: linear (xi) SEQUENCE DESCRIPTION: SEQ ID NO:68:

Gly Cys Gly Pro Lys Glu Asp Gly Arg Thr Gln Lys Asn Asp Gly Asp
1               5                   10                  15

Gly Pro Lys Glu Asp Gly Arg Thr Gln Lys Asn Asp Gly Asp Gly Pro
                20                  25                  30

Lys Glu Asp Gly Arg Thr Gln Lys Asn Asp Gly Asp Gly
        35                  40                  45

(2) INFORMATION FOR SEQ ID NO:69:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:69:

Gly Cys Gly Pro Lys Glu Asp Gly His Thr Gln Lys Asn Asp Gly Asp
1               5                   10                  15

Gly (2) INFORMATION FOR SEQ ID NO:70:

(i) SEQUENCE CHARACTERISTICS:
        (A) LENGTH: 31 amino acids
        (B) TYPE: amino acid
        (C) STRANDEDNESS:
        (D) TOPOLOGY: linear (xi) SEQUENCE DESCRIPTION: SEQ ID NO:70:

Gly Cys Gly Pro Lys Glu Asp Gly His Thr Gln Lys Asn Asp Gly Asp
1               5                   10                  15

Gly Pro Lys Glu Asp Gly His Thr Gln Lys Asn Asp Gly Asp Gly
                20                  25                  30

(2) INFORMATION FOR SEQ ID NO:71:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:71:

Gly Cys Gly Pro Lys Glu Asp Gly His Thr Gln Lys Asn Asp Gly Asp
1               5                   10                  15

Gly Pro Lys Glu Asp Gly His Thr Gln Lys Asn Asp Gly Asp Gly Pro
                20                  25                  30

Lys Glu Asp Gly His Thr Gln Lys Asn Asp Gly Asp Gly
        35                  40                  45

(2) INFORMATION FOR SEQ ID NO:72:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (xi) SEQUENCE DESCRIPTION: SEQ ID NO:72:

GCTGCAGGAA TTCGGCACGA GATTGCTTCC CAGCCCACCT TCGCTATCCA GCCACTCTCG    60

```
CTCTTCTACA TCTCCCACCC CCTCACACCG CCATGGCTTC TTCCCGCAAG GCTTCCAACC    120

CGCACAAGTC GCACCGCAAG CCGAAGCGCT CGTGGAACGT GTACGTGGGC CGCTCGCTGA    180

AGGCGATCAA CGCCCAGATG TCGATGTCGC ACCGCACGAT GAAGATCGTG AACTCGTACG    240

TGAACGACGT GATGGAGCGC ATCTGCACTG AGGCCGCGTC GATTGTTCGC GCGAACAAGA    300

AGCGCACGTT GGGTGCGCGC GAGGTGCAGA CGGCGGTGCG CATTGTGCTG CCGGCGGAGC    360

TCGCGAAGCA TGCCATGGCT GAGGGCACGA AGGCCGTGTC GAGCGCGTCC CGCTAAAGCG    420

GCTTGCCGGA TGCCGTGTGA GTAGGAGGGT GGCTTGCCGC AAACGCTGAC CTCGGCGATT    480

GCGGCGTGGC GCTCCCCTTC TCCTCCTTGT CCGGCGGTGT GTGTCATGCA TTTGCGTGAC    540

TCCTCCCTCT TATAGATGCA AGCTTTTTTT TTCTCTTGAC GTTTTATTTT CTCCTCCCCC    600

TCCCTTAACG TGAAGTGTAT ATGANAGCGT ACTGGACATG ANANAAAAAA AAAANAAACT    660

CGAG                                                                 664

(2) INFORMATION FOR SEQ ID NO:73:

(i) SEQUENCE CHARACTERISTICS:
        (A) LENGTH: 1432 base pairs
        (B) TYPE: nucleic acid
        (C) STRANDEDNESS: single
        (D) TOPOLOGY: linear (xi) SEQUENCE DESCRIPTION: SEQ ID NO:73:

GATGAAGAAG AGGAGGACAC CACCATCAAC AACTCCGACG TGGTGGTGCG CTACAAGAAG     60

GCCGCAACGT GGTGCAATGA AACGTTGCGC GTGCTTATCG ATGCCACAAA ACCTGGCGCC    120

AAGGTGTGCG ACCTGTGCCG CCTCGGTGAT GACACCATCA CCGCCNAGGT CAAGACAATG    180

TTCAAAGGCA CGGAAAAAGG CATCGCTTTC CCGACCTGCA TCTCGGTCAA CAACTGCGTA    240

TGCCACAACA GCCCTGGCGT GTCGGACGAG ACGACGCAGC AAGAGATCGC GATGGGTGAC    300

GTCGTGCACT ACGACCTGGG CATCCACGTG GACGGCTACT GCGCCGTCGT CGCGCACACC    360

ATTCAGGTGA CAGAGGACAA TGAGCTTGGC AAGGACGAGA AGGCGGCGCG CGTCATTACA    420

GCGGCGTACA ACATCCTGAA CACGGCGCTG CGCCAGATGC GTCCCGGTAC GACCATCTAC    480

CAGGTGACAG ACGTAGTTGA GAAGGCTGCG GAGCACTACA AGGTGACTCC GGTAGACGGC    540

GTCCTCTCGC ATATGATGAA CGCTACATC ATAGACNGAT ACCGCTGTAT CCCGCAGCGC    600

AGGGTCGCGG AGCACATGGT GCACGACTAC GATCTCGAGA AAGCGCAGGT GTGGACGCTA    660

GACATTGTCA TGACCTCCGG CAAGGGCAAG CTGAAGGAGC GCGATGCGCG GCCGTGCGTG    720

TTCAAGGTGG CTCTGGACTC CAACTACTCT GTGAAAATGG AAAGCGCGAA GGAGGTTCAG    780

AAGGAAATCG ACTCCNAGTA TGCCACCTTC CCCTTTGCCA TCCGCAACCT GGAGGCCAAG    840

AAGGCCCGCC TCGGTCTCAA CGAGATGGCG AAGCACGGTG CTGTCATCCC GTACCCTATT    900

CTCTTCGAAA AGGAAGGCGA GGTCGTCGCC CATTTCAAGA TTACGGTGCT CATCAGCAAC    960

AAGAAGATTG AGCCGATTAC CGGCCTGAAG CCGCAGAAGG CCCCGGCGCT CGAGCCATAC   1020

ACGGACGAGA TGCTGCTTGC GACGAACAAG CTCTTCGCTG TCGCTAGAGA AGAAGGCGGC   1080

GAAGTAGACG GCCGTGGCAT CCGTGACGCT GTACTGCGAG CTTTCGTAGG CGTACGCCTC   1140

TTGTGAGGCG TACACGTGTG CTGTTTGCGG ACGAGGAGGC ACCCATTCTG TTCCCCTTCT   1200

TCGCTAATCT TCGCGTTTCC TCTGACGCTG GCTTCTYTGC CGGAGTGTGG TGAGGCGCGT   1260

GGGGGAGAAA CGGCCCACTY GCATGCCTGT GCATACGCGA GCACGGTAGG GAGCGCGGTG   1320

TGTGTGTGTG TGGGGGGGCG TGTTACGAGT ACAAAAGAGG CTCGATCTTT GCGATCTTTT   1380
```

```
CTTTCTGTAA ACAGGAACAT AAGTAACCAA AAAAAAAAAA AAAAAACTCG AG          1432
```

(2) INFORMATION FOR SEQ ID NO:74:

(i) SEQUENCE CHARACTERISTICS:
        (A) LENGTH: 873 base pairs
        (B) TYPE: nucleic acid
        (C) STRANDEDNESS: single
        (D) TOPOLOGY: linear (xi) SEQUENCE DESCRIPTION: SEQ ID NO:74:

```
CTTTATTGTC ATCACTGTAA AGCACTGTTT TTTCTTTCAC TTTTTCTTGA GTGTTTTCTT    60

CTATTCACCA TGAGCATTAT CAAGGAGGAC GACGCCGTGG GCTGCTACAT GACGGTGACC   120

CTCGTGGACG ACACCAAGGT GGAGGGTACC ATCTTCACCT ACAATTCCAA GGAGGGCATC   180

ATAGTACTCC TGTCCCTCCG CGACGATCAG ACGAACATGA AGCTAATCCG CACTCCGTAC   240

ATCAAAGACT TCAGCCTTTC ACACGCTGAG GAGGGAGCGC ACCTGCCCCC GGCACTGGAC   300

TCCTTCAACG AGCTTCCGTC CATGCACGCC GGCCGCGACA AGTCCATCTT CAAGCACGCC   360

AGCACGCAGC TCAAGAACGC CGAGGCGAAC CGCGAAAAGC ACTTCAACTC TGTCACGACC   420

GACACACCGA TTGCCACACT TGATGCGTAC CTCAAGCTCC TGCGGCTATA CCCCTTAATT   480

GAGTGGAACA GCGACGAGGG TGTCATCCAG GTCTCGGACA CCGTCATTGT CGTAGGAGAC   540

CCCGACTGGC GGACGCCCAA GGCAATGCTG GTGGACGGCG CCCCTGAGAA GGACAGACCG   600

CTTGTAGATC GCCTGCAGGT TGCGCTCGGM AACGGCAAGA AGTGATTCAG TGTGTAGCGG   660

ACAGAACATC GTGTGCTTGT GTGTCTGTTT GANGTTTGTT TGTTTTCTCT TTGTGGTACT   720

GCGTACGACG GCGCCTTCTC CCGGTGGTGG GTGAGTCCAT AAGCAGTTGA GTTCTYGGTT   780

GTAGNAAVGC CTYACYGCCG ACCATATGGG AGAGGGCGAA CAAATNTTTG ATAGAAGTTG   840

AAAATCCCAA AGTYAAAAGA AAAAAAAAN AAA                                873
```

(2) INFORMATION FOR SEQ ID NO:75:

(i) SEQUENCE CHARACTERISTICS:
        (A) LENGTH: 1238 base pairs
        (B) TYPE: nucleic acid
        (C) STRANDEDNESS: single
        (D) TOPOLOGY: linear (xi) SEQUENCE DESCRIPTION: SEQ ID NO:75:

```
TTTCTGTACT TTATTGAACA TCAGTAGAAC ACGTTCTTCC CGCAAAGATG GCCAAGAAGC    60

ACCTCAAGCG CTTGTATGCG CCCAAGGACT GGATGCTGAG CAAGCTGACC GGCGTGTTCG   120

CGCCGCGTCC GCGTCCGGGT CCGCACAAGC TGCGCGAGTG CCTGCCGCTN CTGGTGATCA   180

TCCGCAACCG GCTGAAGTAC GCGCTGAACG CGCGCGAGGG TGAGATGATC CTGCGCCAGG   240

GTCTGGTGCA CGTGGACAAC CACCCGCGCC GCGACGGCAA GTATCCCGCC GGTTTCATGG   300

ACGTGGTCGA GATCCCGAAG ACGGGCGACC GCTTCCGCCT GATGTACGAC GTCAAGGGCC   360

GCTTCGCGTT GGTGAACCTG TCCGAGGCGG AGGCGCAGAT CAAGCTGATG AAGGTTGTGA   420

ACCTGTACAC GGCCACCGGC CGCGTGCCGG TCGCTGTGAC GCACGACGGC CACCGCATCC   480

GCTACCCGGA CCCGCACACC TCCATTGGTG ACACCATCGT GTACAACGTC AAGGAGAAGA   540

AGTGCGTGGA CCTGATCAAG AACCGCCAGG GCAAGGCCGT GATCGTGACC GGTGGCGCCA   600

ACCGCGGCCG CATCGGCGAG ATCGTGAAGG TGGAGTGCCA CCCCGGTGCG TTCAACATTG   660

CGCACCTGAA GGACGCGTCC GGCGCCGAGT TCGCCACCCG CGCCGCGAAC ATCTTCGTGA   720

TCGGCAAGGA CCTGAACAAC CTGCAGGTAA CGGTGCCGAA GCAGCAGGGC CTGCGCATGA   780
```

```
ACGTGATCCA GGAGCGCGAG GAGCGCCTGA TCGCGGCGGA GGCCCGCAAG AACGCGCCGG      840

CTCGTGGTGC CCGCAGGGCC CGCAAGTGAG GAGGCGATTA CACGCATGCG TGTTTGTGGC      900

TCTGAAGCGA CTTGGCGGGT CGGCTGTGAG GGTTTGAGAG GAGGTGTGTG ATGCGTGTGA      960

AGTCCTTCTC CGTTCTCAGC TCTCTCTGTG CTGTAGCTGT GCCTTTCCCC AGATCGCTTT     1020

ACCGCATTTG CATACATCTG TGTAGTCGCA TGTGCGTGTT TCTGTCTCTC GGTGGGTCTC     1080

CCTCTCCCTC CCTTTCTGCC TCTCTCTTTG AGTGGGTGTG CATGCGTCGC GCGCGACGGG     1140

CTCCGCTTNA GTGATTCTCT CGTGTTTTAN GGCTGTTTTY TTTCTYAGTT NAGCGTTTTY     1200

GTTCATGATT TCCTCAGACC CAAAAAAAAA AAAAAAAA                             1238

(2) INFORMATION FOR SEQ ID NO:76:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (xi) SEQUENCE DESCRIPTION: SEQ ID NO:76:

CTGACGGAGT TCCAGACGAA CCTTGTGCCG TACCCGCGCA TCCACTTCGT GCTGACAAGC       60

TACGCTCCGG TGGTGTCTGC CGAGAAGGCG TACCACGAGC AGCTNTCCGT CGCGGACATC      120

ACGAACTCGG TNTTTGAGCC TGCTGGCATG CTNACAAAGT GCGATCCTCG CCACGGCAAG      180

TACATGTCGT GCTGCCTCAT GTACCGCGGT GATGTCGTGC CGAAGGATGT CAACGCCGCG      240

ATTGCGACGA TCAAGACGAA GCGCACAATT CAGTTCGTGG ACTGGTGCCC GACCGGCTTC      300

AAGTGCGGCA TCAACTACCA GCCGCCGACC GTTGTGCCCG GCGGTGACCT CGCGAAGGTG      360

CAGCGCGCCG TGTGCATGAT TGCCAACTCG ACCGCGATCG CTGAGGTGTT TGCCCGCATC      420

GACCACAAGT TCGACCTGAT GTACAGCAAG CGCGCGTTTG TGCACTGGTA CGTGGGTGAG      480

GGCATGGAGG AGGGCGAGTT CTCCGAGGCG CGCGAGGATC TCGCTGCGCT GGAGAAGGAC      540

TACGAGGAGG TTGGCGCCGA GTCCGCCGAC GACATGGGCG AGGAGGACGT CGAGGAGTAC      600

TAAGGTAGAC TCGTGCCGCG CGCTGATGAT GTAGGTGCAC GCGTGCGTGT GCTGCAGCGG      660

AGCCGCCGCC ACCGCGACTG TGTGTGTGTG CGCGCGTGAC GACCGGCTCG AG             712

(2) INFORMATION FOR SEQ ID NO:77:

(i) SEQUENCE CHARACTERISTICS:
        (A) LENGTH: 1086 base pairs
        (B) TYPE: nucleic acid
        (C) STRANDEDNESS: single
        (D) TOPOLOGY: linear (xi) SEQUENCE DESCRIPTION: SEQ ID NO:77:

CAAGAAGTGG ATCAAGCAGG AGACGAACGC CGATGGCGAG CGCGTGCGCC GCGCGTTCTG       60

CCAGTTCTGC CTAGACCCCA TCTACCAGAT CTTCGACGCT GTGATGAACG AGAAGAAGGA      120

CAAGGTGGAC AAGATGCTCA AGTCGCTGCA CGTGACGCTN ACGGCTGAGG AGCGCGAGCA      180

GGTGCCGAAN AAGCTTCTGA AGACGGTGAT GATGAANTTC CTGCCGGCTG CTGAGACGCT      240

GCTACAGATG ATCGTGGCGC ACCTGCCGTC GCCCAAGAAG GCGCAGGCGT ACCGTGCGGA      300

GATGCTGTAC TCTGGCGAGG CGTCGCCGGA GGACAAGTAC TTCATGGGTA TCAAGAACTG      360

CGACCCCGCT GCGCCGCTCA TGCTGTACAT CAGCAAGATG GTGCCGACGG CCGACCGCGG      420

CCGCTTCTTC GCCTTTGGCC GCATCTTCTC CGGTAAGGTG CGCAGCGGCC AGAAGGTGCG      480
```

-continued

| | |
|---|---|
| CATCATGGGT AACAACTACG TCTACGGCAA GAAGCAGGAC CTGTACGAGG ACAAGCCTGT | 540 |
| GCAGCGCTCC GTGCTGATGA TGGGCCGCTA CCAGGAGGCC GTGGAGGACA TGCCGTGCGG | 600 |
| TAACGTGGTG GGCCTTGTGG GCGTGGACAA GTACATCGTG AAGTCCGCGA CGATCACGGA | 660 |
| CGATGGCGAG AGCCCGCACC CGCTGCGCGA CATGAAGTAC TCTGTGTCGC CCGTCGTGCG | 720 |
| TGTGGCCGTG GAGGCGAAGA ACCCGTCCGA CCTGCCGAAG CTTGTGGAGG GCCTGAAGCG | 780 |
| CCTTGCCAAG TCCGACCCGC TGGTGGTGTG CAGCATTGAG GAGTCTGGCG AGCACATTGT | 840 |
| TGCCGGCGCT GGCGAGCTTC ACCTTGAGAT TTGCCTGAAG GATCTCCAGG AGGACTTCAT | 900 |
| GAACGGCGCG CCGCTNAAGA TCTCCGAGCC GGTGGTGTCG TTCCGCGAGA CGGTGACGGA | 960 |
| TGTGTCGTCG CAGCAGTGCC TGTCGAAGTC TGCGAACAAG CACAACCGTC TCTTCTGCCG | 1020 |
| CGGTGCGCCG CTNACAGAGG ANCTGGCGCT GGCGATNGAN GAAGGCACCG CTGGTCCCGA | 1080 |
| NGCGGA | 1086 |

(2) INFORMATION FOR SEQ ID NO:78:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (xi) SEQUENCE DESCRIPTION: SEQ ID NO:78:

| | |
|---|---|
| CGCATCAACG TCTACTTCGA TNAGTCGACG GGAGGCCGCT ACGTGCCGCG CGCCGTGCTG | 60 |
| ATGGACCTCG AGCCCGGCAC TATGGACTCC GTTCGCGCCG GCCCGTACGG CCAGCTGTTC | 120 |
| CGCCCGGACA ACTTCATCTT TGGTCAGTCC GGCGCTGGCA ACAACTGGGC CAAGGGCCAC | 180 |
| TACACTGAGG GCGCGGAGCT GATCGACTCC GTGCTTGATG TGTGCCGCAA GGAGGCGGAG | 240 |
| AGCTGCGACT GCCTGCAGGG CTTCCAGCTG TCTCACTCCC TCGGCGGCGG CACGGGCTCC | 300 |
| GGCATGGGCA CGCTGCTCAT TTCCAANCTG CGCGANGAGT ACCCGGACCG GATCATGATG | 360 |
| ACCTTCTCCG TCATCCCGTC CCCCCGCGTG TCGGATACCG TTGTGGANCC GTACAACACG | 420 |
| ACCCTCTCTG TGCACCAGCT CGTGGAA | 447 |

(2) INFORMATION FOR SEQ ID NO:79:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (xi) SEQUENCE DESCRIPTION: SEQ ID NO:79:

| | |
|---|---|
| GTAACCCGCT GGTGTACGCA TATGTAGACA CAGACGGGCA GCACGAGACG ACGTTCCTCG | 60 |
| CGATCCCTGT GGTGCTTGGC ATGAATGGAA TCGAGAAGCG CCTGCCGATT GGTCCGCTGC | 120 |
| ACTCGACGGA GGAAACGCTG CTGAAGGCGG CACTGCCGGT GATCAAGAAG AATATCGTGA | 180 |
| AGGGCAGCGA GTTCGCGCGC TCACACCTGT AGCACCTCAG CTTTTTTTTT TTGCGTTAAA | 240 |
| CGGGCGTGGG AAGCACCTCG ATACTTCGCT TCGCGCTGAC GGACCCGCAC GACATCGTTC | 300 |
| GTCATCCCCC TCCCCCTCTT CGGCCCTATA CGCATGAAGG AGTGGAATTA TGCAACAGCA | 360 |
| TGTTNATATC AAGTG | 375 |

(2) INFORMATION FOR SEQ ID NO:80:

(i) SEQUENCE CHARACTERISTICS:
        (A) LENGTH: 107 amino acids

```
          (B) TYPE: amino acid
          (C) STRANDEDNESS:
          (D) TOPOLOGY: linear (xi) SEQUENCE DESCRIPTION: SEQ ID NO:80:

Met Ala Ser Ser Arg Lys Ala Ser Asn Pro His Lys Ser His Arg Lys
1               5                   10                  15

Pro Lys Arg Ser Trp Asn Val Tyr Val Gly Arg Ser Leu Lys Ala Ile
            20                  25                  30

Asn Ala Gln Met Ser Met Ser His Arg Thr Met Lys Ile Val Asn Ser
            35                  40                  45

Tyr Val Asn Asp Val Met Glu Arg Ile Cys Thr Glu Ala Ala Ser Ile
50                  55                  60

Val Arg Ala Asn Lys Lys Arg Thr Leu Gly Ala Arg Glu Val Gln Thr
65                  70                  75                  80

Ala Val Arg Ile Val Leu Pro Ala Glu Leu Ala Lys His Ala Met Ala
            85                  90                  95

Glu Gly Thr Lys Ala Val Ser Ser Ala Ser Arg
            100                 105

(2) INFORMATION FOR SEQ ID NO:81:

(i) SEQUENCE CHARACTERISTICS:
          (A) LENGTH: 381 amino acids
          (B) TYPE: amino acid
          (C) STRANDEDNESS:
          (D) TOPOLOGY: linear (xi) SEQUENCE DESCRIPTION: SEQ ID NO:81:

Asp Glu Glu Glu Asp Thr Thr Ile Asn Asn Ser Asp Val Val Val
1               5                   10                  15

Arg Tyr Lys Lys Ala Ala Thr Trp Cys Asn Glu Thr Leu Arg Val Leu
            20                  25                  30

Ile Asp Ala Thr Lys Pro Gly Ala Lys Val Cys Asp Leu Cys Arg Leu
            35                  40                  45

Gly Asp Asp Thr Ile Thr Ala Xaa Val Lys Thr Met Phe Lys Gly Thr
50                  55                  60

Glu Lys Gly Ile Ala Phe Pro Thr Cys Ile Ser Val Asn Asn Cys Val
65                  70                  75                  80

Cys His Asn Ser Pro Gly Val Ser Asp Glu Thr Thr Gln Gln Glu Ile
            85                  90                  95

Ala Met Gly Asp Val Val His Tyr Asp Leu Gly Ile His Val Asp Gly
            100                 105                 110

Tyr Cys Ala Val Val Ala His Thr Ile Gln Val Thr Glu Asp Asn Glu
            115                 120                 125

Leu Gly Lys Asp Glu Lys Ala Ala Arg Val Ile Thr Ala Ala Tyr Asn
130                 135                 140

Ile Leu Asn Thr Ala Leu Arg Gln Met Arg Pro Gly Thr Thr Ile Tyr
145                 150                 155                 160

Gln Val Thr Asp Val Val Glu Lys Ala Ala Glu His Tyr Lys Val Thr
            165                 170                 175

Pro Val Asp Gly Val Leu Ser His Met Met Lys Arg Tyr Ile Ile Asp
            180                 185                 190

Xaa Tyr Arg Cys Ile Pro Gln Arg Arg Val Ala Glu His Met Val His
            195                 200                 205

Asp Tyr Asp Leu Glu Lys Ala Gln Val Trp Thr Leu Asp Ile Val Met
210                 215                 220
```

```
Thr Ser Gly Lys Gly Lys Leu Lys Glu Arg Asp Ala Arg Pro Cys Val
225                 230                 235                 240

Phe Lys Val Ala Leu Asp Ser Asn Tyr Ser Val Lys Met Glu Ser Ala
                245                 250                 255

Lys Glu Val Gln Lys Glu Ile Asp Ser Xaa Tyr Ala Thr Phe Pro Phe
                260                 265                 270

Ala Ile Arg Asn Leu Glu Ala Lys Lys Ala Arg Leu Gly Leu Asn Glu
                275                 280                 285

Met Ala Lys His Gly Ala Val Ile Pro Tyr Pro Ile Leu Phe Glu Lys
                290                 295                 300

Glu Gly Glu Val Val Ala His Phe Lys Ile Thr Val Leu Ile Ser Asn
305                 310                 315                 320

Lys Lys Ile Glu Pro Ile Thr Gly Leu Lys Pro Gln Lys Ala Pro Ala
                325                 330                 335

Leu Glu Pro Tyr Thr Asp Glu Met Leu Leu Ala Thr Asn Lys Leu Phe
                340                 345                 350

Ala Val Ala Arg Glu Glu Gly Gly Val Asp Gly Arg Gly Ile Arg
                355                 360                 365

Asp Ala Val Leu Arg Ala Phe Val Gly Val Arg Leu Leu
370                 375                 380

(2) INFORMATION FOR SEQ ID NO:82:

(i) SEQUENCE CHARACTERISTICS:
        (A) LENGTH: 191 amino acids
        (B) TYPE: amino acid
        (C) STRANDEDNESS:
        (D) TOPOLOGY: linear (xi) SEQUENCE DESCRIPTION: SEQ ID NO:82:

Met Ser Ile Ile Lys Glu Asp Asp Ala Val Gly Cys Tyr Met Thr Val
1               5                   10                  15

Thr Leu Val Asp Asp Thr Lys Val Glu Gly Thr Ile Phe Thr Tyr Asn
                20                  25                  30

Ser Lys Glu Gly Ile Ile Val Leu Leu Ser Leu Arg Asp Asp Gln Thr
                35                  40                  45

Asn Met Lys Leu Ile Arg Thr Pro Tyr Ile Lys Asp Phe Ser Leu Ser
50                  55                  60

His Ala Glu Glu Gly Ala His Leu Pro Pro Ala Leu Asp Ser Phe Asn
65                  70                  75                  80

Glu Leu Pro Ser Met His Ala Gly Arg Asp Lys Ser Ile Phe Lys His
                85                  90                  95

Ala Ser Thr Gln Leu Lys Asn Ala Glu Ala Asn Arg Glu Lys His Phe
                100                 105                 110

Asn Ser Val Thr Thr Asp Thr Pro Ile Ala Thr Leu Asp Ala Tyr Leu
                115                 120                 125

Lys Leu Leu Arg Leu Tyr Pro Leu Ile Glu Trp Asn Ser Asp Glu Gly
                130                 135                 140

Val Ile Gln Val Ser Asp Thr Val Ile Val Gly Asp Pro Asp Trp
145                 150                 155                 160

Arg Thr Pro Lys Ala Met Leu Val Asp Gly Ala Pro Glu Lys Asp Arg
                165                 170                 175

Pro Leu Val Asp Arg Leu Gln Val Ala Leu Gly Asn Gly Lys Lys
                180                 185                 190
```

(2) INFORMATION FOR SEQ ID NO:83:

(i) SEQUENCE CHARACTERISTICS:
        (A) LENGTH: 273 amino acids
        (B) TYPE: amino acid
        (C) STRANDEDNESS:
        (D) TOPOLOGY: linear (xi) SEQUENCE DESCRIPTION: SEQ ID NO:83:

```
Met Ala Lys Lys His Leu Lys Arg Leu Tyr Ala Pro Lys Asp Trp Met
1               5                   10                  15
Leu Ser Lys Leu Thr Gly Val Phe Ala Pro Arg Pro Arg Pro Gly Pro
            20                  25                  30
His Lys Leu Arg Glu Cys Leu Pro Leu Leu Val Ile Ile Arg Asn Arg
        35                  40                  45
Leu Lys Tyr Ala Leu Asn Ala Arg Glu Gly Glu Met Ile Leu Arg Gln
    50                  55                  60
Gly Leu Val His Val Asp Asn His Pro Arg Arg Asp Gly Lys Tyr Pro
65                  70                  75                  80
Ala Gly Phe Met Asp Val Val Glu Ile Pro Lys Thr Gly Asp Arg Phe
                85                  90                  95
Arg Leu Met Tyr Asp Val Lys Gly Arg Phe Ala Leu Val Asn Leu Ser
            100                 105                 110
Glu Ala Glu Ala Gln Ile Lys Leu Met Lys Val Val Asn Leu Tyr Thr
        115                 120                 125
Ala Thr Gly Arg Val Pro Val Ala Val Thr His Asp Gly His Arg Ile
    130                 135                 140
Arg Tyr Pro Asp Pro His Thr Ser Ile Gly Asp Thr Ile Val Tyr Asn
145                 150                 155                 160
Val Lys Glu Lys Lys Cys Val Asp Leu Ile Lys Asn Arg Gln Gly Lys
                165                 170                 175
Ala Val Ile Val Thr Gly Gly Ala Asn Arg Gly Arg Ile Gly Glu Ile
            180                 185                 190
Val Lys Val Glu Cys His Pro Gly Ala Phe Asn Ile Ala His Leu Lys
        195                 200                 205
Asp Ala Ser Gly Ala Glu Phe Ala Thr Arg Ala Ala Asn Ile Phe Val
    210                 215                 220
Ile Gly Lys Asp Leu Asn Asn Leu Gln Val Thr Val Pro Lys Gln Gln
225                 230                 235                 240
Gly Leu Arg Met Asn Val Ile Gln Glu Arg Glu Arg Leu Ile Ala
                245                 250                 255
Ala Glu Ala Arg Lys Asn Ala Pro Ala Arg Gly Ala Arg Arg Ala Arg
            260                 265                 270
Lys
```

(2) INFORMATION FOR SEQ ID NO:84:

(i) SEQUENCE CHARACTERISTICS:
        (A) LENGTH: 200 amino acids
        (B) TYPE: amino acid
        (C) STRANDEDNESS:
        (D) TOPOLOGY: linear (xi) SEQUENCE DESCRIPTION: SEQ ID NO:84:

```
Leu Thr Glu Phe Gln Thr Asn Leu Val Pro Tyr Pro Arg Ile His Phe
1               5                   10                  15
Val Leu Thr Ser Tyr Ala Pro Val Val Ser Ala Glu Lys Ala Tyr His
            20                  25                  30
```

```
Glu Gln Leu Ser Val Ala Asp Ile Thr Asn Ser Val Phe Glu Pro Ala
             35                  40                  45

Gly Met Leu Thr Lys Cys Asp Pro Arg His Gly Lys Tyr Met Ser Cys
         50                  55                  60

Cys Leu Met Tyr Arg Gly Asp Val Val Pro Lys Asp Val Asn Ala Ala
 65                  70                  75                  80

Ile Ala Thr Ile Lys Thr Lys Arg Thr Ile Gln Phe Val Asp Trp Cys
                 85                  90                  95

Pro Thr Gly Phe Lys Cys Gly Ile Asn Tyr Gln Pro Pro Thr Val Val
             100                 105                 110

Pro Gly Gly Asp Leu Ala Lys Val Gln Arg Ala Val Cys Met Ile Ala
             115                 120                 125

Asn Ser Thr Ala Ile Ala Glu Val Phe Ala Arg Ile Asp His Lys Phe
         130                 135                 140

Asp Leu Met Tyr Ser Lys Arg Ala Phe Val His Trp Tyr Val Gly Glu
145                 150                 155                 160

Gly Met Glu Glu Gly Glu Phe Ser Glu Ala Arg Glu Asp Leu Ala Ala
             165                 170                 175

Leu Glu Lys Asp Tyr Glu Glu Val Gly Ala Glu Ser Ala Asp Asp Met
             180                 185                 190

Gly Glu Glu Asp Val Glu Glu Tyr
             195                 200

(2) INFORMATION FOR SEQ ID NO:85:

(i) SEQUENCE CHARACTERISTICS:
        (A) LENGTH: 361 amino acids
        (B) TYPE: amino acid
        (C) STRANDEDNESS:
        (D) TOPOLOGY: linear (xi) SEQUENCE DESCRIPTION: SEQ ID NO:85:

Lys Lys Trp Ile Lys Gln Glu Thr Asn Ala Asp Gly Glu Arg Val Arg
1                5                  10                  15

Arg Ala Phe Cys Gln Phe Cys Leu Asp Pro Ile Tyr Gln Ile Phe Asp
             20                  25                  30

Ala Val Met Asn Glu Lys Lys Asp Lys Val Asp Lys Met Leu Lys Ser
             35                  40                  45

Leu His Val Thr Leu Thr Ala Glu Arg Glu Gln Val Pro Xaa Lys
         50                  55                  60

Leu Leu Lys Thr Val Met Met Xaa Phe Leu Pro Ala Ala Glu Thr Leu
 65                  70                  75                  80

Leu Gln Met Ile Val Ala His Leu Pro Ser Pro Lys Lys Ala Gln Ala
                 85                  90                  95

Tyr Arg Ala Glu Met Leu Tyr Ser Gly Glu Ala Ser Pro Glu Asp Lys
             100                 105                 110

Tyr Phe Met Gly Ile Lys Asn Cys Asp Pro Ala Ala Pro Leu Met Leu
             115                 120                 125

Tyr Ile Ser Lys Met Val Pro Thr Ala Asp Arg Gly Arg Phe Phe Ala
             130                 135                 140

Phe Gly Arg Ile Phe Ser Gly Lys Val Arg Ser Gly Gln Lys Val Arg
145                 150                 155                 160

Ile Met Gly Asn Asn Tyr Val Tyr Gly Lys Lys Gln Asp Leu Tyr Glu
             165                 170                 175

Asp Lys Pro Val Gln Arg Ser Val Leu Met Met Gly Arg Tyr Gln Glu
```

```
                  180                 185                 190
Ala Val Glu Asp Met Pro Cys Gly Asn Val Val Gly Leu Val Gly Val
            195                 200                 205
Asp Lys Tyr Ile Val Lys Ser Ala Thr Ile Thr Asp Asp Gly Glu Ser
        210                 215                 220
Pro His Pro Leu Arg Asp Met Lys Tyr Ser Val Ser Pro Val Val Arg
225                 230                 235                 240
Val Ala Val Glu Ala Lys Asn Pro Ser Asp Leu Pro Lys Leu Val Glu
                245                 250                 255
Gly Leu Lys Arg Leu Ala Lys Ser Asp Pro Leu Val Val Cys Ser Ile
                260                 265                 270
Glu Glu Ser Gly Glu His Ile Val Ala Gly Ala Gly Glu Leu His Leu
            275                 280                 285
Glu Ile Cys Leu Lys Asp Leu Gln Glu Asp Phe Met Asn Gly Ala Pro
        290                 295                 300
Leu Lys Ile Ser Glu Pro Val Val Ser Phe Arg Glu Thr Val Thr Asp
305                 310                 315                 320
Val Ser Ser Gln Gln Cys Leu Ser Lys Ser Ala Asn Lys His Asn Arg
                325                 330                 335
Leu Phe Cys Arg Gly Ala Pro Leu Thr Glu Xaa Leu Ala Leu Ala Xaa
                340                 345                 350
Xaa Glu Gly Thr Ala Gly Pro Xaa Ala
            355                 360

(2) INFORMATION FOR SEQ ID NO:86:

(i) SEQUENCE CHARACTERISTICS:
        (A) LENGTH: 149 amino acids
        (B) TYPE: amino acid
        (C) STRANDEDNESS:
        (D) TOPOLOGY: linear (xi) SEQUENCE DESCRIPTION: SEQ ID NO:86:

Arg Ile Asn Val Tyr Phe Asp Xaa Ser Thr Gly Gly Arg Tyr Val Pro
1               5                   10                  15
Arg Ala Val Leu Met Asp Leu Glu Pro Gly Thr Met Asp Ser Val Arg
                20                  25                  30
Ala Gly Pro Tyr Gly Gln Leu Phe Arg Pro Asp Asn Phe Ile Phe Gly
            35                  40                  45
Gln Ser Gly Ala Gly Asn Asn Trp Ala Lys Gly His Tyr Thr Glu Gly
        50                  55                  60
Ala Glu Leu Ile Asp Ser Val Leu Asp Val Cys Arg Lys Glu Ala Glu
65                  70                  75                  80
Ser Cys Asp Cys Leu Gln Gly Phe Gln Leu Ser His Ser Leu Gly Gly
                85                  90                  95
Gly Thr Gly Ser Gly Met Gly Thr Leu Leu Ile Ser Xaa Leu Arg Xaa
                100                 105                 110
Glu Tyr Pro Asp Arg Ile Met Met Thr Phe Ser Val Ile Pro Ser Pro
            115                 120                 125
Arg Val Ser Asp Thr Val Val Xaa Pro Tyr Asn Thr Thr Leu Ser Val
        130                 135                 140
His Gln Leu Val Glu
145

(2) INFORMATION FOR SEQ ID NO:87:
```

-continued (i) SEQUENCE CHARACTERISTICS:
    (A) LENGTH: 69 amino acids
    (B) TYPE: amino acid
    (C) STRANDEDNESS:
    (D) TOPOLOGY: linear (xi) SEQUENCE DESCRIPTION: SEQ ID NO:87:

```
Asn Pro Leu Val Tyr Ala Tyr Val Asp Thr Asp Gly Gln His Glu Thr
1               5                  10                  15

Thr Phe Leu Ala Ile Pro Val Val Leu Gly Met Asn Gly Ile Glu Lys
               20                  25                  30

Arg Leu Pro Ile Gly Pro Leu His Ser Thr Glu Glu Thr Leu Leu Lys
               35                  40                  45

Ala Ala Leu Pro Val Ile Lys Lys Asn Ile Val Lys Gly Ser Glu Phe
           50                  55                  60

Ala Arg Ser His Leu
65
```